(12) United States Patent
Robinson et al.

(10) Patent No.: US 7,795,017 B2
(45) Date of Patent: Sep. 14, 2010

(54) DNA EXPRESSION VECTORS AND METHODS OF USE

(75) Inventors: Harriet L. Robinson, Atlanta, GA (US); Rama R. Amara, Atlanta, GA (US); Ted M. Ross, Aspinall, PA (US); Rick A. Bright, Atlanta, GA (US)

(73) Assignee: Emory University, Atlanta, GA (US)

( * ) Notice: Subject to any disclaimer, the term of this patent is extended or adjusted under 35 U.S.C. 154(b) by 679 days.

(21) Appl. No.: 11/009,063

(22) Filed: Dec. 9, 2004

(65) Prior Publication Data

US 2006/0051839 A1 Mar. 9, 2006

Related U.S. Application Data

(63) Continuation of application No. 09/798,675, filed on Mar. 2, 2001, now abandoned.

(60) Provisional application No. 60/186,364, filed on Mar. 2, 2000, provisional application No. 60/251,083, filed on Dec. 1, 2000.

(51) Int. Cl.
*C07H 21/04* (2006.01)
*C12N 15/63* (2006.01)

(52) U.S. Cl. .................. 435/320.1; 536/23.1

(58) Field of Classification Search .............. None
See application file for complete search history.

(56) References Cited

U.S. PATENT DOCUMENTS

| | | |
|---|---|---|
| 5,169,763 A | 12/1992 | Kieny et al. |
| 5,185,146 A | 2/1993 | Altenburger |
| 5,256,767 A | 10/1993 | Salk et al. |
| 5,445,953 A | 8/1995 | Dorner et al. |
| 5,494,807 A | 2/1996 | Paoletti et al. |
| 5,589,466 A | 12/1996 | Felgner et al. |
| 5,593,972 A | 1/1997 | Weiner et al. |
| 5,614,404 A | 3/1997 | Mazzara et al. |
| 5,676,950 A | 10/1997 | Small et al. |
| 5,736,368 A | 4/1998 | Mazzara et al. |
| 5,741,492 A | 4/1998 | Hurwitz et al. |
| 5,747,324 A | 5/1998 | Mazzara et al. |
| 5,747,338 A | 5/1998 | Giese et al. |
| 5,756,103 A | 5/1998 | Paoletti et al. |
| 5,766,599 A | 6/1998 | Paoletti et al. |
| 5,795,577 A | 8/1998 | Kieny et al. |
| 5,817,637 A | 10/1998 | Weiner et al. |
| 5,846,946 A | 12/1998 | Huebner et al. ............... 514/44 |
| 5,849,304 A | 12/1998 | Moss et al. |
| 5,853,725 A | 12/1998 | Salk et al. |
| 5,858,775 A * | 1/1999 | Johnson .................. 435/320.1 |
| 5,863,542 A | 1/1999 | Paoletti et al. |
| 5,879,925 A | 3/1999 | Rovinski et al. |
| 5,911,989 A | 6/1999 | Katinger et al. ......... 424/160.1 |
| 5,928,930 A | 7/1999 | Salk et al. |
| 5,985,641 A | 11/1999 | Haynes et al. |
| 6,051,410 A | 4/2000 | Mazzara et al. |
| 6,077,662 A | 6/2000 | Compans et al. ............... 435/5 |
| 6,080,408 A | 6/2000 | Rovinski et al. |
| 6,086,891 A | 7/2000 | Hurwitz et al. |
| 6,099,847 A | 8/2000 | Tobin et al. |
| 6,103,244 A | 8/2000 | Dorner et al. |
| 6,121,021 A | 9/2000 | Rovinski et al. |
| 6,140,114 A | 10/2000 | Klatzmann et al. |
| 6,156,952 A | 12/2000 | Bryant et al. ................ 800/11 |
| 6,171,596 B1 | 1/2001 | Earl et al. |
| 6,204,250 B1 | 3/2001 | Bot et al. |
| 6,210,663 B1 | 4/2001 | Ertl |
| 6,214,804 B1 | 4/2001 | Felgner et al. |
| 6,265,183 B1 | 7/2001 | Dorner et al. |
| 6,291,157 B1 | 9/2001 | Rovinski et al. |
| 6,448,083 B1 * | 9/2002 | Larocca et al. ............. 435/456 |

(Continued)

FOREIGN PATENT DOCUMENTS

EP 0 335 635 10/1989

(Continued)

OTHER PUBLICATIONS

Letvin (1998, Science, vol. 280, pp. 1875-1880).*

(Continued)

*Primary Examiner*—Celine X Qian
(74) *Attorney, Agent, or Firm*—Fish & Richardson P.C.

(57) ABSTRACT

The present invention relates to novel plasmid constructs useful for the delivery of DNA vaccines. The present invention provides novel plasmids having a transcription cassette capable of directing the expression of a vaccine nucleic acid insert encoding immunogens derived from any pathogen, including fungi, bacteria and viruses. The present invention, however, is particularly useful for inducing in a patient an immune response against pathogenic viruses such as HIV, measles or influenza. Immunodeficiency virus vaccine inserts of the present invention express non-infectious HIV virus-like particles (VLP) bearing multiple viral epitopes. VLPs allow presentation of the epitopes to multiple histocompatability types, thereby reducing the possibility of the targeted virus escaping the immune response. Also described are methods for immunizing a patient by delivery of a novel plasmid of the present invention to the patient for expression of the vaccine insert therein. Optionally, the immunization protocol may include a booster vaccination that may be a live vector vaccine such as a recombinant pox virus or modified vaccinia Arbora vector. The booster live vaccine vector includes a transcription cassette expressing the same vaccine insert as the primary immunizing vector.

10 Claims, 61 Drawing Sheets

U.S. PATENT DOCUMENTS

| | | | | |
|---|---|---|---|---|
| 6,544,527 | B1 | 4/2003 | Rovinski et al. | 424/208.1 |
| 6,663,871 | B1 | 12/2003 | McMichael et al. | |
| 6,841,381 | B1 * | 1/2005 | Robinson et al. | 435/320.1 |

FOREIGN PATENT DOCUMENTS

| | | |
|---|---|---|
| EP | 0 538 496 | 8/1991 |
| WO | WO 89/09620 | 10/1989 |
| WO | WO 89/12095 | 12/1989 |
| WO | WO 91/07425 | 5/1991 |
| WO | WO 97/27311 | 7/1997 |
| WO | WO 98/56919 | 12/1998 |
| WO | WO 99/63098 | 12/1999 |
| WO | WO 00/00216 | 1/2000 |
| WO | WO 01/47955 | 7/2000 |
| WO | WO 01/02607 | 1/2001 |
| WO | WO 01/52886 | 7/2001 |
| WO | WO 01/82962 | 11/2001 |
| WO | WO 01/92470 | 12/2001 |
| WO | WO02/072754 | 9/2002 |
| WO | WO03/004657 | 1/2003 |

OTHER PUBLICATIONS

Feinberg et al. (2002, Nature Medicine, vol. 8, pp. 207-210).*
Burton et al. Why do we not have an HIV vaccine and how can we make one? Nature Medicine, 1998. vol. 4, pp. 495-498.*
Markmeyer et al (Gene, 1990. vol. 93, pp. 129-134).*
Sipsas et al (J. Clin. Invest. 1997, vol. 99, No. 4, pp. 752-762).*
Huang et al., "Human Immunodeficiency Virus Type 1-Specific Immunity . . . " J. of Virology 75:4947-4951, 2001.
Kong et al., "Immunogenicity of Mutliple Gene and Clade Human Immunodeficiency.." J. of Virology 77(23):12764-12772, 2003.
Megede et al., "Increased Expression and Immunogenicity of Sequence-Modified . . . " J. of Virology 74(6):2628-2635, 2000.
Persson et al., "Modifications of HIV-1 Retrovirus-Like Particles to Enhance . . . " Biologicals 26:255-265, 1998.
Smith et al., "Multiprotein HIV Type 1 Clade B DNA/MVA Vaccine: . . . " AIDS Research and Human Retroviruses 20(6):654-665, 2004.
Accession No. AF430344; (XP-002321209); Smith et al., Oct. 9, 2001.
Accession No. AF426288; (XP-002321210); Smith et al., Mar. 12, 2002.
Belyakov et al., "Induction of a Mucosal Cytotoxic T-Lymphocyte Response by . . . " J. of Virology 72(1):8264-8272, 1998.
Davison et al., "Structure of Vaccinia Virus Early Promoters" J. Mol. Biol. 210:749-769, 1989.
Earl, P.L. et al., "Comparison of vaccine strategies using recombinant env-gag-pol MVA with or without an oligomeric env protein boost in the SHIV rhesus macaque model" Virology (2002) 294:270-281.
Girard, M. et al., "New prospects for the development of a vaccine against human immunodeficiency virus type 1. An overview" C.R. Acad. Sci. Paris, Sciences de la Vie/Life Sciences (1999) 322:959-966.
Gomez, C.E. et alk, 2001 "Recombinant proteins produced by vaccinia virus vectors can be incorporated within the virion (IMV form) into different compartments" Arch Virol. 146(5):875-892.
Haffar et al., "The Carboxy Terminus of Human Immunodeficiency Virus Type I gp 160 . . . " J. of Virology 64(6):3100-3103, 1990.
Hanke et al., "Development of a DNA-MVA/HIVA vaccine for Kenya" Vaccine 20:1995-1998, 2002.
Hanke et al., "Effective induction of HIV-specific CTL by multi-epitope using gene gun . . . " Vaccine 17:589-596, 1999.
Hanke et al., "Immunogenicities of intravenous and intramuscular administrations of modified vaccinia . . . " J. of General Virology 79:83-90, 1998.
Hanke et al., "Lack of toxicity and persistence in the mouse associated with administration of candidate . . . " Vaccine 21:108-114, 2002.
Hanke et al., "Pre-clinical development of a multi-CTL epitope-based DNA prime MVA boost vaccine for ADS" Immunology Letters 66:177-181, 1999.

Hirsch, V.M. et al., 1995 "Limited virus replication following SIV challenge of macaques immunized with attenuated MVA vaccinia expressing SIVsm env and gag-pol" Vaccines 95:195-200.
Karacostas, V. et al., 1989 "Human immunodeficiency virus-like particles produced by a vaccinia virus expression vector" PNAS USA 86:8964-8967.
Masternak et al., "cis- and trans-Acting Elements Involved in Reactivation of Vaccinia Virus Early Transcription" J. of Virology 70(12):8737-8746, 1996.
Men, R. et al., "Immunization of rhesus monkeys with a recombinant of modified vaccinia virus Ankara expressing a truncated envelope glycoprotein of dengue type 2 virus induced resistance to dengue type 2 virus challenge" Vaccine (2000) 18:3113-3122.
Moss, B. et al., 2000 "Retroviruses of human AIDS and related animal diseases" in: Colloque des Cent Gardes, 12th, Paris, France, Oct. 25-27, 1999, Meeting Date 1999, 105-107, Eds. M. Girard & B. Dodet, Editions Scientifiques et Medicales Elsevier, Paris, Fr. (Abstract).
Wee et al., "A DNA/MVA-based candidate human immunodeficiency virus for Kenya induces . . . " J. of General Virology 83:75-80, 2002.
Wyatt et al., "Development of a replication-deficient recombinant vaccinia virus vaccine effective against . . . " Vaccine 14(15):1451-1458, 1996.
Wyatt et al., "Priming and boosting immunity to respiratory syncytial virus by recombinant replication-defective . . . " Vaccine 18:392-397, 2000.
Gao et al., "Effects of Mutations in the Polymerase Domain on the Polymerase, . . . " J. Mol. Biol. 277:559-572, 1998.
Ayyavoo et al., "Immunogenicity of a novel DNA vaccine cassette expressing multiple . . . " AIDS 14:1-9, 2000.
Caselli et al., "DNA immunization with HIV-1 tat mutated in the trans activation domain . . . " J. of Immunol. 162:5631-5638, 1999.
Englund et al., "Integration is required for productive infection of monocyte-derived macrophages . . . " J. of Virol. 69(5):3216-3219, 1995.
Le Grice et al., "Active site mutagenesis of the AIDS virus protease and its alleviation . . . " The EMBO J. 7(8):2547-2553, 1988.
Mizrahi et al., "Mutagenesis of the conserved aspartic acid 443, glutamic acid 478 . . . "J. of Biol. Chem 269(30):19245-19249, 1994.
Wakefield et al., "In vitro enzymatic activity of human immunodeficiency virus type 1 . . . " J. of Virol. 66(11):6806-6812, 1992.
Zhang et al., "Nucleocapsid protein effects on the specificity of retrovirus RNA encapsidation" J. of Virol. 69(9):5716-5722, 1995.
Azevedo et al., "Main features of DNA-based immunization vectors" Br. J. of Medic. & Biol. Res. 32:147-153, 1999.
Bowie et al., "Deciphering the message in protein sequences: tolerance to amino acid substitutions" Science 257:1306-1310, 1990.
Davison et al., "New vaccinia cirus recombination plasmids incorporating a synthetic . . . " Nucl. Acids Res. 18(14):4285-4286, 1990.
Earl et al., Immunogenicity and protective efficacy of oligomeric human . . . J. Virol. 75(2):645-653, 2001.
Greenspan et al., "Defining opitopes: it's not as easy as it seems" Nature Biotech. 7:936-837, 1999.
Allen et al., "Induction of AIDS virus-specific CTL activity in fresh, unstimulated peripheral blood lymphocytes from rhesus macaques vaccinated with a DNA prime/modified vaccinia virus Ankara boost regimen," J. Immunol., 164: 4968-4978, 2000.
Amara et al., "Control of a Mucosal Challenge and Prevention of AIDS by a Multiprotein DNA/MVA Vaccine," Science, 292: 69-74, 2001.
Andre et al., "Increased immune response elicited by DNA vaccination with a synthetic gp120 sequence with optimized codon usage," J. Virol., 72: 1497 1503, 1998.
Antoine et al., "The Complete Genomic Sequence of the Modified Vaccinia Ankara Strain: Comparison with Other Orthopoxviruses", Virology, 244: 365-96, 1998.
Asakura et al., "Induction of HIV 1 specific mucosal immune responses by DNA vaccination." Scand. J. Immunol., 46: 326-330, 1997.
Bachmann and Zinkernagel, "Neutralizing antiviral B cell responses." in Ann. Rev. Immunol., 15: 235-270, 1997.

Barouch et al., "Reduction of Simian-human immunodeficiency virus 89.6P viremia in rhesus monkeys by recombinant modified vaccinia virus Ankara vaccination," J. Virol., 75: 5151-5158, 2001.

Barouch et al., "Control of Viremia and prevention of clinical AIDS in rhesis monkeys by cytokine-augmented DNA vaccination," Science, 290: 486-492, 2000.

Barouch et al., "Augmentation of immune responses to HIV-1 and simian immunodeficiency virus DNA caccines by IL-2/IG plasmid administration in rhesus monkeys", Proc. Natl. Acad. Sci. U.S.A., 97:4192-7, Apr. 11, 2000.

Barry et al., "Protection against mycoplasma infection using expression-library immunization," Nature, 377: 632-635, 1995.

Berger, "HIV Entry and Tropism: the chemokine receptor connection," AIDS, 11(Suppl. A): S3-16, 1997.

Benson et al., J. Virol., "Recombinant vaccine-induced protection against the highly pathogenic simian immunodeficiency virus SIV(mac251): dependence on route of challenge exposure," 72: 4170-4182, 1998.

Blanchard et al., "Modified vaccinia virus Ankara undergoes limited replication in human cells and lacks several immunomodulatory proteins: implications for use as a human vaccine," J. Gen. Virol., 79: 1159-1167, 1998.

Bohm et al., "DNA vector constructs that prime hepatitis B surface antigen-specific cytotoxic T lymphocyte and antibody responses in mice after intramuscular injection," J. Immuno. Methods, 193: 29-40, 1996.

Bohm et al., "Routes of plasmid DNA vaccination that prime murine humoral and cellular immune responses," Vaccine, 16: 949-54, 1998.

Bolivar et al., "Construction and Characterization of New Cloning Vehicles: (II. A Multipurpose Cloning System)," Gene, 2: 95-113, 1977.

Boyer et al., "Protection of chimpanzees from high-dose heterologous HIV-1 challenge by DNA vaccination," Nature Med., 3: 526-532, 1997.

Boyle et al., "Influence of cellular location of expressed antigen on the efficacy of DNA vaccination: cytotoxic T lymphocyte and antibody responses are suboptimal when antigen is cytoplasmic after intramuscular DNA immunization," Int. Immunol., 9: 1897-1906, 1997.

Boyle et al., "Enhanced responses to a DNA vaccine encoding a fusion antigen that is directed to sites of immune induction," Nature, 392: 408-411, 1998.

Burton and Montefiori, "The antibody response in HIV-1 infection," AIDS, 11(Suppl A):S87-98, 1997.

Calarota et al., "Cellular cytotoxic response induced by DNA vaccination in HIV-1-infected patients," Lancet, 351: 1320-1325, 1998.

Cardoso et al., "Immunization with Plasmid DNA Encoding for the Measles Virus Hemagglutinin and Nucleoprotein Leads to Humoral and Cell-Mediated Immunity," Virology, 225: 293-299. 1998.

Carroll and Moss, "Heat Range and Cytopathogenicity of the Highly Attenuated MVA Strain of Vaccina Virus: Propagation and Generation of Recombinant Viruses in a Nonhuman Mammalian Cell Line", Virology, 238:198-211, 1997.

Chapman et al., "Effect of intron A from human cytomegalovirus (Towne) immediate-early gene on heterologous expression in mammalian cells," Nucl. Acids Res., 19: 3979-3986, 1991.

Chen et al., "Protective Immunity Induced by Oral Immunization with a Rotavirus DNA Vaccine Encapsulated in Microparticles," J. Virol., 72: 5757-5761, 1998.

Chun et al., "Early establishment of a pool of latently infected, resting CD4+ T cells during primary HIV-1 infection," Proc. Natl. Acad. Sci. USA, 95: 8869-8873, 1998.

Collman et al., "An Infection Molecular Clone of an Unusual Microphage-Tropic and Highly Cytopathic Strain of Human Immunodeficiency Virus Type 1," J. Virol., 66: 7517-7521, 1992.

Condon et al., "DNA-based immunization by in vivo transfection of dendritic cells," Nat Med., 2:1122-1128, 1996.

Corr et al., "Gene Vaccination with Naked Plasmid DNA: Mechanism of CTL Priming," J. Exp. Med., 184: 1555-1560, 1996.

Dempsey et al., C3d of Complement as a Molecular Adjuvant: Bridging Innate and Acquired Immunity, Science, 271: 348-350, 1996.

Durbin et al., "Comparison of the Immunogenicity and efficacy of a replication-defective vaccinia virus expressing antigens of human parainfluenza virus type 3 (HPIV3) with those of a live attenuated HPIV3 vaccine candidate in rhesus monkeys passively immunized with PIV3 antibodies," J. Infect. Dis., 179: 1345-1351, 1999.

Durbin et al., "The immunogenicity and efficacy of intranasally or parenterally administered replication-deficient vaccinia-parainfluenza virus type 3 recombinants in rhesus monkeys", Vaccine, 16: 1324-30, 1998.

Egan et al., "Simian immunodeficiency virus (SIV) gag DNA-vaccinated rhesus monkeys develop secondary cytotoxic T-lymphocyte responses and control viral replication after pathogenic SIV infection," J Virol., 74:7485-7495, 2000.

Endo et al., "Short- and Long-term Clinical Outcomes in Rhesus Monkeys Inoculated with a Highly Pathogenic Chimeric Simian/Human Immunodeficiency Virus", J. Virol., 74:6935-45, 2000.

Esparza and Bhamarapravati, "Accelerating the development and future availability of JTV-1 vaccines: why, when, where, and how?", Lancet, 355: 2061-6, 2000.

Evans DT et al., "Virus-specific T-lymphocyte responses select for amino-acid variation in simian immunodeficiency virus Env and Nef," Nat. Med., 5: 1270-1276, 1999.

Feltquate et al., "Different T Helper Cell Types and Antibody Isotypes Generated by Saline and Gene Gun DNA Immunization," J. Immunol. 158: 2278-2284, 1997.

Finzi et al., "Latent infection of CD4 T cells provides a mechanism for lifelong persistence of HIV-1, even in patients on effective combination therapy", Nat. Med. 5: 1270-6, 1996.

Fomsgaard et al., "Improved Humoral and Cellular Immune Responses Against the gp120 V3 Loop of HIV-1 Following Genetic Immunization with a Chimeric DNA Vaccine Encoding the V3 Inserted into the Hepatitis B Surface Antigen," Scand. J. Immunol., 47:289-295, 1998.

Fu et al., "Priming of Cytotoxic T Lymphocytes by DNA Vaccines: Requirement for Professional Antigen Presenting Cells and Evidence for Antigen Transfer from Myocytes," Mol. Med., 3: 362-371, 1997.

Furci et al., "Antigen-driven C-C Chemokine-mediated HIV-1 Suppression by CD4 T Cells from Exposed Uninfected Individuals Expressing the Wild-type CCR-5 Allele", J. Exp. Med., 186:455-60, 1997.

Fynan et al., "DNA vaccines: Protective immunizations by parenteral, mucosal, and gene-gun inoculations," Proc. Natl. Acad. Sci. USA, 90: 11478-11482, 1993.

Gorelick et al., "Nucleocapsid Protein Zinc-Finger Mutants of Simian Immunodeficiency Virus Strain Mne Produce Virions That are Replication Defective in Vitro and in Vivo", Virology, 259-70, 1999.

Goulder et al., "Anti-HIV cellular immunity: recent advances towards vaccine design", AIDS, 13: S121-36, 1999.

Hakim et al., "A Nine-Amino Acid Peptide from IL-1β Augments Antitumor Immune Responses Induced by Protein and DNA Vaccines," J. Immunol., 157: 5503-5511, 1996.

Hanke, "Effective Induction of Simian Immunodeficiency Virus-Specific Cytotoxic T Lymphocytes in Macaques by Using a Multiepitope Gene and DNA Prime-Modified Vaccinia Virus Ankara Boost Vaccination Regimen," J. Virol., 73: 7524-7532, 1999.

Hanke et al., "Enhancement of MHC class I-restricted peptide-specific T cell induction by a DNA prime/MVA boost vaccination regime," Vaccine, 16: 439-445, 1998a.

Hanke et al., "DNA multi-CTL epitope vaccines for HIV and Plasmodium faciparum: immunogenicity in mice," Vaccine, 16: 426-435, 1998b.

Hartikka et al., "An Improved Plasmid DNA Expression Vector for Direct Injection into Skeletal Muscle," Hum. Gen. Therapy, 7: 1205-1217, 1996.

Hirsch et al., "Prolonged Clinical Latency and Survival of Macaques Given a Whole Inactivated Simian Immunodeficiency Virus Vaccine", J. Infect. Dis., 170:51-9, 1994.

Hofmann-Lehmann et al., "Sensitive and robust one-tube real-time reverse Transcriptase-polymerase chain reaction to quantify SIV RNA load: comparison of one- versus two-enzyme systems," AIDS Res. Hum. Retroviruses, 16: 1247-1257, 2000.

Inchauspe et al., "Plasmid DNA Expressing a Secreted or a Nonsecreted Form of Hepatitis C Virus Nucleocapsid: Comparative Studies of Antibody and T-Helper Responses Following Genetic Immunization," DNA Cell Biol., 16: 185-195, 1997.

Iwasaki et al., "Enhanced CTL responses mediated by plasmid DNA immunogens encoding costimulatory molecules and cytokines," J. Immunol., 158: 4591-4601, 1997a.

Iwasaki et al., "The dominant role of bone-marrow derived cells in CTL induction following plasmid DNA immunization at different sites," J. Immunol., 159: 11-14, 1997b.

Jin et al., "Dramatic Rise in Plasma Viremia after CD8 T Cell Depletion in Simian Immunodeficiency Virus-infected Macaques", J. Exp. Med., 189: 991 8, 1999.

Jones et al., "Poly (DL-lactide-co-glycolide) encapsulated plasmid: DNA elicits systemic and mucosal antibody responses to encoded protein after oral administration." Vaccine, 15: 814-817, 1997.

Karlsson et al., "Characterization of Molecularly Cloned Simian-Human Immunodeficiency Viruses Causing Rapid CD4 Lymphocyte Depletion in Rhesus Monkeys", J. Virol., 71: 4218-25, 1997.

Kawabata et al., "The Fate of Plasmid DNA After Intravenous Injection in Mice: Involvement of Scavenger Receptors in Its Hepatic Uptake," Pharm Res., 12: 825-830, 1995.

Kent et al., "Enhanced T-Cell Immunogenicity and Protective Efficacy of a Human Immunodeficiency Virus Type 1 Vaccine Regimen Consisting of Consecutive Priming with DNA and Recombinant Fowlpox Virus," J. Virol., 72: 10180-10188, 1998.

Kern et al., "Target structures of the CD8(+)-T-cell response to human cytomegalovirus: the 72-kilodalton major immediate-early protein revisited," J. Virol., 73: 8179-8184, 1999.

Knapp et al., "A high frequency of Mamu-A*01 in the rhesus macaque detected by polymerase chain reaction with sequence-specific primers and direct sequencing," Tissue Antigens, 50: 657-661, 1997.

Korber et al., "Epidemiological and Immunological Implications of the Global Variability of HIV" *Retroviral Immunology*, B. Walker, D. Pantaleo, Eds (The Humana Press, Totowa, NH, In press), 2001.

Kuroda et al., "Analysis of Gag-specific Cytotoxic T Lymphocytes in Simian Immunodeficiency Virus-infected Rhesus Monkeys by Cell Staining with a Tetrameric Major Histocompatibility Complex Class I-Peptide Complex," J. Exp. Med., 187: 1373-1381, 1998.

Lau et al., "Cytotoxic T-cell memory without antigen", Nature, 369: 648-52, 1994.

Lechner et al., "Analysis of Successful Immune Responses in Persons Infected with Hepatitis C Virus", J. Exp. Med., 191:1499-1512, 2000.

Letvin et al., "Cytotoxic T lymphocytes specific for the simian immunodeficiency virus", Immunol. Rev., 170: 127-34, 1999.

Letvin et al., "Potent, protective anti-HIV immune responses generated by bimodal HIV envelope DNA plus protein vaccination," Proc. Natl. Acad. Sci. USA, 94: 9378-9383, 1997.

Levy et al., "Controlling HIV pathogenesis: the role of the noncytotoxic anti-HIV response of CD8 T cells", Immunol. Today, 17: 217-24, 1996.

Lew et al., "Cancer Gene Therapy Using Plasmid DNA: Pharmacokinetic Study of DNA Following Injection in Mice," Hum. Gene Ther., 6: 553, 1995.

Lewis, et al., "Limited Protection from a Pathogenic Chimeric Simian-Human Immunodeficiency Virus Challenge following Immunization with Attenuated Simian Immunodeficiency Virus", J. Virol., 73: 1262-70, 1999.

Li et al., "Infection of Cynomolgus Monkeys with a Chimeric HIV-2/$SIV_{mac}$ Virus That Expresses the HIV-1 Envelope Glycoproteins," J. of AIDS, 5: 639-646, 1992.

Lifson et al., "The Extent of Early Viral Replication Is a Critical Determinant of the Natural History of Simian Immunodeficiency Virus Infection", J. Virol., 71: 9508-14, 1997.

Livingston et al., "The Induction of Mucosal Immunity in the Female Genital Tract Using Gene-Gun Technology (Part 1: Antigen Expression)," Ann. New York Acad. Sci., 772: 265-267, 1995.

Lu et al., "SIV DNA vaccine trial in macaques: post-challenge necropsy in vaccine and control groups," Vaccine 15: 920-923, 1997.

Maecker et al., "DNA vaccination with cytokine fusion constructs biases the immune response to ovalbumin," Vaccine, 15: 1687-1696, 1997.

Maecker et al., "Cytotoxic 1 Cell Responses to DNA Vaccination: Dependence on Antigen Presentation via Class II MHC[1]," J. Immunol., 161: 6532-6536, 1998.

Mahnel et al., "[Experiences with immunization against orthopox viruses of humans and animals using vaccine strain MVA]," Berl. Munch Tierarztl Wochenschr, 107: 253-256, 1994. [English Translation of Abstract Attached].

Manthorpe et al., "Gene Therapy by Intramuscular Injection of Plasmid DNA: Studies on Firefly Luciferase Gene Expression in Mice," Hum. Gene Therapy, 4: 419-431, 1993.

Mayr et al., "[The smallpox vaccination strain MVA: marker, genetic structure, experience gained with the parenteral vaccination and behavior in organisms with a debilitated defence mechanism (author's transl)]," Zentralbl. Bakteriol., 167: 375-390, 1978. [English Translation of Abstract Attached].

McCluskie et al., "Direct Gene Transfer to the Respiratory Tract of Mice with Pure Plasmid and Lipid-Formulated DNA", Antisense Nucleic Acid Drug Dev., 8: 401-414, 1998.

Mellors et al., "Prognosis in HIV-1 Infection Predicted by the Quantity of Virus in Plasma" Science, 272:1167-70, 1996.

Montefiori et al., "Neutralizing antibodies in sera from macaques infected with chimeric simian-human immunodeficiency virus containing the envelope glycoproteins of either a laboratory-adapted variant or a primary isolate of human immunodeficiency virus type 1," J. Virol., 72: 3427-3431, 1998.

Montefiori et al., "Evaluation of antiviral drugs and neutralizing antibodies to human immunodeficiency virus by a rapid and sensitive microtiter infection assay," J. Clin. Microbiol., 26: 231-237, 1988.

Montgomery et al., "Heterologous and Homologous Protection Against Influenza A by DNA Vaccination: Optimization of DNA Vectors," DNA Cell Biol., 12: 777-783, 1993.

Moore et al., "HIV-1 neutralization: the consequences of viral adaptation to growth on transformed T cells," AIDS, 9(Suppl. A):S117-136, 1995.

Murali-Krishna et al., "Counting Antigen-Specific CD8 T Cells: A Reevaluation of Bystander Activation during Viral Infection," Immunity, 8:177-187, 1998.

Murali-Krishna et al., "Persistence of Memory CD8T Cells in MHC Class 1-Deficient Mice", Science, 286:1377-81, 1999.

Ourmanov et al., "Comparative efficacy of recombinant modified vaccinia virus Ankara expressing simian immunodeficiency virus (SIV) Gag-Pol and/or Env in macaques challenged with pathogenic SIV," J. Virol., 74: 2740-2751, 2000.

Ourmanov et al., "Recombinant modified vaccinia virus ankara expressing the surface gp120 of simian immunodeficiency virus (SIV) primes for a rapid neutralizing antibody response to SIV infection in macaques," J. Virol., 74: 2960-2965, 2000.

Pal et al., "Inhibition of IIIV-1 Infection by the β-Chemokine MDC", Science, 278: 695-8, 1997.

Pertmer and Robinson, "Studies on Antibody Responses Following Neonatal Immunization with Influenza Hemagglutinen DNA or Protein," Virology, 257:406-414, (1999).

Pertmer et al., "Influenza Virus Nucleoprotein-Specific Immunoglobin G Subclass and Cytokine Responses Elicited by DNA Vaccination Are Dependent on the Route of Vector DNA Delivery." J. Virol.. 70: 6119-6125. 1996.

Pertmer et al., "Gene gun-based nucleic acid immunization: elicitation of humoral and cytotoxic T lymphocyte responses following epidermal delivery of nanogram quantities of DNA," Vaccine, 13: 1427-1430, 1995.

Poignard et al., "Neutralizing Antibodies Have Limited Effects on the Control of Established HIV-1 Infection in Vivo," Immunity, 10: 431-438, 1999.

Porgador et al., "Predominant Role for Directly Transfected Dendritic Cells in Antigen Presentation to CD8+ T Cells after Gene Gun Immunization," J. Exp. Med., 188: 1075-1082, 1998.

Power et al., "A valid ELISPOT assay for enumeration of ex vivo, antigen-specific, IFNγ-producing T cells," J. Immunol. Methods, 227: 99-107, 1999.

Quinn et al., "Viral Load and Heterosexual Transmission of Human Immunodeficiency Virus Type 1", N. Eng. J. Med., 342: 921-9, 2000.

Ramshaw and Ramsey, "The prime-boost strategy: exciting prospects for improved vaccination", Immunol. Today, 21: 163-5, 2000.

Reimann et al., "An *env* Gene Derived from a Primary Human Immunodeficiency Virus Type 1 Isolate Confers High In Vivo Replicative Capacity to a Chimeric Simian/Human Immunodeficiency Virus in Rhesus Monkeys," J. Virol., 70: 3198-3206, 1996.

Reimann et al., "A Chimeric Simian/Human Immunodeficiency Virus Expressing a Primary Patient Human Immunodeficiency Virus Type 1 Isolate *env* Causes an AIDS-Like Disease after In Vivo Passage in Rhesus Monkeys," J. Virol., 70: 6922-6928, 1996.

Richmond et al., "Studies of the Neutralizing Activity and Avidity of Anti-Human Immunodeficiency Virus Type 1 Env Antibody Elicited by DNA Priming and Protein Boosting," J. Virol., 72: 9092-9100, 1998.

Robinson and Pertmer, "DNA Vaccines: Basic Studies and Applications," in *Adv. Virus Res.*, 55: 1-74, 2000.

Robinson et al., "AIDS Vaccines: Heterologous Prime/Boost Strategies for raising Protective T Cell Responses", AIDS Reviews, 2:105-110, 2000.

Robinson and Pertmer, "Nucleic Acid Immunizations," in *Current Protocols in Immunology*, (R. Coico, Ed.), vol. 1, pp. 2.14.1-2.14.19. 3 vols. John Wiley & Sons, Inc., New York, 1998.

Robinson et al., "Protection against a lethal influenza virus challenge by immunization with a haemagglutinin-expressing plasmid DNA," Vaccine, 11: 957-960, 1993.

Robinson et al., "The Scientific Future of DNA for Immunization," American Academy of Microbiology, May 13-Jun. 2, 1996, 1997.

Robinson et al., "Neutralizing antibody-independent containment of immunodeficiency virus challenges by DNA priming and recombinant pox virus booster immunizations," Nature Med., 5: 526, 1999.

Rodriguez et al., "DNA Immunization: Ubiquitination of a Viral Protein Enhances Cytotoxic T-Lymphocyte Induction and Antiviral Protection but Abrogates Antibody Induction," J. Virol., 71: 8497-8503, 1997.

Ross et al., "C3d enhancement of antibodies to hemagglutinin accelerates protection against influenza virus challenge," Nat. Immunology, 1:127-131, 2000.

Ross et al.. "Enhanced Avidity Maturation of Antibody to Human Immunodeficiency Virus Envelope: DNA Vaccination with gp120-C3d Fusion Proteins." AIDS Res. Human Retro., 17(a):829-835, 2001.

Rubbert et al., "Multifactorial nature of non cytolytic CD8+ T cell-mediated suppression of HIV replication: beta-chemokine dependent and independent effects," AIDS Res. Hum. Retroviruses 13: 63-9, 1997.

Sasaki et al., "Comparison of Intranasal and Intramuscular Immunization against Human Immunodeficiency Virus Type 1 with a DNA-Monophosphoryl Lipid A Adjuvant Vaccine," Infect. Immunol., 66: 823-826, 1998.

Sauter et al., "An Internalization Signal in the Simian Immunodeficiency Virus Transmembrane Protein Cytoplasmic Domain Modulates Expression of Envelope Glycoproteins on the Cell Surface", J. Cell Biol., 132: 795-811, 1996.

Schmitz et al., "Control of Viremia in Simian Immunodeficiency Virus Infection by CD8 Lymphocytes", Science, 283: 857-60, 1999.

Schneider et al., "Induction of CD8 cells using heterologous prime-boost immunisation strategies", Immunol. Rev., 170: 29-38, 1999.

Schneider et al., "Enhanced immunogenicity for CD8+ T cell induction and complete protective efficacy of malaria DNA vaccination by boosting with modified vaccinia virus Ankara," Nat. Med., 4: 397-402, 1998.

Scholtissek et al., "A cloning cartridge of $\lambda\ t_o$ to terminator," Nucleic Acids Res., 15: 3185, 1987.

Sizemore et al., "Attenuated *Shigella* as a DNA Delivery Vehicle for DNA-Mediated Immunization," Science, 270: 299-302, 1995.

Sizemore et al., "Attenuated bacteria as a DNA delivery vehicle for DNA-mediated immunization," Vaccine, 15: 804-807, 1997.

Staprans et al., "Simian Immunodeficiency Virus Disease Course Is Predicted by the Extent of Virus replication during Primary Infection", J. Virol., 73:4829-39, 1999.

Staprans et al., "Quantitative Methods to Monitor Viral Load in Simian Immunodeficiency Virus Infections," in *Viral Genome Methods*, K. Adolph, Ed., CRC Press, Boca Raton, FL, pp. 167-184, 1996).

Stittelaar et al., "Protective immunity in macaques vaccinated with a modified vaccinia virus Ankara-based measles virus vaccine in the presence of passively acquired antibodies," J. Virol., 74: 4236-4243, 2000.

Subbarao et al., "Genetic variability of HIV-1," AIDS, 10(Suppl. A):S13-23, 1996.

Sutcliffe, "Complete nucleotide sequence of the *Escherichia coli* plasmid pBR322," Cold Spring Harbor Quant. Biol., 43: 77-90, 1979.

Sutter et al., "Nonreplicating vaccinia vector efficiently expresses recombinant genes," Proc. Natl. Acad Sci. USA, 89: 10847-10851, 1992.

Tang et al.. "Genetic immunization is a simple method for eliciting an immune response," Nature, 356: 152-154, 1992.

Thomson et al., "Delivery of Multiple CD8 Cytotoxic T Cell Epitopes by DNA Vaccination," J. Immunol , 160: 1717-1723, 1998.

Tobery et al., "Targeting of HIV 1 Antigens for Rapid Intracellular Degradation Enhances Cytotoxic T Lymphocyte (CTL) Recognition and the Induction of De Novo CTL Responses In Vivo After Immunization," J. Exp. Med., 185: 909-920. 1997.

Tomaras et al., "CD8 T cell-mediated suppressive activity inhibits HIV-1 after virus entry with kinetics indicating effects on virus gene expression", Proc. Natl. Acad. Sci. U.S.A, 97:3503-8, 2000.

Torres et al., "DNA immunization: effect of secretion of DNA-expressed hemaggutinins on antibody responses," Vaccine, 18: 805-814, 2000.

Torres et al., "Differential Dependence on Target Site Tissue for Gene Gun and Intramuscular DNA Immunizations," J. Immunol., 158: 4529-4532, 1997.

Uchijima et al., "Optimization of Codon Usage of Plasmid DNA Vaccine Is Required for the Effective MHC Class I-Restricted T Cell Responses Against an Intracellular Bacterium," J. Immunol., 161: 5594-5599, 1998.

Ulmer et al., "Heterologous Protection Against Influenza by Injection of DNA Encoding a Viral Protein," Science 259: 1745-1749, 1993.

Villinger et al., "Induction of Long-Term Protective Effects against Heterologous Challenge in SIVhu-Infected Macaques", Virology, 278:194-206, 2000.

Waldrop et al., "Determination of Antigen-specific Memory/Effector CD4 T Cell Frequencies by Flow Cytometry", J. Clin. Invest., 99:1739-50, 1997.

Watson et al., "Plasma Viremia in Macaques Infected with Simian Immunodeficiency Virus: Plasma Viral Load Early in Infection Predicts Survival", J. Virol., 71: 284-90, 1997.

Wild et al., "Polyvalent vaccination against hepatitis B surface and core antigen using a dicistronic expression plasmid," Vaccine, 16: 353-360. 1998.

Wolff et al. "Direct Gene Transfer into Mouse Muscle in Vivo," Science, 247: 1465-1468, 1990.

Wu et al., "Deoxyribonucleic Acid Vaccines Encoding Antigens With Rapid Proteasome-Dependent Degradation Are Highly Efficient Inducers of Cytolytic T Lymphocytes," J. Immunol., 159: 6037-6043, 1997.

Wyand et al., "Protection by live, attenuated simian immunodeficiency virus against heterologous challenge," J. Virol., 73: 8356-8363, 1999.

Wyatt et al., "Marker Rescue of the Host Range Restriction Defects of Modified Vaccinia Virus Ankara," Virology, 251:334-42, 1998.

Xiang et al., "Manipulation of the Immune Response to a Plasmid-Encoded Viral Antigen by Coinoculation with Plasmids Expressing Cytokines," Immunity, 2: 129-135, 1995.

Yamamoto et al., "Highly sensitive qualitative and quantitative detection of reverse transcriptase activity: optimization, validation, and comparative analysis with other detection systems," J. Virol. Methods, 61: 135-143, 1996.

Yang and Walker, "CD8T cells in human immunodeficiency virus type I pathogenesis: cytolytic and noncytolytic inhibition of viral replication," Adv. Immunol., 66: 273-311, 1997.

Zajac et al., "Viral Immune Evasion Due to Presistence of Activated T Cells Without Effector Function", J. Exp. Med., 188:2205-13, 1998.

Burton et al., "Why do we not have an HIV vaccine and how can we make one?" Nature Med. 4:495-498, 1998.

Femberg et al., "AIDS vaccine models" Challenging challenge viruses Nature Med. 8(3):207-210, 2002.

Letvin, N.L. "Progress in the development of an HIV-1 vaccine" Science 280:1875-1880, 1998.

Markmeyer et al., "The pAX plasmids: new gene-fusion vectors for sequencing, mutagenesis and expression of proteins in *E.coli*," *Gene* 93:129-134 (1990).

Mizuno et al., "Mutational analysis of two zinc-finger motifs in HIV type 1 nucleocapsid proteins: effects on proteolytic processing of Gag precursors and particle formation," *Aides Research and Human Retroviruses* 12(9):793-800 (1996).

Wang et al., "Mammalian cell/vaccinia virus expression vectors with increased stability of retroviral sequences in *E. coli*; production of feline immunodeficiency virus envelope protein," *Gene* 153:197 202 (1995).

Amara et al., "Different Patterns of Immune Responses but Similar Control of a Simian-Human Immunodeficiency Virus 89.6P Mucosal Challenge by Modified Vaccinia Virus Ankara (MVA) and DNA/MVA Vaccines," *J. Virology* 76:7625-7631 (2002).

Jacobsen et al., "Characterization of Human Immunodeficiency Virus Type 1 Mutants with Decreased Sensitivity to Proteinase Inhibitor Ro 31-8959," *J. Virology* 206:527-534 (1995).

Meyer et al., "Mapping of deletions in the genome of the highly attenuated vaccinia virus MVA and their influence on virulence," *J. Gen. Virology* 72:1031-1038 (1991).

Smith et al., "Recombinant Vaccinia Viruses as New Live Vaccines," *Biotechnology & Genetic Engineering Reviews* 2:383-407 (1984).

Andersson et al. "Cloning, Structure, and Expression of the Mitochondrial Cytochrome P-450 . . . " J. of Biol. Chem. 264(14):8222-8229, 1989.

Cheonis, N., "Status Report on HIV Vaccine Development" Retrieved from internet <http://www.thebody.com/sfaf/winter00/vaccine.html. Oct. 2001.

Ho, M., "AIDS Vaccines Trials Dangerous" Retrieved from the internet http://www.i-sis.org.uk/isisnews/i-sisnews11-19.php. Oct. 2001.

* cited by examiner

1/4

|  |  |
|---|---|
| 1 | CGACAATATT GCTATTGGCC CATTGCCATAC GTGTATCTA TATCATAATA TGTACATTTA TATTGGCTCA TGTCCAATAT GACCCCCATG TTGACATTGA<br>GCTGTTATAA CCGATAACCG GTAACGTATG CAACATAGAT ATAGTATTAT ACATGTAAAT ATAACCGAGT ACAGGTTATA CTGGCGGTAC AACTGTAACT<br>CMV Promoter |
| 101 | TTATTGACTA GTTATTAATA GTAATCAATT ACGGGTTCAT TAGTTCATAG CCCATATATG GAGTTCCGCG TTACATAACT TACGGTAAAT GGCCCGCCTG<br>AATAACTGAT CAATAATTAT CATTAGTTAA TGCCCAAGTA ATCAAGTATC GGGTATATAC CTCAAGGCGC AATGTATTGA ATGCCATTTA CCGGGCGGAC<br>CMV Promoter |
| 201 | GCTGACCGCC CAACGACCCC CGCCCATTGA CGTCAATAAT GACGTATGTT CCCATAGTAA CGCCAATAGG GACTTTCCAT TGACGTCAAT GGGTGGAGTA<br>CGACTGGCGG GTTGCTGGGG GCGGGTAACT GCAGTTATTA CTGCATACAA GGGTATCATT GCGGTTATCC CTGAAAGGTA ACTGCAGTTA CCCACCTCAT<br>CMV Promoter |
| 301 | TTTAACGGTAA ACTGCCCACT TGGCAGTACA TCAAGTGTAT CATATGCCAA GTCCGCCCCC TATTGACGTC AATGACGGTA AATGGCCCGC CTGGCATTAT<br>AAATGCCATT TGACGGGTGA ACCGTCATGT AGTTCACATA GTATACGGTT CAGGCGGGGG ATAACTGCAG TTACTGCCAT TTACCGGGCG GACCGTAATA<br>CMV Promoter |
| 401 | GCCCAGTACA TGACTTACG GGACTTTCCT ACTTGGCAGT ACATCTACGT ATTAGTCATC GCTATTACCA TGGTGATGCG GTTTTGGCAG TACACCAATG<br>CGGGTCATGT ACTGAATGCC CCTGAAAGGA TGAACCGTCA TGTAGATGCA TAATCAGTAG CGATAATGGT ACCACTACGC CAAAACCGTC ATGTGGTTAC<br>CMV Promoter |
| 501 | GGGTGGAGTA GCGGTTTGAC TCACGGGGAT TTCCAAGTCT CCACCCCATT GACGTCAATG GGAGTTTGTT TTGGCACCAA AATCAACGGG ACTTTCCAAA<br>CCGCACCTAT CGCCAAACTG AGTGCCCCTA AAGGTTCAGA GGTGGGGTAA CTGCAGTTAC CCTCAAACAA AACCGTGGTT TTAGTTGCCC TGAAAGGTTT<br>CMV Promoter |
| 601 | ATGTCGTAAT AACCCCGCCC CGTTGACGCA AATGGGCGGT AGGCGTGTAC GGTGGGAGGT CTATATAAGC AGAGCTCGTT TAGTGAACCG TCAGATCGCC<br>TACAGCATTA TTGGGGCGGG GCAACTGCGT TTACCCGCCA TCCGCACATG CCACCCTCCA GATATATTCG TCTCGAGCAA ATCACTTGGC AGTCTAGCGG |
| 701 | TGGAGACGCC ATCCAGCCTC TTTTGACCTG CATAGAAGAC ACCGGACCG ATCCAGCCTC CGCGGCCGGG AACGGTGCAT TGGAACGCGG ATTCCCGTG<br>ACCTCTGCGG TAGGTCGGAG AAAACTGGAC GTATCTTCTG TGGCCTGGC TAGGTCGGAG GCGCCGGCC TTGCCACGTA ACCTTGCGCC TAAGGGCAC<br>CMV Intron A |
| 801 | CCAAGAGTGA CGTAAGTACC GCCTATAGAG TCTATAGGCA CACCCCTTTG GCTCTTATGC ATGCTATACT GTTTTTGGCT TGGGGCCTAT ACACCCCGC<br>GGTTCTCACT GCATTCATGG CGGATATCTC AGATATCCGT GTGGGGAAAC CGAGAATACG TACGATATGA CAAAAACCGA ACCCGGATA TGTGGGGCG<br>CMV Intron A |
| 901 | TTCCTTATGC TATAGGTGAT GGTATAGCTT AGCCTATAGG TGTGGGTTAT TGACCATTAT TGACCACTCC CCTATTGGTG ACGATACTTT CCATTACTAA<br>AAGGAATACG ATATCCACTA CCATATCGAA TCGGATATCC ACACCCAATA ACTGGTAATA ACTGGTGAGG GGATAACCAC TGCTATGAAA GGTAATGATT<br>CMV Intron A |
| 1001 | TCCATAACAT GGCTCTTTGC CACAACTATC TCTATTGGGT ATATGCCAAT ACTCTGTCCT TCAGAGACTG ACACGGACTC TGTATTTTTA CAGGATGGGG<br>AGGTATTGTA CCGAGAAACG GTGTTGATAG AGATAACCCA TATACGGTTA TGAGACAGGA AGTCTCTGAC TGTGCCTGAG ACATAAAAAT GTCCTACCCC<br>CMV Intron A |
| 1101 | TCCCATTTAT TATTTACAAA TTCACATATA CAACAACGCC GTCCCCCGTG CCCGCAGTTT TTATTAAACA TAGGCGTGGA TCTCCACGCG AATCGCGGT<br>AGGGTAAATA ATAAATGTTT AAGTGTATAT GTTGTTGCGG CAGGGGGCAC GGGCGTCAAA AATAATTTGT ATCCGCACCT AGAGGTGCGC TTAGAGCCCA<br>CMV Intron A |
| 1201 | ACGTGTTCCG GACATGGGCT CTTCTCCGGT AGCGGCGGAG CTTCCACATC CGAGCCCTGG CTCGGGGACC GAAGTGTAG GCTCGGGGAC TCCCATGCCT CCAGCGGCTC ATGGTCGCTC GGCAGCTCCT<br>TGCACAAGGC CTGTACCCGA GAAGAGGCCA TCGCCGCCTC GAAGGTGTAG CGCCGGGACC AGGGTACGAC GGTCGCCGAG TACCAGCGAG CCGTCGAGGA<br>CMV Intron A |

*Fig. 2A*

```
1301  TGCTCCTAAC AGTGGAGCGC AGACTTAGGC ACAGACAAT GCCCACCACC ACCAGTGTGC CGCACAAGGC CGTGCGGTA GGGTATGTGT CTGAAAATGA
      ACGAGGATTG TCACCTCCGG TCTGAATCCG TGTCGTGTTA CGGGTGGTGG TGGTCACACG GCGTGTTCCG GCACCGCCAT CCCATACACA GACTTTTACT
                                                            CMV Intron A 1401  GCTCGGAGAT TGGGCTCGCA CCCGTGACGC AGATGGAAGA CTTAAGGCAG CGGCAGAAGA AGATGCAGGC AGCTGAGTTG TTGTATTCTG ATAAGAGTCA
      CGAGCCTCTA ACCCGAGCGT GGGCGACTGCG TCTACCTTCT GAATTCCGTC GCCGTCTTCT TCTACGTCCG TCGACTCAAC AACATAAGAC TATTCTCAGT
                                                            CMV Intron A 1501  GAGGTAACTC CCGTTGCCGT GCTGTTAACG GTGGAGGGCA GTGTAGTCTG AGCAGTACTC GTTGCTGCCG CGGGGCCAC CAGACATAAT AGCTGACAGA
      CTCCATTGAG GGCAACGGCA CGACAATTGC CACCTCCCGT CACATCAGAC TCGTCATGAG CAACGACGGC GCCCGCGGTG GTCTGTATTA TCGACTGTCT
                                                            CMV Intron A
                                                            BspD I
                                                            Cla I 1601  CTAACAGACT GTTCCTTTCC ATGGGTCTTT TCTGCAGTCA CCATCGATGC TTGCAATCAT GGATCCAATG AAGAGAGGGC TCTGCTGCTG CTGCTGCTG
      GATTGTCTGA CAAGGAAAGG TACCCAGAAA AGACGTCAGT GGTAGCTACG AACGTTAGTA CCTAGGTTAC TTCTCTCCCG AGACGACACA CGACGACGAC
                CMV Intron A                            Nhe I Xma I          M   D   A   M    K   R   G    L   C   C   V    L   L   L
                                                            Sma I                              tpa Leader 1701  TGTGGAGCAG TCTTCGTTC GGCTAGCCCC GGGTGATAAA CGGACCGCGC AATCCCTAGG CTGTGCCTTC TAGTTGCCAG CCATCTGTTG TTTGCCCCTC
      ACACCTCGTC AGAAGCAAAG CCGATCGGGG CCCACTATTT GCCTGGCGCG TTAGGGATCC GACACGGAAG ATCACGGTC GGTAGACAAC AAACGGGGAG
      C   G   A    V   E   F    V   S                                    Bsr II          Ava II
                 tpa Leader 1801  CCCGTGCCT TCCTTGACCC TGGAAGGTGC CACTCCCACT GTCCTTTCCT AATAAAATGA GGAAATTGCA TCGCATTGTC TGAGTAGTG TCATTCTATT
      GGGCACGGA AGGAACTGGG ACCTTCCACG GTGAGGGTGA CAGGAAAGGA TTATTTTACT CCTTTAACGT AGCGTAACAG ACTCATCCAC AGTAAGATAA
                                                            BGH pA 1901  CTGGGGGGTG GGGGGCA GGACAGCAAG GGGAGGATT CCCTCCTAA AGAACTCGT AAGAGGCGA TAGAGGCGA ATCGGGAGCG GCGATACCGT
      GACCCCCCAC CCCCCCGT CCTGTCGTTC CCCTCCTAA GGGAGGATT TCTTGAGCAG TTCTTCCGCT ATCTTCCGCT TAGCCCTCGC CGCTATGGCA
                                                            BGH pA                                  Lambda To Terminator 2001  GCAACCGAGC GTTCGAACG CTAGAGTCGA CAAATTCGA AGAACTCGT GTTTAAGTCT TCTTGAGCAG TTCTTCCGCT ATCTTCCGCT TAGCCCTCGC CGCTATGGCA
      CGTTGGCTCG CAAGCTTGC GATCTCAGCT GTTTAAGTCT CAAATTCAGA AGAACTCGT
                                                            Kanamycin Resistance 2101  AAAGCACGAG GAAGCGGTCA GCCCATTCGC CGCCAAGTTC TTCAGCAATA TCACGGGTAG CCAAGCCTAT GTCCTGATAG CGGTCTGCCA CACCCAGCCG
      TTTCGTGCTC CTTCCGCCAGT CGGGTAAGCG GCGGTTCAAG AAGTCGTTAT AGTGCCCATC GGTTGCGATA CAGGACTATC GCCAGACGGT GTGGGTCGGC
                                                            Kanamycin Resistance 2201  GCCCAGTCG ATGAATTCCG AAAAGCGGCC ATTTTCCACC ATGATATTCG GCAAGCAGGC ATCGCCATGG GTCACGACGA GATCCTCGCC GTCGGGCATG
      CGGGTCAGC TACTTAAGGC TTTTCGCCGG TAAAAGGTGG TACTATAAGC CGTTCGTCCG TAGCGGTACC CAGTGCTGCT CTAGGAGCGG CAGCCCGTAC
                                                            Kanamycin Resistance
```

*Fig. 2B*

```
2301  CTCGCCTTGA GCCTGGCGAA CAGTTCGGCT GGCGCGAGCC CCTGATGCTC TTCGTCCAGA TCATCCTGAT CGACAAGACC GGCTTCCATC CGAGTACGTG
      GAGCGGAACT CGGACCGCTT GTCAAGCCGA CCGCGCTCGG GGACTACGAG AAGCAGGTCT AGTAGGACTA GCTGTTCTGG CCGAAGGTAG GCTCATGCAC
                                                 Kanamycin Resistance
2401  CTCGCTCGAT GCGATGTTTC GCTTGGTGGT CGAATGGGCA GGTAGCCGGA TCAAGCGTAT GCAGCCCCCG CATTGCATCA GCCATGATGG ATACTTTCTC
      GAGCGAGCTA CGCTACAAAG CGAACCACCA GCTTACCCGT CCATCGGCCT AGTTCCGATA CGTCGGGGGC GTAACGTAGT CGGTACTACC TATGAAAGAG
                                                 Kanamycin Resistance
2501  GGCAGGAGCA AGGTGAGATG ACAGGAGATC CTGCCCCGGC ACTTCGCCCA ATAGCAGCCA GTCCCTTCCC GCTTCAGTGA CAACGTCGAG CACAGCTGCG
      CCGTCCTCGT TCCACTCTAC TGTCCTCTAG GACGGGGCCG TGAAGCGGGT TATCGTCGGT CAGGGAAGGG CGAAGTCACT GTTGCAGCTC GTGTCGACGC
                                                 Kanamycin Resistance
2601  CAAGGAACGC CCGTCGTCGC CAGCCACGAT AGCCGCGCTG CCTCGTCTTG CAGTTCATTC AGGGCACCGG ACAGTCGGT CTTGACAAAA AGAACCGGGC
      GTTCCTTGCG GGCAGCAGCG GTCGGTGCTA TCGGCGCGAC GGAGCAGAAC GTCAAGTAAG TCCCGTGGCC TGTCCAGCCA GAACTGTTTT TCTTGGCCCG
                                                 Kanamycin Resistance
2701  GCCCCTGCGC TGACAGCCGG AACACGGGCG CATCAGAGCA GCCGATTGTC TGTTGTGCCC AGTCATAGCC GAATAGCCTC TCCACCCAAG CGGCCGGAGA
      CGGGGACGCG ACTGTCGGCC TTGTGCCCGC GTAGTCTCGT CGGCTAACAG ACAACACGGG TCAGTATCGG CTTATCGGAG AGGTGGGTTC GCCGGCCTCT
                                                 Kanamycin Resistance
2801  ACCTGCGTGC AATCCATCTT GTTCAATCAT GGAAAACGAT CCCTACTCTG TCTCTTGATC AGATCTTGAT CCCCTGCGCC ATCAGATCCT TGGCGGCAAG
      TGGACCACG TTAGGTAGAA CAAGTTAGTA CCTTTGCTA GGGATGAGAC AGAGAACTAG TCTAGAACTA GGGGACGCGG TAGTCTAGGA ACCGCCGTTC
            Kanamycin Resistance                                                                         ColE1
2901  AAAGCCATCC AGTTTACTTT GCAGGGCTTC CCAACCTTAC CAGAGGGCGC CCCAGCTGGC CGGTTTCC GGCTTGCTGT AGCCCAGTAG CTGACATCA TCCGGGTCA
      TTTCGGTAGG TCAAATGAAA CGTCCCGAAG GGTTGGAATG GTCTCCGCGG GGGTCGACCG GCCAAAGGG TTAAGGCACA GCGAACGACA GGTATTTCG CGGTCAGAT
                                                 ColE1
3001  GCTATCGCCA TGTAAGCCA CTGCAAGCTA CCTGCTTTCT CTTTGCGCTT GGTTTTTCC TTGTCCAGAT AGCCCAGTAG CTTAACGTGA GTTTTCGTTC
      CGATAGCGGT ACATTCGGGT GACGTTCGAT GGACGAAAGA GAAACGCGAA CCAAAAGGG AACAGGTCTA TCGGGTCATC GAATTGCACT CAAAGCAAG
                                                 ColE1
3101  GCACCGTTTC TGCGGACTGG CTTTCTACGT CTTTCTACGT GAAAAGGATC TAGGTGAAGA TCCTTTTTGA TAATCTCATG ACCAAAATCC CTTAACGTGA GTTTTCGTTC
      CGTGGCAAAG ACGCCTGACC GAAAGATGCA CTTTTCCTAG ATCCACTTCT AGGAAAAACT ATTAGAGTAC TGGTTTTAGG GAATTGCACT CAAAGCAAG
                                                 ColE1
3201  CACTGAGCGT CAGACCCCGT AGAAAGATCT AAAGGATCTT CTTGAGATCC TTTTTTTCTG CGCGTAATCT GCTGCTTGCA AACAAAAAAA CCACCGCTAC
      GTGACTCGCA GTCTGGGGCA TCTTTCTAGA TTTCCTAGAA GAACTCTAGG AAAAAAAGAC GCGCATTAGA CGACGAACGT TTGTTTTTT GGTGGCGATG
                                                 ColE1
3301  CAGCGGTGGT TTGTTTGCCG GATCAAGAGC TACCAACTCT TTTTCCGAAG GTAACTGGCT TCAGCAGAGC GCAGATACCA AATACTGTTC TTCTAGTGTA
      GTCGCCACCA AACAAACGGC CTAGTTCTCG ATGGTTGAGA AAAAGGCTTC CATTGACCGA AGTCGTCTCG CGTCTATGGT TTATGACAAG AAGATCACAT
                                                 ColE1
3401  GCCGTAGTTA GGCCACCACT TCAAGAACTC TGTAGCACCG CCTACATACC TCGCTCTGCT AATCCTGTTA CCAGTGGCTG CTGCCAGTGG CGATAAGTCG
      CGGCATCAAT CCGGTGGTGA AGTTCTTGAG ACATGTATGG AGCGAGACGA TTAGGACAAT GGTCACCGAC GACGGTCACC GCTATTCAGC
                                                 ColE1
3501  TGTCTTACCG GGTTGGACTC AAGACGATAG TTACCGGATA AGGCGCAGCG TTACCGGCTGA ACGGGGGGTT CGTGCACACA GCCCAGCTTG GAGCGAACGA
      ACAGAATGGC CCAACCTGAG TTCTGCTATC AATGGCCTAT TCCGCGTCGC CAGCCCGACT TGCCCCCAA GCACGTGTGT CGGGTCGAAC CTCGCTTGCT
                                                 ColE1
```

*Fig. 2C*

3601 CCTACACCCGA ACTGAGATAC CTACAGCGTG AGCTATGAGA AAGCGCCACG CTTCCCGAAG GGAGAAAGGC GGACAGGTAT CCGGTAAGCG GCAGGGTCGG
     GGATGTGGCT TGACTCTATG GATGTCGCAC TCGATACTCT TTCGCGGTGC GAAGGGCTTC CCTCTTTCCG CCTGTCCATA GGCCATTCGC CGTCCCAGCC
                                                    CoIE1

3701 AACAGGAGAG CGCACGAGGG AGCTTCCAGG GGGAAACGCC TGGTATCTTT ATAGTCCTGT CGGGTTTCGC CACCTCTGAC TTGAGCGTCG ATTTTTGTGA
     TTGTCCTCTC GCGTGCTCCC TCGAAGGTCC CCCTTTGCGG ACCATAGAAA TATCAGGACA GCCCAAAGCG GTGGAGACTG AACTCGCAGC TAAAAACACT
                                                    CoIE1

3801 TGCTCGTCAG GGGGGCGGAG CCTATGGAAA AACGCCAGCA ACGCGGCCTT TTTACGGTTC CTGGCCTTTT GCTGGCCTTT TGCTCACATG TTGT
     ACGAGCAGTC CCCCCGCCTC GGATACCTTT TTGCGGTCGT TGCGCCGGAA AAATGCCAAG GACCGGAAAA CGACCGGAAA ACGAGTGTAC AACA
                                                    CoIE1

*Fig. 2D*

```
                                                    1/3
   1  CGACAATATT GGCTATTGGC CATTGCATAC GTTGTATCTA TATCATAATA TGTACATTTA TATTGGCTCA TGTCCAATAT GACCGCCATG TTGCACATTGA
      GCTGTTATAA CCGATAACCG GTAACGTATG CAACATAGAT ATAGTATTAT ACATGTAAAT ATAACCGAGT ACAGTTATA CTGGCGGTAC AACTGTAACT
                                                                    CMV Promoter 101  TTATTGACTA GTTATTAATA GTAATCAATT ACGGGGTCAT TAGTTCATAG CCCATATATG GAGTTCCGCG TTACATAACT TACGGTAAAT GGCCCGCCTG
      AATAACTGAT CAATAATTAT CATTAGTTAA TGCCCCAGTA ATCAAGTATC GGGTATATAC CTCAAGGCGC AATGTATTGA ATGCCATTTA CCGGGCGGAC
                                                                    CMV Promoter 201  GCTGACCGCC CAACGACCCC CGCCCATTGA CGTCAATAAT GACGTATGTT CCCATAGTAA CGCCAATAGG GACTTTCCAT TGACGTCAAT GGGTGAGTA
      CGACTGGCGG GTTGCTGGGG GCGGGTAACT GCAGTTATTA CTGCAATACA GGGTATCAT CTGAAAGGTA ACTGCAGTTA CCCACCTCAT
                                                                    CMV Promoter 301  TTTACGGTAA ACTGCCCACT TGGCAGTACA TCAAGTGTAT CATATGCCAA GTCCGCCCC TATTGACGTC AATGACGGTA AATGGCCCGC CTGGCATTAT
      AAATGCCATT TGACGGGTGA ACCGTCATGT AGTTCACATA GTATACGGTT CAGGCGGGGG ATAACTGCAG TTACTGCCAT TTACCGGGCG GACCGTAATA
                                                                    CMV Promoter 401  GCCCAGTACA TGACCTTACG GGACTTTCCT ACTTGGCAGT ACATCTACGT ATTAGTCATC GCTATTACCA TGGTGATGCG GTTTTGGCAG TACACCAATG
      CGGGTCATGT ACTGGAATGC CCTGAAAGGA TGAACCGTCA TGTAGATGCA TAATCAGTAG CGATAATGGT ACCACTACGC CAAAACGTC ATGTGGTTAC
                                                                    CMV Promoter 501  GGCGTGGATA GCGGTTTGAC TCACGGGGAT TTCCAAGTCT CCACCCCATT GACGTCAATG GGAGTTTGTT TTGGCACCAA AATCAACGGG ACTTTCCAAA
      CCGCACCTAT CGCCAAACTG AGTGCCCCTA AAGGTTCAGA GGTGGGGTAA CTGCAGTTAC CCTCAAACAA AACCGTGGTT TTAGTTGCCC TGAAAGGTTT
                                                                    CMV Promoter BspD I
                                                                                                        Cla I
 601  ATGTCGTAAT AACCCCGCCC CGTTGACGCA AATGGGCGGT AGGCGTGTAC GGTGGGAGGT CTATATAAGC AGAGCTCGTT TAGTGAACTC ATTCTATCGA
      TACAGCATTA TTGGGGCGGG GCAACTGCGT TTACCCGCCA TCCGCACATG CCACCCTCCA GATATATTCG TCTCGAGCAA ATCACTTGAG TAAGATAGCT
                                                                    CMV Promoter NheI        SmaI
                                                                                              XmaI        RsrII
                                                                                              AvaI        AvaII
 701  TGCTTGCAAT CATGGATGCA ATGAAGAGAG GGCTCTGCTG TGTGCTGCTG CTGTGTGGAG CAGTCTTCGT TTCGGCTAGC CCCGGGTGAT AAACGGACCG
      ACGAACGTTA GTACCTACGT TACTTCTCTC CCGAGACGAC ACACGACGAC GACACACCTC GTCAGAAGCA AAGCCGATCG GGGCCCACTA TTTGCCTGGC
         AvrII    H  D  A  M  K  R  R   G  L  C  C   V  L  L   L  C  G   A  V  F  V  S
                                              tpa Leader 801  CCCAATCCCT AGGCTGTGCC TTCTAGTTGC CAGCCATCTG TTGTTTGCCC TTGTTTGCCC CCTTCCTTGA CCTTGAAGG TGCCACTCCC ACTGTCCTTT
      GGGTTAGGGA TCCGACACGG AAGATCAACG GTCGGTAGAC AACAAACGG GAGGGGGCAC GGAGGAACAT GGGAACCTTCC ACGGTAGGG TGACAGGAAA
                                              BGH pA 901  CCTAATAAA TGAGGAAATT GCATCGCATT GTCTGAGTAG GTGTCATTCT ATTCTGGGGG GTGGGGTGG GCAGGACACG AAGGGGGAGG ATTGGGAAGA
      GGATTATTTT ACTCCTTTAA CGTAGCGTAA CAGATCCATC CACAGTAAGA TAAGACCCCC CACCCCACCC CGTCCTGTCG TTCCCCCTCC TAACCTTCT
                                                                    BGH pA 1001  CAATAGCAGG CATGCTGGGG ATGCGGTGGG CTCTATGTAA AAAACGCCCG GCGCAACCG AGGGTTCTGA ACGTCTAGAGT CGACAAATTC AGAAGAACTC
      GTTATCGTCC GTACGACCCC TACGCCACCC GAGATATATT TTTTGCGGGC CGCGTTGGCG TCCCAAGACT TGCCATCTCA CCTGTTAAG TCTTCTTGAG
                                              BGH pA                                         Lambda T0 Terminator 1101  GTCAGAAGG CGATAGAAGG CGATGCGCTG CGAATCGGGA GCGGCGATAC CGTAAAGCAC GAGGAAGCGG CGTCCTTCGG GCATTCGGT CCCCGCAAG CTCTTCAGCA
      CAGTTCTTCC GCTATCTTCC GCTACGCGAC GCTTAGCCCT CGCCGCTATG GCATTTCGTG CTCCTTCGCC AGTGGGCTAA CCGGGCGTTC CGAGAAGTCGT
                                              Kanamycin Resistance 1201  ATATCACGGG TAGTCCTGA TATGTCCTGA TATCGGGACT ATCGGAGGA ATCGCCAGAG ATCGGGCGC GCCTGGGCGT ATCGATGAAT C AGCCAGCGTGTC AGTACTTAG GTCTTTTCCC GCAAATATGGA CCATTTGCGA CGGTACTAGG
                                              Kanamycin Resistance
```

*Fig. 4A*

```
1301  TCGGCAAGCA  GGCATCGCCA  TGGGTCACGA  CGAGATCCTC  GCCCTCGGGC  ATGCTCGCCT  TGAGCCTGGC  GAACAGTTCG  GCTGGCGCGA  GCCCCTGATG
      AGCCCGTTCGT  CCGTAGCGGT  ACCCAGTGCT  GCTCTAGGAG  CGGCAGCCCG  TACGAGCCGA  ACTCGGACCG  CTTGTCAAGC  CGACCGCGCT  CGGGACTAC
                                                      Kanamycin Resistance
1401  CTCTTCGTCC  AGATCATCCT  GATCGACAAG  ACCGGCTTCC  ATCCGAGTAC  GTGCTCGCTC  GATGCGATGT  TTCGCTTGGT  GGTCGAATGG  GCAGGTAGCC
      GAGAAGCAGG  TCTAGTAGGA  CTAGCTGTTC  TGGCCGAAGG  TAGGCTCATG  CACGAGCGAG  CTACGCTACA  AAGCGAACCA  CCAGTTACC  CGTCCATCGG
                                                      Kanamycin Resistance
1501  GGATCAAGCG  TATGCAGCCG  CCGCATTGCA  TCAGCCATGA  TGGATACTTT  CTCGGCAGGA  GCAAGGTGAG  ATGAAGGAG  ATCCTGCCCC  GGCACTTCGC
      CCTAGTTCGC  ATACGTCGGC  GGCGTAACGT  AGTCGGTACT  ACCTATGAAA  GAGCCGTCCT  CGTTCCACTC  TACTGTCCTC  TAGGACGGGG  CCGTGAAGCG
                                                      Kanamycin Resistance
1601  CCAATAGCAG  CCAGTCCCTT  CCCGCTTCAG  TGACAACGTC  GAGCAACGCT  GGGCAAGGAA  CGCCCATCGT  GGCCAGCCAC  GATAGCCGCG  CTGCCTCGTC
      GGTTATCGTC  GGTCAGGGAA  GGGCGAAGTC  ACTGTTGCAG  CTCGTTGCGA  CCCGTTCCTT  GCGGGCAGCA  CCGGTCGGTG  CTATCGGCGC  GACGGAGCAG
                                                      Kanamycin Resistance
1701  TTGCAGTTCA  TTCAGGGCAC  CGGACAGGTC  GGTCTTGACA  AAAAGAACCG  GGCGCCCCTG  CGCTGACAGC  CGGAACACGG  CGGCATCAGA  GCAGCCGATT
      AACGTCAAGT  AAGTCCCGTG  GCCTGTCCAG  CCAGAACTGT  TTTTCTTGGC  CCGCGGGGAC  GCGACTGTCG  GCCTTGTGCC  GCCGTAGTCT  CGTCGGCTAA
                                                      Kanamycin Resistance
1801  GTCTGTTGTG  CCCAGTCATA  GCCGAATAGC  CTCCCACCCC  AAGCGGCCGG  AGAACCTGCG  TGCAATCCAT  CTTGTTCAAT  CATGCGAAAC  GATCCTCATC
      CAGACAACAC  GGGTCAGTAT  CGGCTTATCG  GAGGGTGGGG  TTCGCCGGCC  TCTTGGACGC  ACGTTAGGTA  GAACAAGTTA  GTACGCTTTG  CTAGGACTAG
                                                      Kanamycin Resistance      |        ColE1
1901  CTGTCTCTTG  ATCAGATCTT  GATCCCCTGC  GCCATCAGAT  CCTTGGCGCG  AAGAAAGCCA  TCCAGTTTAC  TTTGCAGGGC  TTCCCAACCT  TACCAGAGG
      GACAGAGAAC  TAGTCTAGAA  CTAGGGGACG  CGGTAGTCTA  GGAACCGCGC  TTCTTTCGGT  AGGTCAAATG  AAACGTCCCG  AAGGGTTGGA  ATGGTCTCCC
                                                                              ColE1
2001  CGCCCCAGCT  GGCAATTCCG  GTTCGCTTGC  TGTCCATAAA  ACCGCCCAGT  CTAGCTATCG  CATGTAAGC  CCACTGCAAG  CTACCTGCTT  TCTCTTTGCG
      GCGGGGTCGA  CCGTTAAGGC  CAAGCGAACG  ACAGGTATTT  TGGCGGGTCA  GATCGATAGC  GGTACATTCG  GGTGACGTTC  GATGGACGAA  AGAGAAACGC
                                                                              ColE1
2101  CTTGCGTTTT  CCCTTGTCA  GGGAACAGGT  TAGCTAGCCG  ATCATCCGG  TCATCCGGGG  TCAGCACCGT  TTCTGCGGAC  TGGCTTTCTA  CGTGAAAAGG  ATCTAGGTGA
      GAACGCAAAA  GGGAACAGT  CTATCGGGTC  ATCGACTGTA  AGTAGCCCC  AGTCGTGGCA  AGACGCCTG  AACGCCCTG  ACCGAAACAT  GCACTTTCC  TAGATCCACT
                                                                              ColE1
2201  AGATCCTTTT  TGATAATCTC  ATGACCAAAA  TCCCTTAACG  TGAGTTTTCG  TTCCACTGAG  CGTCAGACCC  CGTAGAAAAG  ATCAAAGGAT  CTTCTTGAGA
      TCTAGGAAAA  ACTATTAGAG  TACTGGTTTT  AGGGAATTGC  ACTCAAAAGC  AAGGTGACTC  GCAGTCTGGG  GCATCTTTTC  TAGTTTCCTA  GAAGAACTCT
                                                                              ColE1
2301  TCCTTTTTTT  CTGCGCGTAA  TCTGCTGCTT  GCAAACAAAA  AACCACCGC  TACCAGCGGT  GGTTTGTTTG  CCGGATCAAG  AGCTACCAAC  TCTTTTTCCG
      AGGAAAAAAA  GACGCGCATT  AGACGACGAA  CGTTTGTTTT  TTGGTGGCG  ATGGTCGCCA  CCAAACAAAC  GGCCTAGTTC  TCGATGGTTG  AGAAAAAGGC
                                                                              ColE1
2401  AAGGTAACTG  GCTTCAGCAG  AGCGCAGATA  CCAAATACTG  TTCTTCTAGT  GTAGCCGTAG  TTAGGCCACC  ACTTCAAGAA  CTCTGTAGCA  CCGCCTACAT
      TTCCATTGAC  CGAAGTCGTC  TCGCGTCTAT  GGTTTATGAC  AAGAAGATCA  CATCGGCATC  AATCCGGTGG  TGAAGTTCTT  GAGACATCGT  GGCGGATGTA
                                                                              ColE1
2501  ACCTCGCTCT  GCTAATCCTG  TTACCAGTGG  CTGCTGCCAG  TGGCGATAAG  TCGTGTCTTA  CCGGGTTGGA  CTCAAGACGA  TAGTTACCGG  ATAAGGCGCA
      TGGAGCCAGA  CGATTAGGAC  AATGGTCACC  GACGACGGTC  ACCGCTATTC  AGCACAGAAT  GGCCCAACCT  GAGTTCTGCT  ATCAATGGCC  TATTCCGCGT
                                                                              ColE1
2601  GCGGTCGGGC  TGAACGGGGG  GTTCGTGCAC  ACAGCCCAGC  TTGGAGCGAA  CGACCTACAC  CGAACTGAGA  TACCTACAGC  GTGAGCTATG  AGAAAGCGCC
      CGCCAGCCCG  ACTTGCCCCC  CAAGCACGTG  TGTCGGGTCG  AACCTCGCTT  GCTGGATGTG  GCTTGACTCT  ATGGATGTCG  CACTCGATAC  TCTTTCGCGG
                                                                              ColE1
2701  ACGCTTCCCG  AAGGGAGAAA  GGCGGACAGG  TATCCGGTAA  GCGGCAGGGT  CGGAACAGGA  GAGCGCACGA  GGGAGCTTCC  AGGGGGAAAC  GCCTGGTATC
      TGCGAAGGGC  TTCCCTCTTT  CCGCCTGTCC  ATAGGCCATT  CGCCGTCCCA  GCCTTGTCCT  CTCGCGTGCT  CCCTCGAAGG  TCCCCCTTTG  CGGACCATAG
                                                                              ColE1
2801  TTTTATAGTCC  TGTCGGGTTT  CGCCACCTCT  GACTTGAGCG  TCGATTTTTG  TGATGCTCGT  CAGGGGGGCG  GAGCGTATGG  AAAAACGCCA  GCAACGCGGC
      AAATATCAGG  ACAGCCCAAA  GCGGTGGAGA  CTGAACTCGC  AGCTAAAAAC  ACTACGAGCA  GTCCCCCGC  CTCGCATACC  TTTTTGCGGT  CGTTGCGCCG
                                                                              ColE1
```

Fig. 4B

```
2901  CCTTTTACGG TTCCTGGCCT TTTGCTGGCC TTTTGCTCAC ATGTTGT
      GGAAAATGCC AAGGACCGGA AAACGACCGG AAAACGAGTG TACAACA
                                 ColE1
```

```
1501  GAGGTAACTC CCGTTGCCGT GCTGTTAACG GTGTAGGGCA GTGTAGTCTG AGCAGTACTC GTTGCTGCCG CCGCGCCCAC CAGACATAAT AGCTGACAGA
      CTCCCATTGAG GGCAACCCCA CGACAATTGC CACCTCCCGT CACATCAGAC TCGTCATGAG CAACGACGGC GCGCGGGTG GTCTGTATTA TCGACTGTCT
                                                                    CMV Intron A
                                                                    HindIII 1601  CTAACAGACT GTTCCTTTCC ATGGGTCTTT TCTGCAGTCA CCGTCCAAGC TTGCAATCAT GGATCGAATG AAGAGAGGGC TCTGCTGCTT GCTGCTGCTG
      GATTGTCTGA CAAGGAACGA TACCCAGAAA AGACGTCAGT GGCAGGTTCG AACGTTAGTA CCTACGTTAC TTCTCTCCCG AGACGACGAC CGACGACGAC
            CMV Intron A                                                                      M  K  R  G    L  L  L
                                                                                                 tpa Leader 1701  TGTGGAGCAG TCTTCGTTTC GGCTAGCCCC GGGTGATAAG GATCCCTCGA ATCCCTAGGC TGTGCCTTCT AGTTGCCAGC CATCTGTTGT TTGCCCCTCC
      ACACCTCGTC AGAAGCAAAG CCGATCGGGG CCCACTATTC CTAGGAGCT TAGGGATCCG ACACGGAAGA TCAACGGTCG GTAGACAACA AACGGGAGG
       C  G  A  V  F  V  S              Nhe I           BamH I    Avr II                                           BGH PA
              tpa Leader                   Xma I
                                          Sma I 1801  CCCGTGCCTT CCTTGACCCT GGAAGGTGCC ACTCCACTG TCCTTCTA ATAAAATGAG GAAATTGCAT CGCATTGTCT GAGTAGTGT CATTCTATTC
      GGGCACGGAA GGAACTGGGA CCTTCCACGG TGAGGTGAC AGGAAGAT TATTTTACTC CTTTAACGTA GCGTAACAGA CTCATCCACA GTAAGATAAG
                                                                  BGH pA                                    Lambda To Terminator 1901  TGGGGGGTGG GGTGGGGCAG GACAGCAAGG GGGAGGATTG GAAGACAAT AGCAGGCATG CTGGGGATGC GGTGGCCTCT ATATAAAAA CGGCCGGGCG
      ACCCCCCACC CCACCCCGTC CTGTCGTTCC CCCTCCTAAC CCTTCTGTTA TCGTCCGTAC GACCCCCTACG CCACCGGAGA TATATTTTT GCCGGCCCGC 2001  CAACCCAGCCG TTCTGAACGC TAGAGTCGAC AAATTCAGAA GAACTCGTCA AGAGGCGAT AGAAGGCGAT GGCTGCGAA TCGGGAGCGG CGATACCGTA
      GTTGGGTCGC AAGACTTGCG ATCTCAGCTG TTTAAGTCTT CTTGAGCAGT TCTTCCGCTA TCCTTCCGCTA CCGACGCTT AGCCCTCGCC GCTATGGCAT
                                                                 Kanamycin Resistance 2101  AAGCACGAGG AAGCGGTCAG CCCATTCGCC GCCAAGCTCT TCAGCAACTG CACGGGTAGC CAACGCTATG TCCTGATAGC GGTCTGCCAC ACCCAGCCGG
      TTCGTGCTCC TTCGCCAGTC GGGTAAGCGG CGGTTCGAGA AGTCGTTGAC GTGCCCATCG GTTGCGATAC AGGACTATCG CCAGACGGTG TGGGTCGGCC
                                                                 Kanamycin Resistance 2201  CCACAGTCGA TGAATCCAGA AAAGCGGCCA TTTTCCACCA TGATATTCGG CAAGCAGGCA TCGCCATGGG TCACGACGAG ATCCTCGCCG TCGGCATGC
      GGTGTCAGCT ACTTAGGTCT TTTCGCCGGT AAAAGGTGGT ACTATAAGCC GTTCGTCCGT AGCGGTACCC AGTGCTGCTC TAGGAGCGGC AGCCCGTACG
                                                                 Kanamycin Resistance 2301  TCGCCTGAG CCTGGCGAAC AGTTCGGCTG GCGCGAGCCC CTGATGCTCT TCGTCCAGAT CATCCTGATC GACAAGACCG GCTTCCATCC GAGTACGTGC
      AGCGGACTC GGACCGCTTG TCAAGCCGAC CGCGCTCGGG GACTACGAGA AGCAGGTCTA GTAGGACTAG CTGTTCTGGC CGAAGGTAGG CTCATCCACG
                                                                 Kanamycin Resistance 2401  TCGCTCGATG CGATGTTTCG CTTGGTGGTC GAATGGGCAG GTAGCCGGAT CAAGCGTATG CAGCCGCCGC ATTGCATCAG CCATGATGGA TACTTTCTCG
      AGCGAGCTAC GCTACAAAGC GAACCACCAG CTTACCCGTC CATCCGGCCTA GTTCGCATAC GTCGGCGGCG TAACGTAGTC GGTACTACCT ATGAAAGAGC
                                                                 Kanamycin Resistance 2501  GCAGGAGCAA GGTGAGATGA CAGGAGATCC TGCCCCGGCA CTTCCGCCAA TAGCAGCCAG TCCCTTCCCG CTTCAGTGAC AACGTCGAGC ACAGCTGCGC
      CGTCCTCGTT CCACTCTACT GTCCTCTAGG ACGGGGCCGT GAAGGCGGTT ATCGTCGGTC AGGGAAGGGC GAAGTCACTG TTGCAGTCG TGTCGACGCG
                                                                 Kanamycin Resistance 2601  AAGGAACCGC CGTCTGCGG AGCCACGATA GCCGCGCTGC CTGTTCATTCA GGGACACCGA CAGGTCCGTC TTGACAAAAA GAACCCCGCG
      TTCCTTGGCG GCAGACGCC TCGGTGCTAT CGGCGCGACG GAGCAGACG TCAAGTAAGT CCCGTGGCCT GTCCAGGCAG AACTGTTTTT CTTGGCCGC
```

*Fig. 6B*

```
                                                                3/3
2701    CCCCTCGCCT GACAGCCGGA ACACGGCGGC ATCAGAGCCAG CCGATTGTCT GTTGTGCCCA GTCATAGCCG AATAGCCTCT CCACCCAAGC GGCCGGAGAA
        GGGGACGGGA CTGTCGGCCT TGTGCCGCCG TAGTCTCGTC GGCTAACAGA CAACACGGGT CAGTATCGGC TTATCGGAGA GGTGGGTTCG CCGGCCTCTT
                                                                                                Kanamycin Resistance
2801    CCTGCGTCGA ATCCATCTTG TTCAATCATG CGAAACGATC CTCATCCTGT CTCTTGATCA GATCTTGATC CCCTGCGCCA TCAGATCCTT GGGGCAAGA
        GGACGCAGCT TAGGTAGAAC AAGTTAGTAC GCTTTGCTAG GAGTAGGACA GAGAACTAGT CTAGAACTAG GGGACGCGGT AGTCTAGGAA CCCGCGTTCT
          Kanamycin Resistance                                                ColE1
2901    AAGCCATCCA GTTTACTTTG CAGGGCTTCC CAACCTTACC AGAGGGGCGC CCAGCTGGCA ATTCCGGTTC GCTTGCTGTC CATAAAACCG CCCAGTCTAG
        TTCGGTAGGT CAAATGAAAC GTCCCGAAGG GTTGGAATGG TCTCCCCGCG GGTCGACCGT TAAGGCCAAG CGAACGACAG GTATTTTGGC GGGTCAGATC
                                                            ColE1
3001    CTATCGCCAT GTAAGCCCAC TGCAAGCTAC CTGCTTTCTC TTTGCGCTTG CGTTTTCCCT TGTCCAGATA GCCCAGTAGC TGACATTCAT CCGGGGTCAG
        GATAGCGGTA CATTCGGGTG ACGTTCGATG GACGAAAGAG AAACGCGAAC GCAAAAGGGA ACAGGTCTAT CGGGTCATCG ACTGTAAGTA GGCCCCAGTC
                                                            ColE1
3101    CACCGTTTCT GGGGACTGGC TTTCTACGTG AAAAGGATCT AGGTGAAGAT CCTTTTTGAT AATCTCATGA CCAAAATCCC TTAACGTGAG TTTTCGTTCC
        GTGGCAAAGA CCCCTGACCG AAAGATGCAC TTTTCCTAGA TCCACTTCTA GGAAAAACTA TTAGAGTACT GGTTTTAGGG AATTGCACTC AAAAGCAAGG
                                                            ColE1
3201    ACTGAGCGTC AGACCCCGTA GAAAAGATCA AAGGATCTTC TTGAGATCCT TTTTTTCTGC GCGTAATCTG CTGCTTGCAA ACAAAAAAAC CACCGCTACC
        TGACTCGCAG TCTGGGGCAT CTTTTCTAGT TTCCTAGAAG AACTCTAGGA AAAAAAGACG CGCATTAGAC GACGAACGTT TGTTTTTTTG GTGGCGATGG
                                                            ColE1
3301    AGCGGTGGTT TGTTTGCCGG ATCAAGAGCT ACCAACTCTT TTTCCGAAGG TAACTGCTTC CAGCAGAGCG CAGATACCAA ATACTGTTCT TCTAGTGTAG
        TCGCCACCAA ACAAACGGCC TAGTTCTCGA TGGTTGAGAA AAAGGCTTCC ATTGACGAAG GTCGTCTCGC GTCTATGGTT TATGACAAGA AGATCACATC
                                                            ColE1
3401    CCGTAGTTAG GCCACCACTT CAAGAACTCT GTAGCACCGC CTACATACCT CGCTCTGCTA ATCCTGTTAC CAGTGGCTGC TGCCAGTGGC GATAAGTCGT
        GGCATCAATC CGGTGGTGAA GTTCTTGAGA CATCGTGGCG GATGTATGGA GCGAGACGAT TAGGACAATG GTCACCGACG ACGGTCACCG CTATTCAGCA
                                                            ColE1
3501    GTCTTACCGG GTTGGACTCA AGACGATAGT TACCGGATAA GGCGCAGCGG TCGGGCTGAA CGGGGGGTTC GTGCACACAG CCCAGCTTGG AGCGAACGAC
        CAGAATGGCC CAACCTGAGT TCTGCTATCA ATGGCCTATT CCGCGTCGCC AGCCCGACTT GCCCCCCAAG CACGTGTGTC GGGTCGAACC TCGCTTGCTG
                                                            ColE1
3601    CTACACCGAA CTGAGATACC TACAGCGTGA GCTATGAGAA AGCGCCACGC TTCCCGAAGG GAGAAAGGCG GACAGGTATC CGGTAAGCGG CAGGGTCGGA
        GATGTGGCTT GACTCTATGG ATGTCGCACT CGATACTCTT TCGCGGTGCG AAGGGCTTCC CTCTTTCCGC CTGTCCATAG GCCATTCGCC GTCCCAGCCT
                                                            ColE1
3701    ACAGGAGAGC GCACGAGGGA GCTTCCAGGG GGAAACGCCT GGTATCTTTA TAGTCCTGTC GGGTTTCGCC ACCTCTGACT TGAGCGTCGA TTTTTGTGAT
        TGTCCTCTCG CGTGCTCCCT CGAAGGTCCC CCTTTGCGGA CCATAGAAAT ATCAGGACAG CCCAAAGCGG TGGAGACTGA ACTCGCAGCT AAAAACACTA
                                                            ColE1
3801    GCTCGTCAGG GGGCCGGAGC CTATGGAAAA ACGCCAGCAA CGCGGCCTTT TTACGGTTCC TGGCCTTTTG CTGGCCTTTT GCTCACATGT TGT
        CGAGCAGTCC CCCCGGCCTCG GATACCTTTT TGCGGTCGTT GCGCCGGAAA AATGCCAAGG ACCGGAAAAA CGACCGGAAA ACGAGTGTACA ACA
                                                            ColE1
```

*Fig. 6C*

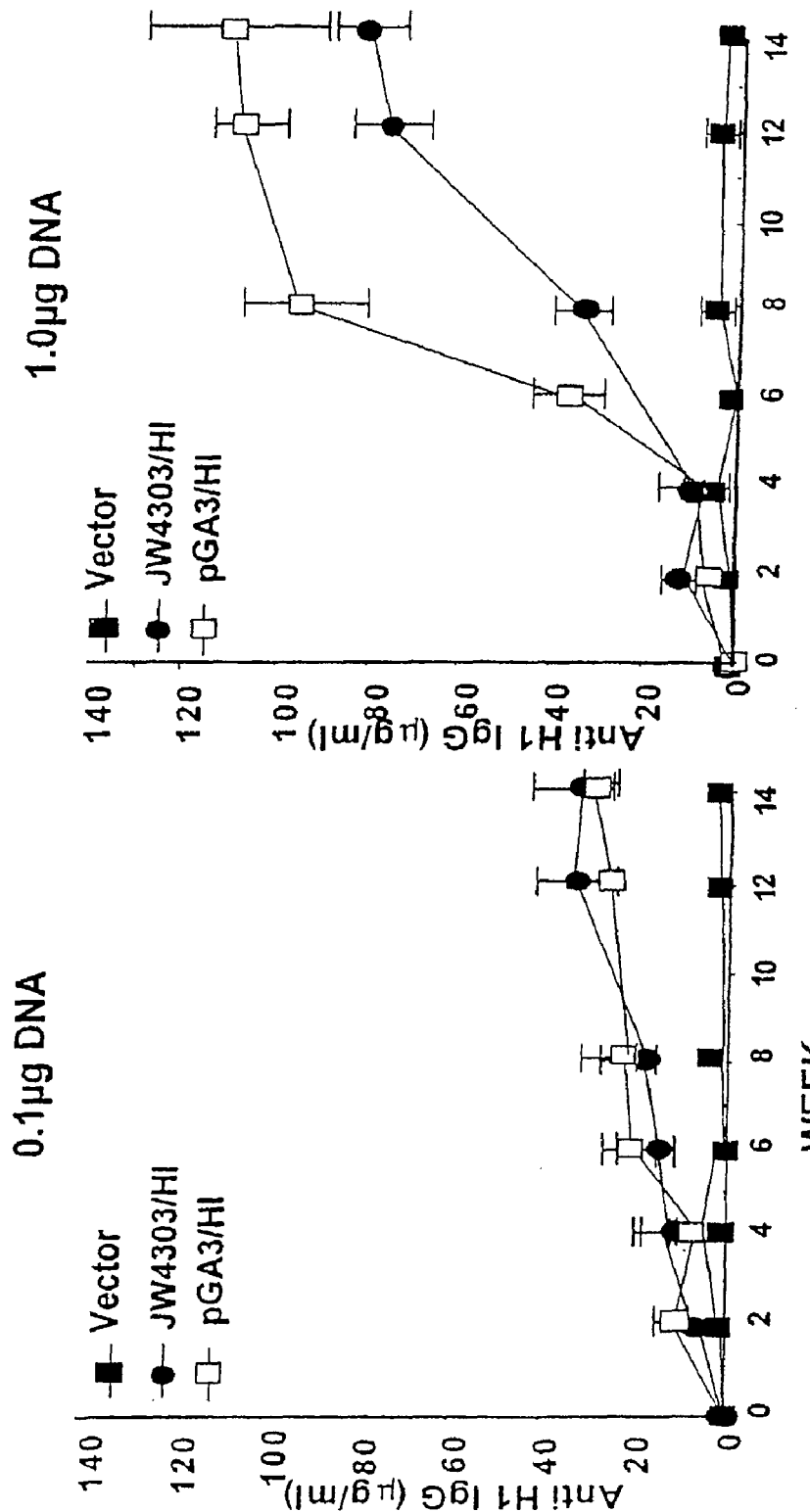

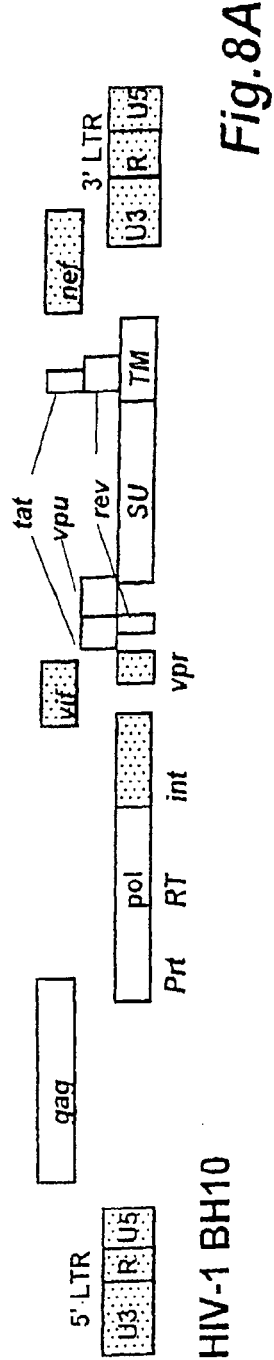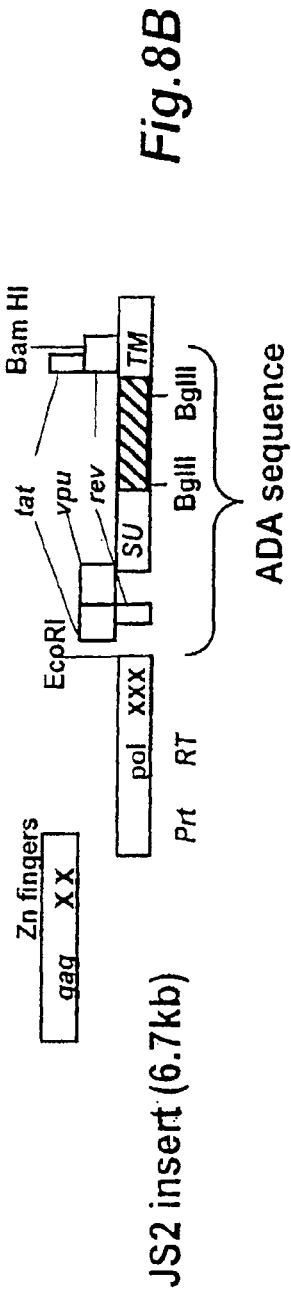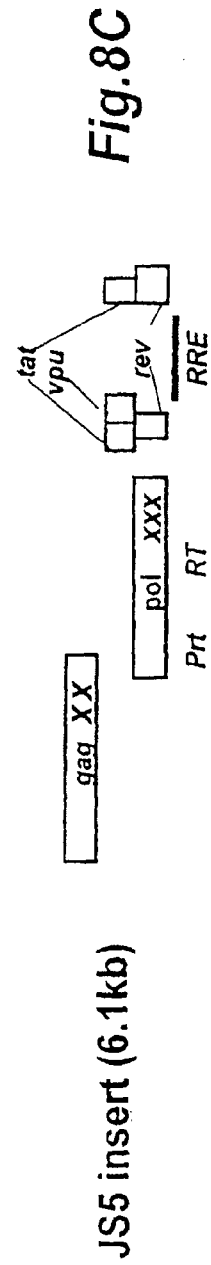

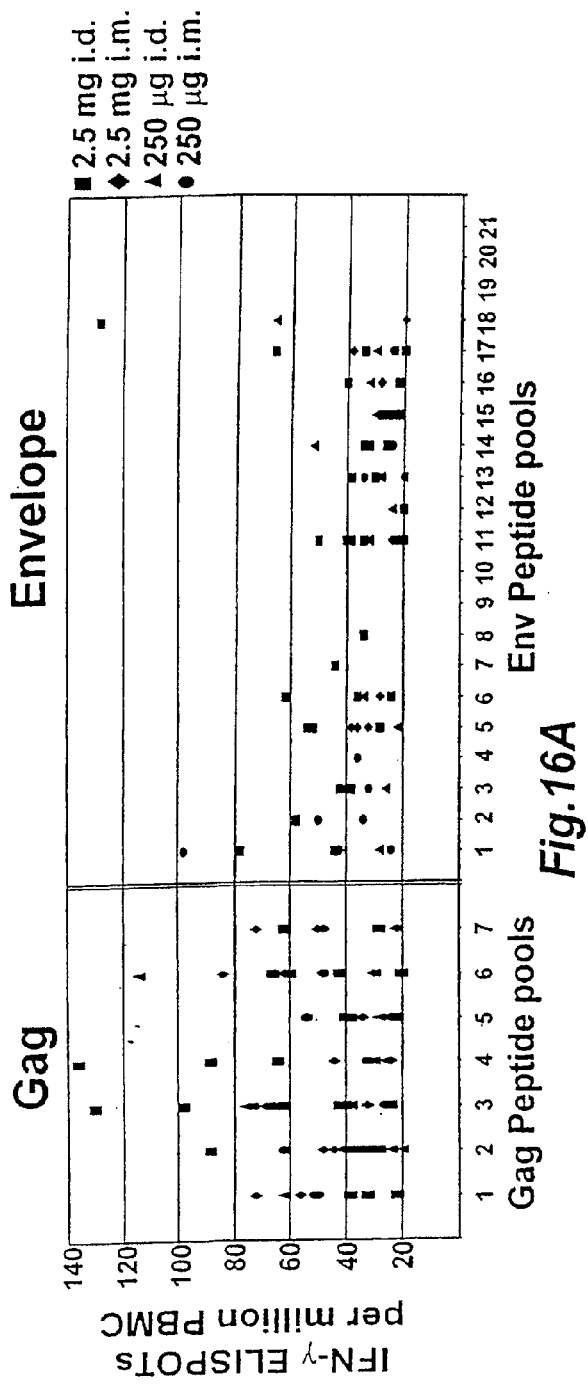

```
GATCTCCACGCGGAATCTCCGGCTACGTGTTCCGGACATGGGCTCCTTCTCCGGTAGCGGGCGGAGCTTCCACATCCGAGCCCTGGTCCCAGCCCATGCCTCATGGTGCTGCTCGGCAGCTCCTTGCTCCTCCTAACAGTGGAGGCCAGACTTAG  9600
                                                                                    pGA1
GCACAGCACAATGCCCACCACCAGTCGTGCCGCACAAGGCCGTGCCGCCGTAGGGTATCGTGTCTGAAAATGAGCTCGGACGCTGACACCGTGACCGAGATTGGGGCTAAGGCAGCGGCAGAGAAGATGCAGGCAGCTGAGTT  9750
                                pGA1                                                                                              NcoI
GTTGTATTCTGATAAGAGTCAGAGGTAACTCCCGTTGCCGTGCTGTGTTAACGGTGAGGGCAGTGTAGTCTGAGCAGTACTCGTTGCTGCCGCCGCCCACCAGACATAATAGCTGACAGACTAACGACTGTTCCTTTCCATGGGTCTT  9900
                                                                                    pGA1
      PstI
TTCTGCAGTCACCGTCCA  9918
         pGA1
```

*Fig. 18G*

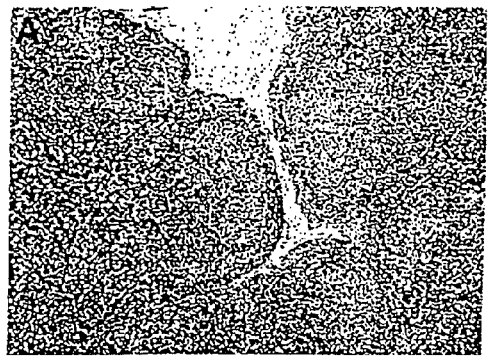
Fig. 21A　　　　Fig. 21B
 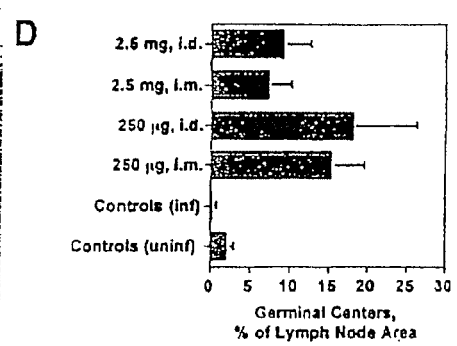
Fig. 21C　　　　Fig. 21D
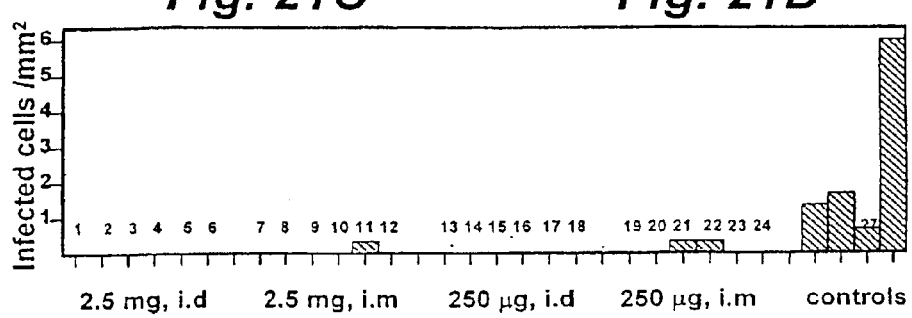
Fig. 21E

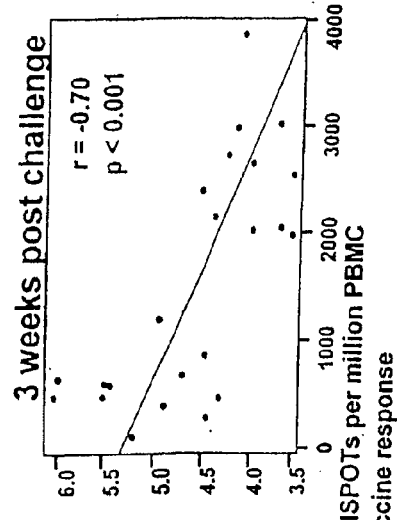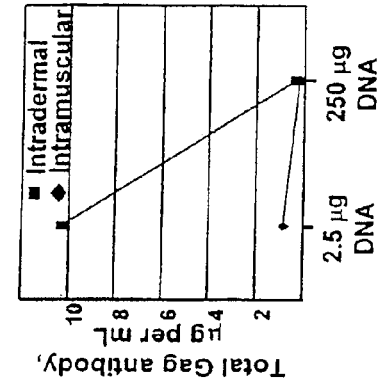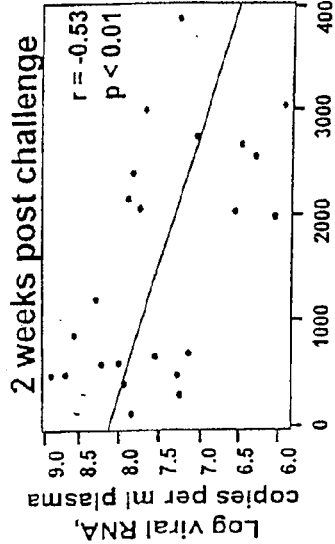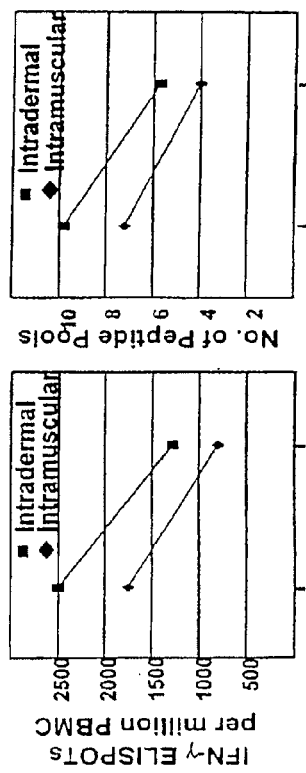
Fig. 23A
Fig. 23B
Fig. 23C
Fig. 23D
Fig. 23E

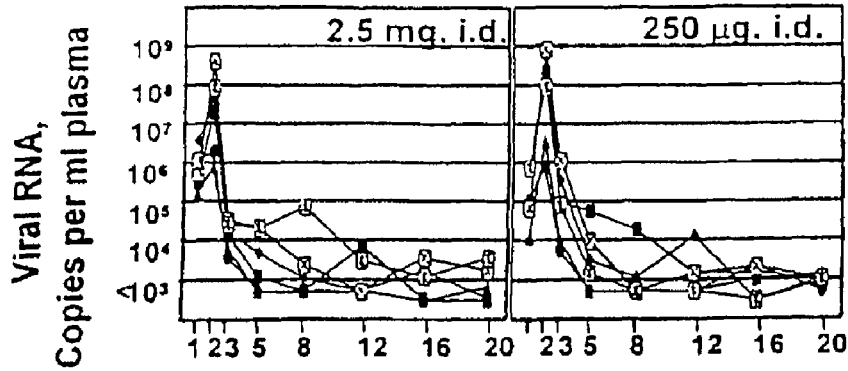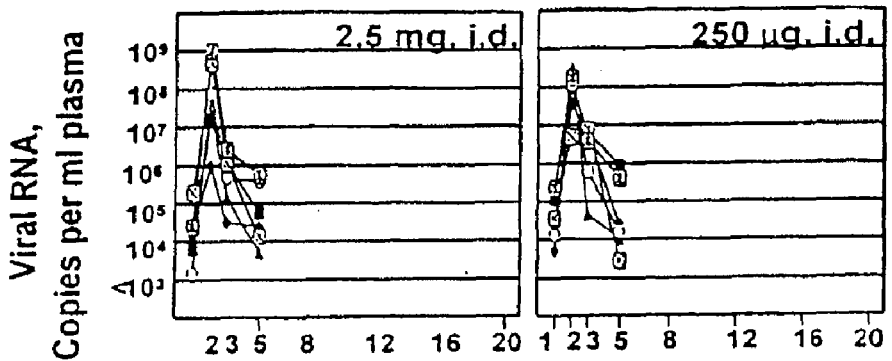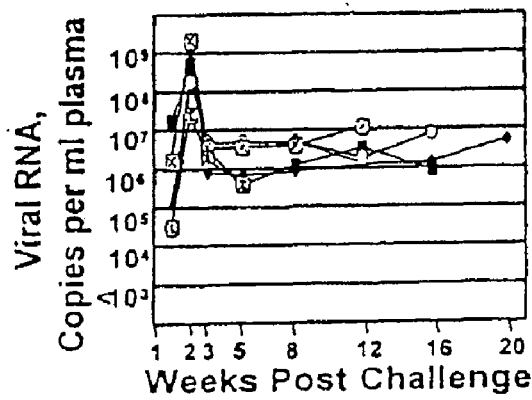
Fig. 28C

SEQUENCE LISTING

<160> NUMBER OF SEQ ID NOS: 46

<210> SEQ ID NO 1
<211> LENGTH: 3894
<212> TYPE: DNA
<213> ORGANISM: Artificial Sequence
<220> FEATURE:
<223> OTHER INFORMATION: vaccine vector pGA1
<220> FEATURE:
<221> NAME/KEY: promoter
<222> LOCATION: (1)...(692)
<223> OTHER INFORMATION: cytomegalovirus intermediate early promoter

<400> SEQUENCE: 1

| | | | | | |
|---|---|---|---|---|---|
| cgacaatatt | ggctattggc | cattgcatac | gttgtatcta | tatcataata | tgtacattta 60 |
| tattggctca | tgtccaatat | gaccgccatg | ttgacattga | ttattgacta | gttattaata 120 |
| gtaatcaatt | acgggttcat | tagttcatag | cccatatatg | gagttccgcg | ttacataact 180 |
| tacggtaaat | ggcccgcctg | gctgaccgcc | caacgacccc | cgcccattga | cgtcaataat 240 |
| gacgtatgtt | cccatagtaa | cgccaatagg | gactttccat | tgacgtcaat | gggtggagta 300 |
| tttacggtaa | actgcccact | ggcagtaca | tcaagtgtat | catatgccaa | gtccgccccc 360 |
| tattgacgtc | aatgacggta | aatggcccgc | ctggcattat | gcccagtaca | tgaccttacg 420 |
| ggactttcct | acttggcagt | acatctacgt | attagtcatc | gctattacca | tggtgatgcg 480 |
| gttttggcag | tacaccaatg | ggcgtggata | gcggtttgac | tcacgggat | ttccaagtct 540 |
| ccaccccatt | gacgtcaatg | ggagtttgtt | ttggcaccaa | aatcaacggg | actttccaaa 600 |
| atgtcgtaat | aaccccgccc | cgttgacgca | aatgggcggt | aggcgtgtac | ggtgggaggt 660 |
| ctatataagc | agagctcgtt | tagtgaaccg | tcagatcgcc | tggagacgcc | atccacgctg 720 |
| ttttgacctc | catagaagac | accgggaccg | atccagcctc | cgcggccggg | aacggtgcat 780 |
| tggaacgcgg | attccccgtg | ccaagagtga | cgtaagtacc | gcctatagac | tctataggca 840 |
| cacccctttg | gctcttatgc | atgctatact | gttttttggct | tggggcctat | acaccccgc 900 |
| ttccttatgc | tataggtgat | ggtatagctt | agcctatagg | tgtgggttat | tgaccattat 960 |
| tgaccactcc | cctattggtg | acgatacttt | ccattactaa | tccataacat | ggctctttgc 1020 |
| cacaactatc | tctattggct | atatgccaat | actctgtcct | tcagagactg | acacggactc 1080 |
| tgtattttta | caggatgggg | tcccatttat | tatttacaaa | ttcacatata | caacaacgcc 1140 |
| gtcccccgtg | cccgcagttt | ttattaaaca | tagcgtggga | tctccacgcg | aatctcgggt 1200 |
| acctgttccg | gacatgggyt | cttctccggt | agcggcggag | cttccacatc | cgagccctgg 1260 |
| tcccatgcct | ccagcggctc | atggtcgctc | ggcagctcct | tgctcctaac | agtggaggcc 1320 |
| agacttaggc | acagcacaat | gcccaccacc | accagtgtgc | cgcacaaggc | cgtggcggta 1380 |
| gggtatgtgt | ctgaaaatga | gctcggagat | tgggctcgca | ccgctgacgc | agatggaaga 1440 |
| cttaaggcag | cggcagaaga | agatgcaggc | agctgagttg | ttgtattctg | ataagagtca 1500 |
| gaggtaactc | ccgttgcggt | gctgttaacg | gtggagggca | gtgtagtctg | agcagtactc 1560 |
| gttgctgccg | cgcgcgccac | cagacataat | agctgacaga | ctaacagact | gttcctttcc 1620 |
| atgggtcttt | tctgcagtca | ccatcgatgc | ttgcaatcat | ggatgcaatg | aagagagggc 1680 |
| tctgctgtgt | gctgctgctg | tgtggagcag | tcttcgtttc | ggctagcccc | gggtgataaa 1740 |
| cggaccgcgc | aatccctagg | ctgtgccttc | tagttgccag | ccatctgttg | tttgcccctc 1800 |
| ccccgtgcct | tccttgaccc | tggaaggtgc | cactcccact | gtcctttcct | aataaaatga 1860 |

-continued

```
ggaaattgca tcgcattgtc tgagtaggtg tcattctatt ctgggggtg gggtggggca      1920
ggacagcaag ggggaggatt gggaagacaa tagcaggcat gctggggatg cggtgggctc      1980
tatataaaaa acgcccggcg gcaaccgagc gttctgaacg ctagagtcga caaattcaga      2040
agaactcgtc aagaaggcga tagaaggcga tgcgctgcga atcgggagcg gcgataccgt      2100
aaagcacgag gaagcggtca gcccattcgc cgccaagctc ttcagcaata tcacgggtag      2160
ccaacgctat gtcctgatag cggtctgcca cacccagccg gccacagtcg atgaatccag      2220
aaaagcggcc attttccacc atgatattcg gcaagcaggc atcgccatgg gtcacgacga      2280
gatcctcgcc gtcgggcatg ctcgccttga gcctggcgaa cagttcggct ggcgcgagcc      2340
cctgatgctc ttcgtccaga tcatcctgat cgacaagacc ggcttccatc cgagtacgtg      2400
ctcgctcgat gcgatgtttc gcttggtggt cgaatgggca ggtagccgga tcaagcgtat      2460
gcagccgccg cattgcatca gccatgatgg atactttctc ggcaggagca aggtgagatg      2520
acaggagatc ctgccccggc acttcgccca atagcagcca gtcccttccc gcttcagtga      2580
caacgtcgag cacagctgcg caaggaacgc ccgtcgtggc cagccacgat agccgcgctg      2640
cctcgtcttg cagttcattc agggcaccgg acaggtcggt cttgacaaaa agaaccgggc      2700
gcccctgcgc tgacagccgg aacacggcgg catcagagca gccgattgtc tgttgtgccc      2760
agtcatagcc gaatagcctc tccacccaag cggccgagaa cctgcgtgc aatccatctt      2820
gttcaatcat gcgaaacgat cctcatcctg tctcttgatc agatcttgat ccctgcgcc      2880
atcagatcct tggcggcaag aaagccatcc agtttacttt gcagggcttc ccaaccttac      2940
cagagggcgc cccagctggc aattccggtt cgcttgctgt ccataaaacc gcccagtcta      3000
gctatcgcca tgtaagccca ctgcaagcta cctgctttct ctttgcgctt gcgttttccc      3060
ttgtccagat agcccagtag ctgacattca tccggggtca gcaccgtttc tgcggactgg      3120
cttttctacgt gaaaaggatc taggtgaaga tccttttga taatctcatg accaaaatcc      3180
cttaacgtga gttttcgttc cactgagcgt cagaccccgt agaaaagatc aaaggatctt      3240
cttgagatcc ttttttctg cgcgtaatct gctgcttgca acaaaaaaa ccaccgctac      3300
cagcggtggt ttgtttgccg gatcaagagc taccaactct ttttccgaag gtaactggct      3360
tcagcagagc gcagatacca aatactgttc ttctagtgta gccgtagtta ggccaccact      3420
tcaagaactc tgtagcaccg cctacatacc tcgctctgct aatcctgtta ccagtggctg      3480
ctgccagtgg cgataagtcg tgtcttaccg ggttggactc aagacgatag ttaccggata      3540
aggcgcagcg gtcgggctga acggggggtt cgtgcacaca gcccagcttg gagcgaacga      3600
cctacaccga actgagatac ctacagcgtg agctatgaga aagcgccacg cttcccgaag      3660
ggagaaaggc ggacaggtat ccggtaagcg gcagggtcgg aacaggagag cgcacgaggg      3720
agcttccagg gggaaacgcc tggtatcttt atagtcctgt cgggtttcgc cacctctgac      3780
ttgagcgtcg attttgtga tgctcgtcag ggggcggag cctatggaaa aacgccagca      3840
acgcggccct ttacggttc ctggcctttt gctggccttt tgctcacatg ttgt           3894
```

<210> SEQ ID NO 2
<211> LENGTH: 2947
<212> TYPE: DNA
<213> ORGANISM: Artificial Sequence
<220> FEATURE:
<223> OTHER INFORMATION: vaccine vector pGA2
<220> FEATURE:
<221> NAME/KEY: promoter
<222> LOCATION: (1)...(682)

<223> OTHER INFORMATION: cytomegalovirus intermediate early promoter

<400> SEQUENCE: 2

```
cgacaatatt ggctattggc cattgcatac gttgtatcta tatcataata tgtacattta      60
tattggctca tgtccaatat gaccgccatg ttgacattga ttattgacta gttattaata     120
gtaatcaatt acggggtcat tagttcatag cccatatatg gagttccgcg ttacataact     180
tacggtaaat ggcccgcctg gctgaccgcc caacgacccc cgcccattga cgtcaataat     240
gacgtatgtt cccatagtaa cgccaatagg gactttccat tgacgtcaat gggtggagta     300
tttacggtaa actgcccact tggcagtaca tcaagtgtat catatgccaa gtccgccccc     360
tattgacgtc aatgacggta aatggcccgc ctggcattat gcccagtaca tgaccttacg     420
ggactttcct acttggcagt acatctacgt attagtcatc gctattacca tggtgatgcg     480
gttttggcag tacaccaatg ggcgtggata gcggtttgac tcacggggat ttccaagtct     540
ccaccccatt gacgtcaatg ggagtttgtt ttggcaccaa aatcaacggg actttccaaa     600
atgtcgtaat aaccccgccc cgttgacgca aatgggcggt aggcgtgtac ggtgggaggt     660
ctatataagc agagctcgtt tagtgaactc attctatcga tgcttgcaat catggatgca     720
atgaagagag ggctctgctg tgtgctgctg ctgtgtggag cagtcttcgt ttcggctagc     780
cccgggtgat aaacgaccg cgcaatccct aggctgtgcc ttctagttgc cagccatctg     840
ttgtttgccc ctcccccgtg ccttccttga ccctggaagg tgccactccc actgtccttt     900
cctaataaaa tgaggaaatt gcatcgcatt gtctgagtag gtgtcattct attctggggg     960
gtggggtggg gcaggacagc aaggggagg attgggaaga caatagcagg catgctgggg    1020
atgcggtggg ctctatataa aaacgcccg gcggcaaccg agcgttctga acgctagagt    1080
cgacaaattc agaagaactc gtcaagaagg cgatagaagg cgatgcgctg cgaatcggga    1140
gcggcgatac cgtaaagcac gaggaagcgg tcagcccatt cgccgccaag ctcttcagca    1200
atatcacggg tagccaacgc tatgtcctga tagcggtctg ccacacccag ccggccacag    1260
tcgatgaatc cagaaaagcg gccatttttcc accatgatat tcggcaagca ggcatcgcca    1320
tgggtcacga cgagatcctc gccgtcgggc atgctcgcct tgagcctggc gaacagttcg    1380
gctggcgcga gccctgatg ctcttcgtcc agatcatcct gatcgacaag accggcttcc    1440
atccgagtac gtgctcgctc gatgcgatgt ttcgcttggt ggtcgaatgg gcaggtagcc    1500
ggatcaagcg tatgcagccg ccgcattgca tcagccatga tggatacttt ctcggcagga    1560
gcaaggtgag atgacaggag atcctgcccc ggcacttcgc ccaatagcag ccagtccctt    1620
cccgcttcag tgacaacgtc gagcacagct gcgcaaggaa cgcccgtcgt ggccagccac    1680
gatagccgcg ctgcctcgtc ttgcagttca ttcagggcac cggacaggtc ggtcttgaca    1740
aaaagaaccg ggcgcccctg cgctgacagc cggaacacgg cggcatcaga gcagccgatt    1800
gtctgttgtg cccagtcata gccgaatagc ctctccaccc aagcggccgg agaacctgcg    1860
tgcaatccat cttgttcaat catgcgaaac gatcctcatc ctgtctcttg atcagatctt    1920
gatccctgc gccatcagat ccttggcgg aagaaagcca tccagtttac tttgcagggc    1980
ttcccaacct taccagaggg cgccccagct ggcaattccg gttcgcttgc tgtccataaa    2040
accgcccagt ctagctatcg ccatgtaagc ccactgcaag ctacctgctt tctctttgcg    2100
cttgcgtttt cccttgtcca gatagcccag tagctgacat tcatccgggg tcagcaccgt    2160
ttctgcggac tggctttcta cgtgaaaagg atctaggtga agatcctttt tgataatctc    2220
atgaccaaaa tcccttaacg tgagttttcg ttccactgag cgtcagaccc cgtagaaaag    2280
```

| | |
|---|---|
| atcaaaggat cttcttgaga tcctttttt ctgcgcgtaa tctgctgctt gcaaacaaaa | 2340 |
| aaaccaccgc taccagcggt ggtttgtttg ccggatcaag agctaccaac tctttttccg | 2400 |
| aaggtaactg gcttcagcag agcgcagata ccaaatactg ttcttctagt gtagccgtag | 2460 |
| ttaggccacc acttcaagaa ctctgtagca ccgcctacat acctcgctct gctaatcctg | 2520 |
| ttaccagtgg ctgctgccag tggcgataag tcgtgtctta ccgggttgga ctcaagacga | 2580 |
| tagttaccgg ataaggcgca gcggtcgggc tgaacgggggg gttcgtgcac acagcccagc | 2640 |
| ttggagcgaa cgacctacac cgaactgaga tacctacagc gtgagctatg agaaagcgcc | 2700 |
| acgcttcccg aagggagaaa ggcggacagg tatccggtaa gcggcagggt cggaacagga | 2760 |
| gagcgcacga gggagcttcc agggggaaac gcctggtatc tttatagtcc tgtcgggttt | 2820 |
| cgccacctct gacttgagcg tcgatttttg tgatgctcgt caggggggcg gagcctatgg | 2880 |
| aaaaacgcca gcaacgcggc ccttttacgg ttcctggcct tttgctggcc ttttgctcac | 2940 |
| atgttgt | 2947 |

<210> SEQ ID NO 3
<211> LENGTH: 3893
<212> TYPE: DNA
<213> ORGANISM: Artificial Sequence
<220> FEATURE:
<223> OTHER INFORMATION: vaccine vector pGA3
<220> FEATURE:
<221> NAME/KEY: promoter
<222> LOCATION: (1)...(690)
<223> OTHER INFORMATION: cytomegalovirus intermediate early promoter

<400> SEQUENCE: 3

| | |
|---|---|
| cgacaatatt ggctattggc cattgcatac gttgtatcta tatcataata tgtacattta | 60 |
| tattggctca tgtccaatat gaccgccatg ttgacattga ttattgacta gttattaata | 120 |
| gtaatcaatt acggggtcat tagttcatag cccatatatg gagttccgcg ttacataact | 180 |
| tacggtaaat ggcccgcctg gctgaccccc caacgacccc cgcccattga cgtcaataat | 240 |
| gacgtatgtt cccatagtaa cgccaatagg gactttccat tgacgtcaat gggtggagta | 300 |
| tttacggtaa actgcccact tggcagtaca tcaagtgtat catatgccaa gtccgccccc | 360 |
| tattgacgtc aatgacggta aatggcccgc ctggcattat gcccagtaca tgaccttacg | 420 |
| ggactttcct acttggcagt acatctacgt attagtcatc gctattacca tggtgatgcg | 480 |
| gttttggcag tacaccaatg ggcgtggata gcggtttgac tcacggggat ttccaagtct | 540 |
| ccaccccatt gacgtcaatg ggagtttgtt ttggcaccaa aatcaacggg actttccaaa | 600 |
| atgtcgtaat aaccccgccc cgttgacgca aatgggcggt aggcgtgtac ggtgggaggt | 660 |
| ctatataagc agagctcgtt tagtgaaccg tcagatcgcc tggagacgcc atccacgctg | 720 |
| ttttgacctc catagaagac accgggaccg atccagcctc cgcggccggg aacggtgcat | 780 |
| tggaacgcgg attccccgtg ccaagagtga cgtaagtacc gcctatagac tctataggca | 840 |
| caccccttg gctctatgc atgctatact gttttggct tggggcctat acaccccgc | 900 |
| ttccttatgc tataggtgat ggtatagctt agcctatagg tgtgggttat tgaccattat | 960 |
| tgaccactcc cctattggtg acgatacttt ccattactaa tccataacat ggctctttgc | 1020 |
| cacaactatc tctattggct atatgccaat actctgtcct tcagagactg acacggactc | 1080 |
| tgtatttta caggatgggg tcccattat tatttacaaa ttcacatata caacaacgcc | 1140 |
| gtccccccgtg cccgcagttt ttattaaaca tagcgtggga tctccacgcg aatctcgggt | 1200 |

-continued

```
acgtgttccg gacatgggct cttctccggt agcggcggag cttccacatc cgagccctgg   1260
tcccatgcct ccagcggctc atggtcgctc ggcagctcct tgctcctaac agtggaggcc   1320
agacttaggc acagcacaat gcccaccacc accagtgtgc cgcacaaggc cgtggcggta   1380
gggtatgtgt ctgaaaatga gctcggagat tgggctcgca ccgctgacgc agatggaaga   1440
cttaaggcag cggcagaaga agatgcaggc agctgagttg ttgtattctg ataagagtca   1500
gaggtaactc ccgttgcggt gctgttaacg gtggagggca gtgtagtctg agcagtactc   1560
gttgctgccg cgcgcgccac cagacataat agctgacaga ctaacagact gttccttccc   1620
atgggtcttt tctgcagtca ccgtccaagc ttgcaatcat ggatgcaatg aagagagggc   1680
tctgctgtgt gctgctgctg tgtggagcag tcttcgtttc ggctagcccc gggtgataag   1740
gatcctcgca atccctaggc tgtgccttct agttgccagc catctgttgt ttgcccctcc   1800
cccgtgcctt ccttgaccct ggaaggtgcc actcccactg tcctttccta ataaaatgag   1860
gaaattgcat cgcattgtct gagtaggtgt cattctattc tggggggtgg ggtggggcag   1920
gacagcaagg gggaggattg gaagacaat agcaggcatg ctggggatgc ggtgggctct   1980
atataaaaaa cgcccggcgg caaccgagcg ttctgaacgc tagagtcgac aaattcagaa   2040
gaactcgtca agaaggcgat agaaggcgat gcgctgcgaa tcgggagcgg cgataccgta   2100
aagcacgagg aagcggtcag cccattcgcc gccaagctct tcagcaatat cacgggtagc   2160
caacgctatg tcctgatagc ggtctgccac acccagccgg ccacagtcga tgaatccaga   2220
aaagcggcca ttttccacca tgatattcgg caagcaggca tcgccatggg tcacgacgag   2280
atcctcgccg tcgggcatgc tcgccttgag cctggcgaac agttcggctg gcgcgagccc   2340
ctgatgctct tcgtccagat catcctgatc gacaagaccg gcttccatcc gagtacgtgc   2400
tcgctcgatg cgatgtttcg cttggtggtc gaatgggcag gtagccggat caagcgtatg   2460
cagccgccgc attgcatcag ccatgatgga tactttctcg gcaggagcaa ggtgagatga   2520
caggagatcc tgccccggca cttcgcccaa tagcagccag tcccttcccg cttcagtgac   2580
aacgtcgagc acagctgcgc aaggaacgcc cgtcgtggcc agccacgata gccgcgctgc   2640
ctcgtcttgc agttcattca gggcaccgga caggtcggtc ttgacaaaaa gaaccgggcg   2700
cccctgcgct gacagccgga acacggcggc atcagagcag ccgattgtct gttgtgccca   2760
gtcatagccg aatagcctct ccacccaagc ggccggagaa cctgcgtgca atccatcttg   2820
ttcaatcatg cgaaacgatc ctcatcctgt ctcttgatca gatcttgatc ccctgcgcca   2880
tcagatcctt ggcggcaaga aagccatcca gtttactttg cagggcttcc aaccttacc   2940
agagggcgcc ccagctggca attccggttc gcttgctgtc cataaaaccg cccagtctag   3000
ctatcgccat gtaagcccac tgcaagctac ctgctttctc tttgcgcttg cgttttccct   3060
tgtccagata gcccagtagc tgacattcat ccggggtcag caccgtttct gcggactggc   3120
tttctacgtg aaaaggatct aggtgaagat ccttttttgat aatctcatga ccaaaatccc   3180
ttaacgtgag ttttcgttcc actgagcgtc agacccgta gaaaagatca aggatcttc    3240
ttgagatcct ttttttctgc gcgtaatctg ctgcttgcaa acaaaaaaac caccgctacc   3300
agcggtggtt tgtttgccgg atcaagagct accaactctt tttccgaagg taactggctt   3360
cagcagagcg cagataccaa atactgttct tctagtgtag ccgtagttag gccaccactt   3420
caagaactct gtagcaccgc ctacatacct cgctctgcta atcctgttac cagtggctgc   3480
tgccagtggc gataagtcgt gtcttaccgg gttggactca agacgatagt taccggataa   3540
ggcgcagcgg tcgggctgaa cggggggttc gtgcacacag cccagcttgg agcgaacgac   3600
```

```
ctacaccgaa ctgagatacc tacagcgtga gctatgagaa agcgccacgc ttcccgaagg   3660
gagaaaggcg gacaggtatc cggtaagcgg cagggtcgga acaggagagc gcacgaggga   3720
gcttccaggg ggaaacgcct ggtatcttta tagtcctgtc gggtttcgcc acctctgact   3780
tgagcgtcga tttttgtgat gctcgtcagg ggggcggagc ctatggaaaa acgccagcaa   3840
cgcggccctt ttacggttcc tggccttttg ctggcctttt gctcacatgt tgt          3893
```

<210> SEQ ID NO 4
<211> LENGTH: 9545
<212> TYPE: DNA
<213> ORGANISM: Artificial Sequence
<220> FEATURE:
<223> OTHER INFORMATION: construct of vaccine vector pGA2 and insert JS2
      expressing clade HIV-1 VL

<400> SEQUENCE: 4

```
atcgatgcag gactcggctt gctgaagcgc gcacggcaag aggcgagggg cggcgactgg     60
tgggtacgcc aaaaattttg actagcggag gctagaagga gagagatggg tgcgagagcg    120
tcagtattaa gcgggggaga attagatcga tgggaaaaaa ttcggttaag gccaggggga    180
aagaaaaaat ataaattaaa acatatagta tgggcaagca gggagctaga acgattcgca    240
gttaatcctg gcctgttaga aacatcagaa ggctgtagac aaatactggg acagctacaa    300
ccatcccttc agacaggatc agaagaactt agatcattat ataatacagt agcaaccctc    360
tattgtgtgc atcaaaggat agagataaaa gacaccaagg aagctttaga caagatagag    420
gaagagcaaa acaaaagtaa gaaaaaagca cagcaagcag cagctgacac aggacacagc    480
agtcaggtca gccaaaatta ccctatagtg cagaacatcc aggggcaaat ggtacatcag    540
gccatatcac ctagaacttt aaatgcatgg gtaaaagtag tagaagagaa ggctttcagc    600
ccagaagtaa tacccatgtt ttcagcatta tcagaaggag ccaccccaca agatttaaac    660
accatgctaa acacagtggg gggacatcaa gcagccatgc aaatgttaaa agagaccatc    720
aatgaggaag ctgcagaatg ggatagagta catccagtgc atgcagggcc tattgcacca    780
ggccagatga gagaaccaag gggaagtgac atagcaggaa ctactagtac ccttcaggaa    840
caaataggat ggatgacaaa taatccacct atcccagtag gagaaattta taaaagatgg    900
ataatcctgg gattaaataa aatagtaaga atgtatagcc ctaccagcat tctggacata    960
agacaaggac caaaagaacc ttttagagac tatgtagacc ggttctataa aactctaaga   1020
gccgagcaag cttcacagga ggtaaaaaat tggatgacag aaaccttgtt ggtccaaaat   1080
gcgaacccag attgtaagac tattttaaaa gcattgggac cagcggctac actagaagaa   1140
atgatgacag catgtcaggg agtaggagga cccggccata aggcaagagt tttggctgaa   1200
gcaatgagcc aagtaacaaa tacagctacc ataatgatgc agagaggcaa ttttaggaac   1260
caaagaaaga tggttaagag cttcaatagc ggcaaagaag ggcacacagc cagaaattgc   1320
agggccccta ggaaaaaggg cagctggaaa agcggaaagg aaggacacca aatgaaagat   1380
tgtactgaga gacaggctaa tttttaggg aagatctggc cttcctacaa gggaaggcca   1440
gggaattttc ttcagagcag accagagcca acagccccac catttcttca gagcagacca   1500
gagccaacag ccccaccaga agagagcttc aggtctgggg tagagacaac aactcccct    1560 cagaagcagg agccgataga caaggaactg tatcctttaa cttccctcag atcactcttt   1620
ggcaacgacc cctcgtcaca ataaagatag gggggcaact aaaggaagct ctattagata   1680
caggagcaga tgatacagta ttagaagaaa tgagtttgcc aggaagatgg aaaccaaaaa   1740
```

```
tgatagggggg aattggaggt tttatcaaag taagacagta tgatcagata ctcatagaaa    1800
tctgtggaca taaagctata ggtacagtat tagtaggacc tacacctgtc aacataattg    1860
gaagaaatct gttgactcag attggttgca ctttaaattt tcccattagc cctattgaga    1920
ctgtaccagt aaaattaaag ccaggaatgg atggcccaaa agttaaacaa tggccattga    1980
cagaagaaaa aataaaagca ttagtagaaa tttgtacaga atggaaaag gaagggaaaa     2040 tttcaaaaat tgggcctgag aatccataca atactccagt atttgccata agaaaaaaag    2100
acagtactaa atggagaaaa ttagtagatt tcagagaact taataagaga actcaagact    2160
tctgggaagt tcaattagga ataccacatc ccgcagggtt aaaaaagaaa aaatcagtaa    2220
cagtactgga tgtgggtgat gcatattttt cagttccctt agatgaagac ttcaggaagt    2280
atactgcatt taccatacct agtataaaca atgagacacc agggattaga tatcagtaca    2340
atgtgcttcc acagggatgg aaaggatcac cagcaatatt ccaaagtagc atgacaaaaa    2400
tcttagagcc ttttaaaaaa caaaatccag acatagttat ctatcaatac atgaacgatt    2460
tgtatgtagg atctgactta gaaatagggc agcatagaac aaaaatagag gagctgagac    2520
aacatctgtt gaggtgggga cttaccacac cagacaaaaa acatcagaaa gaacctccat    2580
tcctttggat gggttatgaa ctccatcctg ataaatggac agtacagcct atagtgctgc    2640
cagaaaaaga cagctggact gtcaatgaca tacagaagtt agtggggaaa ttgaataccg    2700
caagtcagat ttacccaggg attaaagtaa ggcaattatg taaactcctt agaggaacca    2760
aagcactaac agaagtaata ccactaacag aagaagcaga gctagaactg gcagaaaaca    2820
gagagattct aaaagaacca gtacatggag tgtattatga cccatcaaaa gacttaatag    2880
cagaaataca gaagcagggg caaggccaat ggacatatca aatttatcaa gagccattta    2940
aaaatctgaa aacaggaaaa tatgcaagaa tgaggggtgc ccacactaat gatgtaaaac    3000
aattaacaga ggcagtgcaa aaaataacca cagaaagcat agtaatatgg ggaaagactc    3060
ctaaatttaa actacccata caaaaggaaa catgggaaac atggtggaca gagtattggc    3120
aagccacctg gattcctgag tgggagtttg ttaatacccc tcctttagtg aaattatggt    3180
accagttaga gaaagaaccc atagtaggag cagaaacctt ctatgtagat ggggcagcta    3240
acagggagac taaattagga aaagcaggat atgttactaa caaggaaga caaaaggttg    3300 tcccccctaac taacacaaca aatcagaaaa ctcagttaca agcaatttat ctagctttgc    3360
aggattcagg attagaagta aacatagtaa cagactcaca atatgcatta ggaatcattc    3420
aagcacaacc agataaaagt gaatcagagt tagtcaatca aataatagag cagttaataa    3480
aaaaggaaaa ggtctatctg gcatgggtac cagcacacaa aggaattgga ggaaatgaac    3540
aagtagataa attagtcagt gctggaatca ggaaaatact attttagat ggaatagata    3600 aggcccaaga tgaacattag aattctgcaa caactgctgt ttatccattt tcagaattgg    3660
gtgtcgacat agcagaatag gcgttactcg acagaggaga gcaagaaatg gagccagtag    3720
atcctagact agagccctgg aagcatccag gaagtcagcc taaaactgct tgtaccaatt    3780
gctattgtaa aaagtgttgc tttcattgcc aagtttgttt cataacaaaa gccttaggca    3840
tctcctatgg caggaagaag cggagacagc gacgaagacc tcctcaagac agtcagactc    3900
atcaagtttc tctatcaaag cagtaagtag taaatgtaat gcaaccttta caaatattag    3960
caatagtagc attagtagta gcagcaataa tagcaatagt tgtgtggacc atagtattca    4020
tagaatatag gaaaatatta agacaaagaa aaatagacag gttaattgat aggataacag    4080
```

```
aaagagcaga agacagtggc aatgaaagtg aagggga tca ggaagaatta tcagcacttg   4140
tggaaatggg gcatcatgct ccttgggatg ttgatgatct gtagtgctgt agaaaatttg   4200
tgggtcacag tttattatgg ggtacctgtg tggaaagaag caaccaccac tctattttgt   4260
gcatcagatg ctaaagcata tgatacagag gtacataatg tttgggccac acatgcctgt   4320
gtacccacag accccaaccc acaagaagta gtattggaaa atgtgacaga aaattttaac   4380
atgtggaaaa ataacatggt agaacagatg catgaggata taatcagttt atgggatcaa   4440
agcctaaagc catgtgtaaa attaacccca ctctgtgtta ctttaaattg cactgatttg   4500
aggaatgtta ctaatatcaa taatagtagt gagggaatga gaggagaaat aaaaaactgc   4560
tctttcaata tcaccacaag cataagagat aaggtgaaga agactatgc acttttttat   4620
agacttgatg tagtaccaat agataatgat aatactagct ataggttgat aaattgtaat   4680
acctcaacca ttacacaggc ctgtccaaag gtatcctttg agccaattcc catacattat   4740
tgtaccccgg ctggttttgc gattctaaag tgtaaagaca agaagttcaa tggaacaggg   4800
ccatgtaaaa atgtcagcac agtacaatgt acacatggaa ttaggccagt agtgtcaact   4860
caactgctgt taaatggcag tctagcagaa gaagaggtag taattagatc tagtaatttc   4920
acagacaatg caaaaaacat aatagtacag ttgaaagaat ctgtagaaat taattgtaca   4980
agacccaaca acaatacaag gaaaagtata catataggac caggaagagc attttataca   5040
acaggagaaa taataggaga tataagacaa gcacattgca acattagtag aacaaaatgg   5100
aataacactt taaatcaaat agctacaaaa ttaaaagaac aatttgggaa taataaaaca   5160
atagtcttta atcaatcctc aggaggggac ccagaaattg taatgcacag ttttaattgt   5220
ggaggggaat ttttctactg taattcaaca caactgttta atagtacttg gaattttaat   5280
ggtacttgga atttaacaca atcgaatggt actgaaggaa atgacactat cacactccca   5340
tgtagaataa aacaaattat aaatatgtgg caggaagtag gaaaagcaat gtatgcccct   5400
cccatcagag gacaaattag atgctcatca atattacag ggctaatatt aacaagagat   5460
ggtgaaacta acagtagtgg gtccgagatc ttcagacctg ggggaggaga tatgagggac   5520
aattggagaa gtgaattata taaatataaa gtagtaaaaa ttgaaccatt aggagtagca   5580
cccaccaagg caaaagaag agtggtgcag agagaaaaaa gagcagtggg aacgatagga   5640
gctatgttcc ttgggttctt gggagcagca ggaagcacta tgggcgcagc gtcaataacg   5700
ctgacggtac aggccagact attattgtct ggtatagtgc aacagcagaa caatttgctg   5760
agggctattg aggcgcaaca gcatctgttg caactcacag tctggggcat caagcagctc   5820
caggcaagag tcctggctct ggaaagatac ctaagggatc aacagctcct agggatttgg   5880
ggttgctctg gaaaactcat ctgcaccact gctgtgcctt ggaatgctag ttggagtaat   5940
aaaactctgg atatgatttg gataacatg acctggatgg agtgggaaag agaaatcgaa   6000
aattacacag gcttaatata caccttaatt gaagaatcgc agaaccaaca agaaaagaat   6060
gaacaagact tattagcatt agataagtgg gcaagtttgt ggaattggtt tgacatatca   6120
aattggctgt ggtgtataaa aatcttcata atgatagtag gaggcttgat aggtttaaga   6180
atagttttta ctgtactttc tatagtaaat agagttaggc agggatactc accattgtca   6240
tttcagaccc acctcccagc cccgagggga cccgacaggc ccgaaggaat cgaagaagaa   6300
ggtggagaca gagacagaga cagatccgtg cgattagtgg atggatcctt agcacttatc   6360
tgggacgatc tgcggagcct gtgcctcttc agctaccacc gcttgagaga cttactcttg   6420
attgtaacga ggattgtgga acttctggga cgcaggggt gggaagccct caaatattgg   6480
```

```
tggaatctcc tacagtattg gagtcaggag ctaaagaata gtgctgttag cttgctcaat    6540
gccacagcta tagcagtagc tgaggggaca gatagggtta tagaagtagt acaaggagct    6600
tatagagcta ttcgccacat acctagaaga ataagacagg gcttggaaag gattttgcta    6660
taagatgggt ggctagcccc gggtgataaa cggaccgcgc aatccctagg ctgtgccttc    6720
tagttgccag ccatctgttg tttgcccctc cccgtgcct tccttgaccc tggaaggtgc     6780
cactcccact gtcctttcct aataaaatga ggaaattgca tcgcattgtc tgagtaggtg    6840
tcattctatt ctgggggtg gggtggggca ggacagcaag ggggaggatt gggaagacaa     6900
tagcaggcat gctggggatg cggtgggctc tatataaaaa acgcccggcg caaccgagc     6960 gttctgaacg ctagagtcga caaattcaga agaactcgtc aagaaggcga tagaaggcga    7020
tgcgctgcga atcgggagcg gcgataccgt aaagcacgag gaagcggtca gcccattcgc    7080
cgccaagctc ttcagcaata tcacgggtag ccaacgctat gtcctgatag cggtctgcca    7140
cacccagccg gccacagtcg atgaatccag aaaagcggcc attttccacc atgatattcg    7200
gcaagcaggc atcgccatgg gtcacgacga atcctcgcc gtcgggcatg ctcgccttga     7260
gcctggcgaa cagttcggct ggcgcgagcc cctgatgctc ttcgtccaga tcatcctgat    7320
cgacaagacc ggcttccatc cgagtacgtg ctcgctcgat gcgatgtttc gcttggtggt    7380
cgaatgggca ggtagccgga tcaagcgtat gcagccgccg cattgcatca gccatgatgg    7440
atactttctc ggcaggagca aggtgagatg acaggagatc ctgccccggc acttcgccca    7500
atagcagcca gtcccttccc gcttcagtga acgtcgag cacagctgcg caaggaacgc     7560
ccgtcgtggc cagccacgat agccgcgctg cctcgtcttg cagttcattc agggcaccgg    7620
acaggtcggt cttgacaaaa agaaccgggc gcccctgcgc tgacagccgg aacacggcgg    7680
catcagagca gccgattgtc tgttgtgccc agtcatagcc gaatagcctc tccacccaag    7740
cggccggaga acctgcgtgc aatccatctt gttcaatcat gcgaaacgat cctcatcctg    7800
tctcttgatc agatcttgat cccctgcgcc atcagatcct ggcggcgag aaagccatcc     7860 agtttacttt gcagggcttc ccaaccttac cagagggcgc cccagctggc aattccggtt    7920
cgcttgctgt ccataaaacc gcccagtcta gctatcgcca tgtaagccca ctgcaagcta    7980
cctgctttct ctttgcgctt gcgttttccc ttgtccagat agcccagtag ctgacattca    8040
tccggggtca gcaccgtttc tgcggactgg cttctacgt gaaaaggatc taggtgaaga    8100 tccttttttga taatctcatg accaaaatcc cttaacgtga gttttcgttc cactgagcgt   8160
cagaccccgt agaaaagatc aaaggatctt cttgagatcc ttttttttctg cgcgtaatct   8220 gctgcttgca acaaaaaaaa ccaccgctac cagcggtggt ttgtttgccg gatcaagagc    8280
taccaactct tttccgaag gtaactggct tcagcagagc gcagatacca aatactgtcc     8340
ttctagtgta gccgtagtta ggccaccact tcaagaactc tgtagcaccg cctacatacc    8400
tcgctctgct aatcctgtta ccagtggctg ctgccagtgg cgataagtcg tgtcttaccg    8460
ggttggactc aagacgatag ttaccggata aggcgcagcg gtcgggctga acggggggtt    8520
cgtgcacaca gcccagcttg gagcgaacga cctacaccga actgagatac ctacagcgtg    8580
agctatgaga aagcgccacg cttcccgaag gagaaaggc ggacaggtat ccggtaagcg     8640
gcagggtcgg aacaggagag cgcacgaggg agcttccagg gggaaacgcc tggtatcttt    8700
atagtcctgt cgggtttcgc cacctctgac ttgagcgtcg attttgtga tgctcgtcag    8760 gggggcggag cctatggaaa aacgccagca acgcggcctt tttacggttc ctgggctttt    8820
```

-continued

```
gctggccttt tgctcacatg ttgtcgaccg acaatattgg ctattggcca ttgcatacgt    8880
tgtatctata tcataatatg tacatttata ttggctcatg tccaatatga ccgccatgtt    8940
gacattgatt attgactagt tattaatagt aatcaattac ggggtcatta gttcatagcc    9000
catatatgga gttccgcgtt acataactta cggtaaatgg cccgcctcgt gaccgcccaa    9060
cgacccccgc ccattgacgt caataatgac gtatgttccc atagtaacgc aatagggac    9120 tttccattga cgtcaatggg tggagtattt acggtaaact gcccacttgg cagtacatca    9180
agtgtatcat atgccaagtc cgcccctatt gacgtcaatg acggtaaatg cccgcctgg    9240 cattatgccc agtacatgac cttacgggac tttcctactt ggcagtacat ctacgtatta    9300
gtcatcgcta ttaccatggt gatgcggttt tggcagtaca ccaatgggcg tggatagcgg    9360
tttgactcac ggggatttcc aagtctccac cccattgacg tcaatgggag tttgttttgg    9420
caccaaaatc aacgggactt tccaaaatgt cgtaataacc ccgccccgtt gacgcaaatg    9480
ggcggtaggc gtgtacggtg ggaggtctat ataagcagag ctcgtttagt gaaccgtcag    9540
atcgc                                                                9545
```

<210> SEQ ID NO 5
<211> LENGTH: 9918
<212> TYPE: DNA
<213> ORGANISM: Artificial Sequence
<220> FEATURE:
<223> OTHER INFORMATION: construct of vaccine vector pGA1 and vaccine insert expressing clade B HIV-1 Gag-Pol

<400> SEQUENCE: 5

```
atcgatgcag gactcggctt gctgaagcgc gcacggcaag aggcgagggg cggcgactgg      60
tgagtacgcc aaaatttttg actagcggag gctagaagga gagagatggg tgcgagagcg     120
tcagtattaa gcgggggaga attagatcga tgggaaaaaa ttcggttaag gccaggggga     180
aagaaaaaat ataaattaaa acatatagta tgggcaagca gggagctaga acgattcgca     240
gttaatcctg gcctgttaga acatcagaa ggctgtagac aaatactggg acagctacaa      300
ccatcccttc agacaggatc agaagaactt agatcattat ataatacagt agcaaccctc     360
tattgtgtgc atcaaaggat agagataaaa gacaccaagg aagctttaga caagatagag     420
gaagagcaaa acaaaagtaa gaaaaaagca cagcaagcag cagctgacac aggacacagc     480
agtcaggtca gccaaaatta ccctatagtg cagaacatcc aggggcaaat ggtacatcag     540
gccatatcac ctagaacttt aaatgcatgg gtaaaagtag tagaagagaa ggctttcagc     600
ccagaagtaa tacccatgtt ttcagcatta tcagaaggag ccaccccaca agatttaaac     660
accatgctaa acacagtggg gggacatcaa gcagccatgc aaatgttaaa agagaccatc     720
aatgaggaag ctgcagaatg ggatagagta catccagtgc atgcagggcc tattgcacca     780
ggccagatga gagaaccaag gggaagtgac atagcaggaa ctactagtac ccttcaggaa     840
caaataggat ggatgacaaa taatccacct atcccagtag gagaaattta taaaagatgg     900
ataatcctgg gattaaataa aatagtaaga atgtatagcc ctaccagcat tctggacata     960
agacaaggac caaagaaacc ttttagagac tatgtagacc ggttctataa aactctaaga    1020
gccgagcaag cttcacagga ggtaaaaaat tggatgacag aaaccttgtt ggtccaaaat    1080
gcgaacccag attgtaagac tattttaaaa gcattgggac cagcggctac actagaagaa    1140
atgatgacag catgtcaggg agtaggagga cccggccata aggcaagagt tttggctgaa    1200
gcaatgagcc aagtaacaaa tacagctacc ataatgatgc agagaggcaa ttttaggaac    1260
```

```
caaagaaaga tggttaagag cttcaatagc ggcaaagaag ggcacacagc cagaaattgc   1320
agggccccta ggaaaaaggg cagctggaaa agcggaaagg aaggacacca aatgaaagat   1380
tgtactgaga gacaggctaa ttttttaggg aagatctggc cttcctacaa gggaaggcca   1440
gggaattttc ttcagagcag accagagcca acagccccac catttcttca gagcagacca   1500
gagccaacag ccccaccaga agagagcttc aggtctgggg tagagacaac aactccccct   1560
cagaagcagg agccgataga caaggaactg tatcctttaa cttccctcag atcactcttt   1620
ggcaacgacc cctcgtcaca ataaagatag gggggcaact aaaggaagct ctattagata   1680
caggagcaga tgatacagta ttagaagaaa tgagtttgcc aggaagatgg aaaccaaaaa   1740 tgatagggggg aattggaggt tttatcaaag taagacagta tgatcagata ctcatagaaa   1800
tctgtggaca taaagctata ggtacagtat tagtaggacc tacacctgtc aacataattg   1860
gaagaaatct gttgactcag attggttgca ctttaaattt tcccattagc cctattgaga   1920
ctgtaccagt aaaattaaag ccaggaatgg atggcccaaa agttaaacaa tggccattga   1980
cagaagaaaa aataaaagca ttagtagaaa tttgtacaga aatggaaaag gaagggaaaa   2040
tttcaaaaat tgggcctgag aatccataca atactccagt atttgccata agaaaaaag   2100 acagtactaa atggagaaaa ttagtagatt tcagagaact aataagaga actcaagact   2160 tctgggaagt tcaattagga ataccacatc ccgcagggtt aaaaagaaa aaatcagtaa   2220 cagtactgga tgtgggtgat gcatattttt cagttccctt agatgaagac ttcaggaagt   2280
atactgcatt taccatacct agtataaaca atgagacacc agggattaga tatcagtaca   2340
atgtgcttcc acagggatgg aaaggatcac cagcaatatt ccaaagtagc atgacaaaaa   2400
tcttagagcc ttttaaaaaa caaaatccag acatagttat ctatcaatac atgaacgatt   2460
tgtatgtagg atctgactta gaaatagggc agcatagaac aaaaatagag gagctgagac   2520
aacatctgtt gaggtgggga cttaccacac cagacaaaaa acatcagaaa gaacctccat   2580
tcctttggat gggttatgaa ctccatcctg ataaatggac agtacagcct atagtgctgc   2640
cagaaaaaga cagctggact gtcaatgaca tacagaagtt agtggggaaa ttgaataccg   2700
caagtcagat ttacccaggg attaaagtaa ggcaattatg taaactcctt agaggaacca   2760
aagcactaac agaagtaata ccactaacag aagaagcaga gctagaactg gcagaaaaca   2820
gagagattct aaaagaacca gtacatggag tgtattatga cccatcaaaa gacttaatag   2880
cagaaataca gaagcagggg caaggccaat ggacatatca aatttatcaa gagccattta   2940
aaaatctgaa aacaggaaaa tatgcaagaa tgaggggtgc ccacactaat gatgtaaaac   3000
aattaacaga ggcagtgcaa aaaataacca cagaaagcat agtaatatgg ggaaagactc   3060
ctaaatttaa actacccata caaaaggaaa catgggaaac atggtggaca gagtattggc   3120
aagccacctg gattcctgag tgggagtttg ttaatacccc tcctttagtg aaattatggt   3180
accagttaga gaaagaaccc atagtaggag cagaaacctt ctatgtagat ggggcagcta   3240
acagggagac taaattagga aaagcaggat atgttactaa caaaggaaga caaaaggttg   3300 tcccctaac taacacaaca aatcagaaaa ctcagttaca agcaatttat ctagctttgc   3360
aggattcagg attagaagta aacatagtaa cagactcaca atatgcatta ggaatcattc   3420
aagcacaacc agataaaagt gaatcagagt tagtcaatca aataatagag cagttaataa   3480
aaaaggaaaa ggtctatctg gcatgggtac cagcacacaa aggaattgga ggaaatgaac   3540
aagtagataa attagtcagt gctggaatca ggaaaatact attttagat ggaatagata   3600 aggcccaaga tgaacattag aattctgcaa caactgctgt ttatccattt tcagaattgg   3660
```

```
gtgtcgacat agcagaatag gcgttactcg acagaggaga gcaagaaatg gagccagtag   3720
atcctagact agagccctgg aagcatccag gaagtcagcc taaaactgct tgtaccaatt   3780
gctattgtaa aaagtgttgc tttcattgcc aagtttgttt cataacaaaa gccttaggca   3840
tctcctatgg caggaagaag cggagacagc gacgaagacc tcctcaaggc agtcagactc   3900
atcaagtttc tctatcaaag cagtaagtag tacatgtaat gcaacctata caaatagcaa   3960
tagtagcatt agtagtagca ataataatag caatagttgt gtggtccata gtaatcatag   4020
aatataggaa atatattaaga caaagaaaaa tagacaggtt aattgataga ctaatagaaa   4080
gagcagaaga cagtggcaat gagagtgaag gagaaatatc agcacttgtg gagatggggg   4140
tggagatggg gcaccatgct ccttgggatg ttgatgatct gtagtgctac agaaaaattg   4200
tgggtcacag tctattatgg ggtacctgtg tggaaggaag caaccaccac tctatttttgt   4260 gcatcagatg ctaaagcata tgatacagag gtacataatg tttgggccac acatgcctgt   4320
gtacccacag accccaaccc acaagaagta gtattggtaa atgtgacaga aaatttaac    4380 atgtggaaaa atgacatggt agaacagatg catgaggata taatcagttt atgggatcaa   4440
agcctaaagc catgtgtaaa attaacccca ctctgtgtta gtttaaagtg cactgatttg   4500
aagaatgata ctaataccaa tagtagtagc gggagaatga taatggagaa aggagagata   4560
aaaaactgct ctttcaatat cagcacaagc ataagaggta aggtgcagaa agaatatgca   4620
tttttttata aacttgatat aataccaata gataatgata ctaccagcta tacgttgaca   4680
agttgtaaca cctcagtcat tacacaggcc tgtccaaagg tatcctttga gccaattccc   4740
atacattatt gtgccccggc tggttttgcg attctaaaat gtaataataa gacgttcaat   4800
ggaacaggac catgtacaaa tgtcagcaca gtacaatgta cacatggaat taggccagta   4860
gtatcaactc aactgctgtt aaatggcagt ctggcagaag aagaggtagt aattagatct   4920
tcagacctgg aggaggagat atgagggaca attggagaag tgaattatat aaatataaag   4980
tagtaaaaat tgaaccatta ggagtagcac ccaccaaggc aaagagaaga gtggtgcaga   5040
gagaaaaaag agcagtggga ataggagctt tgttccttgg gttcttggga gcagcaggaa   5100
gcactatggg cgcagcgtca atgacgctga cggtacaggc cagacaatta ttgtctggta   5160
tagtgcagca gcagaacaat ttgctgaggg ctattgaggc gcaacagcat ctgttgcaac   5220
tcacagtctg gggcatcaag cagctccagg caagaatcct ggctgtggaa agatacctaa   5280
aggatcaaca gctcctgggg atttggggtt gctctggaaa actcatttgc accactgctg   5340
tgccttggaa tgctagttgg agtaataaat ctctggaaca gatttggaat aacatgacct   5400
ggatggagtg ggacagagaa attaacaatt acacaagctt aatacactcc ttaattgaag   5460
aatcgcaaaa ccagcaagaa aagaatgaac aagaattatt ggaattagat aaatgggcaa   5520
gtttgtggaa ttggtttaac ataacaaatt ggctgtggta tataaaatta ttcataatga   5580
tagtaggagg cttggtaggt ttaagaatag ttttttgctgt actttctgta gtgaatagag   5640
ttaggcagga atattcacca ttatcgtttc agacccacct cccaatcccg aggggacccg   5700
acaggcccga aggaatagaa gaagaaggtg gagagagaga cagagacaga tccattcgat   5760
tagtgaacgg atccttagca cttatctggg acgatctgcg gagcctgtgc ctcttcagct   5820
accaccgctt gagagactta ctcttgattg taacgaggat tgtggaactt ctgggacgca   5880
gggggtggga agccctcaaa tattggtgga atctcctaca gtattggagt caggagctaa   5940
agaatagtgc tgttagcttg ctcaatgcca cagctatagc agtagctgag gggacagata   6000
```

```
gggttataga agtagtacaa ggagcttata gagctattcg ccacatacct agaagaataa    6060
gacagggctt ggaaaggatt ttgctataag atgggtggct agccccgggt gataaacgga    6120
ccgcgcaatc cctaggctgt gccttctagt tgccagccaa actgttgttt gcccctcccc    6180
cgtgccttcc ttgaccctgg aaggtgccac tcccactgtc ctttcctaat aaaatgagga    6240
aattgcatcg cattgtctga gtaggtgtca ttctattctg gggggtgggg tgggcagga     6300 cagcaagggg gaggattggg aagacaatag caggcatgct ggggatgcgg tgggctctat    6360
ataaaaaacg cccggcggca accgagcgtt ctgaacgcta gagtcgacaa attcagaaga    6420
actcgtcaag aaggcgatag aaggcgatgc gctgcgaatc gggagcggcg ataccgtaaa    6480
gcacgaggaa gcggtcagcc cattcgccgc caagctcttc agcaatatca cgggtagcca    6540
acgctatgtc ctgatagcgg tccgccacac ccagccggcc acagtcgatg aatcagaaa    6600 agcggccatt ttccaccatg atattcggca agcaggcatc gccatgggtc acgacgagat    6660
cctcgccgtc gggcatgctc gccttgagcc tggcgaacag ttcggctggc gcgagcccct    6720
gatgctcttc gtccagatca tcctgatcga caagaccggc ttccatccga gtacgtgctc    6780
gctcgatgcg atgtttcgct tggtggtcga atgggcaggt agccggatca agcgtatgca    6840
gccgccgcat tgcatcagcc atgatggata cttttctcggc aggagcaagg tgagatgaca    6900
ggagatcctg ccccggcact cgcccaata gcagccagtc ccttccccgct tcagtgacaa    6960 cgtcgagcac agctgcgcaa ggaacgcccg tcgtggccag ccacgatagc cgcgctgcct    7020
cgtcttgcag ttcattcagg gcaccggaca ggtcggtctt gacaaaaaga accgggcgcc    7080
cctgcgctga cagccggaac acggcggcat cagagcagcc gattgtctgt tgtgcccagt    7140
catagccgaa tagcctctcc acccaagcgg ccggagaacc tgcgtgcaat ccatcttgtt    7200
caatcatgcg aaacgatcct catcctgtct cttgatcaga tcttgatccc ctgcgccatc    7260
agatccttgg cggcgagaaa gccatccagt ttactttgca gggcttccca accttaccag    7320
agggcgcccc agctggcaat tccggttcgc ttgctgtcca taaaaccgcc cagtctagct    7380
atcgccatgt aagcccactg caagctacct gctttctctt tgcgcttgcg ttttcccttg    7440
tccagatagc ccagtagctg acattcatcc ggggtcagca ccgtttctgc ggactggctt    7500
tctacgtgaa aaggatctag gtgaagatcc ttttttgataa tctcatgacc aaaatccctt    7560
aacgtgagtt ttcgttccac tgagcgtcag accccgtaga aagatcaaa ggatcttctt     7620 gagatccttt ttttctgcgc gtaatctgct gcttgcaaac aaaaaaacca ccgctaccag    7680
cggtggtttg tttgccggat caagagctac caactctttt tccgaaggta actggcttca    7740
gcagagcgca gataccaaat actgtccttc tagtgtagcc gtagttaggc caccacttca    7800
agaactctgt agcaccgcct acatacctcg ctctgctaat cctgttacca gtggctgctg    7860
ccagtggcga taagtcgtgt cttaccgggt tggactcaag acgatagtta ccggataagg    7920
cgcagcggtc gggctgaacg gggggttcgt gcacacagcc cagcttggag cgaacgacct    7980
acaccgaact gagataccta cagcgtgagc tatgagaaag cgccacgctt cccgaaggga    8040
gaaaggcgga caggtatccg gtaagcggca gggtcggaac aggagagcgc acgagggagc    8100
ttccaggggg aaacgcctgg tatctttata gtcctgtcgg gtttcgccac ctctgacttg    8160
agcgtcgatt tttgtgatgc tcgtcagggg ggcggagcct atggaaaaac gccagcaacg    8220
cggccttttt acggttcctg gccttttgct ggccttttgc tcacatgttg tcgaccgaca    8280
atattggcta ttggccattg catacgttgt atctatatca taatatgtac atttatattg    8340
gctcatgtcc aatatgaccg ccatgttgac attgattatt gactagttat taatagtaat    8400
```

```
caattacggg gtcattagtt catagcccat atatggagtt ccgcgttaca taacttacgg    8460
taaatggccc gcctcgtgac cgcccaacga ccccgccca ttgacgtcaa taatgacgta     8520
tgttcccata gtaacgccaa tagggacttt ccattgacgt caatgggtgg agtatttacg    8580
gtaaactgcc cacttggcag tacatcaagt gtatcatatg ccaagtccgc ccctattgac    8640
gtcaatgacg gtaaatggcc cgcctggcat tatgcccagt acatgacctt acgggacttt    8700
cctacttggc agtacatcta cgtattagtc atcgctatta ccatggtgat gcggttttgg    8760
cagtacacca atgggcgtgg atagcggttt gactcacggg gatttccaag tctccacccc    8820
attgacgtca atgggagttt gttttggcac caaaatcaac gggactttcc aaaatgtcgt    8880
aataaccccg ccccgttgac gcaaatgggc ggtaggcgtg tacggtggga ggtctatata    8940
agcagagctc gtttagtgaa ccgtcagatc gcctggagac gccatccacg ctgttttgac    9000
ctccatagaa gacaccggga ccgatccagc ctccgcggcc gggaacggtg cattggaacg    9060
cggattcccc gtgccaagag tgacgtaagt accgcctata gactctatag gcacacccct    9120
ttggctctta tgcatgctat actgtttttg gcttggggcc tatacacccc cgctccttat    9180
gctataggtg atggtatagc ttagcctata ggtgtgggtt attgaccatt attgaccact    9240
cccctattgg tgacgatact ttccattact aatccataac atggctcttt gccacaacta    9300
tctctattgg ctatatgcca atactctgtc cttcagagac tgacacggac tctgtatttt    9360
tacaggatgg ggtcccattt attatttaca aattcacata tacaacaacg ccgtcccccg    9420
tgcccgcagt ttttattaaa catagcgtgg gatctccacg cgaatctcgg gtacgtgttc    9480
cggacatggg ctcttctccg gtagcggcgg agcttccaca tccgagccct ggtcccatgc    9540
ctccagcggc tcatggtcgc tcggcagctc cttgctccta acagtggagg ccagacttag    9600
gcacagcaca atgcccacca ccaccagtgt gccgcacaag gccgtggcgg tagggtatgt    9660
gtctgaaaat gagctcggag attgggctcg caccgtgacg cagatggaag acttaaggca    9720
gcggcagaag aagatgcagg cagctgagtt gttgtattct gataagagtc agaggtaact    9780
cccgttgcgg tgctgttaac ggtggagggc agtgtagtct gagcagtact cgttgctgcc    9840
gcgcgcgcca ccagacataa tagctgacag actaacagac tgttcctttc catgggtctt    9900
ttctgcagtc accgtcca                                                  9918
```

<210> SEQ ID NO 6
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 6
ataaaaaacg cccggcggca accgagcgtt ctgaa                               35

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
ccgtcagatc gcatcgatac gccatccacg                                     30

<210> SEQ ID NO 8

```
-continued

<211> LENGTH: 30
<212> TYPE: DNA
<213> ORGANISM: Artificial Sequence
<220> FEATURE:
<223> OTHER INFORMATION: primer

<400> SEQUENCE: 8
cgtggatggc gtatcgatgc gatctgacgg                                      30

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
gagctctatc gatgcaggac tcggcttgc                                       29

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
ggcaggtttt aatcgctagc ctatgctctc c                                    31

<210> SEQ ID NO 11
<211> LENGTH: 17
<212> TYPE: DNA
<213> ORGANISM: Artificial Sequence
<220> FEATURE:
<223> OTHER INFORMATION: primer

<400> SEQUENCE: 11
gggcaggagt gctagcc                                                    17

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
ccacactact ttcggaccgc tagccaccc                                       29

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
ggttaagagc ttcaatagcg gcaaagaagg gc                                   32

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
```

-continued gcccttctttt gccgctattg aagctcttaa cc                              32

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
gggcagctgg aaaagcggaa aggaagg                                     27

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
ccttcctttc cgcttttcca gctgccc                                     27

<210> SEQ ID NO 17
<211> LENGTH: 44
<212> TYPE: DNA
<213> ORGANISM: Artificial Sequence
<220> FEATURE:
<223> OTHER INFORMATION: primer

<400> SEQUENCE: 17
ccagacatag ttatctatca atacatgaac gatttgtatg tagg                  44

<210> SEQ ID NO 18
<211> LENGTH: 44
<212> TYPE: DNA
<213> ORGANISM: Artificial Sequence
<220> FEATURE:
<223> OTHER INFORMATION: primer

<400> SEQUENCE: 18
cctacataca aatcgttcat gtattgatag ataactatgt ctgg                  44

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
ggggaaattg aataccgcaa gtcagattta ccc                              33

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
gggtaaatct gacttgcggt attcaatttc ccc                              33

<210> SEQ ID NO 21
<211> LENGTH: 40
<212> TYPE: DNA

-continued

```
<213> ORGANISM: Artificial Sequence
<220> FEATURE:
<223> OTHER INFORMATION: primer

<400> SEQUENCE: 21
ccctaactaa cacaacaaat cagaaaactc agttacaagc                             40

<210> SEQ ID NO 22
<211> LENGTH: 40
<212> TYPE: DNA
<213> ORGANISM: Artificial Sequence
<220> FEATURE:
<223> OTHER INFORMATION: primer

<400> SEQUENCE: 22
gcttgtaact gagttttctg atttgttgtg ttagttaggg                             40

<210> SEQ ID NO 23
<211> LENGTH: 34
<212> TYPE: DNA
<213> ORGANISM: Artificial Sequence
<220> FEATURE:
<223> OTHER INFORMATION: primer

<400> SEQUENCE: 23
ggcaactaaa ggaagctcta ttagccacag gagc                                   34

<210> SEQ ID NO 24
<211> LENGTH: 34
<212> TYPE: DNA
<213> ORGANISM: Artificial Sequence
<220> FEATURE:
<223> OTHER INFORMATION: primer

<400> SEQUENCE: 24
gctcctgtgg ctaatagagc ttcctttagt tgcc                                   34

<210> SEQ ID NO 25
<211> LENGTH: 512
<212> TYPE: PRT
<213> ORGANISM: Artificial Sequence
<220> FEATURE:
<223> OTHER INFORMATION: protein encoded by construct of vaccine vector
      pGA2 and insert JS2 expressing clade HIV-1 VL

<400> SEQUENCE: 25

Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Ser Gln Val
        115                 120                 125
```

```
Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Thr Ala Thr Ile Met Met Gln Arg Gly Asn Phe Arg
370                 375                 380

Asn Gln Arg Lys Met Val Lys Ser Phe Asn Ser Gly Lys Glu Gly His
385                 390                 395                 400

Thr Ala Arg Asn Cys Arg Ala Pro Arg Lys Lys Gly Ser Trp Lys Ser
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
            435                 440                 445

Leu Gln Ser Arg Pro Glu Pro Thr Ala Pro Pro Phe Leu Gln Ser Arg
450                 455                 460

Pro Glu Pro Thr Ala Pro Pro Glu Ser Phe Arg Ser Gly Val Glu
465                 470                 475                 480

Thr Thr Thr Pro Pro Gln Lys Gln Glu Pro Ile Asp Lys Glu Leu Tyr
                485                 490                 495

Pro Leu Thr Ser Leu Arg Ser Leu Phe Gly Asn Asp Pro Ser Ser Gln
            500                 505                 510

<210> SEQ ID NO 26
<211> LENGTH: 739
<212> TYPE: PRT
<213> ORGANISM: Artificial Sequence
<220> FEATURE:
<223> OTHER INFORMATION: protein encoded by construct of vaccine vector
```

-continued pGA2 and insert JS2 expressing clade HIV-1 VL

<400> SEQUENCE: 26

```
Phe Phe Arg Glu Asp Leu Ala Phe Leu Gln Gly Lys Ala Arg Glu Phe
 1               5                  10                  15

Ser Ser Glu Gln Thr Arg Ala Asn Ser Pro Thr Ile Ser Ser Glu Gln
            20                  25                  30

Thr Gly Ala Asn Ser Pro Thr Arg Arg Glu Leu Gln Val Trp Gly Arg
        35                  40                  45

Asp Asn Asn Ser Pro Ser Glu Ala Gly Ala Asp Arg Gln Gly Thr Val
    50                  55                  60

Ser Phe Asn Phe Pro Gln Ile Thr Leu Trp Gln Arg Pro Leu Val Thr
65                  70                  75                  80

Ile Lys Ile Gly Gly Gln Leu Lys Glu Ala Leu Leu Asp Thr Gly Ala
                85                  90                  95

Asp Asp Thr Val Leu Glu Glu Met Ser Leu Pro Gly Arg Trp Lys Pro
            100                 105                 110

Lys Met Ile Gly Gly Ile Gly Gly Phe Ile Lys Val Arg Gln Tyr Asp
        115                 120                 125

Gln Ile Leu Ile Glu Ile Cys Gly His Lys Ala Ile Gly Thr Val Leu
    130                 135                 140

Val Gly Pro Thr Pro Val Asn Ile Ile Gly Arg Asn Leu Leu Thr Gln
145                 150                 155                 160

Ile Gly Cys Thr Leu Asn Phe Pro Ile Ser Pro Ile Glu Thr Val Pro
                165                 170                 175

Val Lys Leu Lys Pro Gly Met Asp Gly Pro Lys Val Lys Gln Trp Pro
            180                 185                 190

Leu Thr Glu Glu Lys Ile Lys Ala Leu Val Glu Ile Cys Thr Glu Met
        195                 200                 205

Glu Lys Glu Gly Lys Ile Ser Lys Ile Gly Pro Glu Asn Pro Tyr Asn
    210                 215                 220

Thr Pro Val Phe Ala Ile Lys Lys Lys Asp Ser Thr Lys Trp Arg Lys
225                 230                 235                 240

Leu Val Asp Phe Arg Glu Leu Asn Lys Arg Thr Gln Asp Phe Trp Glu
                245                 250                 255

Val Gln Leu Gly Ile Pro His Pro Ala Gly Leu Lys Lys Lys Lys Ser
            260                 265                 270

Val Thr Val Leu Asp Val Gly Asp Ala Tyr Phe Ser Val Pro Leu Asp
        275                 280                 285

Glu Asp Phe Arg Lys Tyr Thr Ala Phe Thr Ile Pro Ser Ile Asn Asn
    290                 295                 300

Glu Thr Pro Gly Ile Arg Tyr Gln Tyr Asn Val Leu Pro Gln Gly Trp
305                 310                 315                 320

Lys Gly Ser Pro Ala Ile Phe Gln Ser Ser Met Thr Lys Ile Leu Glu
                325                 330                 335

Pro Phe Lys Lys Gln Asn Pro Asp Ile Val Ile Tyr Gln Tyr Met Asn
            340                 345                 350

Asp Leu Tyr Val Gly Ser Asp Leu Glu Ile Gly Gln His Arg Thr Lys
        355                 360                 365

Ile Glu Glu Leu Arg Gln His Leu Leu Arg Trp Gly Leu Thr Thr Pro
    370                 375                 380

Asp Lys Lys His Gln Lys Glu Pro Pro Phe Leu Trp Met Gly Tyr Glu
385                 390                 395                 400
```

-continued

```
Leu His Pro Asp Lys Trp Thr Val Gln Pro Ile Val Leu Pro Glu Lys
                405                 410                 415
Asp Ser Trp Thr Val Asn Asp Ile Gln Lys Leu Val Gly Lys Leu Asn
            420                 425                 430
Thr Ala Ser Gln Ile Tyr Pro Gly Ile Lys Val Arg Gln Leu Cys Lys
        435                 440                 445
Leu Leu Arg Gly Thr Lys Ala Leu Thr Glu Val Ile Pro Leu Thr Glu
    450                 455                 460
Glu Ala Glu Leu Glu Leu Ala Glu Asn Arg Glu Ile Leu Lys Glu Pro
465                 470                 475                 480
Val His Gly Val Tyr Tyr Asp Pro Ser Lys Asp Leu Ile Ala Glu Ile
                485                 490                 495
Gln Lys Gln Gly Gln Gly Gln Trp Thr Tyr Gln Ile Tyr Gln Glu Pro
            500                 505                 510
Phe Lys Asn Leu Lys Thr Gly Lys Tyr Ala Arg Met Arg Gly Ala His
        515                 520                 525
Thr Asn Asp Val Lys Leu Leu Thr Glu Ala Val Gln Lys Ile Thr Thr
    530                 535                 540
Glu Ser Ile Val Ile Trp Gly Lys Thr Pro Lys Phe Lys Leu Pro Ile
545                 550                 555                 560
Gln Lys Glu Thr Trp Glu Thr Trp Trp Thr Glu Tyr Trp Gln Ala Thr
                565                 570                 575
Trp Ile Pro Glu Trp Glu Phe Val Asn Thr Pro Pro Leu Val Lys Leu
            580                 585                 590
Trp Tyr Gln Leu Glu Lys Glu Pro Ile Val Gly Ala Glu Thr Phe Tyr
        595                 600                 605
Val Asp Gly Ala Ala Asn Arg Glu Thr Lys Leu Gly Lys Ala Gly Tyr
    610                 615                 620
Val Thr Asn Lys Gly Arg Gln Lys Val Val Pro Leu Thr Asn Thr Thr
625                 630                 635                 640
Asn Gln Lys Thr Gln Leu Gln Ala Ile Tyr Leu Ala Leu Gln Asp Ser
                645                 650                 655
Gly Leu Glu Val Asn Ile Val Thr Asp Ser Gln Tyr Ala Leu Gly Ile
            660                 665                 670
Ile Gln Ala Gln Pro Asp Lys Ser Glu Ser Glu Leu Val Asn Gln Ile
        675                 680                 685
Ile Glu Gln Leu Ile Lys Lys Glu Lys Val Tyr Leu Ala Trp Val Pro
    690                 695                 700
Ala His Lys Gly Ile Gly Gly Asn Glu Gln Val Asp Lys Leu Val Ser
705                 710                 715                 720
Ala Gly Ile Arg Lys Ile Leu Phe Leu Asp Gly Ile Asp Lys Ala Gln
                725                 730                 735
Asp Glu His
```

<210> SEQ ID NO 27
<211> LENGTH: 72
<212> TYPE: PRT
<213> ORGANISM: Artificial Sequence
<220> FEATURE:
<223> OTHER INFORMATION: protein encoded by construct of vaccine vector
pGA2 and insert JS2 expressing clade HIV-1 VL

<400> SEQUENCE: 27

```
Met Glu Pro Val Asp Pro Arg Leu Glu Pro Trp Lys His Pro Gly Ser
 1               5                  10                  15
```

-continued

```
Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Asp Ser Gln Thr
    50                  55                  60

His Gln Val Ser Leu Ser Lys Gln
65                  70

<210> SEQ ID NO 28
<211> LENGTH: 25
<212> TYPE: PRT
<213> ORGANISM: Artificial Sequence
<220> FEATURE:
<223> OTHER INFORMATION: protein encoded by construct of vaccine vector
      pGA2 and insert JS2 expressing clade HIV-1 VL

<400> SEQUENCE: 28

Met Ala Gly Arg Ser Gly Asp Ser Asp Glu Asp Leu Leu Lys Thr Val
 1               5                  10                  15

Arg Leu Ile Lys Phe Leu Tyr Gln Ser
            20                  25

<210> SEQ ID NO 29
<211> LENGTH: 852
<212> TYPE: PRT
<213> ORGANISM: Artificial Sequence
<220> FEATURE:
<223> OTHER INFORMATION: protein encoded by construct of vaccine vector
      pGA2 and insert JS2 expressing clade HIV-1 VL

<400> SEQUENCE: 29

Met Lys Val Lys Gly Ile Arg Lys Asn Tyr Gln His Leu Trp Lys Trp
 1               5                  10                  15

Gly Ile Met Leu Leu Gly Met Leu Met Ile Cys Ser Ala Val Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Val Thr Asn Ile Asn Asn Ser Ser Glu
    130                 135                 140

Gly Met Arg Gly Glu Ile Lys Asn Cys Ser Phe Asn Ile Thr Thr Ser
145                 150                 155                 160

Ile Arg Asp Lys Val Lys Lys Asp Tyr Ala Leu Phe Tyr Arg Leu Asp
                165                 170                 175

Val Val Pro Ile Asp Asn Asp Asn Thr Ser Tyr Arg Leu Ile Asn Cys
            180                 185                 190

Asn Thr Ser Thr Ile Thr Gln Ala Cys Pro Lys Val Ser Phe Glu Pro
        195                 200                 205
```

-continued

Ile Pro Ile His Tyr Cys Thr Pro Ala Gly Phe Ala Ile Leu Lys Cys
210                 215                 220

Lys Asp Lys Lys Phe Asn Gly Thr Gly Pro Cys Lys Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Val Val Ile Arg Ser Ser Asn
            260                 265                 270

Phe Thr Asp Asn Ala Lys Asn Ile Ile Val Gln Leu Lys Glu Ser Val
        275                 280                 285

Glu Ile Asn Cys Thr Arg Pro Asn Asn Asn Thr Arg Lys Ser Ile His
290                 295                 300

Ile Gly Pro Gly Arg Ala Phe Tyr Thr Thr Gly Glu Ile Ile Gly Asp
305                 310                 315                 320

Ile Arg Gln Ala His Cys Asn Ile Ser Arg Thr Lys Trp Asn Asn Thr
                325                 330                 335

Leu Asn Gln Ile Ala Thr Lys Leu Lys Glu Gln Phe Gly Asn Asn Lys
            340                 345                 350

Thr Ile Val Phe Asn Gln Ser Ser Gly Gly Asp Pro Glu Ile Val Met
        355                 360                 365

His Ser Phe Asn Cys Gly Gly Glu Phe Phe Tyr Cys Asn Ser Thr Gln
370                 375                 380

Leu Phe Asn Ser Thr Trp Asn Phe Asn Gly Thr Trp Asn Leu Thr Gln
385                 390                 395                 400

Ser Asn Gly Thr Glu Gly Asn Asp Thr Ile Thr Leu Pro Cys Arg Ile
                405                 410                 415

Lys Gln Ile Ile Asn Met Trp Gln Glu Val Gly Lys Ala Met Tyr Ala
            420                 425                 430

Pro Pro Ile Arg Gly Gln Ile Arg Cys Ser Ser Asn Ile Thr Gly Leu
        435                 440                 445

Ile Leu Thr Arg Asp Gly Gly Thr Asn Ser Ser Gly Ser Glu Ile Phe
450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Lys
                485                 490                 495

Ala Lys Arg Arg Val Val Gln Arg Glu Lys Arg Ala Val Gly Thr Ile
            500                 505                 510

Gly Ala Met Phe Leu Gly Phe Leu Gly Ala Ala Gly Ser Thr Met Gly
        515                 520                 525

Ala Ala Ser Ile Thr Leu Thr Val Gln Ala Arg Leu Leu Leu Ser Gly
530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
                565                 570                 575

Val Leu Ala Leu Glu Arg Tyr Leu Arg Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ala Ser Trp Ser Asn Lys Thr Leu Asp Met Ile Trp Asp Asn Met Thr
610                 615                 620

Trp Met Glu Trp Glu Arg Glu Ile Glu Asn Tyr Thr Gly Leu Ile Tyr

-continued 625 630 635 640

Thr Leu Ile Glu Glu Ser Gln Asn Gln Gln Glu Lys Asn Glu Gln Asp
645 650 655

Leu Leu Ala Leu Asp Lys Trp Ala Ser Leu Trp Asn Trp Phe Asp Ile
660 665 670

Ser Asn Trp Leu Trp Cys Ile Lys Ile Phe Ile Met Ile Val Gly Gly
675 680 685

Leu Ile Gly Leu Arg Ile Val Phe Thr Val Leu Ser Ile Val Asn Arg
690 695 700

Val Arg Gln Gly Tyr Ser Pro Leu Ser Phe Gln Thr His Leu Pro Ala
705 710 715 720

Pro Arg Gly Pro Asp Arg Pro Glu Gly Ile Glu Glu Glu Gly Gly Asp
725 730 735

Arg Asp Arg Asp Arg Ser Val Arg Leu Val Asp Gly Ser Leu Ala Leu
740 745 750

Ile Trp Asp Asp Leu Arg Ser Leu Cys Leu Phe Ser Tyr His Arg Leu
755 760 765

Arg Asp Leu Leu Leu Ile Val Thr Arg Ile Val Glu Leu Leu Gly Arg
770 775 780

Arg Gly Trp Glu Ala Leu Lys Tyr Trp Trp Asn Leu Leu Gln Tyr Trp
785 790 795 800

Ser Gln Glu Leu Lys Asn Ser Ala Val Ser Leu Leu Asn Ala Thr Ala
805 810 815

Ile Ala Val Ala Glu Gly Thr Asp Arg Val Ile Glu Val Val Gln Gly
820 825 830

Ala Tyr Arg Ala Ile Arg His Ile Pro Arg Arg Ile Arg Gln Gly Leu
835 840 845

Glu Ile Leu Leu
850

<210> SEQ ID NO 30
<211> LENGTH: 512
<212> TYPE: PRT
<213> ORGANISM: Artificial Sequence
<220> FEATURE:
<223> OTHER INFORMATION: protein encoded by construct of vaccine vector pGA1 and vaccine insert expressing clade B HIV-1 Gag-Pol

<400> SEQUENCE: 30

Met Gly Ala Arg Ala Ser Val Leu Ser Gly Gly Glu Leu Asp Arg Trp
1 5 10 15

Glu Lys Ile Arg Leu Arg Pro Gly Gly Lys Lys Lys Tyr Lys Leu Lys
20 25 30

His Ile Val Trp Ala Ser Arg Glu Leu Glu Arg Phe Ala Val Asn Pro
35 40 45

Gly Leu Leu Glu Thr Ser Glu Gly Cys Arg Gln Ile Leu Gly Gln Leu
50 55 60

Gln Pro Ser Leu Gln Thr Gly Ser Glu Glu Leu Arg Ser Leu Tyr Asn
65 70 75 80

Thr Val Ala Thr Leu Tyr Cys Val His Gln Arg Ile Glu Ile Lys Asp
85 90 95

Thr Lys Glu Ala Leu Asp Lys Ile Glu Glu Glu Gln Asn Lys Ser Lys
100 105 110

Lys Lys Ala Gln Gln Ala Ala Ala Asp Thr Gly His Ser Ser Gln Val
115 120 125

```
Ser Gln Asn Tyr Pro Ile Val Gln Asn Ile Gln Gly Gln Met Val His
        130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Thr Ala Thr Ile Met Met Gln Arg Gly Asn Phe Arg
370                 375                 380

Asn Gln Arg Lys Met Val Lys Ser Phe Asn Ser Gly Lys Glu Gly His
385                 390                 395                 400

Thr Ala Arg Asn Cys Arg Ala Pro Arg Lys Lys Gly Ser Trp Lys Ser
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Phe Leu Gln Ser Arg
    450                 455                 460

Pro Glu Pro Thr Ala Pro Pro Glu Glu Ser Phe Arg Ser Gly Val Glu
465                 470                 475                 480

Thr Thr Thr Pro Pro Gln Lys Gln Glu Pro Ile Asp Lys Glu Leu Tyr
                485                 490                 495

Pro Leu Thr Ser Leu Arg Ser Leu Phe Gly Asn Asp Pro Ser Ser Gln
            500                 505                 510

<210> SEQ ID NO 31
<211> LENGTH: 739
<212> TYPE: PRT
<213> ORGANISM: Artificial Sequence
<220> FEATURE:
```

<223> OTHER INFORMATION: protein encoded by construct of vaccine vector
pGA1 and vaccine insert expressing clade B HIV-1
Gag-Pol

<400> SEQUENCE: 31

Phe Phe Arg Glu Asp Leu Ala Phe Leu Gln Gly Lys Ala Arg Glu Phe
1 5 10 15

Ser Ser Glu Gln Thr Arg Ala Asn Ser Pro Thr Ile Ser Ser Glu Gln
20 25 30

Thr Gly Ala Asn Ser Pro Thr Arg Arg Glu Leu Gln Val Trp Gly Arg
35 40 45

Asp Asn Asn Ser Pro Ser Glu Ala Gly Ala Asp Arg Gln Gly Thr Val
50 55 60

Ser Phe Asn Phe Pro Gln Ile Thr Leu Trp Gln Arg Pro Leu Val Thr
65 70 75 80

Ile Lys Ile Gly Gly Gln Leu Lys Glu Ala Leu Leu Asp Thr Gly Ala
85 90 95

Asp Asp Thr Val Leu Glu Glu Met Ser Leu Pro Gly Arg Trp Lys Pro
100 105 110

Lys Met Ile Gly Gly Ile Gly Gly Phe Ile Lys Val Arg Gln Tyr Asp
115 120 125

Gln Ile Leu Ile Glu Ile Cys Gly His Lys Ala Ile Gly Thr Val Leu
130 135 140

Val Gly Pro Thr Pro Val Asn Ile Ile Gly Arg Asn Leu Leu Thr Gln
145 150 155 160

Ile Gly Cys Thr Leu Asn Phe Pro Ile Ser Pro Ile Glu Thr Val Pro
165 170 175

Val Lys Leu Lys Pro Gly Met Asp Gly Pro Lys Val Lys Gln Trp Pro
180 185 190

Leu Thr Glu Glu Lys Ile Lys Ala Leu Val Glu Ile Cys Thr Glu Met
195 200 205

Glu Lys Glu Gly Lys Ile Ser Lys Ile Gly Pro Glu Asn Pro Tyr Asn
210 215 220

Thr Pro Val Phe Ala Ile Lys Lys Lys Asp Ser Thr Lys Trp Arg Lys
225 230 235 240

Leu Val Asp Phe Arg Glu Leu Asn Lys Arg Thr Gln Asp Phe Trp Glu
245 250 255

Val Gln Leu Gly Ile Pro His Pro Ala Gly Leu Lys Lys Lys Lys Ser
260 265 270

Val Thr Val Leu Asp Val Gly Asp Ala Tyr Phe Ser Val Pro Leu Asp
275 280 285

Glu Asp Phe Arg Lys Tyr Thr Ala Phe Thr Ile Pro Ser Ile Asn Asn
290 295 300

Glu Thr Pro Gly Ile Arg Tyr Gln Tyr Asn Val Leu Pro Gln Gly Trp
305 310 315 320

Lys Gly Ser Pro Ala Ile Phe Gln Ser Ser Met Thr Lys Ile Leu Glu
325 330 335

Pro Phe Lys Lys Gln Asn Pro Asp Ile Val Ile Tyr Gln Tyr Met Asn
340 345 350

Asp Leu Tyr Val Gly Ser Asp Leu Glu Ile Gly Gln His Arg Thr Lys
355 360 365

Ile Glu Glu Leu Arg Gln His Leu Leu Arg Trp Gly Leu Thr Thr Pro
370 375 380

Asp Lys Lys His Gln Lys Glu Pro Pro Phe Leu Trp Met Gly Tyr Glu

```
                    385                 390                 395                 400

Leu His Pro Asp Lys Trp Thr Val Gln Pro Ile Val Leu Pro Glu Lys
                405                 410                 415

Asp Ser Trp Thr Val Asn Asp Ile Gln Lys Leu Val Gly Lys Leu Asn
            420                 425                 430

Thr Ala Ser Gln Ile Tyr Pro Gly Ile Lys Val Arg Gln Leu Cys Lys
        435                 440                 445

Leu Leu Arg Gly Thr Lys Ala Leu Thr Glu Val Ile Pro Leu Thr Glu
    450                 455                 460

Glu Ala Glu Leu Glu Leu Ala Glu Asn Arg Glu Ile Leu Lys Glu Pro
465                 470                 475                 480

Val His Gly Val Tyr Tyr Asp Pro Ser Lys Asp Leu Ile Ala Glu Ile
                485                 490                 495

Gln Lys Gln Gly Gln Gly Gln Trp Thr Tyr Gln Ile Tyr Gln Glu Pro
            500                 505                 510

Phe Lys Asn Leu Lys Thr Gly Lys Tyr Ala Arg Met Arg Gly Ala His
        515                 520                 525

Thr Asn Asp Val Lys Leu Leu Thr Glu Ala Val Gln Lys Ile Thr Thr
    530                 535                 540

Glu Ser Ile Val Ile Trp Gly Lys Thr Pro Lys Phe Lys Leu Pro Ile
545                 550                 555                 560

Gln Lys Glu Thr Trp Glu Thr Trp Trp Thr Glu Tyr Trp Gln Ala Thr
                565                 570                 575

Trp Ile Pro Glu Trp Glu Phe Val Asn Thr Pro Pro Leu Val Lys Leu
            580                 585                 590

Trp Tyr Gln Leu Glu Lys Glu Pro Ile Val Gly Ala Glu Thr Phe Tyr
        595                 600                 605

Val Asp Gly Ala Ala Asn Arg Glu Thr Lys Leu Gly Lys Ala Gly Tyr
    610                 615                 620

Val Thr Asn Lys Gly Arg Gln Lys Val Val Pro Leu Thr Asn Thr Thr
625                 630                 635                 640

Asn Gln Lys Thr Gln Leu Gln Ala Ile Tyr Leu Ala Leu Gln Asp Ser
                645                 650                 655

Gly Leu Glu Val Asn Ile Val Thr Asp Ser Gln Tyr Ala Leu Gly Ile
            660                 665                 670

Ile Gln Ala Gln Pro Asp Lys Ser Glu Ser Glu Leu Val Asn Gln Ile
        675                 680                 685

Ile Glu Gln Leu Ile Lys Lys Glu Lys Val Tyr Leu Ala Trp Val Pro
    690                 695                 700

Ala His Lys Gly Ile Gly Gly Asn Glu Gln Val Asp Lys Leu Val Ser
705                 710                 715                 720

Ala Gly Ile Arg Lys Ile Leu Phe Leu Asp Gly Ile Asp Lys Ala Gln
                725                 730                 735

Asp Glu His

<210> SEQ ID NO 32
<211> LENGTH: 72
<212> TYPE: PRT
<213> ORGANISM: Artificial Sequence
<220> FEATURE:
<223> OTHER INFORMATION: protein encoded by construct of vaccine vector
      pGA1 and vaccine insert expressing clade B HIV-1
      Gag-Pol

<400> SEQUENCE: 32
```

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
                35                  40                  45

Arg Lys Lys Arg Arg Gln Arg Arg Pro Pro Gln Gly Ser Gln Thr
50                  55                  60

His Gln Val Ser Leu Ser Lys Gln
65                  70

<210> SEQ ID NO 33
<211> LENGTH: 25
<212> TYPE: PRT
<213> ORGANISM: Artificial Sequence
<220> FEATURE:
<223> OTHER INFORMATION: protein encoded by construct of vaccine vector
      pGA1 and vaccine insert expressing clade B HIV-1
      Gag-Pol

<400> SEQUENCE: 33

Met Ala Gly Arg Ser Gly Asp Ser Asp Glu Asp Leu Leu Lys Thr Val
1               5                   10                  15

Arg Leu Ile Lys Phe Leu Tyr Gln Ser
                20                  25

<210> SEQ ID NO 34
<211> LENGTH: 8
<212> TYPE: PRT
<213> ORGANISM: Artificial Sequence
<220> FEATURE:
<223> OTHER INFORMATION: synthetically generated peptide

<400> SEQUENCE: 34

Ser Ile Ile Asn Phe Glu Lys Leu
1               5

<210> SEQ ID NO 35
<211> LENGTH: 281
<212> TYPE: PRT
<213> ORGANISM: Artificial Sequence
<220> FEATURE:
<223> OTHER INFORMATION: protein encoded by construct of vaccine vector
      pGA1 and vaccine insert expressing clade B HIV-1
      Gag-Pol

<400> SEQUENCE: 35

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
                35                  40                  45

Thr Thr Thr Leu Phe Cys Ala Ser Asp Ala Lys Ala Tyr Asp Thr Glu
50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110
```

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Tyr Gln Lys Glu Tyr Ala Phe Phe
                165                 170                 175

Tyr Lys Leu Asp Ile Ile Pro Ile Asp Asn Asp Thr Thr Ser Tyr Thr
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Ser Asp Leu Glu Glu Glu Ile
        275                 280

<210> SEQ ID NO 36
<211> LENGTH: 21
<212> TYPE: PRT
<213> ORGANISM: Artificial Sequence
<220> FEATURE:
<223> OTHER INFORMATION: tpa leader sequence of pGA1 and pGA2

<400> SEQUENCE: 36

Met Asp Ala Met Lys Arg Gly Leu Cys Cys Val Leu Leu Leu Cys Gly
 1               5                  10                  15

Ala Val Phe Val Ser
            20

<210> SEQ ID NO 37
<211> LENGTH: 3894
<212> TYPE: DNA
<213> ORGANISM: Artificial Sequence
<220> FEATURE:
<223> OTHER INFORMATION: complementary strand of vaccine vector pGA1

<400> SEQUENCE: 37
acaacatgtg agcaaaaggc cagcaaaagg ccaggaaccg taaaagggcc gcgttgctgg     60 cgttttttcca taggctccgc cccctgacg agcatcacaa aaatcgacgc tcaagtcaga    120
ggtggcgaaa cccgacagga ctataaagat accaggcgtt tccccctgga agctccctcg    180
tgcgctctcc tgttccgacc ctgccgctta ccggatacct gtccgccttt ctcccttcgg    240
gaagcgtggc gctttctcat agctcacgct gtaggtatct cagttcggtg taggtcgttc    300
gctccaagct gggctgtgtg cacgaacccc cgttcagcc cgaccgctgc gccttatccg    360
gtaactatcg tcttgagtcc aacccggtaa gacacgactt atcgccactg gcagcagcca    420
ctggtaacag gattagcaga gcgaggtatg taggcggtgc tacagagttc ttgaagtggt    480
ggcctaacta cggctacact agaagaacag tatttggtat ctgcgctctg ctgaagccag    540
ttaccttcgg aaaaagagtt ggtagctctt gatccggcaa acaaaccacc gctggtagcg    600

-continued

```
gtggttttttt tgtttgcaag cagcagatta cgcgcagaaa aaaaggatct caagaagatc    660
ctttgatctt ttctacgggg tctgacgctc agtggaacga aaactcacgt taagggattt    720
tggtcatgag attatcaaaa aggatcttca cctagatcct tttcacgtag aaagccagtc    780
cgcagaaacg gtgctgaccc cggatgaatg tcagctactg ggctatctgg acaagggaaa    840
acgcaagcgc aaagagaaag caggtagctt gcagtgggct tacatggcga tagctagact    900
gggcggtttt atggacagca agcgaaccgg aattgccagc tggggcgccc tctggtaagg    960
ttgggaagcc ctgcaaagta aactggatgg ctttcttgcc gccaaggatc tgatggcgca   1020
ggggatcaag atctgatcaa gagacaggat gaggatcgtt tcgcatgatt gaacaagatg   1080
gattgcacgc aggttctccg gccgcttggg tggagaggct attcggctat gactgggcac   1140
aacagacaat cggctgctct gatgccgccg tgttccggct gtcagcgcag gggcgcccgg   1200
ttcttttttgt caagaccgac ctgtccggtg ccctgaatga actgcaagac gaggcagcgc   1260
ggctatcgtg gctggccacg acgggcgttc cttgcgcagc tgtgctcgac gttgtcactg   1320
aagcgggaag ggactggctg ctattgggcg aagtgccggg gcaggatctc ctgtcatctc   1380
accttgctcc tgccgagaaa gtatccatca tggctgatgc aatgcggcgg ctgcatacgc   1440
ttgatccggc tacctgccca ttcgaccacc aagcgaaaca tcgcatcgag cgagcacgta   1500
ctcggatgga agccggtctt gtcgatcagg atgatctgga cgaagagcat caggggctcg   1560
cgccagccga actgttcgcc aggctcaagg cgagcatgcc cgacggcgag gatctcgtcg   1620
tgacccatgg cgatgcctgc ttgccgaata tcatggtgga aaatggccgc ttttctggat   1680
tcatcgactg tggccggctg ggtgtggcag accgctatca ggacatagcg ttggctaccc   1740
gtgatattgc tgaagagctt ggcggcgaat gggctgaccg cttcctcgtg ctttacggta   1800
tcgccgctcc cgattcgcag cgcatcgcct tctatcgcct tcttgacgag ttcttctgaa   1860
tttgtcgact ctagcgttca gaacgctcgg ttgccgccgg gcgttttta tatagagccc   1920
accgcatccc cagcatgcct gctattgtct tcccaatcct cccccttgct gtcctgcccc   1980
accccacccc ccagaataga atgacaccta ctcagacaat gcgatgcaat ttcctcattt   2040
tattaggaaa ggacagtggg agtggcacct tccagggtca aggaaggcac ggggaggggg   2100
caaacaacag atggctggca actagaaggc acagccctagg gattgcgcgg tccgtttatc   2160
acccgggggct agccgaaacg aagactgctc cacacagcag cagcacacag cagagccctc   2220
tcttcattgc atccatgatt gcaagcatcg atggtgactg cagaaaagac ccatggaaag   2280
gaacagtctg ttagtctgtc agctattatg tctggtggcg cgcgcggcag caacgagtac   2340
tgctcagact acactgccct ccaccgttaa cagcaccgca acgggagtta cctctgactc   2400
ttatcagaat acaacaactc agctgcctgc atcttcttct gccgctgcct taagtcttcc   2460
atctgcgtca gcggtgcgag cccaatctcc gagctcattt tcagacacat accctaccgc   2520
cacggccttg tgcggcacac tggtggtggt gggcattgtg ctgtgcctaa gtctggcctc   2580
cactgttagg agcaaggagc tgccgagcga ccatgagccg ctggaggcat gggaccaggg   2640
ctcggatgtg gaagctccgc cgctaccgga gaagayccca tgtccggaac aggtacccga   2700
gattcgcgtg gagatcccac gctatgttta ataaaaactg cgggcacggg gacggcgtt   2760
gttgtatatg tgaatttgta aataataaat gggaccccat cctgtaaaaa tacagagtcc   2820
gtgtcagtct ctgaaggaca gagtattggc atatagccaa tagagatagt tgtggcaaag   2880
agccatgtta tggattagta atggaaagta tcgtcaccaa taggggagtg gtcaataatg   2940
gtcaataacc cacacctata ggctaagcta taccatcacc tatagcataa ggaagcgggg   3000
```

| | |
|---|---|
| gtgtataggc cccaagccaa aaacagtata gcatgcataa gagccaaagg ggtgtgccta | 3060 |
| tagagtctat aggcggtact tacgtcactc ttggcacggg gaatccgcgt tccaatgcac | 3120 |
| cgttcccggc cgcggaggct ggatcggtcc cggtgtcttc tatggaggtc aaaacagcgt | 3180 |
| ggatggcgtc tccaggcgat ctgacggttc actaaacgag ctctgcttat atagacctcc | 3240 |
| caccgtacac gcctaccgcc catttgcgtc aacggggcgg ggttattacg acattttgga | 3300 |
| aagtcccgtt gattttggtg ccaaaacaaa ctcccattga cgtcaatggg gtggagactt | 3360 |
| ggaaatcccc gtgagtcaaa ccgctatcca cgcccattgg tgtactgcca aaaccgcatc | 3420 |
| accatggtaa tagcgatgac taatacgtag atgtactgcc aagtaggaaa gtcccgtaag | 3480 |
| gtcatgtact gggcataatg ccaggcgggc catttaccgt cattgacgtc aatagggggc | 3540 |
| ggacttggca tatgatacac ttgatgtact gccaagtggg cagtttaccg taaatactcc | 3600 |
| acccattgac gtcaatggaa agtccctatt ggcgttacta tgggaacata cgtcattatt | 3660 |
| gacgtcaatg gcggggggtc gttgggcggt cagccaggcg ggccatttac cgtaagttat | 3720 |
| gtaacgcgga actccatata tgggctatga actaatgaac ccgtaattga ttactattaa | 3780 |
| taactagtca ataatcaatg tcaacatggc ggtcatattg gacatgagcc aatataaatg | 3840 |
| tacatattat gatatagata caacgtatgc aatggccaat agccaatatt gtcg | 3894 |

<210> SEQ ID NO 38
<211> LENGTH: 2947
<212> TYPE: DNA
<213> ORGANISM: Artificial Sequence
<220> FEATURE:
<223> OTHER INFORMATION: complementary strand of vaccine vector pGA2

<400> SEQUENCE: 38

| | |
|---|---|
| acaacatgtg agcaaaaggc cagcaaaagg ccaggaaccg taaagggcc gcgttgctgg | 60 |
| cgttttccca taggctccgc cccctgacg agcatcacaa aaatcgacgc tcaagtcaga | 120 |
| ggtggcgaaa cccgacagga ctataaagat accaggcgtt tcccctgga agctccctcg | 180 |
| tgcgctctcc tgttccgacc ctgccgctta ccggatacct gtccgccttt ctcccttcgg | 240 |
| gaagcgtggc gctttctcat agctcacgct gtaggtatct cagttcggtg taggtcgttc | 300 |
| gctccaagct gggctgtgtg cacgaacccc ccgttcagcc cgaccgctgc gccttatccg | 360 |
| gtaactatcg tcttgagtcc aacccggtaa gacacgactt atcgccactg gcagcagcca | 420 |
| ctggtaacag gattagcaga gcgaggtatg taggcggtgc tacagagttc ttgaagtggt | 480 |
| ggcctaacta cggctacact agaagaacag tatttggtat ctgcgctctg ctgaagccag | 540 |
| ttaccttcgg aaaaagagtt ggtagctctt gatccggcaa acaaaccacc gctggtagcg | 600 |
| gtggtttttt tgtttgcaag cagcagatta cgcgcagaaa aaaaggatct caagaagatc | 660 |
| ctttgatctt ttctacgggg tctgacgctc agtggaacga aaactcacgt taagggattt | 720 |
| tggtcatgag attatcaaaa aggatcttca cctagatcct tttcacgtag aaagccagtc | 780 |
| cgcagaaacg gtgctgaccc cggatgaatg tcagctactg ggctatctgg acaagggaaa | 840 |
| acgcaagcgc aaagagaaag caggtagctt gcagtgggct tacatggcga tagctagact | 900 |
| gggcggtttt atgacagca agcgaaccgg aattgccagc tggggcgccc tctggtaagg | 960 |
| ttgggaagcc ctgcaaagta aactggatgg ctttcttgcc gccaaggatc tgatggcgca | 1020 |
| ggggatcaag atctgatcaa gagacaggat gaggatcgtt tcgcatgatt gaacaagatg | 1080 |
| gattgcacgc aggttctccg gccgcttggg tggagaggct attcggctat gactgggcac | 1140 |

```
aacagacaat cggctgctct gatgccgccg tgttccggct gtcagcgcag gggcgcccgg    1200 ttcttttgt  caagaccgac ctgtccggtg ccctgaatga actgcaagac gaggcagcgc    1260
ggctatcgtg gctggccacg acgggcgttc cttgcgcagc tgtgctcgac gttgtcactg    1320
aagcgggaag ggactggctg ctattgggcg aagtgccggg gcaggatctc ctgtcatctc    1380
accttgctcc tgccgagaaa gtatccatca tggctgatgc aatgcggcgg ctgcatacgc    1440
ttgatccggc tacctgccca ttcgaccacc aagcgaaaca tcgcatcgag cgagcacgta    1500
ctcggatgga agccggtctt gtcgatcagg atgatctgga cgaagagcat caggggctcg    1560
cgccagccga actgttcgcc aggctcaagg cgagcatgcc cgacgcgag  gatctcgtcg    1620 tgacccatgg cgatgcctgc ttgccgaata tcatggtgga aaatggccgc ttttctggat    1680
tcatcgactg tggccggctg ggtgtggcag accgctatca ggacatagcg ttggctaccc    1740
gtgatattgc tgaagagctt ggcggcgaat gggctgaccg cttcctcgtg ctttacggta    1800
tcgccgctcc cgattcgcag cgcatcgcct tctatcgcct tcttgacgag ttcttctgaa    1860
tttgtcgact ctagcgttca gaacgctcgg ttgccgccgg gcgttttta  tatagagccc    1920 accgcatccc cagcatgcct gctattgtct tcccaatcct cccccttgct gtcctgcccc    1980
accccacccc ccagaataga atgacaccta ctcagacaat gcgatgcaat tcctcatttt    2040
tattaggaaa ggacagtggg agtggcacct tccagggtca aggaaggcac ggggaggggg    2100
caaacaacag atggctggca actagaaggc acagcctagg gattgcgcgg tccgtttatc    2160
acccggggct agccgaaacg aagactgctc cacacagcag cagcacacag cagagccctc    2220
tcttcattgc atccatgatt gcaagcatcg atagaatgag ttcactaaac gagctctgct    2280
tatatagacc tcccaccgta cacgcctacc gcccatttgc gtcaacgggg cggggttatt    2340
acgacatttt ggaaagtccc gttgattttg gtgccaaaac aaactcccat tgacgtcaat    2400
ggggtggaga cttggaaatc cccgtgagtc aaaccgctat ccacgcccat tggtgtactg    2460
ccaaaaccgc atcaccatgg taatagcgat gactaatacg tagatgtact gccaagtagg    2520
aaagtcccgt aaggtcatgt actgggcata atgccaggcg ggccatttac cgtcattgac    2580
gtcaataggg ggcggacttg gcatatgata cacttgatgt actgccaagt gggcagttta    2640
ccgtaaatac tccacccatt gacgtcaatg gaaagtccct attggcgtta ctatgggaac    2700
atacgtcatt attgacgtca atgggcgggg tcgttgggc  ggtcagccag gcgggccatt    2760
taccgtaagt tatgtaacgc ggaactccat atatgggcta tgaactaatg accccgtaat    2820
tgattactat taataactag tcaataatca atgtcaacat ggcggtcata ttggacatga    2880
gccaatataa atgtacatat tatgatatag atacaacgta tgcaatggcc aatagccaat    2940
attgtcg                                                             2947
```

<210> SEQ ID NO 39
<211> LENGTH: 3893
<212> TYPE: DNA
<213> ORGANISM: Artificial Sequence
<220> FEATURE:
<223> OTHER INFORMATION: complementary strand of vaccine vector pGA3

<400> SEQUENCE: 39

```
acaacatgtg agcaaaaggc cagcaaaagg ccaggaaccg taaaagggcc gcgttgctgg      60 cgttttttcca taggctccgc cccctgacg  agcatcacaa aaatcgacgc tcaagtcaga    120
ggtggcgaaa cccgacagga ctataaagat accaggcgtt tccccctgga agctccctcg    180
tgcgctctcc tgttccgacc ctgccgctta ccggatacct gtccgccttt ctcccttcgg    240
```

-continued

```
gaagcgtggc gctttctcat agctcacgct gtaggtatct cagttcggtg taggtcgttc      300
gctccaagct gggctgtgtg cacgaacccc ccgttcagcc cgaccgctgc gccttatccg      360
gtaactatcg tcttgagtcc aacccggtaa gacacgactt atcgccactg gcagcagcca      420
ctggtaacag gattagcaga gcgaggtatg taggcggtgc tacagagttc ttgaagtggt      480
ggcctaacta cggctacact agaagaacag tatttggtat ctgcgctctg ctgaagccag      540
ttaccttcgg aaaaagagtt ggtagctctt gatccggcaa acaaaccacc gctggtagcg      600
gtggtttttt tgtttgcaag cagcagatta cgcgcagaaa aaaggatctc aagaagatc       660
ctttgatctt ttctacgggg tctgacgctc agtggaacga aaactcacgt taagggattt      720
tggtcatgag attatcaaaa aggatcttca cctagatcct tttcacgtag aaagccagtc      780
cgcagaaacg tgctgacccc cggatgaatg tcagctactg ggctatctgg acaagggaaa      840
acgcaagcgc aaagagaaag caggtagctt gcagtgggct tacatggcga tagctagact      900
gggcggtttt atggacagca agcgaaccgg aattgccagc tggggcgccc tctggtaagg      960
ttgggaagcc ctgcaaagta aactggatgg cttttcttgcc gccaaggatc tgatggcgca      1020
ggggatcaag atctgatcaa gagacaggat gaggatcgtt tcgcatgatt gaacaagatg      1080
gattgcacgc aggttctccg gccgcttggg tggagaggct attcggctat gactgggcac      1140
aacagacaat cggctgctct gatgccgccg tgttccggct gtcagcgcag ggcgcccgg       1200
ttcttttttgt caagaccgac ctgtccggtg ccctgaatga actgcaagac gaggcagcgc     1260
ggctatcgtg gctggccacg acgggcgttc cttgcgcagc tgtgctcgac gttgtcactg     1320
aagcgggaag ggactggctg ctattgggcg aagtgccggg gcaggatctc ctgtcatctc     1380
accttgctcc tgccgagaaa gtatccatca ggctgatgca atgcggcgg ctgcatacgc       1440
ttgatccggc tacctgccca ttcgaccacc aagcgaaaca tcgcatcgag cgagcacgta     1500
ctcggatgga agccggtctt gtcgatcagg atgatctgga cgaagagcat caggggctcg     1560
cgccagccga actgttcgcc aggctcaagg cgagcatgcc cgacggcgag gatctcgtcg     1620
tgacccatgg cgatgcctgc ttgccgaata tcatggtgga aaatggccgc ttttctggat     1680
tcatcgactg tggccggctg ggtgtggcag accgctatca ggacatagcg ttggctaccc     1740
gtgatattgc tgaagagctt ggcggcgaat gggctgaccg cttcctcgtg ctttacggta     1800
tcgccgctcc cgattcgcag cgcatcgcct tctatcgcct tcttgacgag ttcttctgaa     1860
tttgtcgact ctagcgttca gaacgctcgg ttgccgccgg gcgttttta tatagagccc      1920
accgcatccc cagcatgcct gctattgtct tcccaatcct cccccttgct gtcctgcccc     1980
accccacccc ccagaataga atgacaccta ctcagacaat gcgatgcaat tcctcatttt     2040
tattaggaaa ggacagtggg agtggcacct tccagggtca aggaaggcac ggggggagggg    2100
caaacaacag atggctggca actagaaggc acagccctagg gattgcgagg atccttatca    2160
cccgggggcta gccgaaacga agactgctcc acacagcagc agcacacagc agagccctct   2220
cttcattgca tccatgattg caagcttgga cggtgactgc agaaaagacc catgaaaagg      2280
aacagtctgt tagtctgtca gctattatgt ctggtggcgc gcgcggcagc aacgagtact     2340
gctcagacta cactgccctc caccgttaac agcaccgcaa cgggagttac ctctgactct    2400
tatcagaata caacaactca gctgcctgca tcttcttctg ccgctgcctt aagtcttcca    2460
tctgcgtcag cggtgcgagc ccaatctccg agctcatttt cagacacata ccctaccgcc    2520
acggccttgt gcggcacact ggtggtggtg ggcattgtgc tgtgcctaag tctggcctcc    2580
```

-continued

```
actgttagga gcaaggagct gccgagcgac catgagccgc tggaggcatg ggaccagggc   2640
tcggatgtgg aagctccgcc gctaccggag aagagcccat gtccggaaca cgtacccgag   2700
attcgcgtgg agatcccacg ctatgtttaa taaaaactgc gggcacgggg gacggcgttg   2760
ttgtatatgt gaatttgtaa ataataaatg ggaccccatc ctgtaaaaat acagagtccg   2820
tgtcagtctc tgaaggacag agtattggca tatagccaat agagatagtt gtggcaaaga   2880
gccatgttat ggattagtaa tggaaagtat cgtcaccaat aggggagtgg tcaataatgg   2940
tcaataaccc acacctatag gctaagctat accatcacct atagcataag gaagcggggg   3000
tgtataggcc ccaagccaaa aacagtatag catgcataag agccaaaggg gtgtgcctat   3060
agagtctata ggcggtactt acgtcactct tggcacgggg aatccgcgtt ccaatgcacc   3120
gttcccggcc gcggaggctg gatcggtccc ggtgtcttct atggaggtca aaacagcgtg   3180
gatggcgtct ccaggcgatc tgacggttca ctaaacgagc tctgcttata tagacctccc   3240
accgtacacg cctaccgccc atttgcgtca acggggcggg gttattacga cattttggaa   3300
agtcccgttg attttggtgc caaaacaaac tcccattgac gtcaatgggg tggagacttg   3360
gaaatccccg tgagtcaaac cgctatccac gcccattggt gtactgccaa aaccgcatca   3420
ccatggtaat agcgatgact aatacgtaga tgtactgcca agtaggaaag tcccgtaagg   3480
tcatgtactg ggcataatgc caggcgggcc atttaccgtc attgacgtca atagggggcg   3540
gacttggcat atgatacact tgatgtactg ccaagtgggc agtttaccgt aaatactcca   3600
cccattgacg tcaatggaaa gtccctattg gcgttactat gggaacatac gtcattattg   3660
acgtcaatgg gcgggggtcg ttgggcggtc agccaggcgg gccatttacc gtaagttatg   3720
taacgcggaa ctccatatat gggctatgaa ctaatgaccc cgtaattgat tactattaat   3780
aactagtcaa taatcaatgt caacatggcg gtcatattgg acatgagcca atataaatgt   3840
acatattatg atatagatac aacgtatgca atggccaata gccaatattg tcg          3893
```

```

<210> SEQ ID NO 40
<211> LENGTH: 11
<212> TYPE: PRT
<213> ORGANISM: Artificial Sequence
<220> FEATURE:
<223> OTHER INFORMATION: protein encoded by construct of vaccine vector
      pGA2 and insert JS2 expressing clade HIV-1 VL

<400> SEQUENCE: 40

Val Glu Thr Glu Thr Glu Thr Asp Pro Cys Asp
 1               5                  10

<210> SEQ ID NO 41
<211> LENGTH: 73
<212> TYPE: PRT
<213> ORGANISM: Artificial Sequence
<220> FEATURE:
<223> OTHER INFORMATION: protein encoded by construct of vaccine vector
      pGA2 and insert JS2 expressing clade HIV-1 VL

<400> SEQUENCE: 41

Arg Trp Arg Gln Arg Gln Arg Gln Ile Arg Ala Ile Ser Gly Trp Ile
 1               5                  10                  15

Leu Ser Thr Tyr Leu Gly Arg Ser Ala Glu Pro Val Pro Leu Gln Leu
            20                  25                  30

Pro Pro Leu Glu Arg Leu Thr Leu Asp Cys Asn Glu Asp Cys Gly Thr
        35                  40                  45

Ser Gly Ser Gln Gly Val Gly Ser Pro Gln Ile Leu Val Glu Ser Pro
```

```
                    50                  55                  60
Thr Val Leu Glu Ser Gln Ala Lys Glu
 65                  70

<210> SEQ ID NO 42
<211> LENGTH: 5
<212> TYPE: PRT
<213> ORGANISM: Artificial Sequence
<220> FEATURE:
<223> OTHER INFORMATION: protein encoded by construct of vaccine vector
      pGA1 and vaccine insert expressing clade B HIV-1
      Gag-Pol

<400> SEQUENCE: 42

Thr Gly Pro Lys Glu
 1               5

<210> SEQ ID NO 43
<211> LENGTH: 81
<212> TYPE: PRT
<213> ORGANISM: Artificial Sequence
<220> FEATURE:
<223> OTHER INFORMATION: protein encoded by construct of vaccine vector
      pGA1 and vaccine insert expressing clade B HIV-1
      Gag-Pol

<400> SEQUENCE: 43

Gln Ala Arg Arg Asn Arg Arg Arg Arg Trp Arg Glu Arg Gln Arg Gln
 1               5                  10                  15

Ile His Ser Ile Ser Glu Arg Ile Leu Ser Thr Tyr Leu Gly Arg Ser
                20                  25                  30

Ala Glu Pro Val Pro Leu Gln Leu Pro Pro Leu Glu Arg Leu Thr Leu
            35                  40                  45

Asp Cys Asn Glu Asp Cys Gly Thr Ser Gly Thr Gln Gly Val Gly Ser
        50                  55                  60

Pro Gln Ile Leu Val Glu Ser Pro Thr Val Leu Glu Ser Gly Ala Lys
 65                  70                  75                  80

Glu

<210> SEQ ID NO 44
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 44

Cys Thr Pro Tyr Asp Ile Asn Gln Met
 1               5

<210> SEQ ID NO 45
<211> LENGTH: 6
<212> TYPE: PRT
<213> ORGANISM: HIV-1

<400> SEQUENCE: 45

Val Ala Pro Thr Arg Ala
 1               5

<210> SEQ ID NO 46
<211> LENGTH: 18
<212> TYPE: PRT
<213> ORGANISM: Artificial Sequence
<220> FEATURE:
```

```
-continued

<223> OTHER INFORMATION: tpa leader sequence of pGA3

<400> SEQUENCE: 46

Met Lys Arg Gly Leu Cys Cys Val Leu Leu Leu Cys Gly Ala Val Phe
1               5                   10                  15

Val Ser
```

DNA EXPRESSION VECTORS AND METHODS OF USE

This application is a continuation of U.S. application Ser. No. 09/798,675, filed on Mar. 2, 2001 now abandoned, which claims the benefit of priority from U.S. provisional application Ser. No. 60/186,364, filed on Mar. 2, 2000 and Ser. No. 60/251,083, filed on Dec. 1, 2000.

GOVERNMENT SUPPORT

Work described herein may have been supported in part by National Institutes of Health Grant 5 P01 AI43045 and National Institutes of Health/National Institute of Allergy and Infectious Diseases Grant R21 AI44325-01. The U.S. Government may have certain rights in this invention.

FIELD OF THE INVENTION

The present invention is directed generally to the fields of molecular genetics and immunology. More particularly, the present invention describes novel DNA expression vectors, novel vectors comprising DNA encoding an immunogenic protein, and novel methods of immunizing animals including humans by administering the novel vectors comprising DNA encoding an immunogenic protein.

BACKGROUND OF THE INVENTION

Vaccines have had profound and long lasting effects on world health. Small pox has been eradicated, polio is near elimination, and diseases such as diphtheria, measles, mumps, pertussis, and tetanus are contained. Nonetheless, microbes remain major killers with current vaccines addressing only a handful of the infections of man and his domesticated animals. Common infectious diseases for which there are no vaccines cost the United States $120 billion dollars per year (Robinson et al., 1997). In first world countries, emerging infections such as immunodeficiency viruses, as well as reemerging diseases like drug resistant forms of tuberculosis, pose new threats and challenges for vaccine development. The need for both new and improved vaccines is even more pronounced in third world countries where effective vaccines are often unavailable or cost-prohibitive. Recently, direct injections of antigen-expressing DNAs have been shown to initiate protective immune responses.

DNA-based vaccines use bacterial plasmids to express protein immunogens in vaccinated hosts. Recombinant DNA technology is used to clone cDNAs encoding immunogens of interest into eukaryotic expression plasmids. Vaccine plasmids are then amplified in bacteria, purified, and directly inoculated into the hosts being vaccinated. DNA typically is inoculated by a needle injection of DNA in saline, or by a gene gun device that delivers DNA-coated gold beads into skin. The plasmid DNA is taken up by host cells, the vaccine protein is expressed, processed and presented in the context of self-major histocompatibility (MHC) class I and class II molecules, and an immune response against the DNA-encoded immunogen is generated.

The historical foundations for DNA vaccines (also known as "genetic immunization") emerged concurrently from studies on gene therapy and studies using retroviral vectors. Gene therapy studies on DNA delivery into muscle revealed that pure DNA was as effective as liposome-encapsulated DNA at mediating transfection of skeletal muscle cells (Wolff et al., 1990). This unencapsulated DNA was termed "naked DNA," a fanciful term that has become popular for the description of the pure DNA used for nucleic acid vaccinations. Gene guns, which had been developed to deliver DNA into plant cells, were also used in gene therapy studies to deliver DNA into skin. In a series of experiments testing the ability of plasmid-expressed human growth hormone to alter the growth of mice, it was realized that the plasmid inoculations, which had failed to alter growth, had elicited antibody (Tang, De Vit, and Johnston, 1992). This was the first demonstration of the raising of an immune response by an inoculated plasmid DNA. At the same time, experiments using retroviral vectors, demonstrated that protective immune responses could be raised by very few infected cells (on the order of $10^4$-$10^5$). Direct tests of the plasmid DNA that had been used to produce infectious forms of the retroviral vector for vaccination, performed in an influenza model in chickens, resulted in protective immunizations (Robinson, Hunt, and Webster, 1993).

HIV-1 is projected to infect 1% of the world's population by the year 2000, making vaccine development for this recently emergent agent a high priority for world health. Preclinical trials on DNA vaccines have demonstrated that DNA alone can protect against highly attenuated HIV-1 challenges in chimpanzees (Boyer et al., 1997), but not against more virulent SIV challenges in macaques (Lu et al., 1997). A combination of DNA priming plus an envelope glycoprotein boost has raised a neutralizing antibody-associated protection against a homologous challenge with a non-pathogenic chimera between SIV and HIV (SHIV-IIIb) (Letvin et al., 1997). More recently, a comparative trial testing eight different protocols for the ability to protect against a series of challenges with SHIV-s (chimeras between simian and human immunodeficiency viruses) revealed the best containment of challenge infections by an immunization protocol that included priming by intradermal inoculation of DNA and boosting with recombinant fowl pox virus vectors (Robinson et al., 1999). This containment of challenge infections was independent of the presence of neutralizing antibody to the challenge virus. Protocols which proved less effective at containing challenge infections included immunization by both priming and boosting by intradermal or gene gun DNA inoculations, immunization by priming with intradermal or gene gun DNA inoculations and then boosting with a protein subunit; immunization by priming with gene gun DNA inoculations and boosting with recombinant fowl pox virus, immunization with protein only, and immunization with recombinant fowl pox virus only (Robinson et al, 1999). Early clinical trials of DNA vaccines in humans have revealed no adverse effects (MacGregor et al., 1996) and the raising of cytolytic T-cells (Calarota et al., 1998). A number of studies have screened for the ability of co-transfected lymphokines and co-stimulatory molecules to increase the efficiency of immunization (Robinson and Pertmer, in press).

Disadvantages of DNA vaccine approaches include the limitation of immunizations to products encoded by DNA (e.g., proteins) and the potential for atypical processing of bacterial and parasitic proteins by eukaryotic cells. Another significant problem with existing approaches to DNA vaccines is the instability of some vaccine insert sequences during the growth and amplification of DNA vaccine plasmids in bacteria. One possible cause of instability is exposure during plasmid growth of secondary structures in vaccine inserts or the plasmid backbone that can be recognized by bacterial endonucleases.

A need exists, therefore, for DNA expression vectors that exhibit improved stability in bacterial hosts and may be safely used in animals, including humans; for eukaryotic expression of immunogenic proteins useful as vaccines against a variety of infectious diseases, including HIV-1.

SUMMARY OF THE INVENTION

The present invention provides novel pGA constructs. The novel pGA constructs are useful as vectors for the delivery of DNA vaccines.

The present invention also provides novel pGA constructs having vaccine inserts. The pathogen vaccine inserts can include the DNA transcription unit of any virus, bacteria, parasite and/or fungi.

The present invention describes novel methods of immunizing patients by administering therapeutically effective amounts of the novel pGA constructs comprising pathogen vaccine inserts.

The present invention describes novel methods of immunizing patients by administering therapeutically effective amounts of the novel pGA constructs comprising pathogen vaccine inserts followed by booster immunizations with live vectored vaccines such as recombinant modified vaccinia Ankara (MVA) vectors comprising the same vaccine inserts.

The present invention also describes novel methods of raising mult-epitope CD8 T-cell responses by administering therapeutically effective amounts of the novel pGA constructs comprising pathogen vaccine inserts followed by booster immunizations with a live vectored vaccine such as recombinant modified vaccinia Ankara (MVA) vectors comprising the same vaccine inserts.

The present invention is described in more detail below.

BRIEF DESCRIPTION OF THE DRAWINGS

FIG. 2 illustrates the DNA sequence SEQ ID NO: 1 of the novel pGA1 construct shown in FIG. 1. The positions of elements in the plasmid are indicated below the nucleotide sequence.

FIG. 4 illustrates the DNA sequence SEQ ID NO: 2 of the novel pGA2 construct shown in FIG. 3. The positions of elements in the plasmid are indicated below the nucleotide sequence.

Figure 6A:
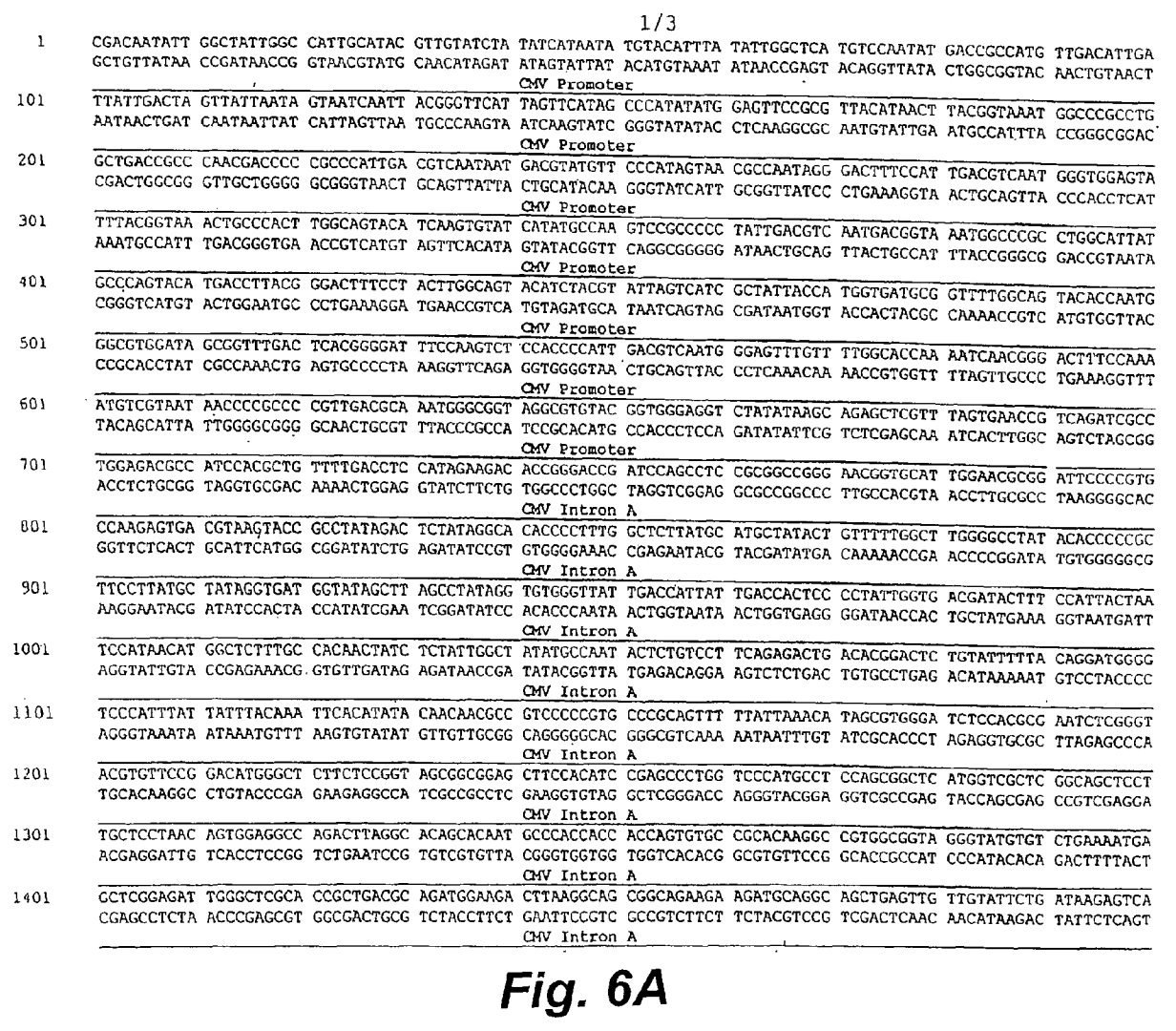

FIG. 6 is illustrates of the DNA sequence SEQ ID NO: 3 of the novel pGA3 construct shown in FIG. 5, and the protein sequence encoded thereby (SEQ ID NO:46). The complementary strand is also shown (SEQ ID NO:39). The position of elements in the plasmid are indicated below the nucleotide sequence.

FIG. 7 compares the levels of anti-HA IgG raised by the influenza H1 hemagglutinin expressed in a pGA vector (pGA3/H1) and in the pJW4303 research vector (pJW4303/H1). BALB/c mice were immunized and boosted with a low dose (0.1 µg) or a high dose (1 µg), of the indicated plasmids using gene gun inoculations. A priming immunization was followed by a booster immunization at 4 weeks.

FIG. 8A presents a schematic of the parent wt BH10 provirus from which constructs producing non-infectious virus like particles (VLPs) were produced. Dotted regions indicate sequences that were deleted in the VLP constructs. Positions and designations of the various regions of the BH10 provirus are indicated in the rectangular boxes. The U3RU5 regions which encode the long terminal repeats contain transcriptional control elements. All other indicated regions encode proteins. For clarity, products expressed by pol (Prt, RT, Int) and env (SU and TM) are indicated.

FIG. 8B depicts the JS2 vaccine insert. This 6.7 kb vaccine insert expresses the Gag, Prt, and RT sequences of the BH10 strain of HIV-1-IIIb, Tat and Vpu proteins that are from ADA, and Rev and Env proteins that are chimeras of ADA and BH10 sequences. The Gag sequences include mutations of the zinc fingers to limit packaging of viral RNA. The RT sequences encompass three point mutations to eliminate reverse transcriptase activity. Designations are the same as in FIG. 8A. The bracketed area indicates the region of BH10 in which sequences from ADA have been substituted for the BH10 sequences to introduce a CCR-5 using Env. The x's indicate safety mutations.

FIG. 8C depicts the JS5 insert. JS5 is a 6 kb vaccine insert that expresses Gag, Prt, RT, Vpu Tat, and Rev. JS5 is comprised of the same sequences as JS2 except that sequences in Env have been deleted. The deleted sequences are indicated in FIG. 8B as a filled rectangle. Designations are the same as in FIGS. 8A and 8B. The Rev responsive element (RRE) which is in the 3' region of Env is retained in the construct.

FIG. 15A: Gag-specific CD8 T Cell responses raised by DNA priming and rMVA booster immunization. The schematic presents Gag-CM9-tetramer data generated in the high-dose i.d. DNA-immunized animals.

FIG. 15B: Gag-CM9-Mamu-A*01 tetramer-specific T cells in Mamu-A*01 vaccinated and control macaques at various times before challenge and at two weeks after challenge. The number at the upper right corner of each plot represents the frequency of tetramer-specific CD8 T cells as a % of total CD8 T cells. The numbers above each column of plots designate individual animals. FIG. 15C: Gag-specific IFN-γ ELISPOTs in A*01 and non-A*01 (hatched bars) vaccinated and non-vaccinated macaques at various times before challenge and at two weeks after challenge. Three pools of approximately 10-13 Gag peptides (22-mers overlapping by 12) were used for the analyses. The numbers above data bars represent the arithmetic mean± the standard deviation for the ELISPOTs within each group. The numbers at the top of the graphs designate individual animals. *, data not available; #, <20 ELISPOTs per $1 \times 10^6$ PBMC.

FIGS. 16A-16B shows the height and breadth of IFN-γ-producing ELISPOTs against Gag and Env in the DNA/MVA memory response. FIG. 16A: Responses against individual Gag and Env peptide pools. Data for animals within a group are designated by the same symbol. FIG. 16B: Averages of the height and breadth of ELISPOT responses for the different groups. The heights are the mean±the standard deviation for the sums of the Gag and Env ELISPOTs for animals in each group. The breadths are the mean±the standard deviation for the number of Gag and Env pools recognized by animals in each group. ELISPOT responses were determined in PBMC, during the memory phase, at 25 weeks after the rMVA booster (four weeks prior to challenge) using 7 pools of Gag peptides (approximately seven 22-mers overlapping by 12) representing about 70 amino acids of Gag sequence, and 21 pools of Env peptides (approximately ten 15-mers overlapping by 11) representing about 40 amino acids of Env sequence.

Figure 17A:
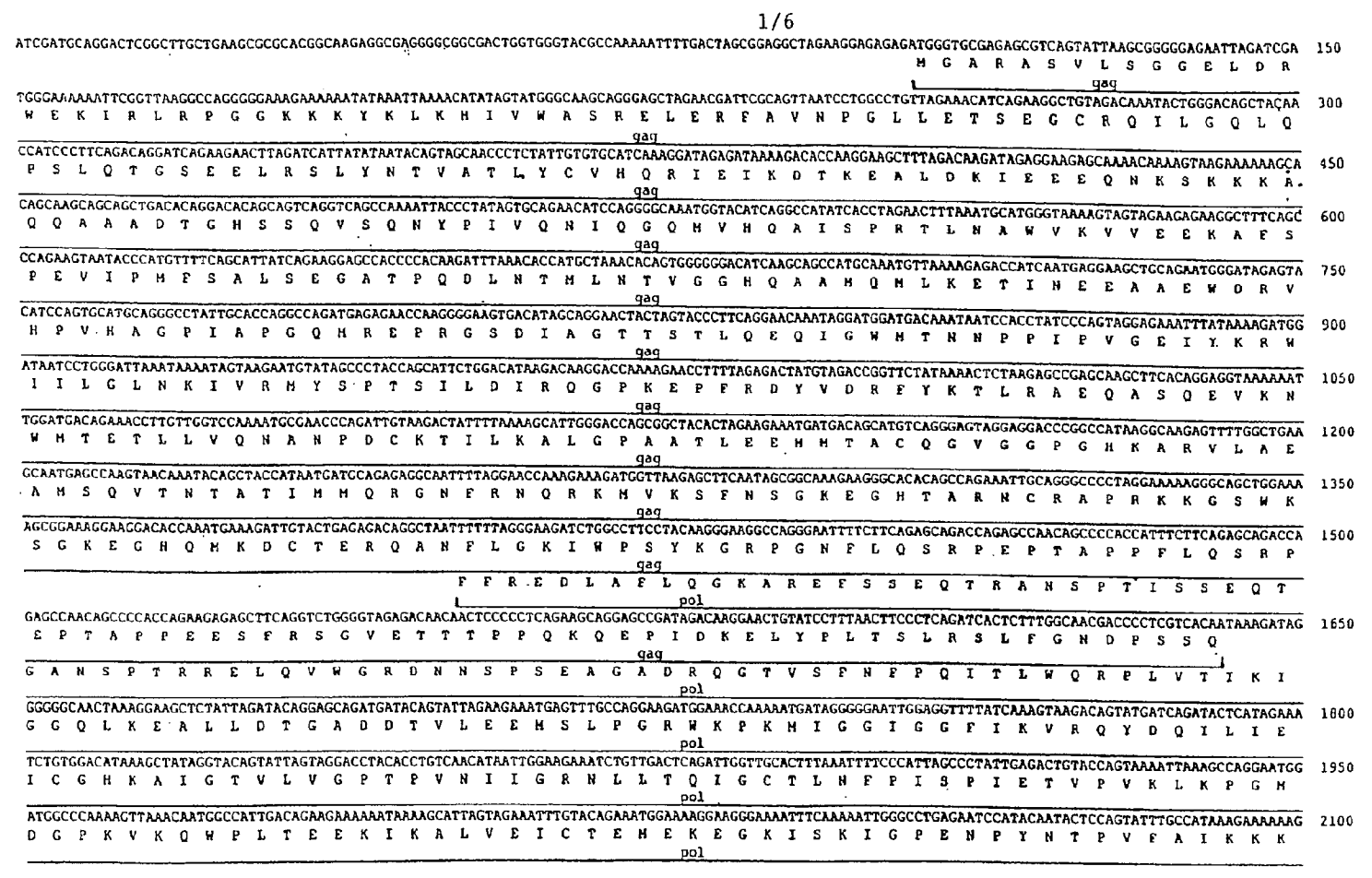
Figure 17B:
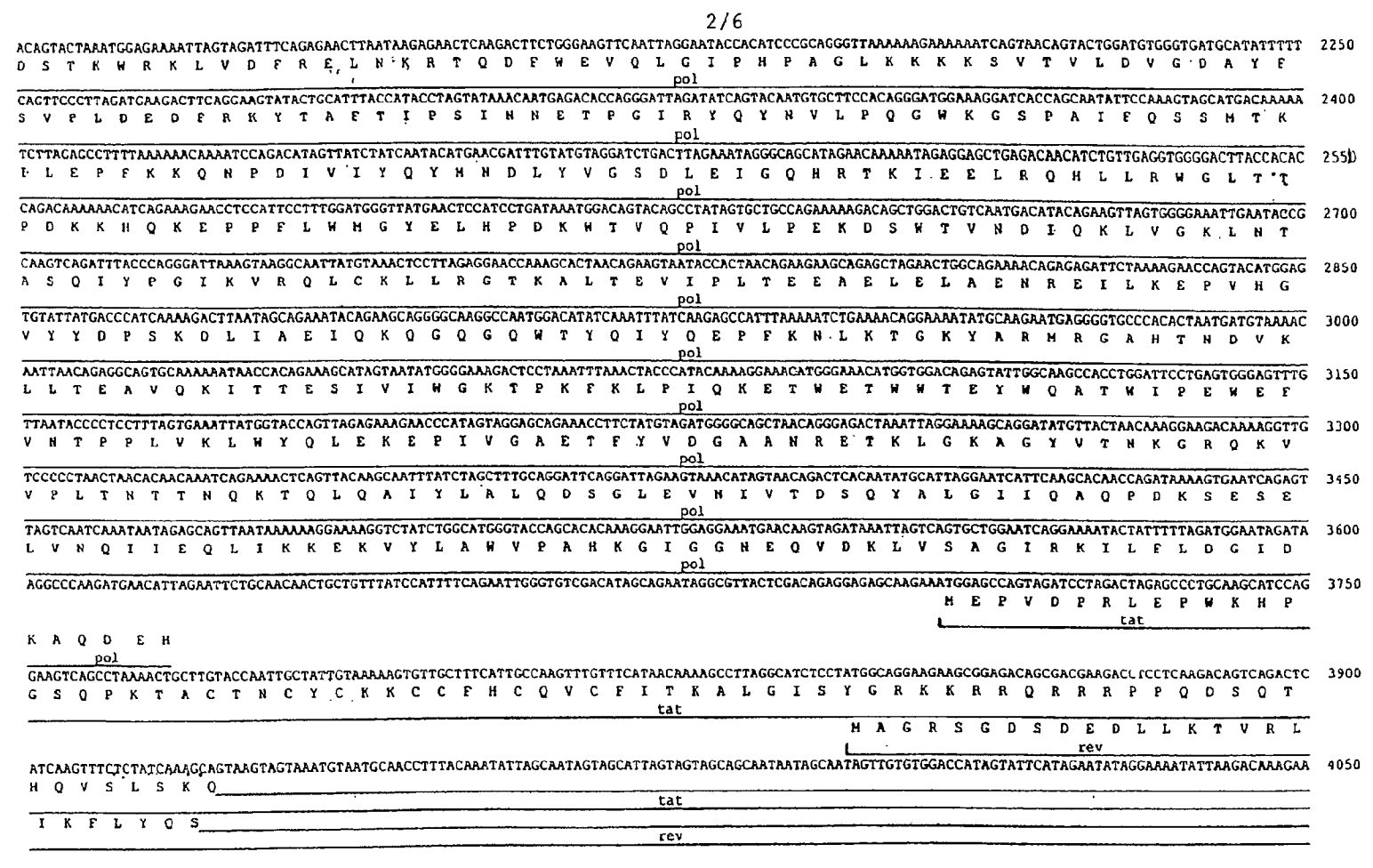
Figure 17C:
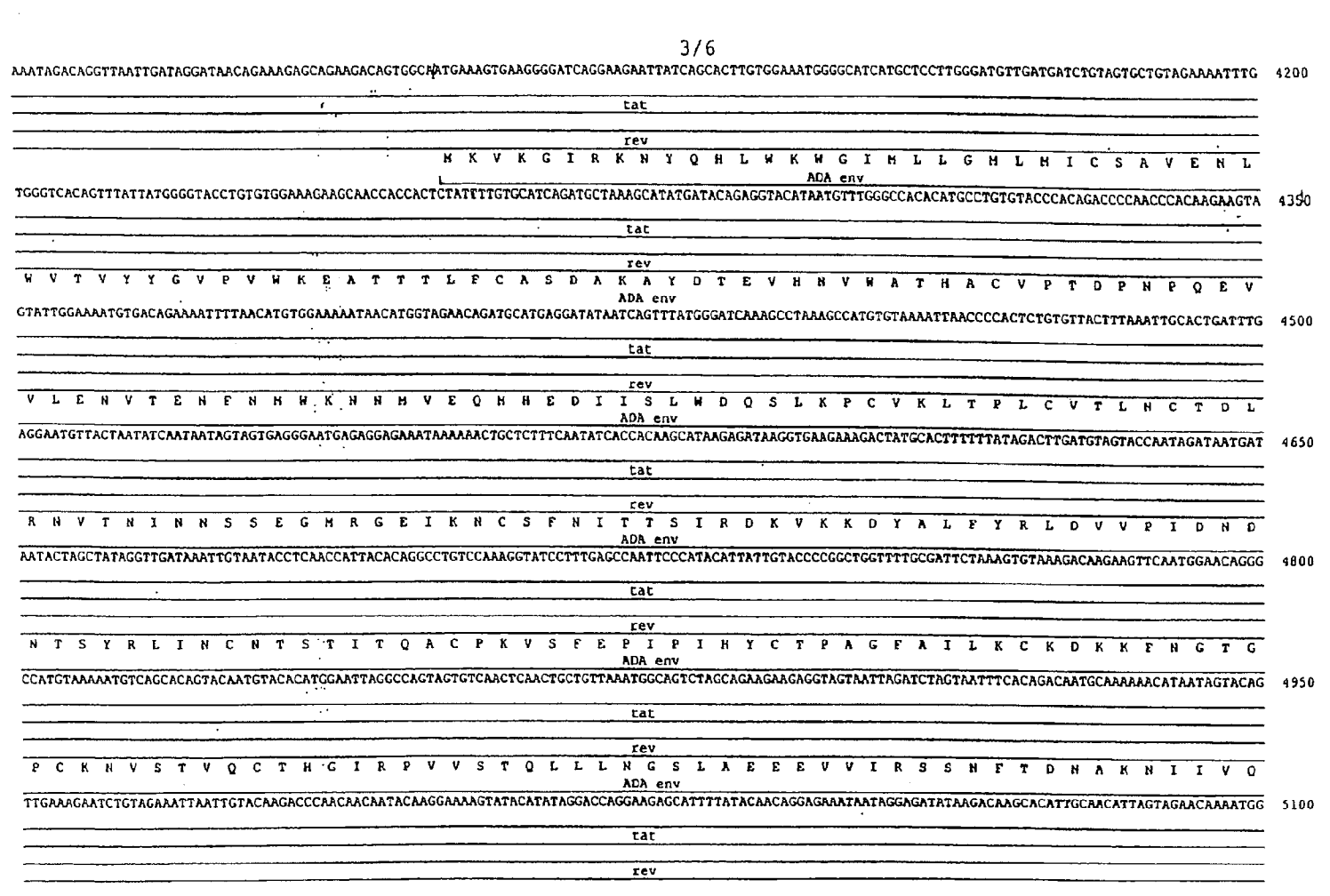
Figure 17D:
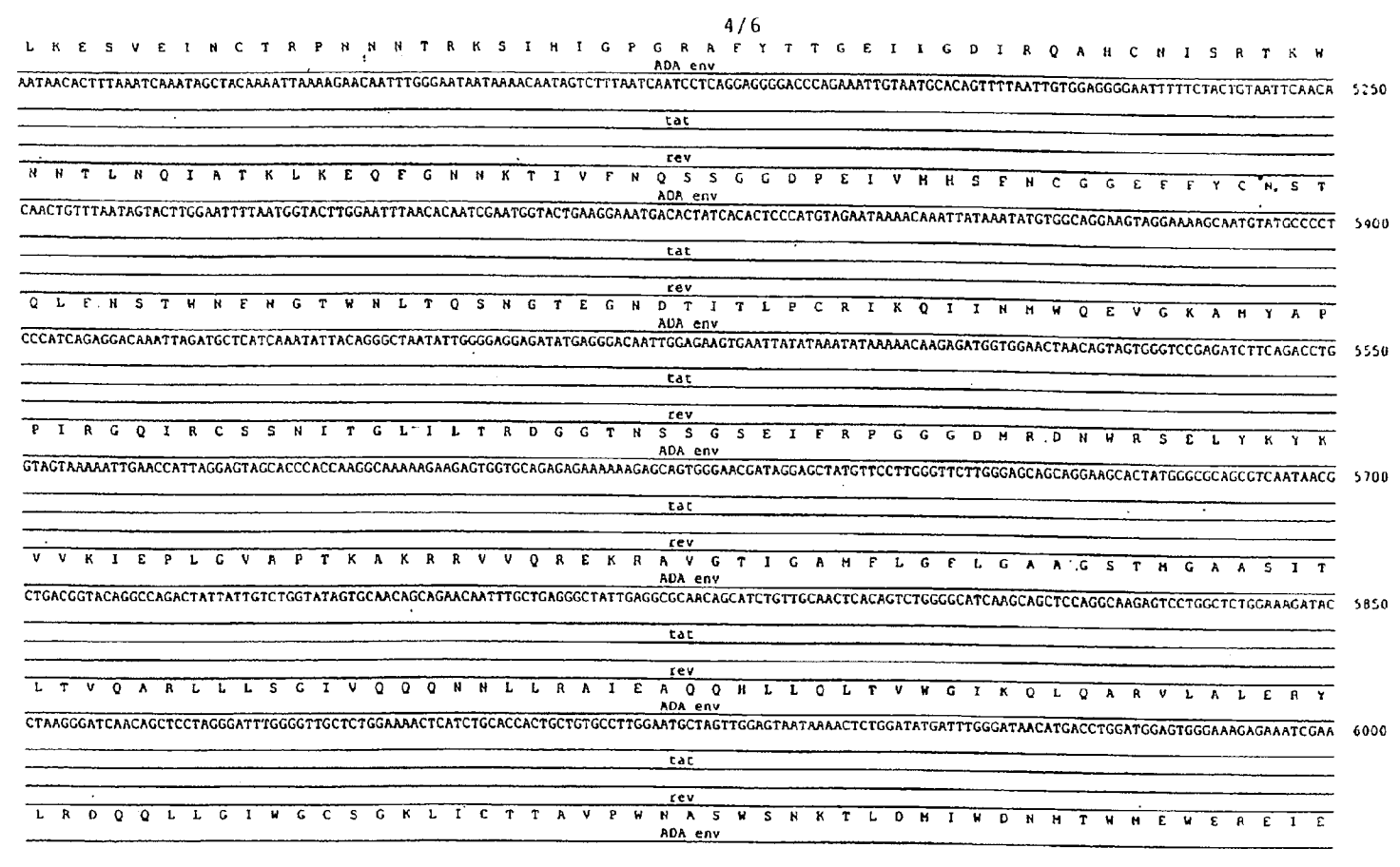
Figure 17E:
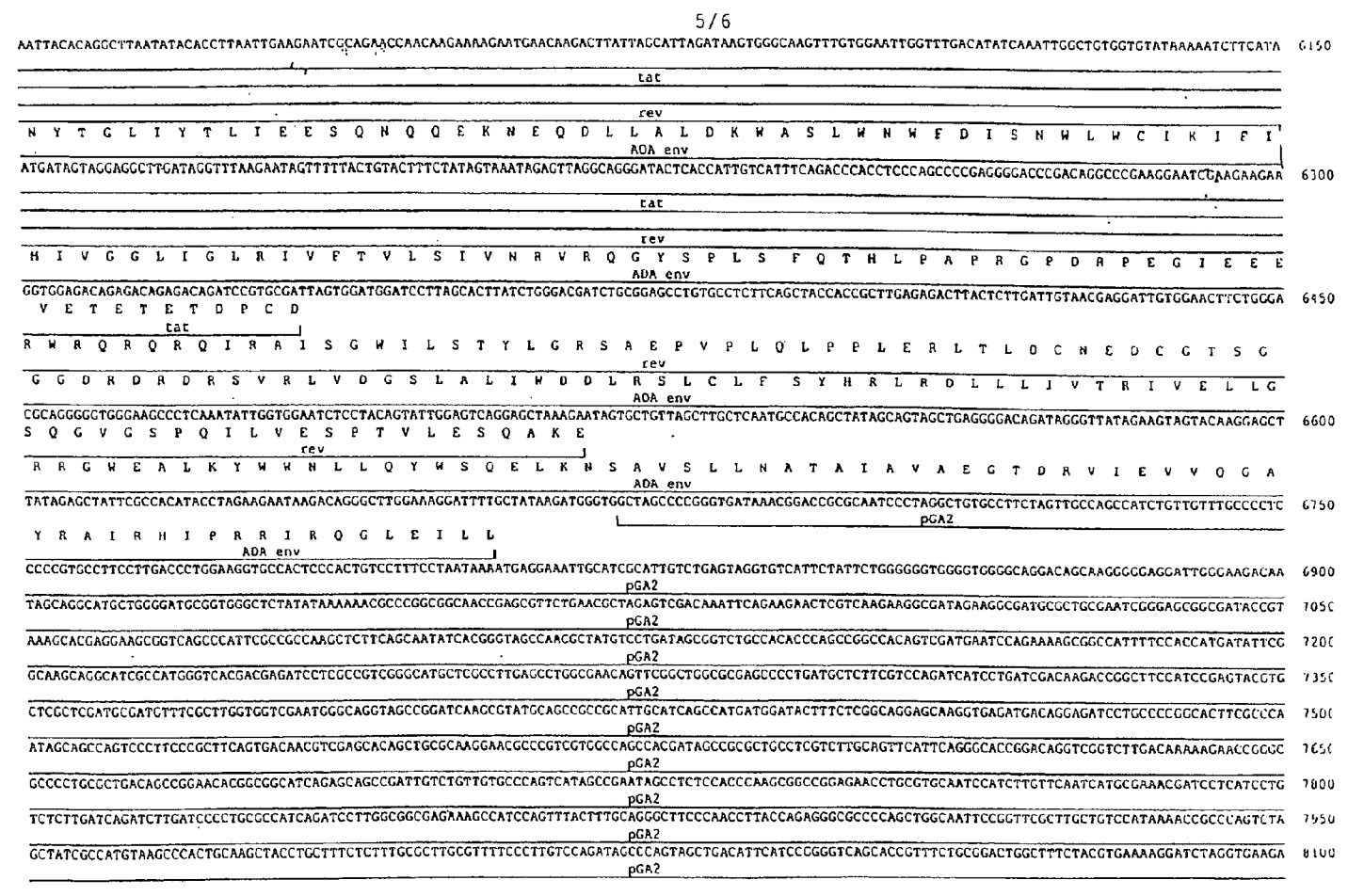
Figure 17F:
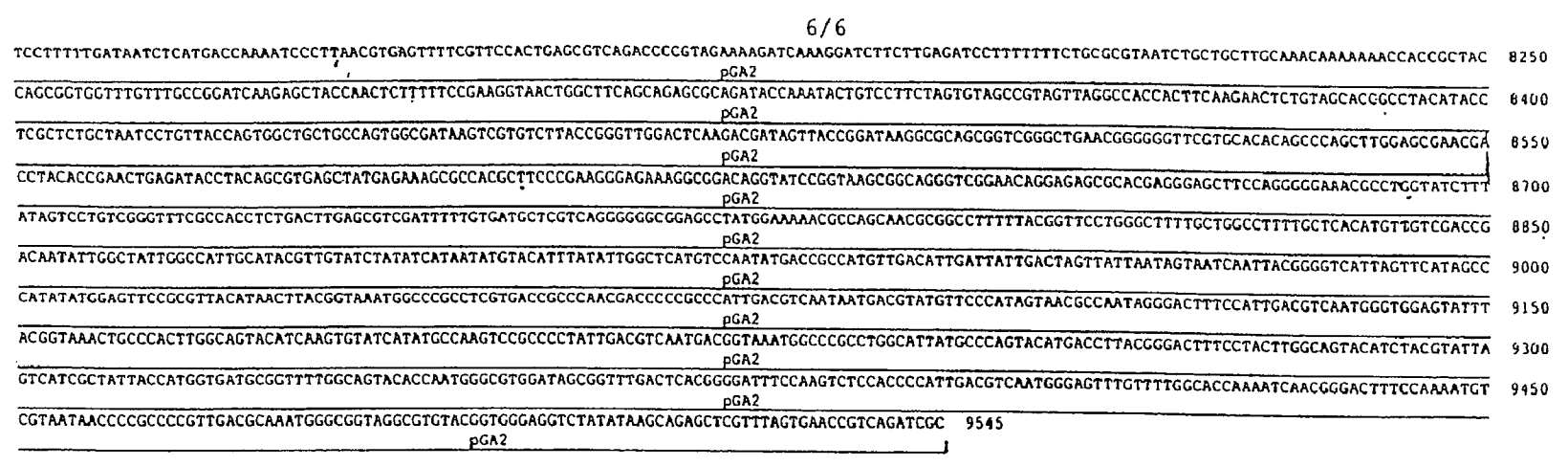

FIG. 17 shows the DNA sequence SEQ ID NO:4 of a pGA2 construct comprising the vaccine insert, where the pathogen vaccine insert. JS2 expresses Glade B HIV-1 VLP. Both the nucleotide sequence and encoded proteins (SEQ ID NOs:25-29, 40, and 41) are indicated.

Figure 18A:
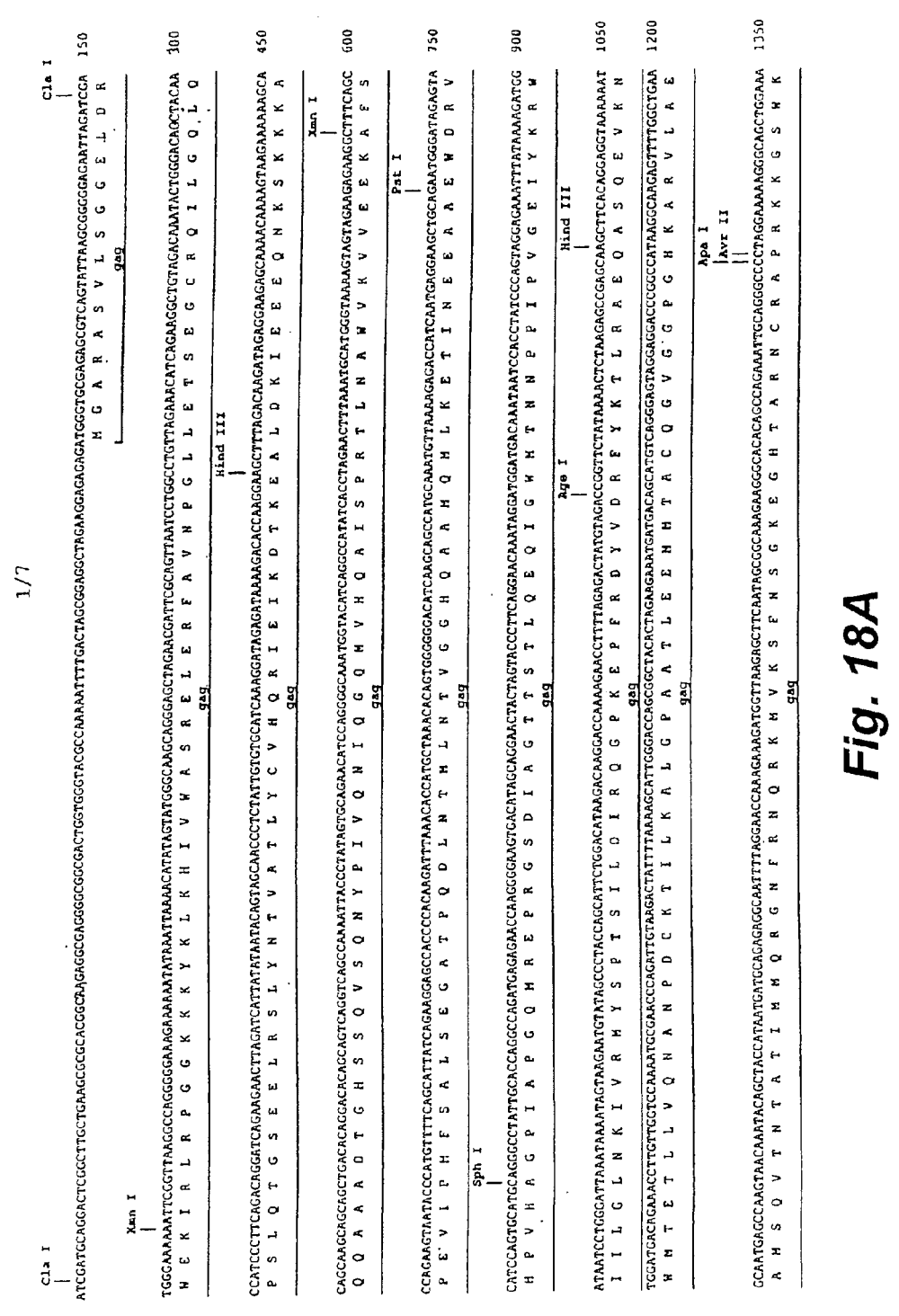
Figure 18B:
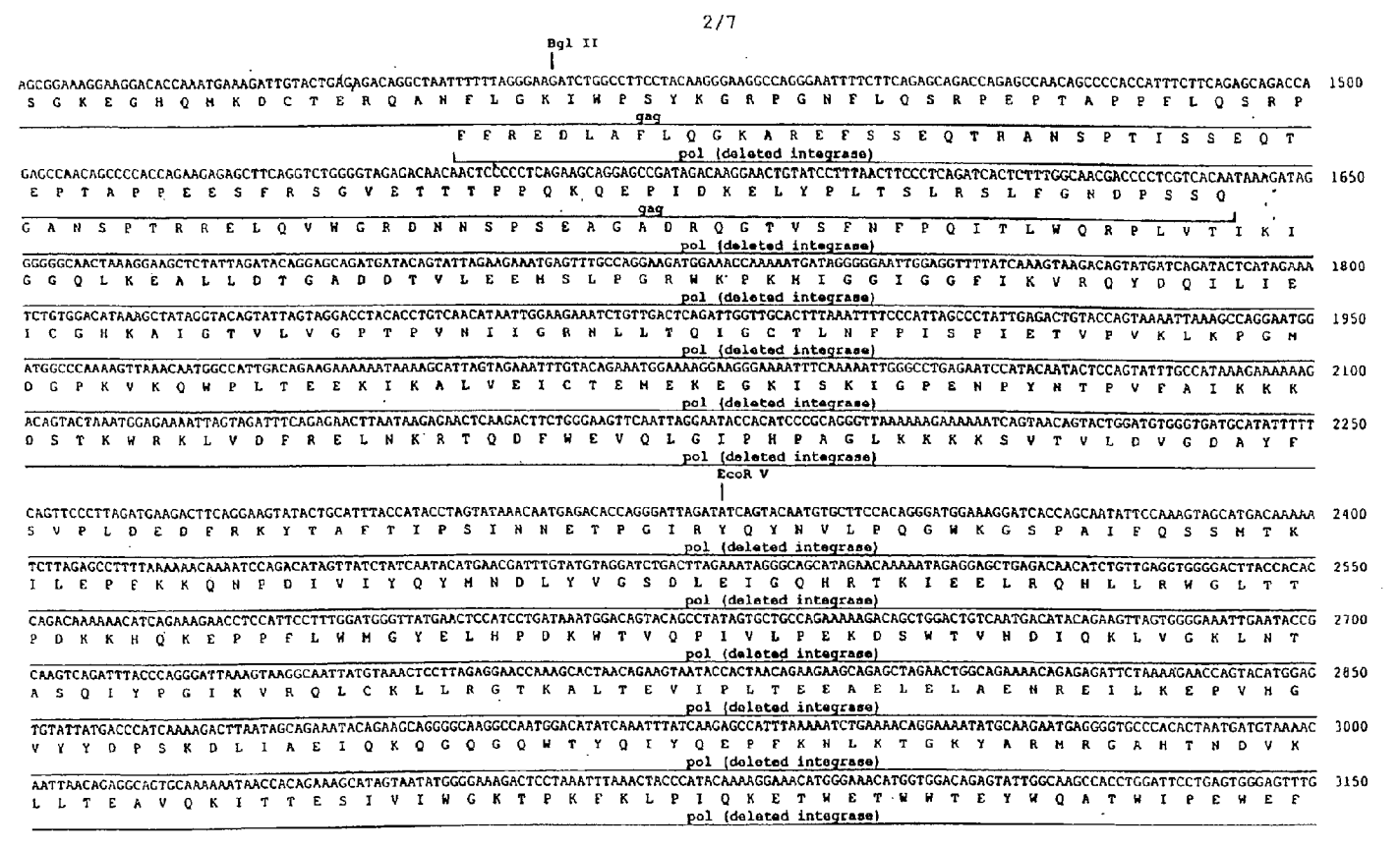
Figure 18C:
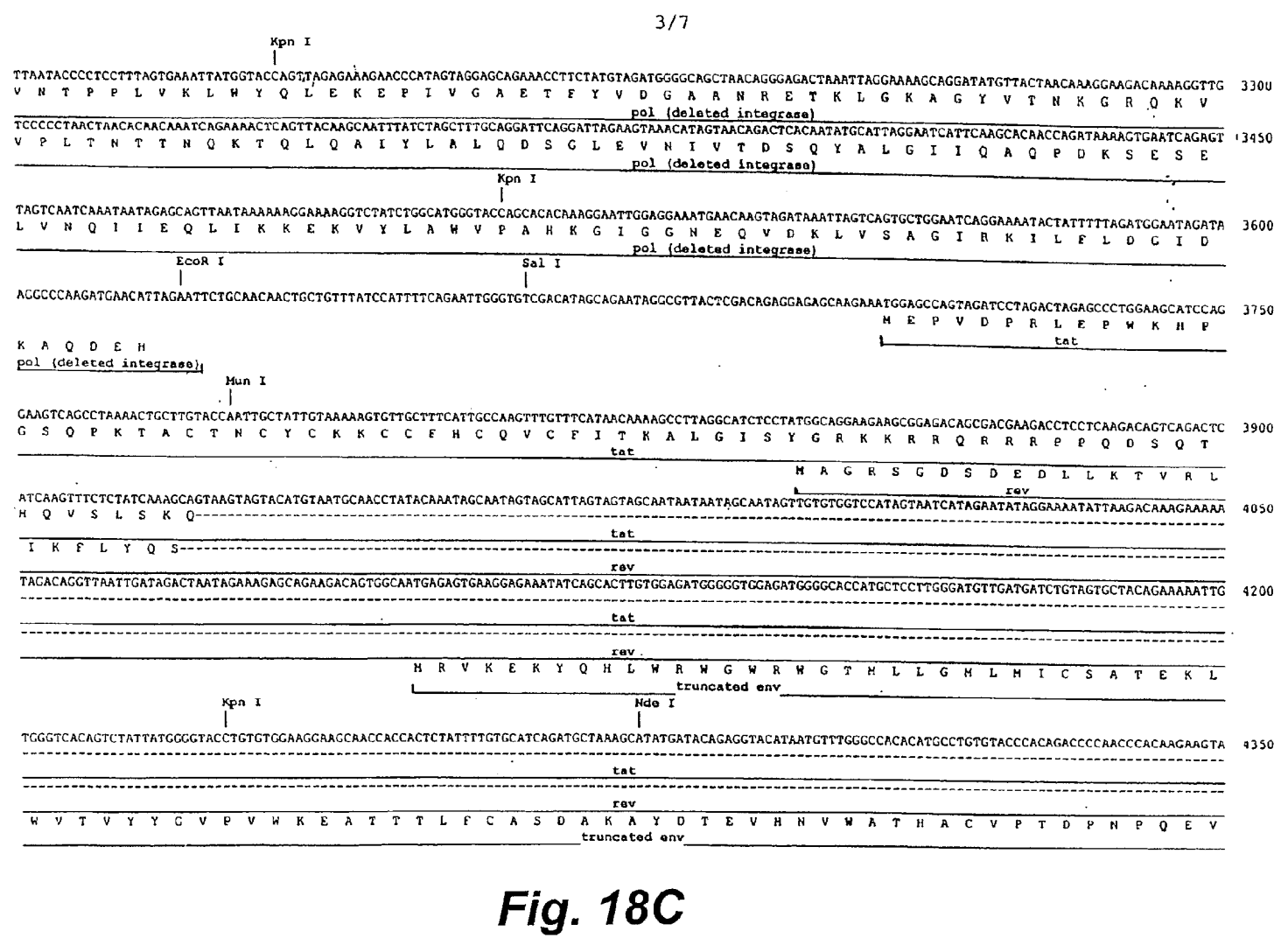
Figure 18D:
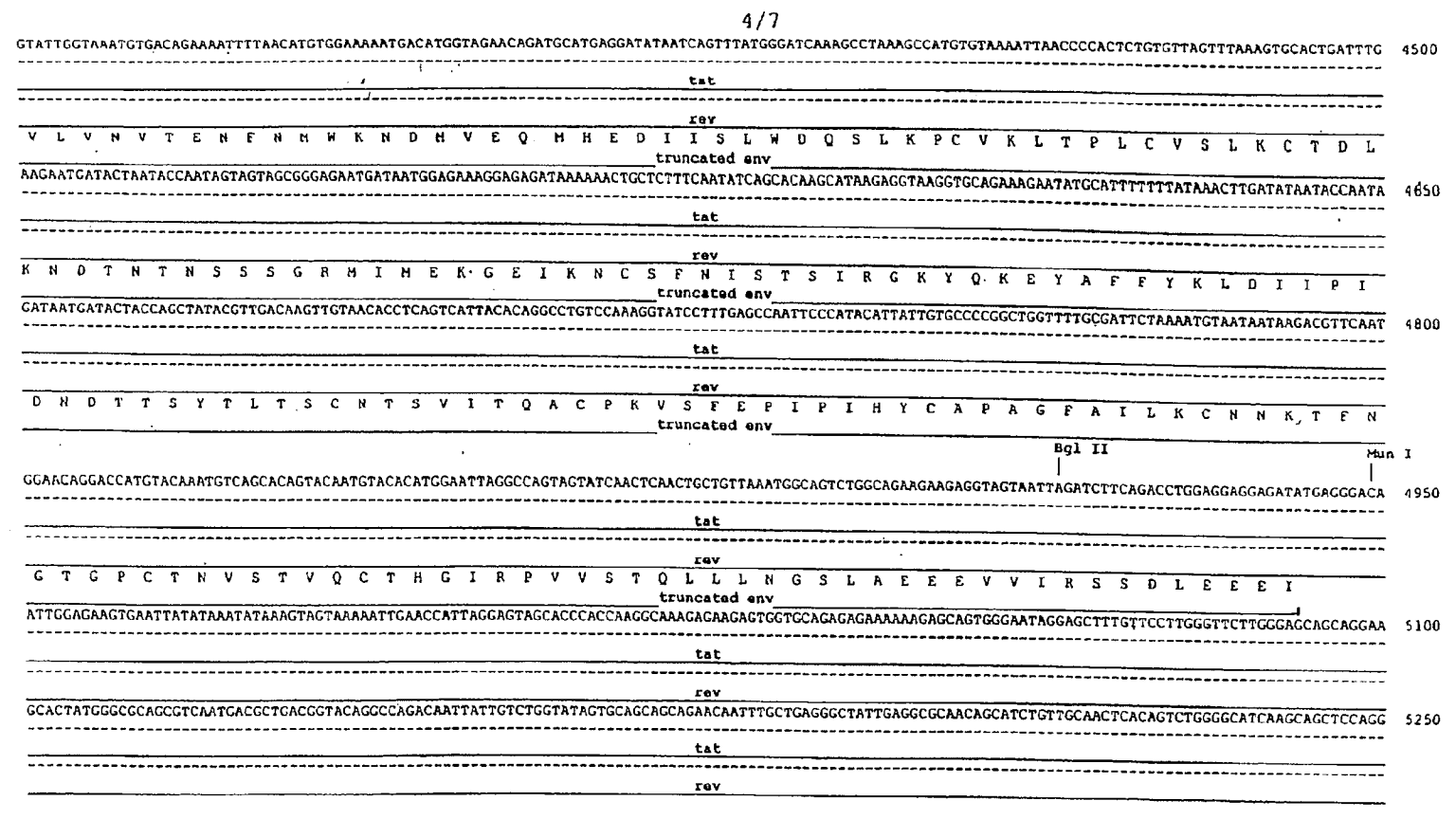
Figure 18E:
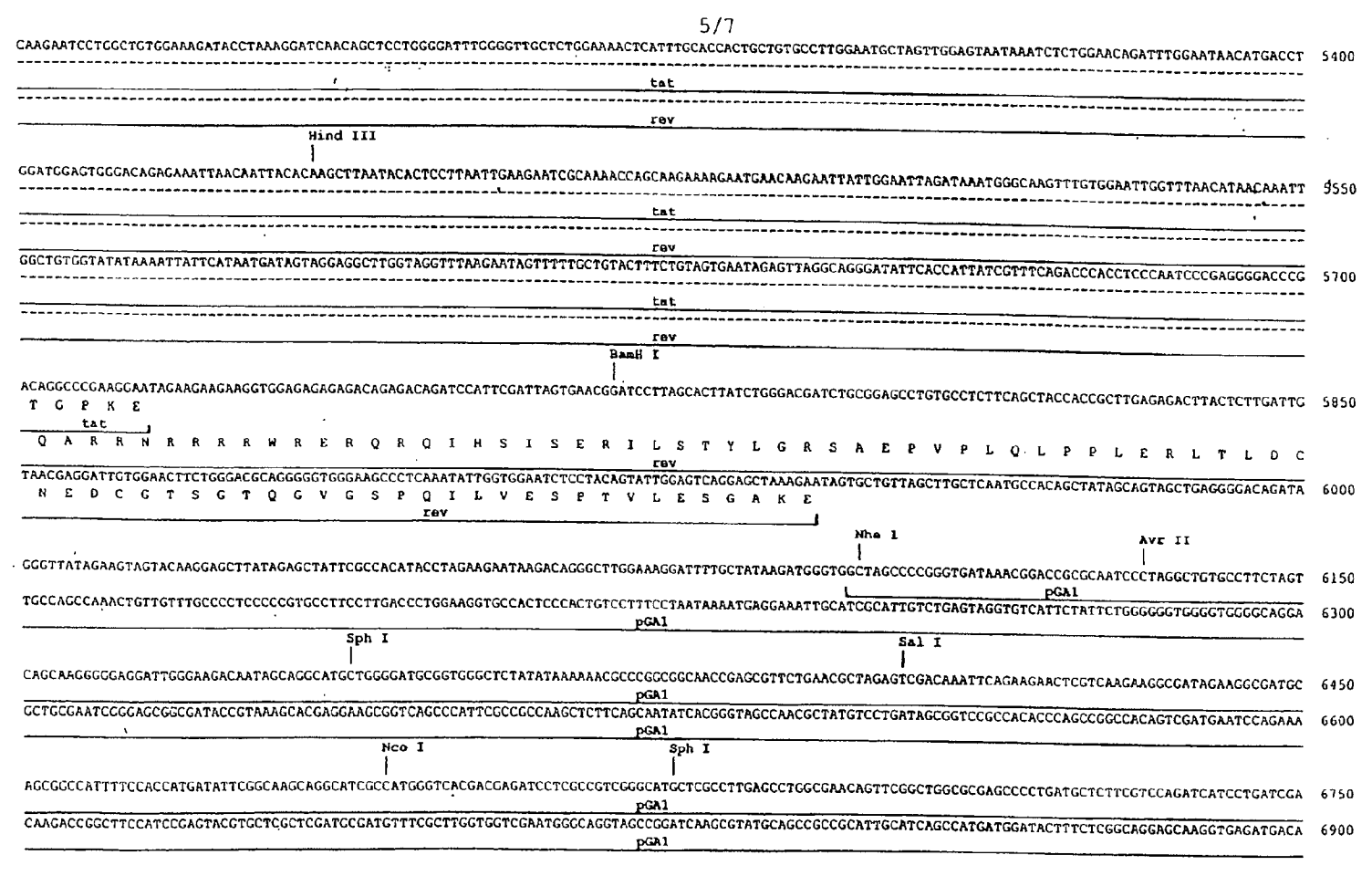
Figure 18F:
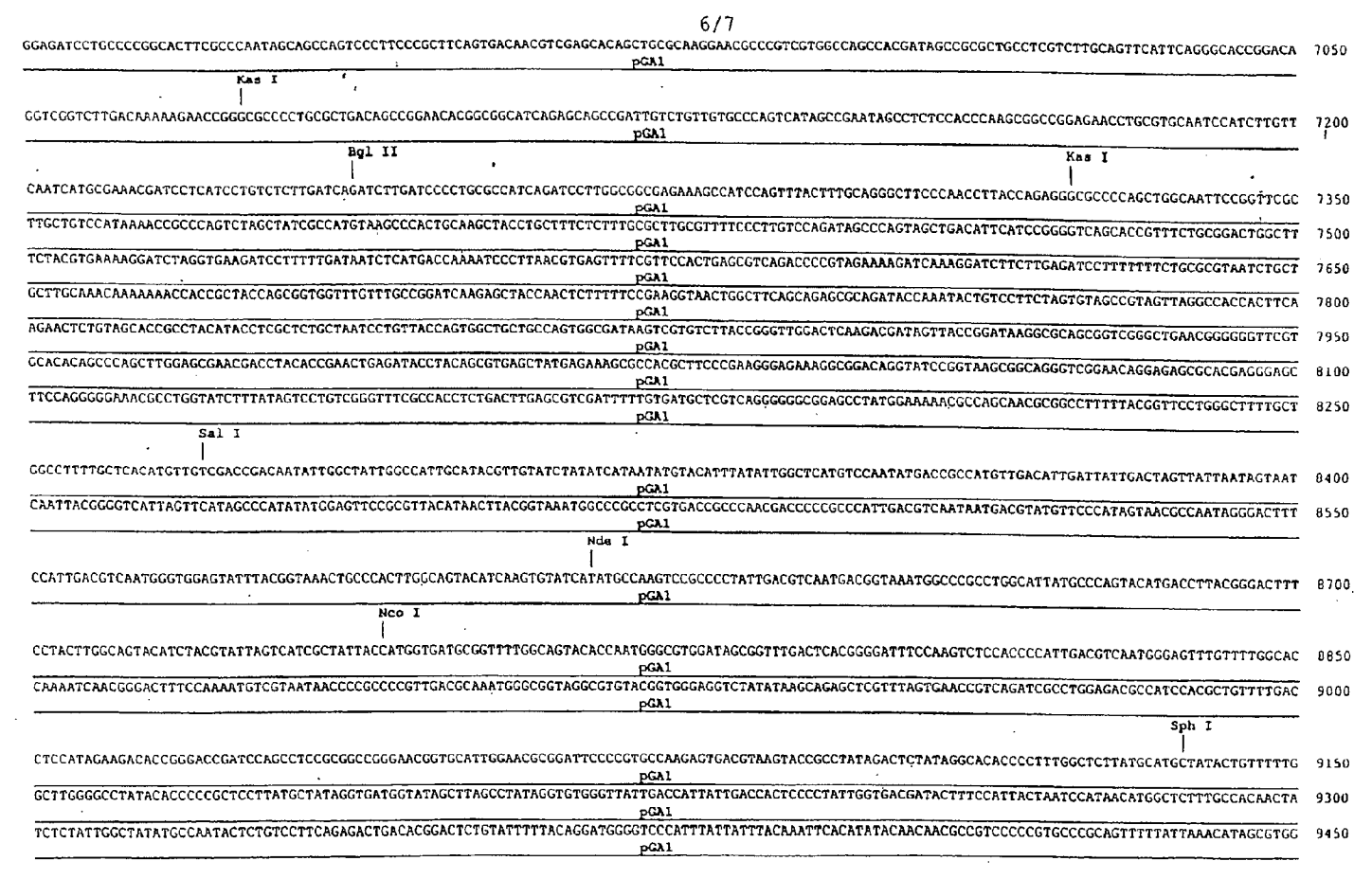

FIG. 18 shows the DNA sequence of a pGA1 construct comprising the pathogen vaccine insert, where the pathogen vaccine insert. JS5 expresses clade B HIV-1 Gag-pol insert (SEQ ID NO: 5). Both the sequence and the encoded proteins (SEQ ID NOs:30-36, 42 and 43) are shown.

FIG. 19A: Geometric mean viral loads and FIG. 19B: geometric mean CD4 counts for vaccine and control groups at various weeks post-challenge. The key for the groups is in panel B. FIG. 19C: Survival curve for vaccinated and control animals. The dotted line represents all 24 vaccinated animals. FIG. 19D: viral loads and FIG. 19E: CD4 counts for individual animals in the vaccine and control groups. The key to animal numbers is presented in FIG. 19E. Assays for the first 12 weeks post challenge had a background of 1000 copies of RNA per ml of plasma. Animals with loads below 1000 were scored with a load of 500. For weeks 16 and 20, the background for detection was 300 copies of RNA/ml. Animals with levels of virus below 300 were scored at 300.

FIG. 20A: temporal tetramer+ cells and viral loads. FIG. 20B: Intracellular cytokine assays for IFN-γ production in response to stimulation with the Gag-CM9 peptide at two weeks post-challenge. This ex vivo assay allows evaluation of the functional status of the peak post-challenge tetramer+cells displayed in FIG. 15A. FIG. 20C: Proliferation assay at 12 weeks post-challenge. Gag-Pol-Env (open bars) and Gag-Pol (hatched bars) produced by transient transfections were used for stimulation. Supernatants from mock-transfected cultures served as control antigen. Proteins were used at approximately 1 μg per ml of p27 Gag for stimulations. Stimulation indices are the growth of cultures in the presence of viral antigens divided by the growth of cultures in the presence of mock antigen.

FIGS. 21A-21E show lymph node histomorphology and viral loads at 12 weeks post-challenge. FIG. 21A: Typical lymph node from a vaccinated macaque showing evidence of follicular hyperplasia characterized by the presence of numerous secondary follicles with expanded germinal centers and discrete dark and light zones. FIG. 21B: Typical lymph node from an infected control animal showing follicular depletion and paracortical lymphocellular atrophy. FIG. 21C: A representative lymph node from an age-matched, uninfected macaque displaying non-reactive germinal centers. FIG. 21D: The percent of the total lymph node area occupied by germinal centers was measured to give a non-specific indicator of follicular hyperplasia. Data for uninfected controls are for four age-matched rhesus macaques. FIG. 21E: Lymph node virus burden was determined by in situ hybridization using an antisense riboprobe cocktail that was complementary to SHIV-89.6 gag and pol. All of the examined nodes were inguinal lymph nodes.

FIGS. 23A-23E show correlations and dose response curves for the vaccine trial (FIGS. 23A and B). Inverse correlations between peak vaccine raised IFN-γ ELISPOTs and viral loads at 2 (FIG. 23A) and 3 (FIG. 23B) weeks post-challenge. Only twenty-three of the 24 vaccinated animals are included in the correlations because of the loss of the peak DNA/MVA ELISPOT sample for animal 3 (see FIG. 15C). (FIG. 23C) Dose response curves for the average height of Gag ELISPOTS at the peak DNA-MVA response (data from FIG. 15C). (FIG. 23D) Dose response curve for the breadth of the DNA/MVA memory ELISPOT response (data from FIG. 16B). (FIG. 23E) Dose response curves for the peak anti-Gag antibody response post the MVA booster (data from FIG. 22A). The different doses of DNA raised different levels of ELISPOT and antibody responses (P<0.05). The route of DNA inoculation had a significant effect on the antibody (P=0.02), but not the ELISPOT response.

FIGS. 28A-28D illustrates the importance of including Env in vaccines administered to animals challenged interectally with SHIV-89.6P.

DETAILED DESCRIPTION OF THE INVENTION

Figure 1:
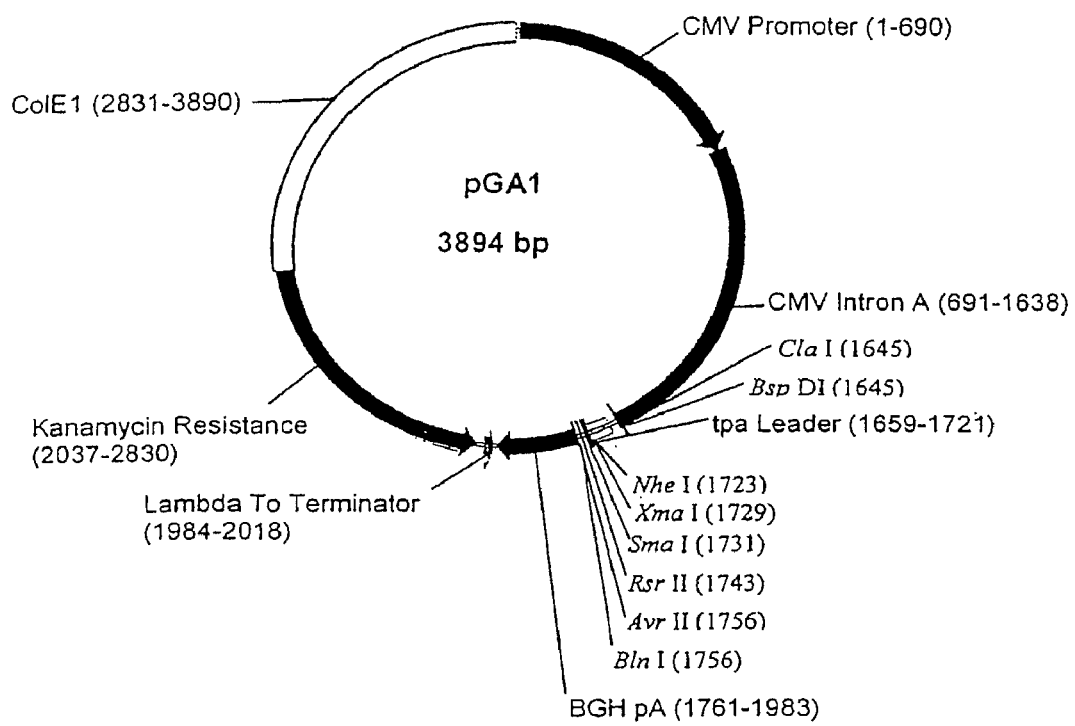
FIG. 1 illustrates a novel pGA1 construct of the present invention. Designations are identities and positions of elements in the vector. Designations in italic print are unique restriction endonuclease sites useful for cloning vaccine inserts into the vector.

This invention relates to novel vectors, novel vectors comprising pathogen vaccine inserts, and novel methods of immunizing patients against a pathogen. The novel immunization methods elicit both cell-mediated and humoral immune responses that may limit the infection, spread or growth of the pathogen and result in protection against subsequent challenge by the pathogen.

Classic references for DNA vaccines include the first demonstration of the raising of an immune response (Tang, De Vit, and Johnston, 1992); the first demonstration of cytotoxic T-cell (Tc)-mediated immunity (Ulmer et al., 1993); the first demonstration of the protective efficacy of intradermal (i.d.), intramuscular (i.m.), intravenous (i.v.), intranasal (i.n.), and gene gun (g.g.) immunizations (Fynan et al., 1993; Robinson, Hunt, and Webster, 1993); the first use of genetic adjuvants (Xiang and Ertl, 1995); the first use of library immunizations (Barry, Lai, and Johnston, 1995); and the first demonstration of the ability to modulate the T-helper type of an immune response by the method of DNA delivery (Feltquate et al., 1997). A highly useful web site compiling DNA vaccine information can be found at http://www.genweb.com/Dnavax/dnavax.html.

For convenience, certain terms employed in the specification, examples, and appended claims are collected here.

DEFINITIONS

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not, identical to that of any fragment of a naturally occurring genomic nucleic acid spanning more than three separate genes, and includes DNA, RNA, or derivatives or variants thereof. The term includes, but is not limited to, the following: (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring.

It is advantageous for some purposes that a nucleotide sequence is in purified form. The term "purified" in reference to nucleic acid represents that the sequence has increased purity relative to the natural environment.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology, isolated from an appropriate source, or are synthesized. The term "polypeptides" further contemplates polypeptides as defined above that include chemically modified amino acids or amino acids covalently or noncovalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes", "heterologous genes" or "exogenous genes" and genes that are naturally a part of a particular organism's genome are referred to as "endogenous genes".

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein or polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The term "transcription regulatory sequences" as used herein refers to nucleotide sequences that are associated with a gene nucleic acid sequence and which regulate the transcriptional expression of the gene. The "transcription regulatory sequences" may be isolated and incorporated into a vector nucleic acid to enable regulated transcription in appropriate cells of portions of the vector DNA. The "transcription regulatory sequence" may precede, but are not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "coding region" as used herein refers to a continuous linear arrangement of nucleotides that may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, or any other label that is well known in the art.

The term "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that may further include at least one regulatory sequence operably linked to a nucleotide sequence coding for the Mago protein. Regulatory sequences are well recognized in the art and may be selected to ensure good expression of the linked nucleotide sequence without undue experimentation by those skilled in the art. As used herein, the term "regulatory sequences" includes promoters, enhancers, and other elements that may control expression. Standard molecular biology textbooks such as *Sambrook* et al. eds "Molecular Cloning: A Laboratory Manual" 2nd ed. Cold Spring Harbor Press (1989) may be consulted to design suitable expression vectors, promoters, and other expression control elements. It should be recognized, however, that the choice of a suitable expression vector depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only a calcium or magnesium salt, an electric field, detergent, or liposome mediated transfection, to render the host cell competent for the uptake of the nucleic acid molecules.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell can harbor a vector that is extragenomic. An extragenomic nucleic acid vector does not insert into the cell's genome. A recombinant cell can further harbor a vector or a portion thereof that is intragenomic. The term intragenomic defines a nucleic acid construct incorporated within the recombinant cell's genome.

The term "recombinant nucleic acid" as used herein refers to combinations of at least two nucleic acid sequences that are not naturally found in a eukaryotic or prokaryotic cell. The nucleic acid sequences may include, but are not limited to nucleic acid vectors, gene expression regulatory elements, origins of replication, sequences that when expressed confer antibiotic resistance, and protein-encoding sequences. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The term "patients," as used herein, refers to animals, preferably mammals, and more preferably humans.

The term "immunizing" or "immunization," as used herein, refers to the production of an immune response in a patient that protects (partially or totally) from the manifestations of infection (i.e., disease) caused by a pathogen. A patient immunized by the present invention will not be infected by the pathogen or will be infected to a lesser extent than would occur without immunization. Immunizations may be either prophylactic or therapeutic in nature. That is, both previously uninfected and infected patients may be immunized with the present invention.

The term "DNA transcription unit" as used herein "refers to a polynucleotide sequence that includes at least two components: antigen-encoding DNA and transcriptional promoter elements. A DNA transcription unit may optionally include additional sequences, such as enhancer elements, splicing signals, termination and polyadenylation signals, viral replicons, and/or bacterial plasmid sequences. The DNA transcription unit can be produced by a number of known methods. For example, DNA encoding the desired antigen can be inserted into an expression vector to construct the DNA transcription unit, as described in Maniatis et al, *Molecular Cloning: A Laboratory Manual,* 2d, Cold Spring Harbor Laboratory Press (1989), the disclosure of which is incorporated by reference in its entirety.

The term "vaccine insert" as used herein refers to the DNA transcription unit of a pathogen. Preferably, the vaccine insert is a DNA transcription unit that can generate an immune responses in a patient. For example, th evaccine insert is a pathogen vaccine insert encoding antigens derived from any virus, bacteria, parasite and/or fungi. Exemplary viruses include herpesvirus, orthomyxoviruses, rhinoviruses, picornaviruses, adenoviruses, paramyxoviruses, coronaviruses, rhabdoviruses, togaviruses, flaviviruses, bunyaviruses, rubella virus, reovirus, measles, hepadna viruses, Ebola, retroviruses (including human immunodeficiency virus), and the like. Exemplary bacteria include tuberculosis, mycobateria, spirochetes, rickettsias, chlamydia, mycoplasma and the like. Exemplary parasites include malaria and the like. Exemplary fungi include yeasts, molds, and the like. One skilled in the art will appreciate that this list does not include all potential pathogens against which a protective immune response can be generated by the methods described herein.

The term "antigen" as used herein refers to any protein, carbohydrate, or other moiety expressed by a pathogen that is capable of eliciting a protective response against a pathogen. The antigen may or may not be a structural component of the pathogen. Also contemplated to be within the term "antigen" are encoded antigens that can be translation products or polypeptides of various lengths. Antigens undergo normal host cell modifications such as glycosylation, myristoylation or phosphorylation. In addition, they can be designed to undergo intracellular, extracellular or cell-surface expression. Furthermore, they can be designed to undergo assembly and release from cells.

As used herein, the term "adjuvant" means a substance added to a vaccine to increase a vaccine's immunogenicity. The mechanism of how an adjuvant operates is not entirely known. Some adjuvants are believed to enhance the immune response by slowly releasing the antigen, while other adjuvants are strongly immunogenic in their own right and are believed to function synergistically. Known vaccine adjuvants include, but are not limited to, oil and water emulsions (for example, complete Freund's adjuvant and incomplete Freund's adjuvant), *Corynebacterium parvum*, Bacillus Calmette Guerin, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N,N-dioctadecyl-N',N'-bis(2-hydroxyethyl)-propanediamine), paraffin oil, and muramyl dipeptide. Adjuvants also encompass genetic adjuvants such as immunomodulatory molecules encoded in a co-inoculated DNA. The co-inoculated DNA can be in the same vaccine construct as the vaccine immunogen or in a separate-DNA vector.

As used herein, the term "pharmaceutically acceptable carrier" means a vehicle for containing the vaccine that can be injected into a bovine host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

The terms "selectable marker gene" as used herein refer to an expressed gene that allows for the selection of a population of cells containing the selectable marker gene from a population of cells not having the expressed selectable marker gene. For example, the "selectable marker gene" may be an "antibiotic resistance gene" that can confer tolerance to a specific antibiotic by a microorganism that was previously adversely affected by the drug. Such resistance may result from a mutation or the acquisition of resistance due to plasmids containing the resistance gene transforming the microorganism.

The term "terminator sequence" or "terminator" as used herein refers to nucleotide sequences that function to stop transcription. The terms "transcription" or "transcribe" as used herein refers to the process by which RNA molecules are formed upon DNA templates by complementary base pairing. This process is mediated by RNA polymerase.

The term "VLP" as used herein refers to virus-like particles and, as used, also refers to aggregates of viral proteins.

The major immunological advantage of DNA-based immunizations is the ability of the immunogen to be presented by both MHC class I and class II molecules. Endogenously synthesized proteins readily enter processing pathways for the loading of peptide epitopes onto MHC I as well as MHC II molecules. MHC I-presented epitopes raise cytotoxic T-cells (Tc) responses whereas MHC II-presented epitopes raise helper T-cells (Th). By contrast, immunogens that are not synthesized in cells are largely restricted to the loading of MHC II epitopes and the raising of Th but not Tc. When compared with live attenuated vaccines or recombinant viral vectors that produce immunogens in cells and raise both Th and Tc, DNA vaccines have the advantages of not being infectious and of focusing the immune response on only those antigens desired for immunization. DNA vaccines also are advantageous because they can be manipulated relatively easily to raise type 1 or type 2 T-cell help. This allows a vaccine to be tailored for the type of immune response that will be mobilized to combat an infection. DNA vaccines are also cost effective because of the ease with which plasmids can be constructed using recombinant DNA technology, the ability to use a generic method for vaccine production (growth and purification of plasmid DNA), and the stability of DNA over a wide range of temperatures.

The best immune responses are achieved using highly active expression vectors modeled on those developed for the production of recombinant proteins (Robinson and Pertmer, 1998). The most frequently used transcriptional control elements include a strong promoter. One such promoter suitable for use is the cytomegalovirus (CMV) intermediate early promoter, although other promoters may be used in a DNA vaccine without departing from the scope the present invention. Other transcriptional control elements useful in the present invention include a strong polyadenylation signal such as, for example, that derived from a bovine growth hormone encoding gene, or a rabbit β globin polyadenylation signal (Bohm et al., 1996; Chapman et al., 1991; Hartikka et al., 1996; Manthorpe et al., 1993; Montgomery et al., 1993). The CMV immediate early promoter may be used with or without intron A (Chapman et al., 1991). The presence of intron A increases the expression of many antigens from RNA viruses, bacteria, and parasites, presumably by providing the expressed RNA with sequences which support processing and function as an eukaryotic mRNA. It will be appreciated that expression also may be enhanced by other methods known in the art including, but not limited to, optimizing the codon usage of prokaryotic mRNAs for eukaryotic cells (Andre et al., 1998; Uchijima et al., 1998). Multi-cistronic vectors may be used to express more than one immunogen or an immunogen and a immunostimulatory protein (Iwasaki et al., 1997a; Wild et al., 1998).

Immunogens can also be engineered to be more or less effective for raising antibody or Tc by targeting the expressed antigen to specific cellular compartments. For example, antibody responses are raised more effectively by antigens that are displayed on the plasma membrane of cells, or secreted therefrom, than by antigens that are localized to the interior of cells (Boyle, Koniaras, and Lew, 1997; Inchauspe et al., 1997). Tc responses may be enhanced by using N-terminal ubiquitination signals which target the DNA-encoded protein to the proteosome causing rapid cytoplasmic degradation and more efficient peptide loading into the MHC I pathway (Rodriguez, Zhang, and Whitton, 1997; Tobery and Siliciano, 1997; Wu and Kipps, 1997). For a review on the mechanistic basis for DNA-raised immune responses, refer to Robinson and Pertmer, *Advances in Virus Research*, vol. 53, Academic Press (2000), the disclosure of which is incorporated herein by reference in its entirety.

The effects of different conformational forms of proteins on antibody responses, the ability of strings of MHC I epitopes (minigenes) to raise Tc responses, and the effect of fusing an antigen with immune-targeting proteins have been evaluated using defined inserts. Ordered structures such as virus-like particles appear to be more effective than unordered structures at raising antibody (Fomsgaard et al., 1998). This is likely to reflect the regular array of an immunogen being more effective than a monomer of an antigen at cross-linking Ig-receptors and signaling a B-cell to multiply and produce antibody. Recombinant DNA molecules encoding a string of MHC epitopes from different pathogens can elicit Tc responses to a number of pathogens (Hanke et al., 1998b). These strings of Tc epitopes are most effective if they also include a Th epitope (Maecker et al., 1998; Thomson et al., 1998).

Another approach to manipulating immune responses is to fuse immunogens to immunotargeting or immunostimulatory molecules. To date, the most successful of these fusions have targeted secreted immunogens to antigen presenting cells (APC) or lymph nodes (Boyle, Brady, and Lew, 1998). Fusion of a secreted form of human IgG with CTLA-4 increased antibody responses to the IgG greater than 1000-fold and changed the bias of the response from complement (C'-) dependent to C'-independent antibodies.

Fusions of human IgG with L-selectin also increased antibody responses but did not change the C'-binding characteristics of the raised antibody. The immunogen fused with L-selectin was presumably delivered to lymph nodes by binding to the high endothelial venules, which serve as portals. Fusions between antigens and cytokine cDNAs have resulted in more moderate increases in antibody, Th, and Tc responses (Hakim, Levy, and Levy, 1996; Maecker et al., 1997). IL-4-fusions have increased antibody responses, whereas IL-12 and IL-1β have enhanced T-cell responses.

Two approaches to DNA delivery are injection of DNA in saline using a hypodermic needle or gene gun delivery of DNA-coated gold beads. Saline injections deliver DNA into extracellular spaces, whereas gene gun deliveries bombard DNA directly into cells. The saline injections require much larger amounts of DNA (100-1000 times more) than the gene gun (Fynan et al., 1993). These two types of delivery also differ in that saline injections bias responses towards type 1 T-cell help, whereas gene gun deliveries bias responses towards type 2 T-cell help (Feltquate et al., 1997; Pertmer, Roberts, and Haynes, 1996). DNAs injected in saline rapidly spread throughout the body. DNAs delivered by the gun are more localized at the target site. Following either method of inoculation, extracellular plasmid DNA has a short half life on the order of 10 minutes (Kawabata, Takakura, and Hashida, 1995; Lew et al., 1995). Vaccination by saline injections can be intramuscular (i.m.) or intradermal (i.d.) (Fynan et al., 1993).

Although intravenous and subcutaneous injections have met with different degrees of success for different plasmids (Bohm et al., 1998; Fynan et al., 1993), intraperitoneal injections have not met with success (Bohm et al., 1998; Fynan et al., 1993). Gene gun deliveries can be administered to the skin or to surgically exposed muscle. Methods and routes of DNA delivery that are effective at raising immune responses in mice are effective in other species.

Immunization by mucosal delivery of DNA has been less successful than immunizations using parenteral routes of inoculation. Intranasal administration of DNA in saline has met with both good (Asakura et al., 1997; Sasaki et al., 1998b) and limited (Fynan et al., 1993) success. The gene gun has successfully raised IgG following the delivery of DNA to the vaginal mucosa (Livingston et al., 1995). Some success at delivering DNA to mucosal surfaces has also been achieved using liposomes (McCluskie et al., 1998), microspheres (Chen et al., 1998a; Jones et al., 1997) and recombinant Shigella vectors (Sizemore, Branstrom, and Sadoff, 1995; Sizemore, Branstrom, and Sadoff, 1997).

The dose of DNA needed to raise a response depends upon the method of delivery, the host, the vector, and the encoded antigen. The most profound effect is seen for the method of delivery. From 10 μg to 1 mg of DNA is generally used for saline injections of DNA, whereas from 0.2 μg to 20 μg of DNA is used for gene gun deliveries of DNA. In general, lower doses of DNA are used in mice (10-100 μg for saline injections and 0.2 μg to 2 μg for gene gun deliveries), and higher doses in primates (100 μg to 1 mg for saline injections and 2 μg to 20 μg for gene gun deliveries). The much lower amount of DNA required for gene gun deliveries reflect the gold beads directly delivering DNA into cells.

An example of the marked effect of an antigen on the raised response can be found in studies comparing the ability to raise antibody responses in rabbits of DNAs expressing the influenza hemagglutinin or an immunodeficiency virus envelope glycoprotein (Env) (Richmond et al., 1998). Under similar immunization conditions, the hemagglutinin-expressing DNA raised long lasting, high avidity, high titer antibody (~100 μg per ml of specific antibody), whereas the Env-expressing DNA raised only transient, low avidity, and low titer antibody responses (<10 μg per ml of specific antibody). These differences in raised antibody were hypothesized to reflect the hemagglutinin being a T-dependent antigen and the highly glycosylated immunodeficiency virus Env behaving as a T-independent antigen.

Both protein and recombinant viruses have been used to boost DNA-primed immune responses. Protein boosts have been used to increase neutralizing antibody responses to the HIV-1 Env. Recombinant pox virus boosts have been used to increase both humoral and cellular immune responses.

For weak immunogens, such as the immunodeficiency virus Env, for which DNA-raised antibody responses are only a fraction of those in naturally infected animals, protein boosts have provided a means of increasing low titer antibody responses (Letvin et al., 1997; Richmond et al., 1998). In a study in rabbits, the protein boost increased both the titers of antibody and the avidity and the persistence of the antibody response (Richmond et al., 1998). Consistent with a secondary immune response to the protein boost, DNA primed animals showed both more rapid increases in antibody, and higher titers of antibody following a protein boost than animals receiving only the protein. However, by a second protein immunization, the kinetics and the titer of the antibody response were similar in animals that had, and had not, received DNA priming immunizations.

Recombinant pox virus boosts have proved to be a highly successful method of boosting DNA-primed CD8+ cell responses (Hanke et al., 1998a; Kent et al., 1998; Schneider et al., 1998). Following pox virus boosters, antigen-specific CD8+ cells have been increased by as much as 10-fold in DNA primed mice or macaques. Studies testing the order of immunizations reveal that the DNA must be delivered first (Schneider et al., 1998). This has been hypothesized to reflect the DNA focusing the immune response on the desired immunogens. The larger increases in CD8+ cell responses following pox virus boosts has been hypothesized to reflect both the larger amount of antigen expressed by the pox virus vector, as well as pox virus-induced cytokines augmenting immune responses (Kent et al., 1998; Schneider et al., 1998).

A number of different pox viruses can be used for the pox boost. A vaccinia virus termed modified vaccinia Ankara (MVA) has been particularly effective in mouse models (Schneider et al., 1998). This may reflect MVA, which is replication defective in mammalian models, being attenuated for the ability to evade host immune responses.

Responses raised by a DNA prime followed by pox virus boost can be highly effective at raising protective cell-mediated immune responses. In mice, intramuscular injections of DNA followed by recombinant pox boosts have protected against a malaria challenge (Schneider et al., 1998). In macaques, intradermal., but not gene gun DNA primes, followed by recombinant pox virus boosters have contained challenges with chimeras of simian and human immunodeficiency viruses (Robinson et al., 1999).

DNA vaccines for immunodeficiency viruses such as HIV-1 encounter the challenge of sufficiently limiting an incoming infection such that the inexorable long-term infections that lead to AIDS are prevented. Complicating this is that neutralizing antibodies is both difficult to raise and specific against particular viral strains (Burton and Montefiori, 1997; Moore and Ho, 1995). Given the problems with raising neutralizing antibody, much effort has focused on raising cell-mediated responses of sufficient strength to severely curtail infections. To date, the best success at raising high titers of Tc have come from immunization protocols using DNA primes followed by recombinant pox virus boosters. The efficacy of this protocol has been evaluated by determining the level of specific Tc using assays for cytolytic activity (Kent et al., 1998), by staining with MHC-specific tetramers for specific SIV Gag epitopes and by challenge with SIVs or SHIVs (Hanke, 1999).

A number of salient findings are emerging from preclinical trials using DNA primes and recombinant pox virus boosts. The first is that challenge infections can be contained below the level that can be detected using quantitative RT-PCR analyses for plasma viral RNA (Robinson et al., 1999). The second is that this protection is long lasting and does not require the presence of neutralizing antibody (Robinson et al., 1999). The third is that intradermal DNA priming with saline injections of DNA is superior to gene gun priming for raising protective immunity (P=0.01, Fisher's exact test) (Robinson et al., 1999).

The novel pGA vectors of the present invention have a prokaryotic origin of replication, a selective marker gene for plasmid selection, and a transcription cassette for eukaryotic cells. Unique to the pGA vectors of the present invention is the inclusion of the lambda terminator in the same transcriptional orientation, and following, the selective marker gene. This terminator sequence prevents read-through from the kanamycin cassette into vaccine sequences while the plasmid is being produced in bacteria. Prevention of transcriptional read-through stabilizes vaccine insert sequences by limiting the exposure of secondary structures that can be recognized by bacterial endonucleases.

A transcription cassette as incorporated in the pGA vectors of the present invention uses sequences from the cytomegalovirus immediate early promoter (CMVIE) and from the bovine growth hormone polyadenylation sequences (BGHpA) to control transcription. A leader sequence that is a synthetic homolog of the tissue plasminogen activator gene leader sequence (tPA) is optional in the transcription cassette.

Figure 3:
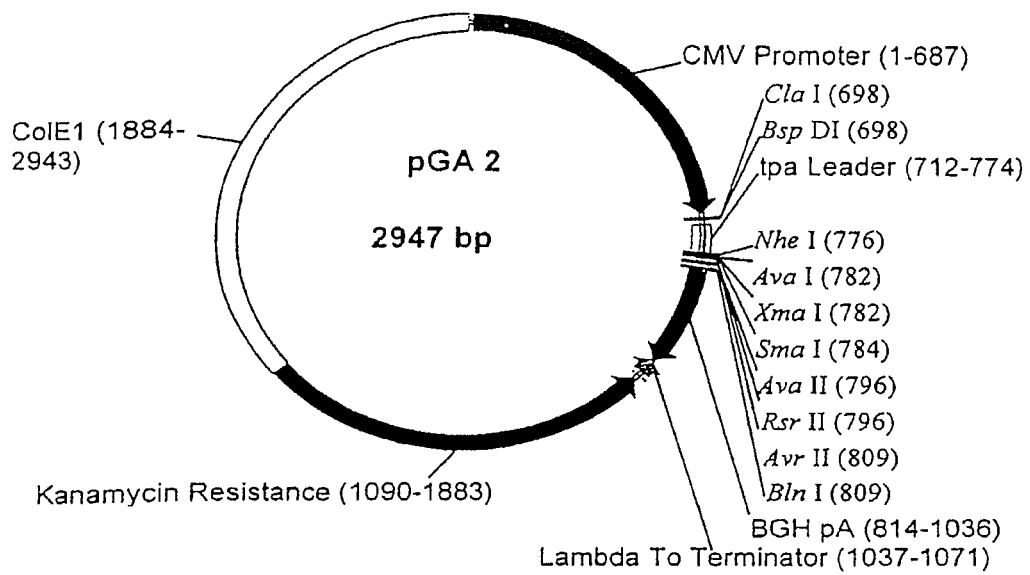
FIG. 3 illustrates a novel pGA2 construct of the present invention. Designations are identities and positions of elements in the vector. Designations in italic print are unique restriction endonuclease sites useful for cloning vaccine inserts into the vector.
Figure 5:
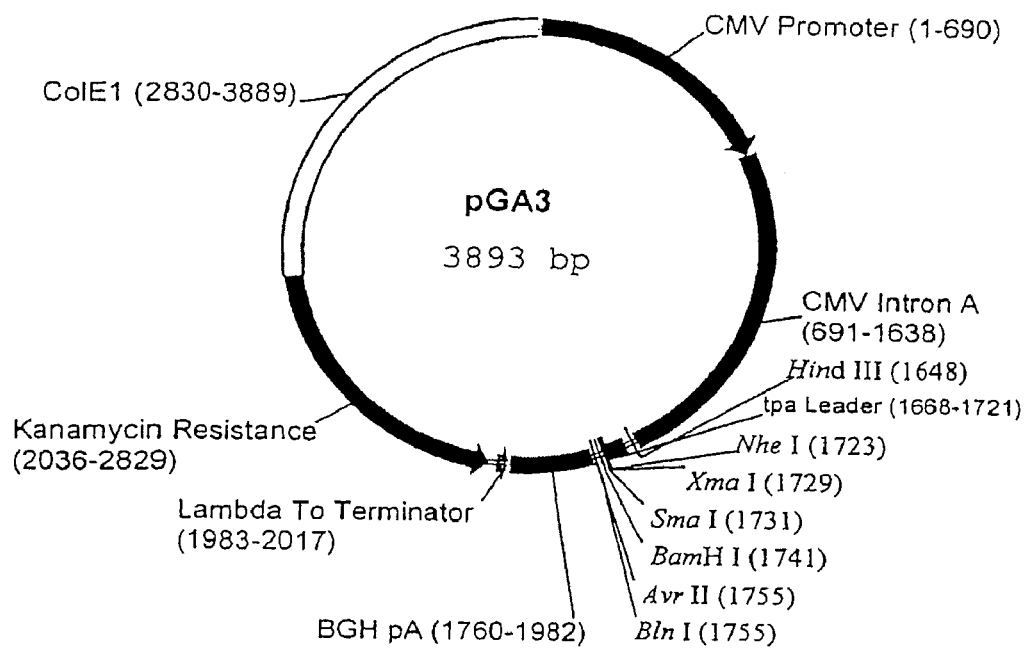
FIG. 5 illustrates a novel pGA3 construct of the present invention. Designations are identities and positions of elements in the vector. Designations in italic print are unique restriction endonuclease sites useful for cloning vaccine inserts into the vector.

The vectors of the present invention differ in the sites that can be used for accepting vaccine inserts and in whether the transcription cassette includes intron A sequences in the CMVIE promoter. Both intron A and the tPA leader sequence have been shown in certain instances to supply a strong expression advantage to vaccine inserts (Chapman et al., 1991).

pGA1 is a 3894 bp plasmid. pGA1 comprises a promoter (bp 1-690), the CMV-intron A (bp 691-1638), a synthetic mimic of the tPA leader sequence (bp 1659-1721), the bovine growth hormone polyadenylation sequence (bp1761-1983), the lambda T0 terminator (bp 1984-2018), the kanamycin resistance gene (bp 2037-2830) and the ColEI replicator (bp 2831-3890). The DNA sequence of the pGA1 construct (SEQ ID NO: 1) is shown in FIG. 2. In FIG. 1, the indicated restriction sites are single cutters useful for the cloning of vaccine inserts. The ClaI or BspD1 sites are used when the 5' end of a vaccine insert is cloned upstream of the tPA leader. The NheI site is used for cloning a sequence in frame with the tPA leader sequence. The sites listed between SmaI and BlnI are used for cloning the 3' terminus of a vaccine insert.

pGA2 is a 2947 bp plasmid lacking the 947 bp of intron A sequences found in pGA1. pGA2 is the same as pGA1, except for the deletion of intron A sequences. pGA2 is valuable for cloning sequences which do not require an upstream intron for efficient expression, or for cloning sequences in which an upstream intron might interfere with the pattern of splicing needed for good expression. FIG. 3 presents a map of pGA2 with useful restriction sites for cloning vaccine inserts, and FIG. 4 shows the DNA sequence SEQ ID NO: 2. The use of restriction sites for cloning vaccine inserts into pGA2 is the same as that used for cloning fragments into pGA1.

pGA3 is a 3893 bp plasmid that contains intron A. pGA3 is the same as pGA1 except for the cloning sites that can be used for the introduction of vaccine inserts. In pGA3, inserts cloned upstream of the tPA leader sequence use a Hind III site. Sequences cloned downstream from the tPA leader sequence use sites between the SmaI and the BlnI site. In pGA3, these sites include a BamHI site. FIG. 5 shows the map for pGA3, and FIG. 6 shows the DNA sequence SEQ ID NO: 3.

In view of the teachings herein, one skilled in the art will recognize that any vaccine insert known in the art can be used in the novel pGA constructs described herein, including but not limited to viral pathogens like HIV, influenza, measles, herpes, Ebola, and the like.

For example, the present invention contemplates inserts from immunodeficiency virus, more preferably HIV, including all clades of HIV-1 and HIV-2 and modifications thereof; influenza virus genes including all subtypes and modifications thereof; and vaccine inserts derived from measles genes. One skilled in the art will appreciate that the discussion about inserts derived from immunodeficiency virus; influenza virus; measles virus; and modifications thereof are exemplary in nature and provided for the sake of illustration only.

The immunodeficiency virus vaccine inserts of the present invention were designed to express non-infectious virus like particles (VLPs) from a single DNA. This was achieved using the subgenomic splicing elements normally used by immunodeficiency viruses to express multiple gene products from a single viral RNA. Important to the subgenomic splicing patterns are (i) splice sites and acceptors present in full length viral RNA, (ii) the Rev responsive element (RRE) and (iii) the Rev protein. The splice sites in retroviral RNAs use the canonical sequences for splice sites in eukaryotic RNAs. The RRE is an ~200 bp RNA structure that interacts with the Rev protein to allow transport of viral RNAs from the nucleus to the cytoplasm. In the absence of Rev, the ~10 kb RNA of immunodeficiency virus undergoes splicing to the mRNAs for the regulatory genes Tat, Rev, and Nef. These genes are encoded by exons present between RT and Env and at the 3' end of the genome. In the presence of Rev, the singly spliced mRNA for Env and the unspliced mRNA for Gag and Pol are expressed in addition to the multiply spliced mRNAs for Tat, Rev, and Nef.

The expression of non-infectious VLPs from a single DNA affords a number of advantageous features to an immunodeficiency virus vaccine. The expression of a number of proteins from a single DNA affords the vaccinated host the opportunity to respond to the breadth of T- and B-cell epitopes encompassed in these proteins. The expression of proteins containing multiple epitopes affords the opportunity for the presentation of epitopes by diverse histocompatibility types. By using whole proteins, one offers hosts of different histocompatibility types the opportunity to raise broad-based T-cell responses. Such may be essential for the effective containment of immunodeficiency virus infections, whose high mutation rate supports ready escape from immune responses (Evans et al., 1999) (Poignard et al., 1999, Evans, et al., 1995). Just as in drug therapy, multi-epitope T-cell responses that require multiple mutations for escape will provide better protection than single epitope T-cell responses that require only a single mutation for escape.

Antibody responses are often best primed by multi-valent vaccines that present an ordered array of an epitope to responding B-cells (Bachmann, Zinkernagel, 1997). Virus-like particles, by virtue of the multivalency of Env in the virion membrane, will facilitate the raising of anti-Env antibody responses. These particles will also present non-denatured and normal forms of Env to the immune system.

The novel vectors of the present invention can be administered to a patient in the presence of adjuvants or other substances that have the capability of promoting DNA uptake or recruiting immune system cells to the site of the inoculation. Embodiments include combining the DNA vaccine with conventional adjuvants or genetic adjuvants. Conventional adjuvants, including reagents that favor the stability and uptake of the DNA, recruit immune system cells to the site of inoculation, or facilitate the immune activation of responding lymphoid cells, include but are not limited to oil and water emulsions (for example, complete Freund's adjuvant and incomplete Freund's adjuvant), *Corynebacterium parvum*, Bacillus Calmette Guerin, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N,N-dioctadecyl-N', N'-bis(2-hydroxyethyl)-propanediamine), paraffin oil, and muramyl dipeptide. The present invention also contemplates the use of genetic adjuvants such as immunomodulatory molecules encoded in a co-inoculated DNA. The co-inoculated DNA can be in the same vaccine construct as the vaccine immunogen or in a separate DNA vector.

A vaccine according to the present invention can be administered in a variety of ways including through any parenteral or topical route. For example, an individual can be inoculated by intravenous, intraperitoneal, intradermal, subcutaneous or intramuscular methods. Inoculation can be, for example, with a hypodermic needle, needleless delivery devices such as those that propel a stream of liquid into the target site, or with the use of a gene gun that bombards DNA on gold beads into the target site. The vector comprising the pathogen vaccine insert can be administered to a mucosal surface by a variety of methods including intranasal administration, i.e., nose drops or inhalants, or intrarectal or intravaginal administration by solutions, gels, foams, or suppositories. Alternatively, the vector comprising the vaccine insert can be orally administered in the form of a tablet, capsule, chewable tablet, syrup, emulsion, or the like. In an alternate embodiment, vectors can be administered transdermally, by passive skin patches, iontophoretic means, and the like.

Any appropriate physiologically acceptable medium is suitable for introducing the vector comprising the pathogen vaccine insert into the patient. For example, suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

The present invention is further illustrated by the following examples, which are provided by way of illustration and should not be construed as limiting. The contents of all references, published patents and patents cited throughout the present application are hereby incorporated by reference in their entirety.

EXAMPLE 1

Structure and Sequence of PGA1 pGA1 as illustrated in FIG. 1 and FIG. 2 contains the ColE1 origin of replication, the kanamycin resistance gene for antibiotic selection, the lambda T0 terminator, and a eukaryotic expression cassette including an upstream intron. The ColE1 origin of replication is a 600 nucleotide DNA fragment that contains the origin of replication (ori), encodes an RNA primer, and encodes two negative regulators of replication initiation. All enzymatic functions for replication of the plasmid are provided by the bacterial host. The original constructed plasmid that contained the ColE1 replicator was pBR322 (Bolivar, et al. 1977; Sutcliffe, et al. 1978).

The kanamycin resistance gene is an antibiotic resistance gene for plasmid selection in bacteria. The lambda T0 terminator prevents read through from the kanamycin resistance gene into the vaccine transcription cassette during prokaryotic growth of the plasmid (Scholtissek and Grosse, 1987). By preventing read through into the vaccine expression cassette, the terminator helps stabilize plasmid inserts during growth in bacteria.

The eukaryotic expression cassette is comprised of the CMV immediate early promoter including intron A (CMVIE-IA) and termination sequences from the bovine growth hormone polyadenylation sequence (BGHpA). A synthetic mimic of the leader sequence for tissue plasminogen activator (tPA) is included as an option within the transcription cassette. Cassettes with these elements have proven to be highly effective for expressing foreign genes in eukaryotic cells (Chapman et al., 1991). Cloning sites within the transcription cassette include a ClaI site upstream of the tPA leader, a NheI site for cloning in frame with the tPA leader, and XmnI, SmaI, RsrII, AvrII, and BlnI sites for cloning prior to the BGHpA.

The ColE1 replicator, the Kanamycin resistance gene and transcriptional control elements for eukaryotic cells were combined in one plasmid using polymerase chain reaction (PCR) fragments from a commercial vector, pZErO-2 (Invitrogen, Carlsbad, Calif.) and a eukaryotic expression vector, pJW4303 (Lu et al., 1997).

A 1853 bp fragment from pZErO2 from nt 1319 to nt 3178 included the ColE1 origin of replication and the kanamycin resistance gene. A 2040 bp fragment from pJW4303 from nt 376 to nt 2416 included the CMVIE promoter with intron A, a synthetic homolog of the tissue plaminogen activator leader (tPA), and the bovine growth hormone polyadenylation site (BGHpA). Fragments were amplified by polymerase chain reaction (PCR) with oligonucleotide primers containing SalI sites. A ligation product with the transcription cassettes for Kanamycin resistance from pZeRO2 and the eukaryotic transcription cassette form pJW4303 in opposite transcriptional orientations was identified for further development. Nucleotide numbering for this parent for the pGA vectors was started from the first bp of the 5' end of the CMV promoter.

The T0 terminator was introduced into this parent for the pGA vectors by PCR amplification of a 391 by fragment with a BamH 1 restriction endonuclease site at its 5' end and an Xba I restriction endonuclease site at its 3' end. The initial 355 by of the fragment were sequences in the BGHpA sequence derived from the pJW4303 transcription cassette, the next 36 bases in a synthetic oligonucleotide introduced the T0 sequence and the Xba I site. The introduced T0 terminator sequences comprised the sequence:

(SEQ ID NO: 6)
5'-ATAAAAAACGCCCGGCGGCAACCGAGCGTTCTGAA-3'.

The T0 terminator containing BamH1-XbaI fragment was substituted for the homologous fragment without the T0 terminator in the plasmid created from pXeRO 2 and pJW4303. The product was sequenced to verify the TO orientation.

A region in the eukaryotic transcription cassette between nucleotides 1755-1845 contained the last 30 bp of the reading frame for SIV nef. This region was removed from pGA by mutating the sequence at nt1858 and generating an Avr II restriction endonuclease site. A naturally occurring Avr II site is located at nt1755. Digestion with Avr II enzyme and then religation with T4 DNA ligase allowed for removal of the SIV segment of DNA between nucleotides 1755-1845. To facilitate cloning of HIV-1 sequences, into pGA vectors a ClaI site was introduced at bp1645 and an RsrII site at bp 1743 using site directed mutagenesis. Constructions were verified by sequence analyses.

EXAMPLE 2

Structure and Sequence of PGA2 pGA2, as illustrated in FIG. 3, and FIG. 4, is identical to pGA1 except for delation of the intron A sequence from the CMVIE promoter. pGA2 was created from pGA1 by introducing a Cla I site 8 by downstream from the mRNA cap site in the CMVIE promoter. The Cla I site was introduced using oligonucleotide-directed mutagenesis using the complimentary primers (SEQ ID NO: 7)
5'-CCGTCAGATCGCATCGATACGCCATCCACG-3'
and (SEQ ID NO: 8)
5'-CGTGGATGGCGTATCGATGCGATCTGACGG-3'.

After insertion of the new Cla I site, pGA1 was digested with Cla Ito remove the 946 by Cla I fragment from pGA1, and then religated to yield pGA2.

EXAMPLE 3

Structure and Sequence of PGA3 pGA3 as shown in FIG. 5 and FIG. 6 is identical to pGA1 except for the introduction of a HindIII site in stead of the ClaI site at nt 1645 and a BamHI site instead of the RsrII site at nucleotide 1743.

EXAMPLE 4

Comparative Expression and Immunogenicity of PGA3 and pJW4303

To determine the efficacy of the pGA plasmids as vaccine vectors, a pGA plasmid was compared to the previously described vaccine vector pJW4303. The pJW4303 plasmid has been used for DNA vaccinations in mice, rabbits, and rhesus macaques (Robinson et al. 1999; Robinson et al., 1997; Pertmer, et al., 1995; Feltquate, et al. 1997; Torres, et al. 1999). Comparisons were done with pGA3 with a vaccine insert encoding the normal, plasma-membrane form of the A/PR/8/34 (H1N1) influenza virus hemagglutinin (pGA3/H1) and pJW4303 encoding the same fragment (pJW4303/H1). Both pGA3 and pJW4303 contain intron A upstream of influenza H1 sequences.

The pGA3/H1 and pJW4303/H1 vaccine plasmids expressed similar levels of H1 in eukaryotic cells, as summarized below:

TABLE 5

In Vitro Expression Levels of HA plasmids.

| Plasmids | Relative HA Units | |
|---|---|---|
| | Supernatant | Cell Lysate |
| PGA3/H1 | 0.1 ± 0.1 | 5.7 ± 0.6 |
| pGA vector | 0.0 ± 0.0 | 0.2 ± 0.1 |
| PJW4303/H1 | 0.3 ± 0.05 | 4.8 ± 0.5 |
| pJW4303 | 0.0 ± 0.0 | 0.1 ± 0.1 |

Human embryonic kidney 293T cells were transiently transfected with 2 μg of plasmid and the supernatants and cell lysates assayed for H1 using an antigen-capture ELISA. The capture antibody was a polyclonal rabbit serum against H1, and the detection antibody, polyclonal mouse sera against H1. pGA3/H1 expressed slightly more H1 than pJW4303/H1 (5.8 HA units as opposed to 5.1 H1 units (Table 6). As expected, 90% of the H1 antigen was in the cell lysates. A comparative immunization study using pGA3/H1, and pJW4303/H1 demonstrated comparable or better immunogenicity for pGA3/H1 than pJW4303/H1 (FIG. 7). Immunogenicity was assessed in BALB/c mice. In this example, mice were vaccinated with DNA coated gold particles via gene gun. Mice were primed and boosted with a low dose (0.1 μg) or a high dose (1 μg) of the plasmid DNAs. The booster immunization was given at 4 weeks after the priming immunization. The amount of anti-H1 IgG raised in response to immunizations was as high or higher following immunization with pGA3/H1 than following immunization with pJW4303/H1 (FIG. 7). Thus the pGA vector proved to be as effective, or more effective, than the pJW4303 vector at raising immune responses.

EXAMPLE 5

Immunodeficiency Virus Vaccine Inserts in pGA Vectors

Immunodeficiency virus vaccine inserts expressing virus like particles have been developed in pGA1 and pGA2. The VLP insert was designed with clade B HIV-1 sequences so that it would match HIV-1 sequences that are endemic in the United States. Within clade B, different isolates exhibit clustal diversity, with each isolate having overall similar diversity from the consensus sequence for the clade (Subbarao, Schochetman, 1996). Thus, any clade B isolate can be used as a representative sequence for other clade B isolates. HIV-1 isolates use different chemokine receptors as co-receptors. The vast majority of viruses that are undergoing transmission use the CCR-5 co-receptor (Berger, E. A., 1997). Therefore the vaccine insert was designed to have a CCR-5 using Env.

The expression of VLPs with an R5-Env by a HIV-1 DNA vaccine also has the advantage of supporting Env-mediated entry of particles into professional antigen presenting cells (APCs) such as dendritic cells and macrophages. Both dendritic cells and macrophages express the CD4 receptor and the CCR-5 co-receptor used by CCR-5-tropic (R5) HIV-1 Envs. By using an R5 Env in the vaccine, the VLP expressed in a transfected non-professional APC (for example keratinocyte or muscle cells) can gain entry into the cytoplasm of an APC by Env-mediated entry. Following entry into the cytoplasm of the APC, the VLP will be available for processing and presentation by class I histocompatibility antigens. DNA-based immunizations rely on professional APCs for antigen presentation (Corr et al., 1996; Fu, et al., 1997; Iwasaki A, et al., 1997). Much of DNA-based immunization is accomplished by direct transfection of professional APC (Condon et al., 1996; Porgador et al., 1998). Transfected muscle cells or keratinocytes serve as factories of antigen but do not directly raise immune response (Torres et al., 1997). By using an expressed antigen that is assembled and released from transfected keratinocytes or muscle cells and then actively enters professional APC, the efficiency of the immunization may be increased.

Goals in the construction of pGA2/JS2 were (i) to achieve a CCR-5-using clade B VLP with high expression, (ii) to produce a VLP that was non infectious and (iii) to minimize the size of the vaccine plasmid. Following the construction of the CCR-5-using VLP (pGA2/JS2), a derivative of JS2 was prepared that expresses an Env-defective VLP. This plasmid insert was designated JS5. Although it is anticipated that this sequence will be a less effective vaccine than the Env-containing JS2 VLP, the non-Env containing VLP offers certain advantages for vaccination. These include the ability to monitor vaccinated populations for infection by sero-conversion to Env. Deletion of Env sequences also reduces the size of the vaccine plasmid. The DNA sequence of pGA2/JS2 is shown in FIG. 17 and that of pGA1/JS5 in FIG. 18.

To achieve a VLP plasmid with high expression, candidate vaccines were constructed from 7 different HIV-1 sequences, as shown in the following table:

TABLE I

Comparison of candidate vaccine inserts

| Plasmid designation | Sequences tested | Ability to grow plasmid | Expression of Gag | Expression of Env | Comment |
|---|---|---|---|---|---|
| BH10-VLP | BH10 | good | good | good | X4 Env |
| 6A-VLP | 6A env in BH10-VLP | poor | not tested | not tested | |
| BAL-VLP | BAL env in BH10-VLP | good | poor | poor | |
| ADA-VLP | ADA env in BH10-VLP | good | good | good | chosen for vaccine, renamed pGA1/JS1 |
| CDC-A-VLP | CDC-A env in BH10-VLP | good | good | poor | |
| CDC-B-VLP | CDC-B-env in BH10-VLP | good | good | good | not as favorable expression as ADA |
| CDC-C-VLP | CDC -C env in BH10-VLP | good | good | good | not as favorable expression as ADA |

An initial construct, pBH10-VLP, was prepared from IIIb sequences that are stable in bacteria and have high expression in eukaryotic cells. The BH10 sequences were obtained from the NIH-sponsored AIDS Repository (catalog #90). The parental pBH10 was used as the template for PCR reactions to construct pBH10-VLP.

Primers were designed to yield a Gag-Rt PCR product (5' PCR product) encompassing from 5' to 3' 105 by of the 5' untranslated leader sequence and gag and pol sequences from the start codon for Gag to the end of the RT coding sequence. The oligonucleotide primers introduced a ClaI site at the 5' end of the PCR product and EcoRI and NheI sites at the 3' end of the PCR product. Sense primer 1 (5'-GAGCTCTATCGAT-GCAGGACTCGGCTTGC-3' (SEQ ID NO: 9)) and antisense primer 2 (5'-GGCAGGTTTTAATCGCTAGCCTAT-GCTCTCC-3' (SEQ ID NO: 10)) were used to amplify the 5' PCR product.

The PCR product for the env region of HIV-1 (3' PCR product) encompassed the vpu, tat, rev, and env sequences and the splice acceptor sites necessary for proper processing and expression of their respective mRNAs. An EcoRI site was introduced at the 5' end of this product and NheI and RsrII sites were introduced into the 3' end. Sense primer 3 (5'-GGGCAGGAGTGCTAGCC-3' (SEQ ID NO: 11)) and antisense primer 4 (5'-CCACACTACTTTCGGACCGCTAGC-CACCC-3' (SEQ ID NO: 12)) were used to amplify the 3' PCR product.

The 5' PCR product was cloned into pGA1 at the ClaI and NheI sites and the identity of the construct confirmed by sequencing. The 3' PCR product was then inserted into the 5' clone at the EcoRI and NheI sites to yield pBH10-VLP. The construction of this VLP resulted in proviral sequences that lacked LTRs, integrase, vif, and vpr sequences (see FIG. 8A).

Because the BH10-VLP had an X4 rather than an R5 Env, sequences encoding six different R5 Envs were substituted for env sequences in BH10-VLP. This was done by cloning EcoRI to BamHI fragments encompassing tat, rev, vpu and env coding sequences from different viral genomes into pBH10-VLP. The resulting env and rev sequences were chimeras for the substituted sequences and BH10 sequences (for example see FIG. 8B). In the case of the ADA envelope, a BamHI site was introduced into the ADA sequence to facilitate substituting an EcoRI to BamHI fragment for the EcoRI to BamHI region of the BH10-VLP (FIG. 8). The results of these constructions are summarized in Table 1. Of the six sequences tested, one, the 6A-VLP was found to be associated with poor plasmid growth in transformed bacteria. This plasmid was not used for further vaccine development (Table 1).

Figures 9A, 9B:
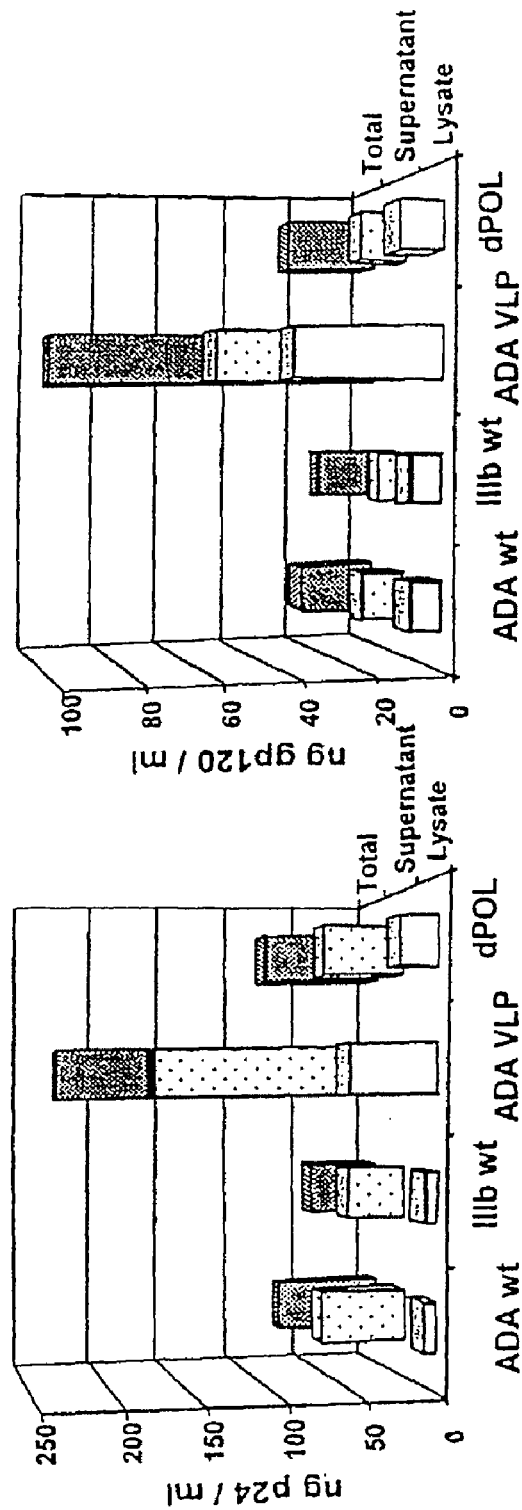
FIGS. 9A and 9B show Gag and Env expression, respectively, for intermediates in the construction of the JS2 vaccine insert. Data are from transient transfections in 293T cells. pGA1/JS1 (ADA VLP) produced higher levels of both Gag (FIG. 9A) and Env (FIG. 9B) than wild type HIV-1 ADA or HIV-1 IIIb proviruses, and a VLP-producing DNA (dPol) used in previous studies.

Among the plasmids exhibiting good growth in bacteria, the best expression of the VLP was found for the ADA-VLP (Table 1). In transient transfections in 293T cells, the expression of the ADA-VLP was higher than that of wt proviruses for ADA or IIIb (FIG. 9). Expression was also higher than for a previous VLP-vaccine (dpol) (Richmond et al., 1998) that had successfully primed cytotoxic T-cell (Tc) responses in rhesus macaques (Kent et al., 1998).

EXAMPLE 6

Safety Mutations

Once the ADA-VLP had been identified as a favorable candidate for further vaccine development, this plasmid was mutated to increase its safety for use in humans. Further mutations disabled the Zinc fingers in NC that are active in the encapsidation of viral RNA, and added point mutations to inactivate the activity of the viral reverse transcriptase and the viral protease (FIG. 8). The following table summarizes the location of the safety point mutations

TABLE 2

Location of safety point mutations in pGA/JS2 and pGA/JS5 to inhibit viral RNA packaging and abolish reverse transcriptase activity in vaccine constructs

| GENE | REGION | FUNCTION | AMINO ACID CHANGE[1] | LOCATION[2] |
|---|---|---|---|---|
| Gag | Zn finger | Viral RNA packaging | C392S | 1285/1287 |
| Gag | Zn finger | Viral RNA packaging | C395S | 1294/1296 |
| Gag | Zn finger | Viral RNA packaging | C413S | 1348/1350 |
| Gag | Zn finger | Viral RNA packaging | C416S | 1357/1359 |
| Pol | RT | Polymerase activity | D185N | 2460/2462 |
| Pol | RT | Strand transfer | W266T | 2703/2704/2705 |
| Pol | RNAse H | RNAse activity | E478Q | 3339 |

Figure 10:
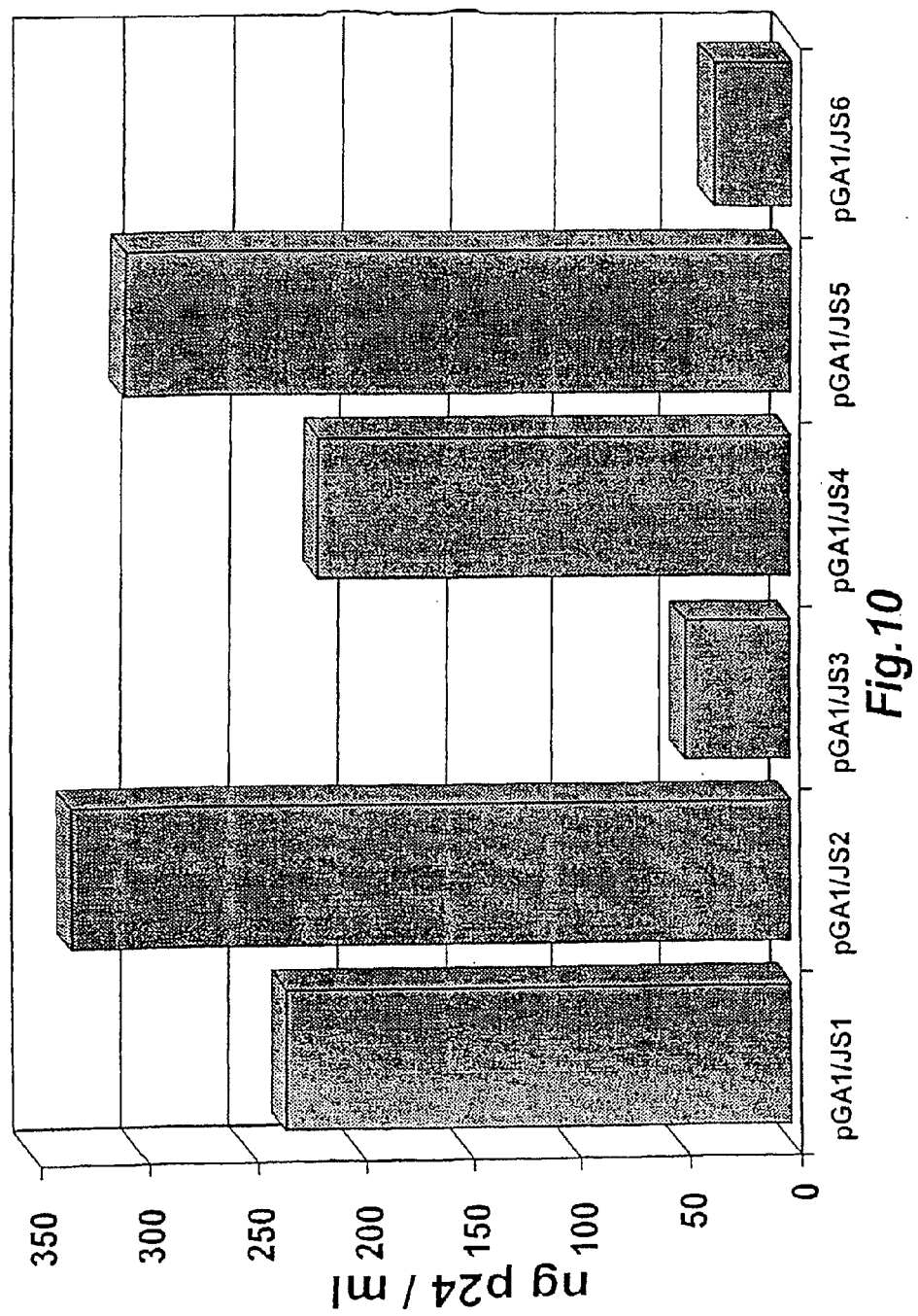
FIG. 10 shows the expression of p24 capsid in transiently transfected cells by vaccine vectors expressing inserts without safety mutations (JS1 and JS4), inserts with point mutations in the zinc fingers and in RT (JS2 and JS5), and point mutations in the zinc fingers, RT, and protease (JS3 and JS6). Note that the safety mutations in the zinc fingers and RT supported active VLP expression whereas the safety mutation in Prt did not. JS2 and JS5 were chosen for continued vector development based on their high levels of expression in the presence of safety mutations.

[1]Amino acid number corresponds to individual genes in HIV-1 BH10 sequence;
[2]Nucleotide number in wt HIV-1 BH10 sequence The mutations were made using a site directed mutagenesis kit (Stratagene) following the manufacturer's protocol. All mutations were confirmed by sequencing. Primer pairs used for the mutagenesis were:

```
(A) C15S ZN1
5'-GGTTAAGAGCTTCAATAGCGGCAAAGAAGGGC-3' (SEQ ID NO: 13)
    C15S ZN2
5'-GCCCTTCTTTGCCGCTATTGAAGCTCTTAACC-3' (SEQ ID NO: 14)

(B) C36S ZN3
5'-GGGCAGCTGGAAAAGCGGAAAGGAAGG-3' (SEQ ID NO: 15)
    C36S ZN4
5'-CCTTCCTTTCCGCTTTTCCAGCTGCCC-3' (SEQ ID NO: 16)

(C) D185N RT1
5'-CCAGACATAGTTATCTATCAATACATGAACGATTTGTATGTAGG-3' (SEQ ID NO: 17)
    D185N RT2
5'-CCTACATACAAATCGTTCATGTATTGATAGATAACTATGTCTGG-3' (SEQ ID NO: 18)

(D) W266T RT3
5'-GGGGAAATTGAATACCGCAAGTCAGATTTACCC-3' (SEQ ID NO: 19)
    W266T RT4
5'GGGTAAATCTGACTTGCGGTATTCAATTTCCCC-3' (SEQ ID NO: 20)

(E) E478Q RT5
5'-CCCTAACTAACACAACAAATCAGAAAACTCAGTTACAAGC-3' (SEQ ID NO: 21)
    E478Q RT6
5'-GCTTGTAACTGAGTTTTCTGATTTGTTGTGTTAGTTAGGG-3' (SEQ ID NO: 22)

(F) D25A Prt1
5'-GGCAACTAAAGGAAGCTCTATTAGCCACAGGAGC-3' (SEQ ID NO: 23)
    D25A prt2
5'-GCTCCTGTGGCTAATAGAGCTTCCTTTAGTTGCC-3' (SEQ ID NO: 24)
```

The ADA-VLP with the zinc finger and RT mutations was found to express Gag and Env more effectively than the VLP plasmid without the mutations (FIG. 10). The mutation that inactivated the protease gene markedly reduced VLP expression (FIG. 10) and was not included in the further development of the vaccine plasmid. The ADA-VLP without mutations was designated JS 1 and the ADA-VLP with mutations, JS2.

EXAMPLE 7

Construction of the JS5 Vaccine Insert

The JS5 insert, a plasmid expressing Gag, RT, Tat, and Rev was constructed from JS2 by deleting a BglII fragment in the ADA Env (FIG. 8). This deletion removed sequences from nt 4906-5486 of the pGA2/JS2 sequence and results in a premature stop codon in the env gene leading to 269 out of the 854 amino acids of Env being expressed while leaving the tat, rev, and vpu coding regions the RRE and splice acceptor sites intact. The DNA sequence of pGA1/JS5 is shown in FIG. 18.

EXAMPLE 8

Minimizing the Size of the JS2 and JS5 Vaccine Plasmids

Figure 11A:
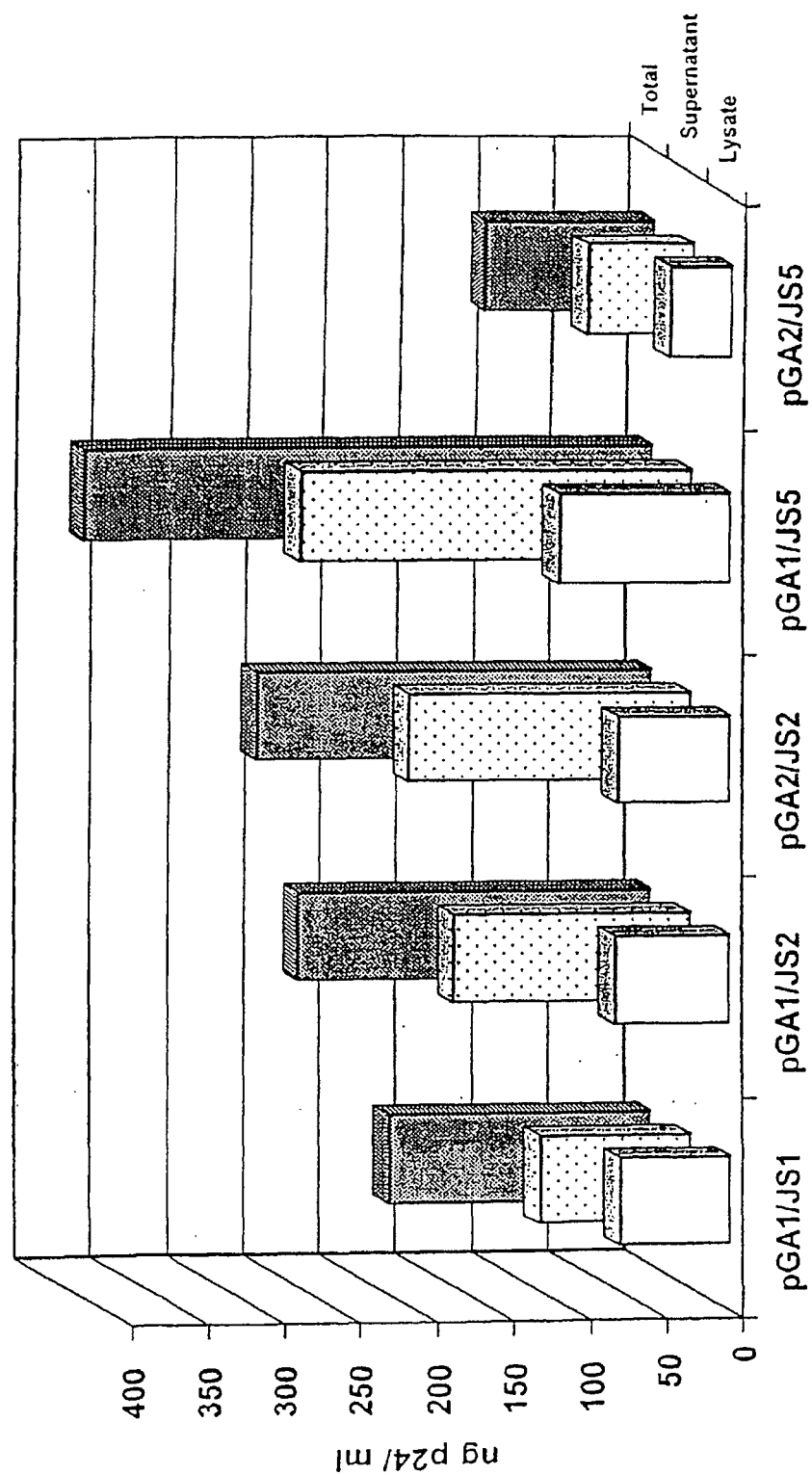
FIGS. 11A and 11B show Gag and Env expression, respectively, of novel candidate vaccine constructs expressed by pGA vectors with and without intron A. PGA1 but not pGA2 contains intron A. pGA2/JS2 and pGA1/JS5 were chosen for use in vaccines based on their favorable levels of expression.
Figure 11B:
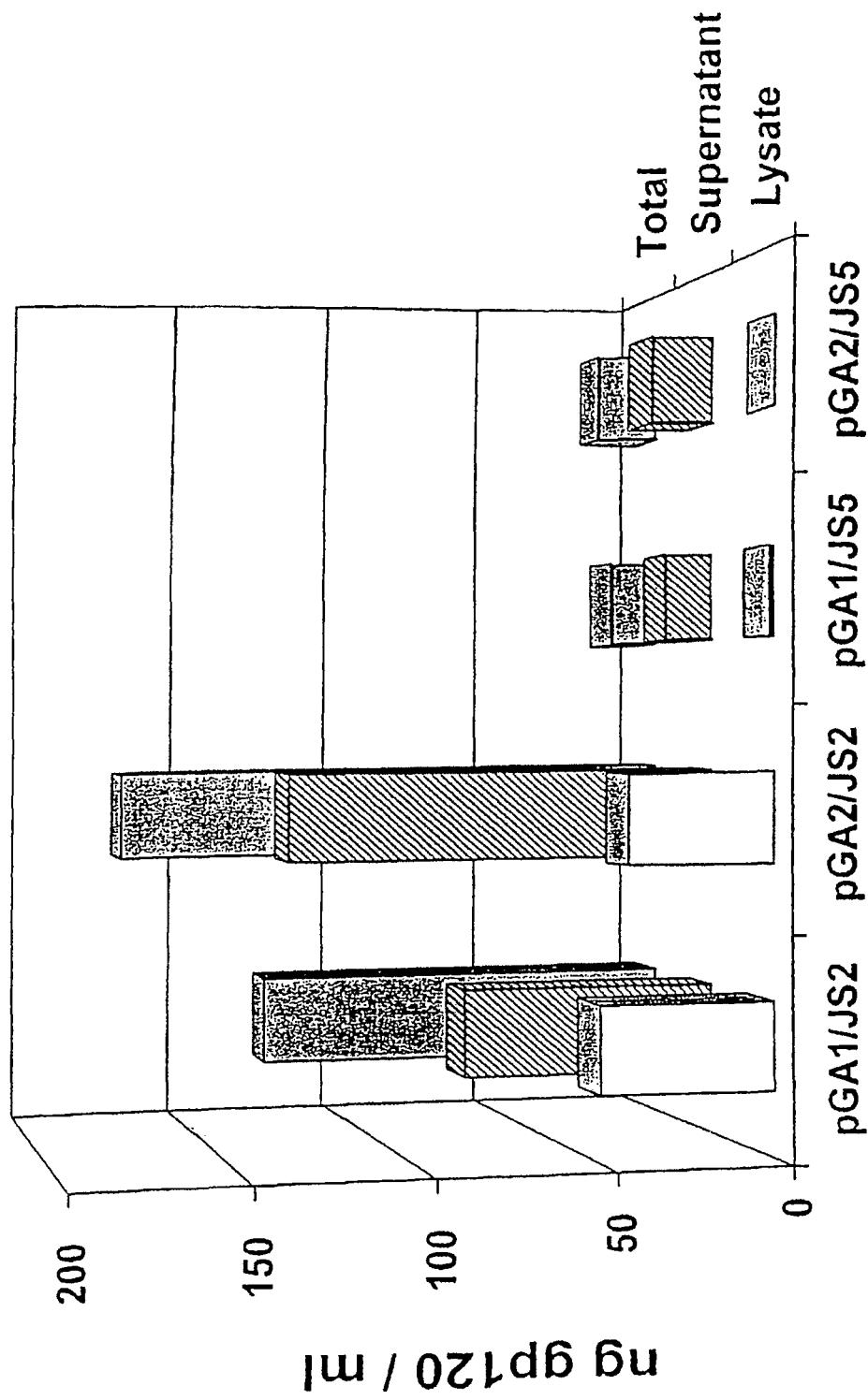

The JS2 and JS5 vaccine inserts were originally constructed in pGA1, a vector that contains the ~1 kb intron A of the CMVIE promoter upstream of the vaccine insert. To determine whether this intron was necessary for high levels of vaccine expression, pGA2 vectors lacking intron A were constructed expressing the JS2 and JS5 vaccine inserts. In expression tests, pGA2 proved to have as good an expression pattern as pGA1 for JS2 (FIG. 11). In contrast to this result, JS5 was expressed much more effectively by pGA1 than pGA2 (FIG. 11). For the JS5 insert, the absence of intron A resulted in 2-3-fold lower levels of expression than in the presence of intron A.

EXAMPLE 9

Testing for the Efficacy of the Safety Mutations in the Vaccine Inserts JS2 and JS5

The three point mutations in RT (Table 2) completely abolished detectable levels of reverse transcriptase activity for JS2 and JS5. A highly sensitive reverse transcriptase assay was used in which the product of reverse transcription was amplified by PCR (Yamamoto, Folks, Heneine, 1996). This assay can detect reverse transcriptase in as few as 10 viral particles. Reverse transcriptase assays were conducted on the culture supernatants of transiently transfected cells. Reverse transcriptase activity was readily detected for as few as 10 particles ($4 \times 10^{-3}$ pg of p 24) in the JS 1 vaccine but could not be detected for the JS2 or JS5 inserts.

The deletions and zinc finger mutations in the JS2 and JS5 vaccine inserts (Table 2) reduced the levels of viral RNA in particles by at least 1000-fold. Particles pelleted from the supernatants of transiently transfected cells were tested for the efficiency of the packaging of viral RNA. The VLPs were treated with DNase, RNA was extracted and the amount of RNA standardized by p24 levels before RT PCR. The RT PCR reaction was followed by nested PCR using primers specific for viral sequences. End point dilution of the VLP RNA was compared to the signal obtained from RNA packaged in wt HIV-1 Bal virus.

Packaging for both JS2 and JS5 was restricted by the deletions in the plasmid by 500-1000-fold, as summarized below:

TABLE 3

Packaging of viral RNA is reduced in pGA2/JS2 and pGA1/JS5 VLPs

| Vaccine Construct | Deletions/Mutations | Copies vRNA relative to wt HIV-1 bal |
|---|---|---|
| HIV-1 bal | Wt | 1 |
| pGA1/JS1 VLP | Deleted: LTRs, int, vif, vpr, nef | .002 |
| pGA1/JS2 VLP | Deleted: LTRs, int, vif, vpr, nef, Mutations in Zn fingers and RT | .0001 |
| pGA1/JS4 VLP | Deleted: LTRs, int, vif, vpr, nef | .001 |
| pGA1/JS5 VLP | Deleted: LTRs, int, vif, vpr, nef, env; Mutations in Zn fingers and RT | .001 |

The zinc finger mutations decreased the efficiency of packaging for the JS2 particles a further 20-fold but did not further affect the efficiency of packaging for the JS5 particles. This pattern of packaging was reproducible for particles produced in independent transfections.

EXAMPLE 10

Western Blot Analyses of Protein Expression

Figure 12A:
FIGS. 12A-12D shows Western blots of cell lysates and tissue culture supernatants from 293T cells transfected with (1) mock, (2) pGA2/JS2, and (3) pGA1/JS5, where the primary antibody was pooled from anti-HIV Ig from infected patients (FIG. 12A), anti-p24 (FIG. 12B), anti-gp120 (FIG. 12C), and anti-RT (FIG. 12D) respectively.
Figure 12B:
Figure 12C:
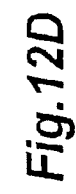
Figure 12D:

Western blot analyses, shown in FIGS. 12A-D, revealed the expected patterns of expression of pGA2/JS2 and pGA1/JS5. Both immature and mature proteins were observed in cell lysates, whereas only the mature forms of Gag and Env were found in the VLP-containing lysates (FIGS. 12B and 12C). Reverse transcriptase was readily detected in cell lysates (FIG. 12D).

EXAMPLE 11 pGA2/89.6 SHIV Vector Construction

Figure 13:
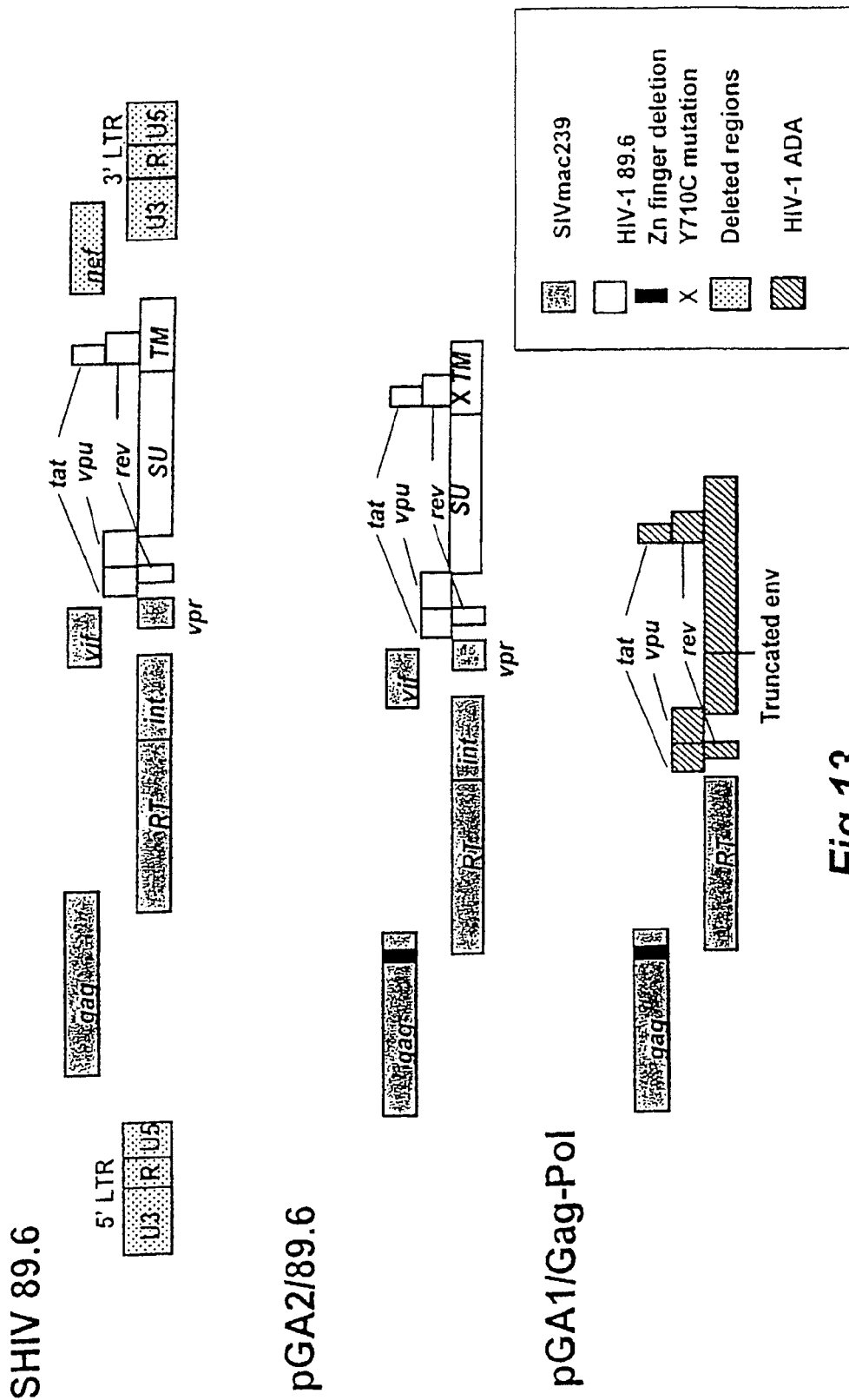
FIG. 13 illustrates pGA.

Initial immunogenicity trials have been conducted with a SHIV-expressing VLP rather than the HIV-1-expressing vaccine plasmids. SHIVs are hybrids of simian and human immunodeficiency virus sequences that grow well in macaques (Li et al., 1992). By using a SHIV, vaccines that are at least partially of HIV-1 origin can be tested for efficacy in macaque models.

pGA2/89.6 (also designated as pGA2/M2) expresses sequences from SHIV-89.6 (Reimann, Li, Voss, et al., 1996; Reimann, Li, Veazey, et al., 1996). The 89.6 Env represents a patient isolate (Collman et al., 1992). The SHIV-89.6 virus is available as a highly pathogenic challenge stock, designated SHIV-89.6P (Reimann, Li, Voss, et al., 1996; Reimann, Li, Veazey, et al., 1996), which allows a rapid determination of vaccine efficacy. The SHIV-89.6P challenge can be administered via both intrarectal and intravenous routes. SHIV-89.6 and SHIV-89.6P do not generate cross-neutralizing antibody.

pGA2/89.6 (FIG. 13) has many of the design features of pGA2/JS2. Both express immunodeficiency virus VLPs: HIV-1 VLP in the case of pGA2/JS2, while the VLP expressed by pGA2/89.6 is a SHIV VLP. The gag-pol sequences in pGA2/89.6 are from SIV239, while the tat, rev, and env sequences are from HIV-1-89.6. pGA2/89.6 also differs from pGA2/JS2 in that the integrase, vif and vpr sequences have not been deleted, nor has the reverse transcriptase gene been inactivated by point mutations. Finally, the zinc fingers in NC have been inactivated by a deletion and not by point mutations.

pGA1/Gag-Pol was also constructed to allow evaluation of the protective efficacy of a Gag-Pol expressing vector with the Gag-Pol-Env expresssing pGA2/89.6. This vector was constructed from pGA1/JS5 and pGA2/89.6 (FIG. 13).

EXAMPLE 12

Figure 14:
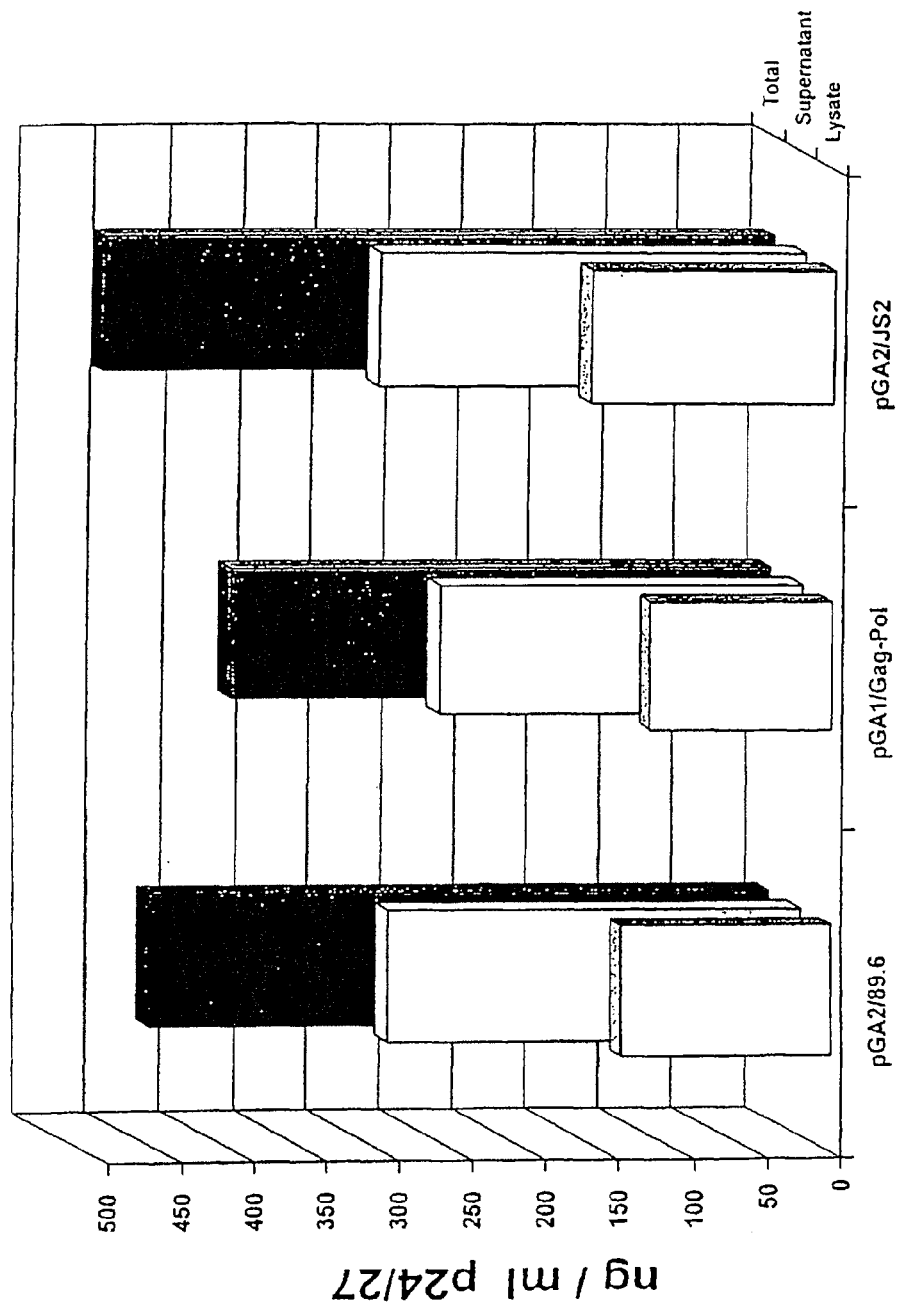
FIG. 14 compares Gag expression levels between pGA2/89.6, pGA1/Gag-Pol and pGA2/JS2. Comparative studies for expression were performed on transiently transfected 293T cells.

Comparison of the Expression of PGA2/89.6 SHIV Plasmid with pGA2/JS2 Expression Both pGA2/89.6 and pGA1/Gag-Pol expressed similar levels of Gag as pGA2/JS2. Comparative studies for expression were performed on transiently transfected 293T cells. Analyses of the lysates and supernatants of transiently transfected cells revealed that both plasmids expressed similar levels of capsid antigen (FIG. 14). The capsid proteins were quantified using commercial antigen capture ELISA kits for HIV-1 p24 and SIV p27.

EXAMPLE 13 pGA2/89.6 SHIV Vaccine Protocol

A rhesus macaque model was used to investigate the ability of systemic DNA priming followed by a recombinant MVA (rMVA) booster to protect against a mucosal challenge with the SHIV-89.6P challenge strain (Amara et al, 2001).

The DNA component of the vaccine (pGA2/89.6) was made as described in Example 11 and and expressed eight immunodeficiency virus proteins (SIV Gag, Pol, Vif, Vpx, and Vpr and HIV Env, Tat, and Rev) from a single transcript using the subgenomic splicing mechanisms of immunodeficiency viruses. The rMVA booster (89.6-MVA) was provided by Dr. Bernard Moss (NIH) and expresses both the HIV 89.6 Env and the SIV 239 Gag-Pol, inserted into deletion II and deletion III of MVA respectively, under the control of vaccinia virus early/late promoters (Wyatt and Moss, unpublished results). The 89.6 Env protein was truncated for the C-terminal 115 amino acids of gp41. The modified H5 promoter controlled the expression of both foreign genes.

The vaccination trial compared i.d. and i.m. administration of the DNA vaccine and the ability of a genetic adjuvant, a plasmid expressing macaque GM-CSF, to enhance the immune response raised by the vaccine inserts. Vaccination was accomplished by priming with DNA at 0 and 8 weeks and boosting with rMVA at 24 weeks. For co-delivery of a plasmid expressing GM-CSF, 1-100 µl i.d. inoculation was given with a solution containing 2.5 mg of pGA2/89.6 and 2.5 mg per ml of pGM-CSF.

I.d. and i.m. deliveries of DNA were compared for two doses, 2.5 mg and 250 µg of DNA. Four vaccine groups of six rhesus macaques were primed with either 2.5 mg (high-dose) or 250 µg (low-dose) of DNA by intradermal (i.d.) or intramuscular (i.m.) routes using a needleless jet injection device (Bioject, Portland Oreg.). The 89.6-MVA booster immunization ($2 \times 10^8$ pfU) was injected with a needle both i.d. and i.m. A control group included two mock immunized animals and two naive animals. The vaccination protocol is summarized as follows:

TABLE 4

Vaccination Trial

| Group, (# macaque) | Prime at 0 and 8 weeks | Immunogen | Boost at 24 weeks | Immunogen |
|---|---|---|---|---|
| 1 (6) | i.d. bioject | 2.5 mg VLP DNA | i.d. + i.m. | MVA gag-pol-env |
| 2 (6) | i.m. bioject | 2.5 mg VLP DNA | i.d. + i.m. | MVA gag-pol-env |
| 3 (6) | i.d bioject | 250 ug VLP DNA | i.d. + i.m | MVA gag-pol-env |
| 4 (6) | i.m. bioject | 250 ug VLP DNA | i.d. + i.m. | MVA gag-pol-env |
| 5 (6) | i.d. bioject | 2.5 mg gag-pol DNA | i.d. + i.m. | MVA gag-pol |
| 6 (6) | i.d. bioject | 250 ug gag-pol DNA | i.d. + i.m. | MVA gag-pol |
| 7 (6) | i.d bioject | 250 ug VLP DNA + 250 ug GM-CSF DNA | i.d. + i.m. | MVA gag-pol-env |
| 8 (5) | i.d. bioject i.d. + i.m.control MVA | 2.5 mg control DNA control MVA | i.d. + i.m. | control MVA |
| 9 (4) | i.d., bioject | 250 ug control DNA + 250 ug GM-CSF DNA | i.d. + i.m. | MVA gag-pol-env |
| 10 (6) | i.d. + i.m. | MVA gag-pol-env | i.d. + i.m. | MVA gag-pol-env |

VLP DNA expresses all SHIV-89.6 proteins except Nef, truncated for LTRs, $2^{nd}$ ZN++ finger, mutated to express cell surface Env; gag-pol DNA expresses SIV mac 239 gag-pol; MVA gag-pol-env expresses 89.6 truncated env and SIV mac 239 gag-pol; MVA gag-pol expresses SIVmac239 gag-pol; MVA dose is $1 \times 10^8$ pfu Animals were challenged seven months after the rMVA booster to test whether the vaccine had generated long-term immunity. Because most HIV-1 infections are transmitted across mucosal surfaces, an intrarectal challenge was administered to test whether the vaccine could control a mucosal immunodeficiency virus challenge. Briefly, the challenge stock ($5.7 \times 10^9$ copies of viral RNA per ml) was produced by one i.v. followed by one intrarectal passage in rhesus macaques of the original SHIV-89.6P stock. Lymphoid cells were harvested from the intrarectally infected animal at peak viremia, CD8-depleted and mitogen-stimulated for stock production. Prior to intrarectal challenge, fasted animals were anesthetized (ketamine, 10 mg/kg) and placed on their stomach with the pelvic region slightly elevated. A feeding tube [8Fr (2.7 mm)×16 inches (41 cm), Sherwood Medical, St. Louis, Mo.] was inserted into the rectum for a distance of 15-20 cm. Following insertion of the feeding tube, a syringe containing 20 intrarectal infectious doses in two ml of RPMI-1640 plus 10% fetal bovine serum (FBS) was attached to the tube and the inoculum slowly injected into the rectum. Following delivery of the inoculum, the feeding tube was flushed with 3.0 ml of RPMI without fetal calf serum and then slowly withdrawn. Animals were left in place, with pelvic regions slightly elevated, for a period of ten minutes following the challenge.

EXAMPLE 14

Vaccine-Raised T-Cell Responses

DNA priming followed by rMVA boosting generated high frequencies of virus-specific T cells that peaked at one week following the rMVA booster, as shown in FIG. 15. The frequencies of T cells recognizing the Gag-CM9 epitope were assessed using Mamu-A*01-tetramers; and the frequencies of T cells recognizing epitopes throughout Gag and Env, using pools of overlapping Gag and Env peptides and an enzyme linked immunospot (ELISPOT) assay.

For tetramer analyses, approximately $1 \times 10^6$ PBMC were surface stained with antibodies to CD3 (FN-18, Biosource International, Camarillo, Calif.), CD8 (SK1, Becton Dickinson, San Jose, Calif.), and Gag-CM9 (CTPYDINQM)-Mamu-A*01 tetramer conjugated to FITC, PerCP and APC respectively, in a volume of 100 µl at 8-10° C. for 30 min. Cells were washed twice with cold PBS containing 2% FBS, fixed with 1% paraformaldehyde in PBS and analyses acquired within 24 hrs. on a FACScaliber (Becton Dickinson, San Jose, Calif.). Cells were initially gated on lymphocyte populations using forward scatter and side scatter and then on CD3 cells. The CD3 cells were then analyzed for CD8 and tetramer-binding cells. Approximately 150,000 lymphocytes were acquired for each sample. Data were analyzed using FloJo software (Tree Star, Inc. San Carlos, Calif.).

For IFN-γ ELISPOTs, MULTISCREEN 96 well filtration plates (Millipore Inc. Bedford, Mass.) were coated overnight with anti-human IFN-γ antibody (Clone B27, Pharmingen, San Diego, Calif.) at a concentration of 2 µg/ml in sodium bicarbonate buffer (pH 9.6) at 8-10° C. Plates were washed two times with RPMI medium then blocked for one hour with complete medium (RPMI containing 10% FBS) at 37° C. Plates were washed five more times with plain RPMI medium and cells were seeded in duplicate in 100 µl complete medium at numbers ranging from $2 \times 10^4$ to $5 \times 10^5$ cells per well. Peptide pools were added to each well to a final concentration of 2 µg/ml of each peptide in a volume of 100 µl in complete medium. Cells were cultured at 37° C. for about 36 hrs under 5% $CO_2$. Plates were washed six times with wash buffer (PBS with 0.05% Tween-20) and then incubated with 1 µg of biotinylated anti-human IFN-γ antibody per ml (clone 7-86-1, Diapharma Group Inc., West Chester, Ohio) diluted in wash buffer containing 2% FBS. Plates were incubated for 2 hrs at 37° C. and washed six times with wash buffer. Avidin-HRP (Vector Laboratories Inc, Burlingame, Calif.) was added to each well and incubated for 30-60 min at 37° C. Plates were washed six times with wash buffer and spots were developed using stable DAB as substrate (Research Genetics Inc., Huntsville, Ala.). Spots were counted using a stereo dissecting microscope. An ovalbumin peptide (SIINFEKL) was included as a control in each analysis. Background spots for the ovalbumin peptide were generally <5 for $5 \times 10^5$ PBMC s. This background when normalized for $1 \times 10^6$ PBMC is <10. Only ELISPOT counts of twice the background ($\geq 20$) were considered significant. The frequencies of ELISPOTs are approximate because different dilutions of cells have different efficiencies of spot formation in the absence of feeder cells (34). The same dilution of cells was used for all animals at a given time point, but different dilutions were used to detect memory and peak effector responses.

Simple linear regression was used to estimate correlations between post-booster and post-challenge ELISPOT responses, between memory and post-challenge ELISPOT responses, and between log viral loads and ELISPOT frequencies in vaccinated groups. Comparisons between vaccine and control groups were performed by means of 2-sample t-tests using log viral load and log ELISPOT responses. Comparisons of ELISPOTs or log viral loads between A*01 and non A*01 macaques were done using 2-sample t-tests. Two-way analyses of variance were used to examine the effects of dose and route of administration on peak DNA/MVA ELISPOTs, memory DNA/MVA ELISPOTs, and on logarithmically transformed Gag antibody data.

Figure 15A:
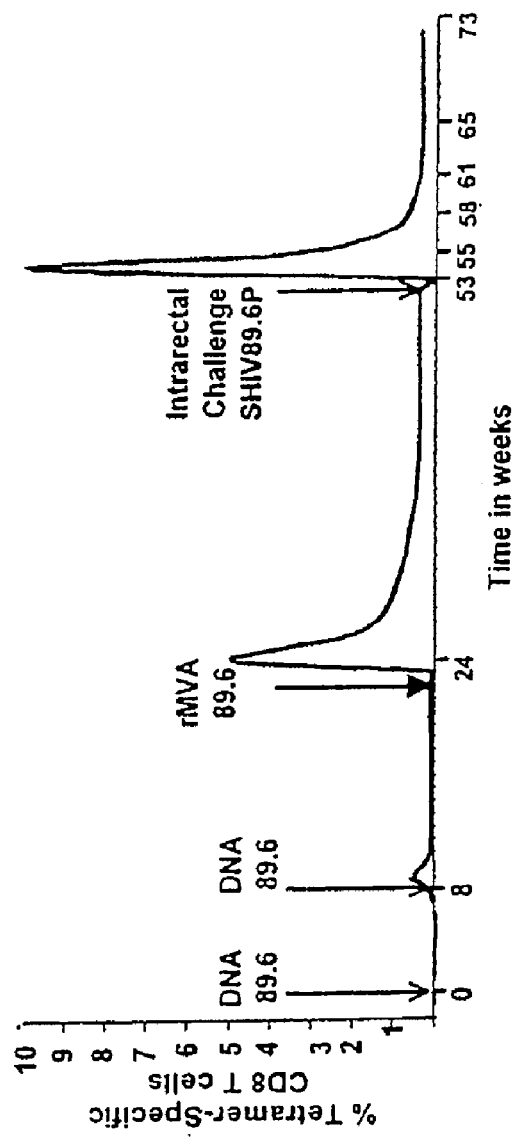
FIGS. 15A-15C show the temporal frequencies of Gag-specific T cells.
Figure 15B:
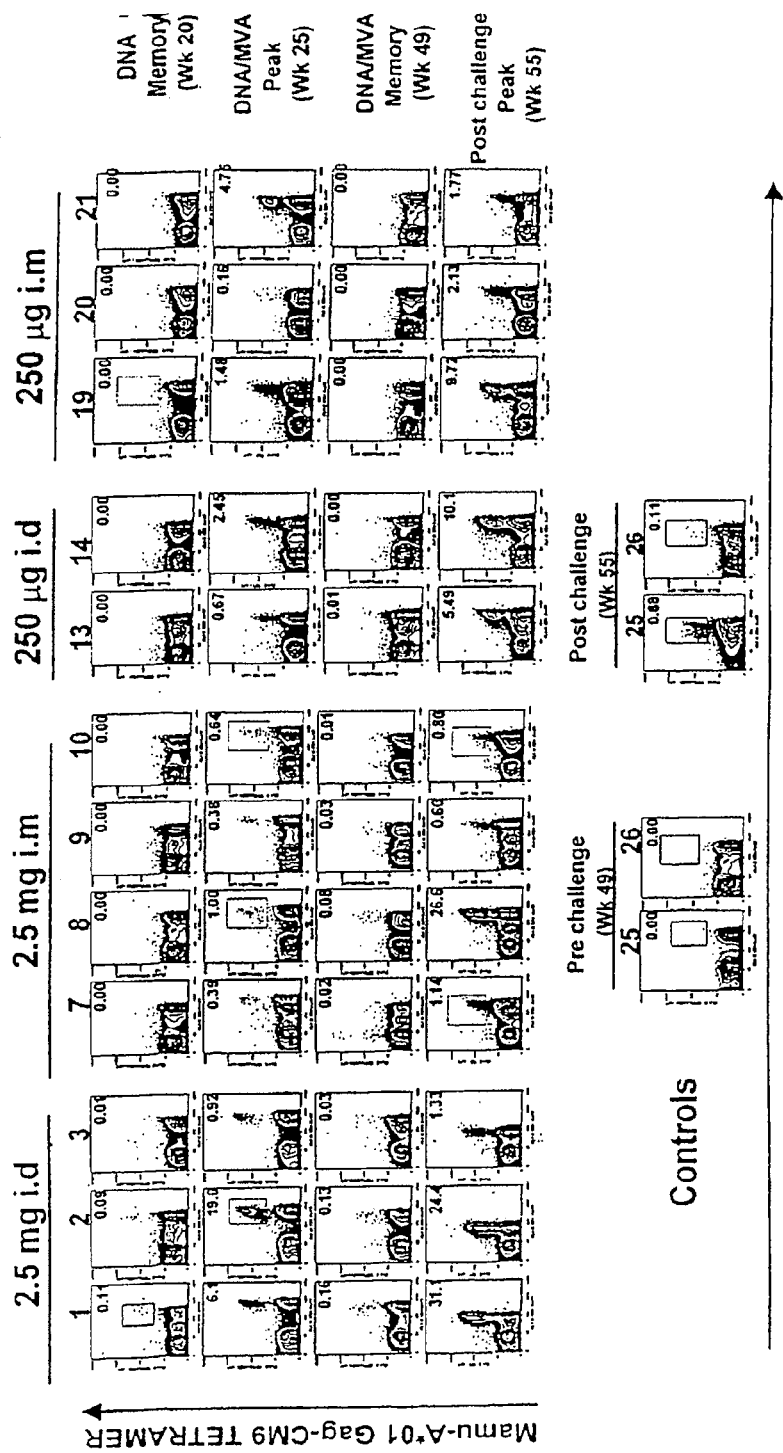
Figure 15C:
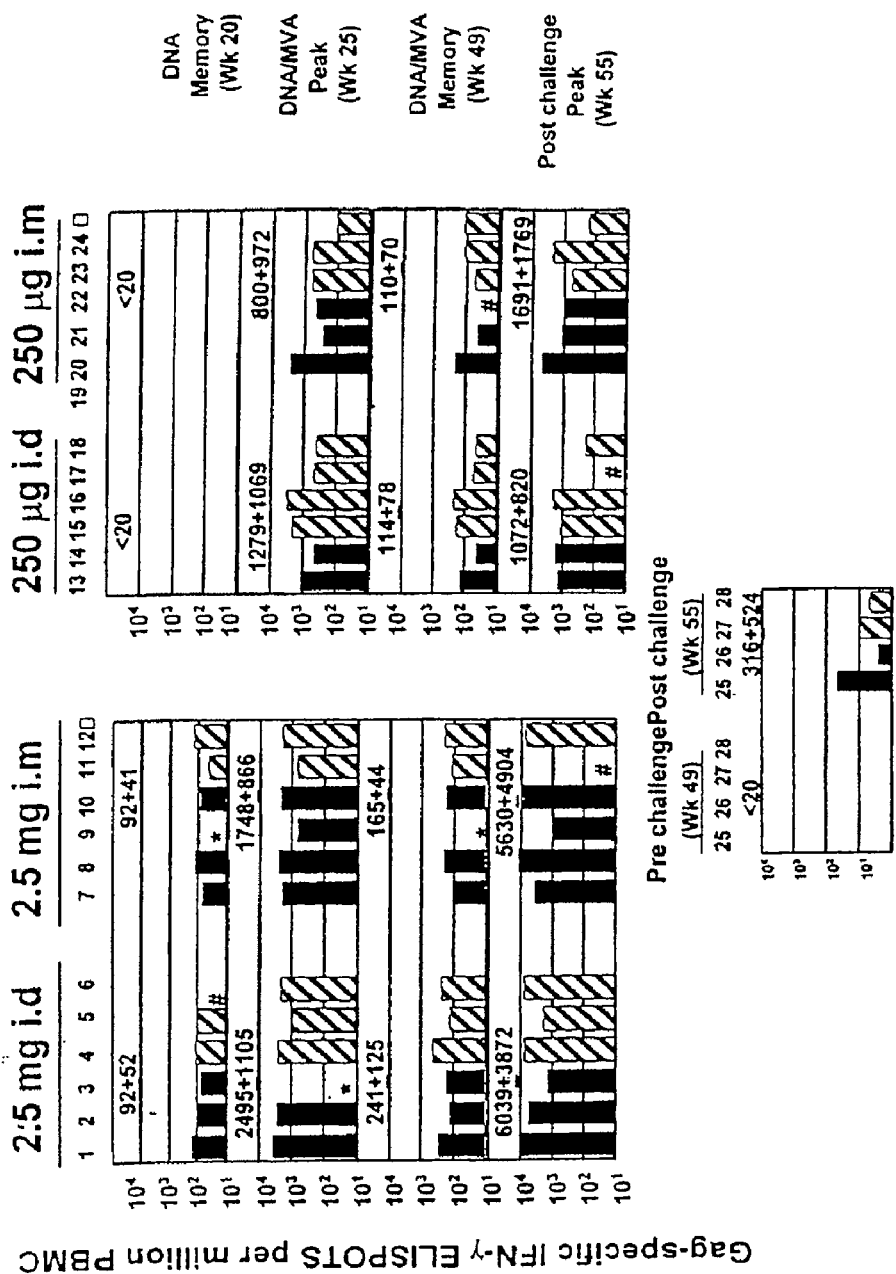

Gag-CM9 tetramer analyses were restricted to macaques that expressed the Mamu-A*01 histocompatibility type, whereas ELISPOT responses did not depend on a specific histocompatibility type. Temporal T cell assays were designed to score both the acute (peak of effector cells) and long-term (memory) phases of the T cell response (FIG. 15A). As expected, the DNA immunizations raised low levels of memory cells that expanded to high frequencies within one week of the rMVA booster (FIG. 15). In Mamu-A*01 macaques, cells specific to the Gag-CM9 epitope expanded to frequencies as high as 19% of total CD8 T cells (see animal 2 FIG. 15B). This peak of specific cells underwent a >10-fold contraction into the DNA/MVA memory pool (FIGS. 15A and B). ELISPOTs for three pools of Gag peptides also underwent a major expansion (frequencies up to 4000 spots for $1 \times 10^6$ PBMC) before contracting into the DNA/MVA memory response (FIG. 15C). The frequencies of ELISPOTs were the same in macaques with and without the A*01 histocompatibility type (P>0.2.). At both peak and memory phases of the vaccine response, the rank order for the height of the ELISPOTs in the different vaccine groups was 2.5 mg i.d.>2.5 mg i.m.>250 µg i.d.>250 µg i.m. (FIG. 15C). The IFN-γ-ELISPOTs included both CD4 and CD8 cells (work in progress). Gag-CM9-specific CD8 cells had good lytic activity following restimulation with peptide (data not shown).

Impressively, in the outbred population of animals, pools of peptides throughout Gag and Env stimulated IFN-γ-ELISPOTs (FIG. 16A). The breadth of the cellular response was tested at 25 weeks after the rMVA boost, a time when vaccine-raised T cells were in memory. Seven out of 7 pools of Gag peptides and 16 out of 21 pools of Env peptides were recognized by T cells in vaccinated animals. Of the five Env pools that were not recognized, two have been recognized in a macaque DNA/MVA vaccine trial at the U.S. Centers for Disease Control (data not shown). The remaining three (pools 19-21) had been truncated in our immunogens (Amara et al, 2001, submitted) and served as negative controls. Gag and Env ELISPOTs had overall similar frequencies in the DNA/MVA memory response (FIG. 16B). The greatest breadth, of response was in high-dose i.d. DNA-primed animals where on average 10 peptide pools (4.5 Gag and 5.3 Env) were recognized. The rank order of the vaccine groups for breadth was the same as for the peak DNA/MVA response: 2.5 mg i.d.>2.5 mg i.m.>250 µg i.d.>250 µg i.m. (FIG. 16B).

EXAMPLE 15

Challenge and Protection Against Aids

The highly pathogenic SHIV-89.6P challenge was administered intrarectally at 7 months after the rMVA booster, when vaccine-raised T cells were in memory (FIG. 15).

Determination of SHIV copy number: viral RNA from 150 µl of ACD anticoagulated plasma was directly extracted with the QIAamp Viral RNA kit (Qiagen), eluted in 60 µl AVE buffer, and frozen at −80° C. until SHIV RNA quantitation was performed. 5 µl of purified plasma RNA was reverse transcribed in a final 20 µl volume containing 50 mM KCl, 10 mM Tris-HCl, pH 8.3, 4 mM $MgCl_2$, 1 mM each dNTP, 2.5 µM random hexamers, 20 units MultiScribe RT, and 8 units RNase inhibitor. Reactions were incubated at 25° C. for 10 min., followed by incubation at 42° C. for 20 min. and inactivation of reverse transcriptase at 99° C. for 5 min. The reaction mix was adjusted to a final volume of 50 µl containing 50 mM KCl, 10 mM Tris-HCl, pH 8.3, 4 mM $MgCl_2$, 0.4 mM each dNTP, 0.2 µM forward primer, 0.2 µM reverse primer, 0.1 µM probe and 5 units AmpliTaq Gold DNA polymerase (all reagents from Perkin Elmer Applied Biosystems, Foster City, Calif.). The primer sequences within a conserved portion of the SIV gag gene are the same as those described previously (Staprans, S., et al., 1996).

A Perkin Elmer Applied Biosystems 7700 Sequence Detection System was used with the PCR profile: 95° C. for 10 min., followed by 40 cycles at 93° C. for 30 sec., 59.5° C. for 1 min. PCR product accumulation was monitored using the 7700 sequence detector and a probe to an internal conserved gag gene sequence, where FAM and Tamra denote the reporter and quencher dyes. SHIV RNA copy number was determined by comparison to an external standard curve consisting of virion-derived SIVmac239 RNA quantified by the SIV bDNA method (Bayer Diagnostics, Emeryville, Calif.). All specimens were extracted and amplified in duplicate, with the mean result reported. With a 0.15-ml plasma input, the assay has a sensitivity of $10^3$ copies RNA/ml plasma, and a linear dynamic range of $10^3$ to $10^8$ RNA copies ($R^2$=0.995). The intra-assay coefficient of variation is <20% for samples containing >$10^4$ SHIV RNA copies/ml, and <25% for samples containing $10^3$-$10^4$ SHIV RNA copies/ml. In order to more accurately quantitate low SHIV RNA copy number in vaccinated animals at weeks 16 and 20, the following modifications to increase the sensitivity of the SHIV RNA assay were made: 1) Virions from ≦1 ml of plasma were concentrated by centrifugation at 23,000 g, 10° C. for 150 minutes and viral RNA was extracted; 2) A one-step RT-PCR method was used. Absolute SHIV RNA copy numbers were determined by comparison to the same SIVmac239 standards. These changes provided a reliable quantitation limit of 300 SHIV RNA copies/ml, and gave SHIV RNA values that were highly correlated to those obtained by the first method used (r=0.91, p<0.0001).

Challenge results: The challenge infected all of the vaccinated and control animals. However, by two weeks post-challenge, titers of plasma viral RNA were at least 10-fold lower in the vaccine groups (geometric means of $1 \times 10^7$ to $5 \times 10^7$) than in the control animals (geometric mean of $4 \times 10^8$) (FIG. 19A). By 8 weeks post-challenge, both high-dose DNA-primed groups and the low-dose i.d. DNA-primed group had reduced their geometric mean loads to about 1000 copies of viral RNA per ml. At this time the low-dose i.m. DNA-primed group had a geometric mean of $6 \times 10^3$ copies of viral RNA and the non-vaccinated controls, a geometric mean of $2 \times 10^6$. By 20 weeks post-challenge, even the low-dose i.m. group had reduced its geometric mean copies of viral RNA to 1000. At this time, the unvaccinated controls were succumbing to AIDS. Among the 24 vaccinated animals, only one animal, in the low dose i.m. group, had intermittent viral loads above $1 \times 10^4$ copies per ml (FIG. 19D).

Figure 19B:
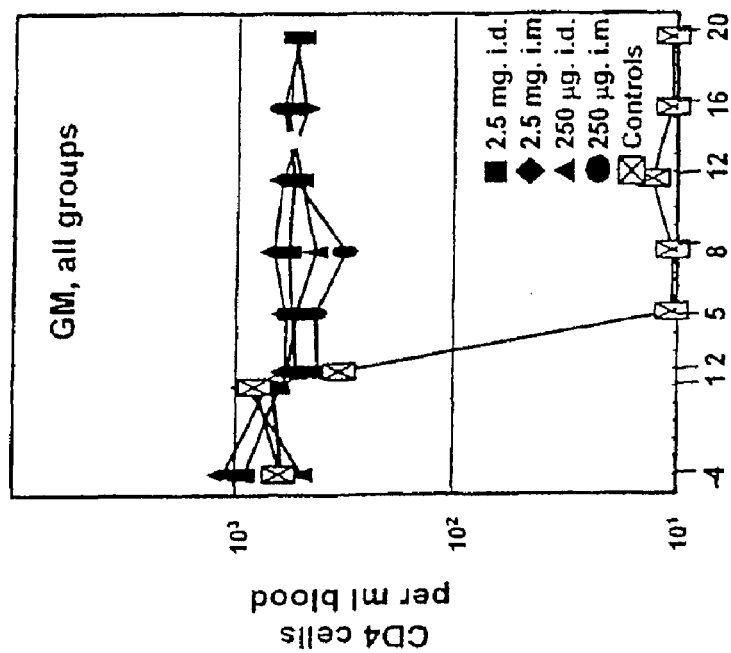
FIGS. 19A-19E show temporal viral loads, CD4 counts and survival after challenge of vaccinated and control animals.
Figure 19A:
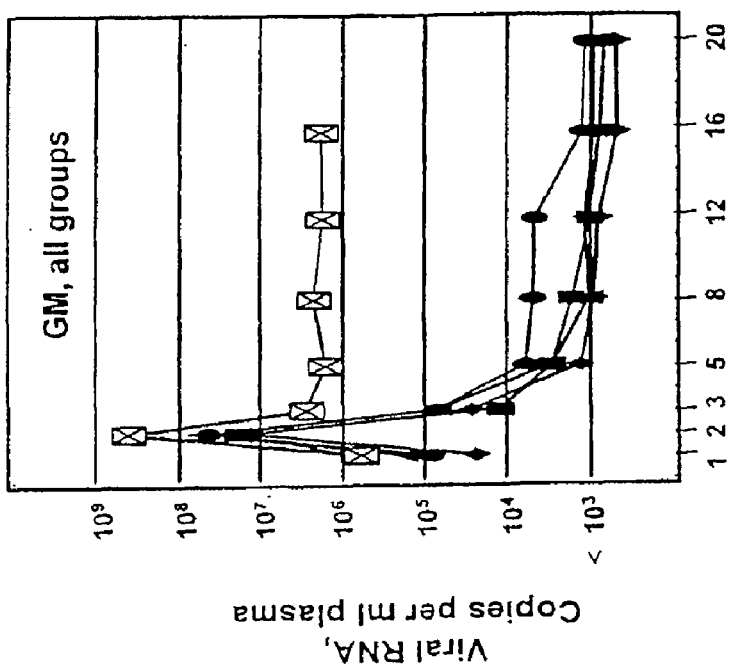
Figure 19C:
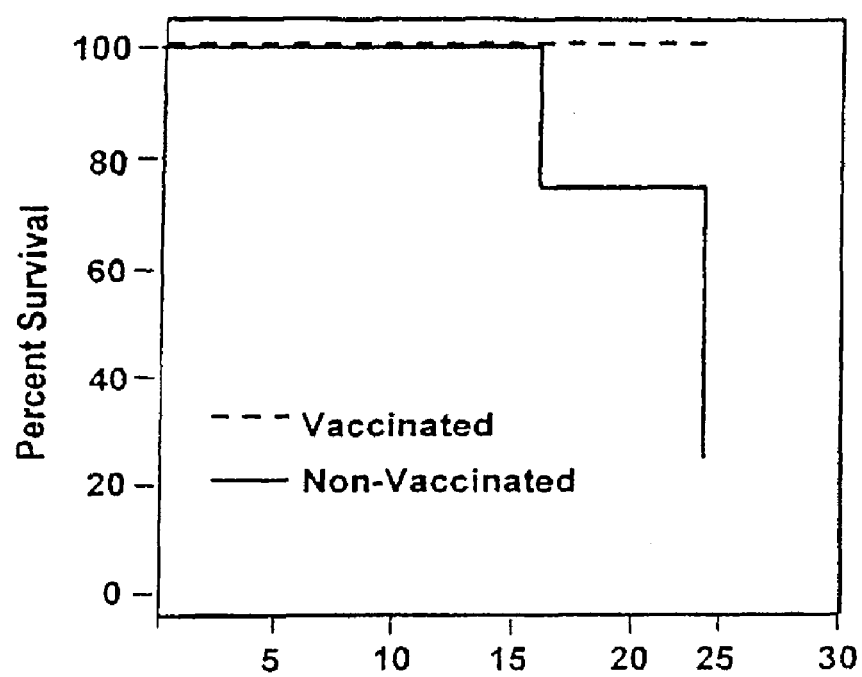
Figure 19D:
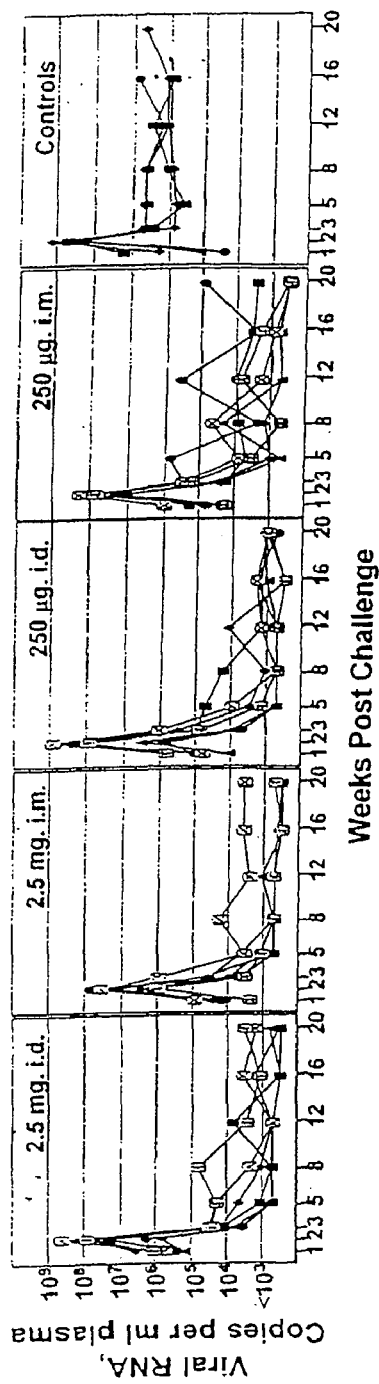
Figure 19E:
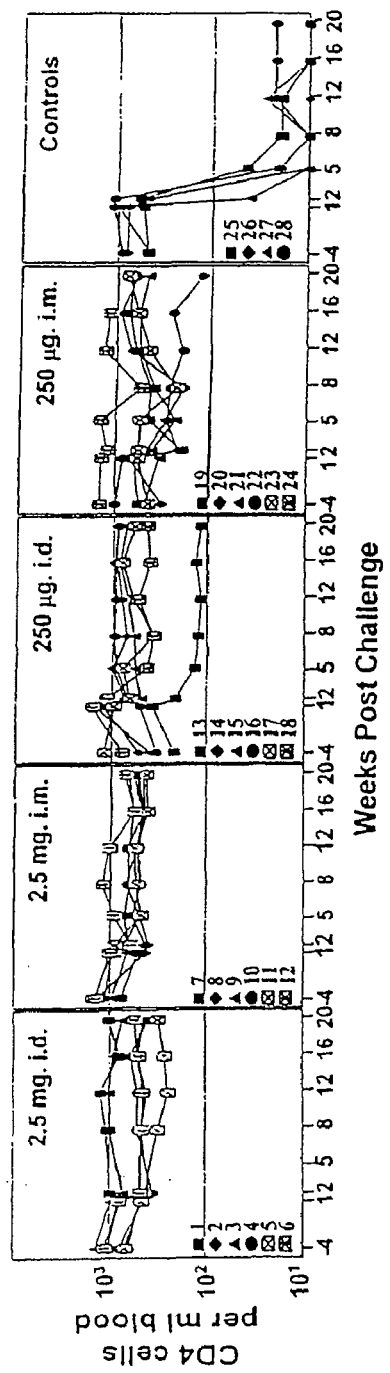

The rapid reduction of viral loads protected the vaccinated macaques against the loss of CD4 cells and the rapid onset of AIDS (FIGS. 19B, 19C, 19E). By 5 weeks post-challenge, all of the non-vaccinated controls had undergone the profound depletion of CD4 cells that is characteristic of SHIV-89.6P infections (FIG. 19B). All of the vaccinated animals maintained their CD4 cells with the exception of animal 22 (see above), which underwent a slow CD4 decline (FIG. 19E). By 23 weeks post-challenge, three of the four control animals had succumbed to AIDS (FIG. 19C). These animals had variable degrees of enterocolitis with diarrhea, cryptosporidiosis, colicystitis, enteric campylobacter infection, spenomegaly, lymphadenopathy, and SIV-associated giant cell pneumonia. In contrast, all 24 vaccinated animals have maintained their health.

Intracellular cytokine assays: Approximately $1 \times 10^6$ PBMC; were stimulated for one hour at 37° C. in 5 ml polypropylene tubes with 100 µg of Gag-CM9 peptide (CT-PYDINQM; SEQ ID NO:44) per ml in a volume of 100 µl RPMI containing 0.1% BSA and anti-human CD28 and anti-human CD49d (Pharmingen, Inc. San Diego, Calif.) costimulatory antibodies (1 µg/ml). 900 RPMI containing 10% FBS and monensin (10 µg/ml) was added and the cells cultured for an additional 5 hrs at 37° C. at an angle of 5 degrees under 5% $CO_2$. Cells were surface stained with antibodies to CD8 conjugated to PerCP (clone SK1, Becton Dickinson) at 8°-10° C. for 30 min., washed twice with cold PBS containing 2% FBS, fixed and permeabilized with Cytofix/Cytoperm solution (Pharmingen, Inc.). Cells were then incubated with antibodies to human CD3 (clone FN-18, Biosource International, Camarillo, Calif.) and IFN—γ (Clone B27, Pharmingen) conjugated to FITC and PE, respectively, in Perm wash solution (Pharmingen) for 30 min at 4° C. Cells were washed twice with Perm wash, once with plain PBS, and resuspended in 1% para-formaldehyde in PBS. Approximately 150,000 lymphocytes were acquired on the FACScaliber and analyzed using FloJo software.

Proliferation assay: Approximately 0.2 million PBMC were stimulated with appropriate antigen in triplicate in a volume of 200 µl for five days in RPMI containing 10% FCS at 37° C. under 5% $CO_2$. Supernatants from 293T cells transfected with the DNA expressing either SHIV-89.6 Gag and Pol or SHIV-89.6 Gag, Pol and Env were used directly as antigens. Supernatants from mock DNA (vector alone) transfected cells served as negative controls. On day six cells were pulsed with 1 µCi of tritiated-thymidine per well for 16-20 hrs. Cells were harvested using an automated cell harvester (TOMTEC, Harvester 96, Model 1010, Hamden, Conn.) and counted using a Wallac 1450 MICROBETA Scintillation counter (Gaithersburg, Md.). Stimulation indices are the counts of tritiated-thymidine incorporated in PBMC stimulated with 89.6 antigens divided by the counts of tritiated-thymidine incorporated by the same PBMC stimulated with mock antigen.

Figure 20A:
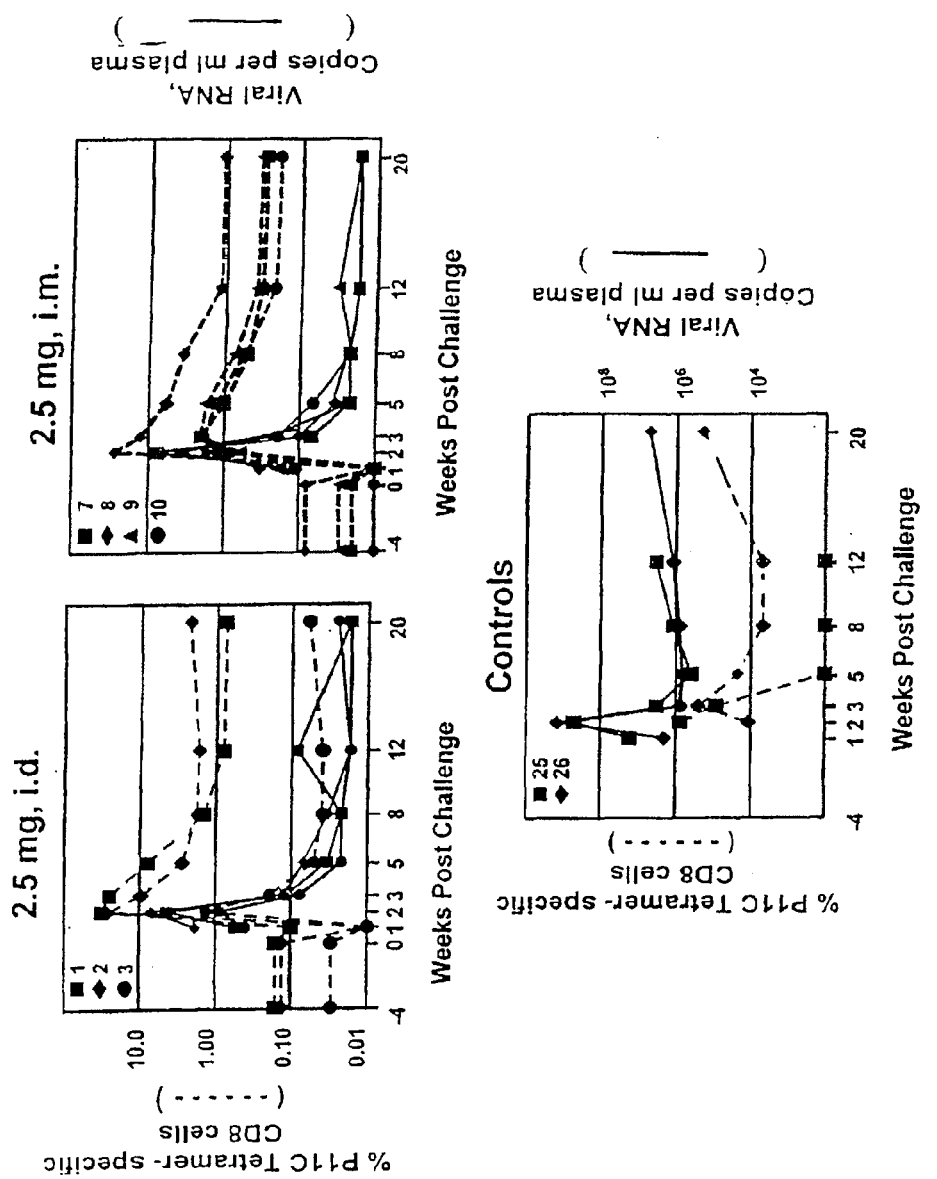
FIGS. 20A-20C show Post-challenge T-cell responses in vaccine and control groups.
Figure 20B:
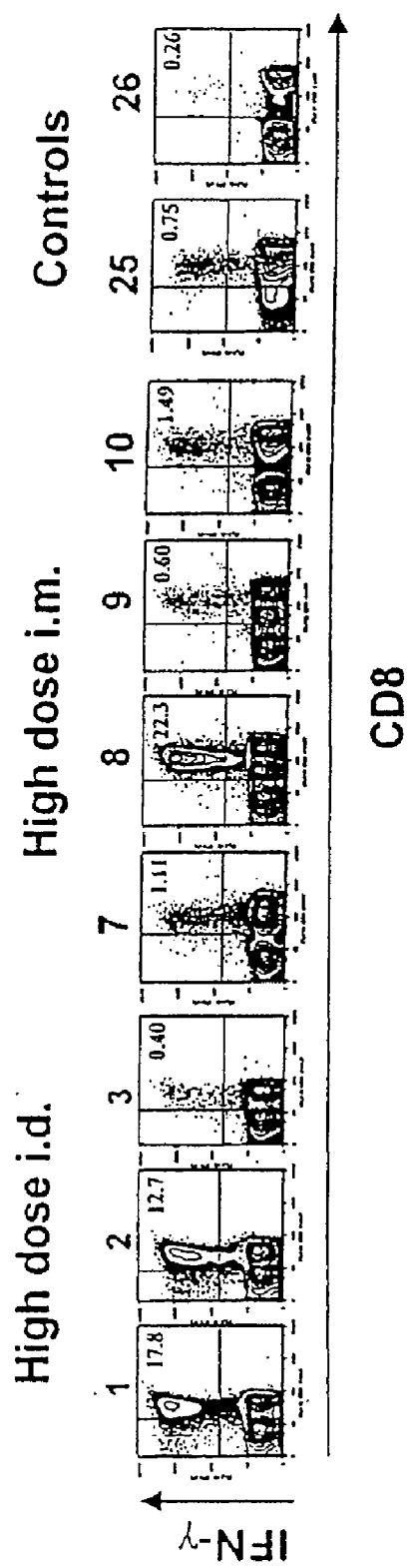

Post-challenge T cell results: Containment of the viral challenge was associated with a burst of antiviral T cells (FIG. 15; FIG. 20A). At one-week post challenge, the frequency of tetramer+ cells in the peripheral blood had decreased, potentially reflecting the recruitment of specific T cells to the site of infection (FIG. 20A). However, by two weeks post-challenge, tetramer+ cells in the peripheral blood had expanded rapidly, to frequencies as high, or higher, than after the MVA booster (FIGS. 15, 20A). The majority of the tetramer+ cells produced IFN-γ in response to a 6-hour stimulation with peptide Gag-CM9 (FIG. 20B) and did not have the "stunned" IFN-γ negative phenotype sometimes observed in chronic viral infections. The post-challenge burst of T cells contracted concomitant with the decline of the viral load. By 12 weeks post-challenge, virus-specific T cells were present at approximately one tenth of their peak height (FIGS. 15A, 20A, and data not shown). The height of the peak DNA/MVA-induced ELISPOTs presaged the height of the post-challenge T cell response as measured by ELISPOTs (r=+0.79, P<0.0001). In contrast to the vigorous secondary response in the vaccinated animals, the naive animals mounted a modest primary response (FIGS. 15B, 15C and 20A). Tetramer+ cells peaked at less than 1% of total CD8 cells (FIG. 20A), and IFN-γ-producing T cells were present at a mean frequency of about 300 as opposed to the much higher frequencies of 1000 to 6000 in the vaccine groups (FIG. 15C) (P<0.05). The tetramer+cells in the control group, like those in the vaccine group, were largely IFN-γ producing following stimulation with the Gag-CM9 peptide (FIG. 20B). By 12 weeks post challenge, 3 of the 4 controls had undetectable levels of IFN-γ-producing T cells (data not shown). This rapid loss of anti-viral CD8 cells in the presence of high viral loads may reflect the lack of CD4 help.

Figure 20C:
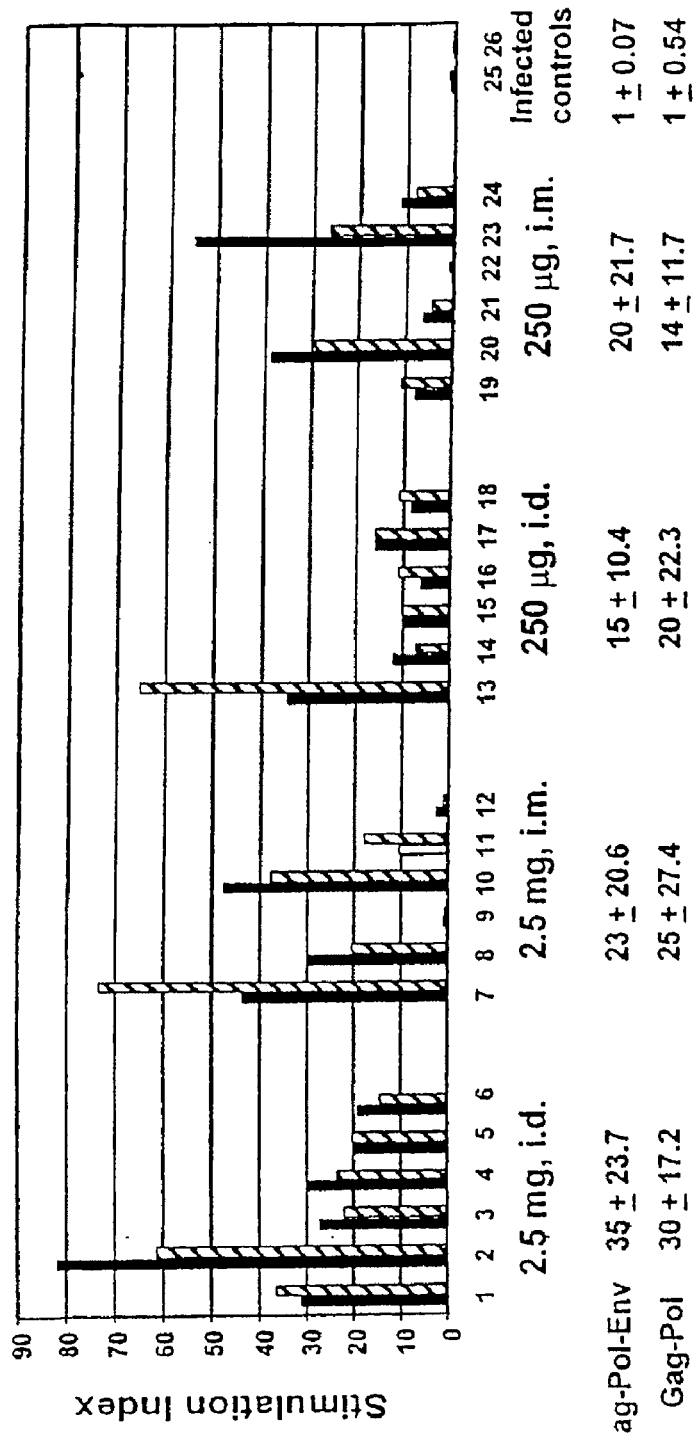

T cell proliferative responses demonstrated that virus-specific CD4 cells had survived the challenge and were available to support the antiviral immune response (FIG. 20C). At 12 weeks post-challenge, mean stimulation indices for Gag-Pol-Env or Gag-Pol proteins ranged from 35 to 14 in the vaccine groups but were undetectable in the control group. Consistent with the proliferation assays, intracellular cytokine assays demonstrated the presence of virus-specific CD4 cells in vaccinated but not control animals (data not shown). The overall rank order of the vaccine groups for the magnitude of the proliferative response was 2.5 mg i.d.>2.5 mg i.m.>250 μg i.d.>250 μg i.m.

Preservation of lymph nodes: At 12 weeks post-challenge, lymph nodes from the vaccinated animals were morphologically intact and responding to the infection whereas those from the infected controls had been functionally destroyed (FIG. 5). Nodes from vaccinated animals contained large numbers of reactive secondary follicles with expanded germinal centers and discrete dark and light zones (FIG. 5A). By contrast, lymph nodes from the non-vaccinated control animals showed follicular and paracortical depletion (FIG. 5B), while those from unvaccinated and unchallenged animals displayed normal numbers of minimally reactive germinal centers (FIG. 5C). Germinal centers occupied <0.05% of total lymph node area in the infected controls, 2% of the lymph node area in the uninfected controls, and up to 18% of the lymph node area in the vaccinated groups (FIG. 5D). The lymph node area occupied by germinal centers was about two times greater for animals receiving low-dose DNA priming than for those receiving high-dose DNA priming, suggesting more vigorous immune reactivity in the low-dose animals (FIG. 5D). At 12 weeks post-challenge, in situ hybridization for viral RNA revealed rare virus-expressing cells in lymph nodes from 3 of the 24 vaccinated macaques, whereas virus-expressing cells were readily detected in lymph nodes from each of the infected control animals (FIG. 5E). In the controls, which had undergone a profound depletion in CD4 T cells, the cytomorphology of infected lymph node cells was consistent with a macrophage phenotype (data not shown).

Temporal antibody response: ELISAs for total anti-Gag antibody used bacterial produced SIV gag p27 to coat wells (2 μg per ml in bicarbonate buffer). ELISAs for anti-Env antibody used 89.6 Env produced in transiently transfected 293T cells captured with sheep antibody against Env (catalog number 6205; International Enzymes, Fairbrook Calif.). Standard curves for Gag and Env ELISAs were produced using serum from a SHIV-89.6-infected macaque with known amounts of anti-Gag or anti-Env IgG. Bound antibody was detected using goat anti-macaque IgG-PO (catalog # YNGMOIGGFCP, Accurate Chemical, Westbury, N.Y.) and TMB substrate (Catalog # T3405, Sigma, St. Louis, Mo.). Sera were assayed at 3-fold dilutions in duplicate wells. Dilutions of test sera were performed in whey buffer (4% whey and 0.1% tween 20 in 1×PBS). Blocking buffer consisted of whey buffer plus 0.5% non-fat dry milk. Reactions were stopped with 2M $H_2SO_4$ and the optical density read at 450 nm. Standard curves were fitted and sample concentrations were interpolated as μg of antibody per ml of serum using SOFTmax 2.3 software (Molecular Devices, Sunnyvale, Calif.).

Results showed that the prime/boost strategy raised low levels of anti-Gag antibody and undetectable levels of anti-Env antibody (FIG. 22). However, post-challenge, antibodies to both Env and Gag underwent anamnestic responses with total Gag antibody reaching heights approaching one mg per ml and total Env antibody reaching heights of up to 100 μg per ml (FIGS. 22A and B).

Figure 22A:
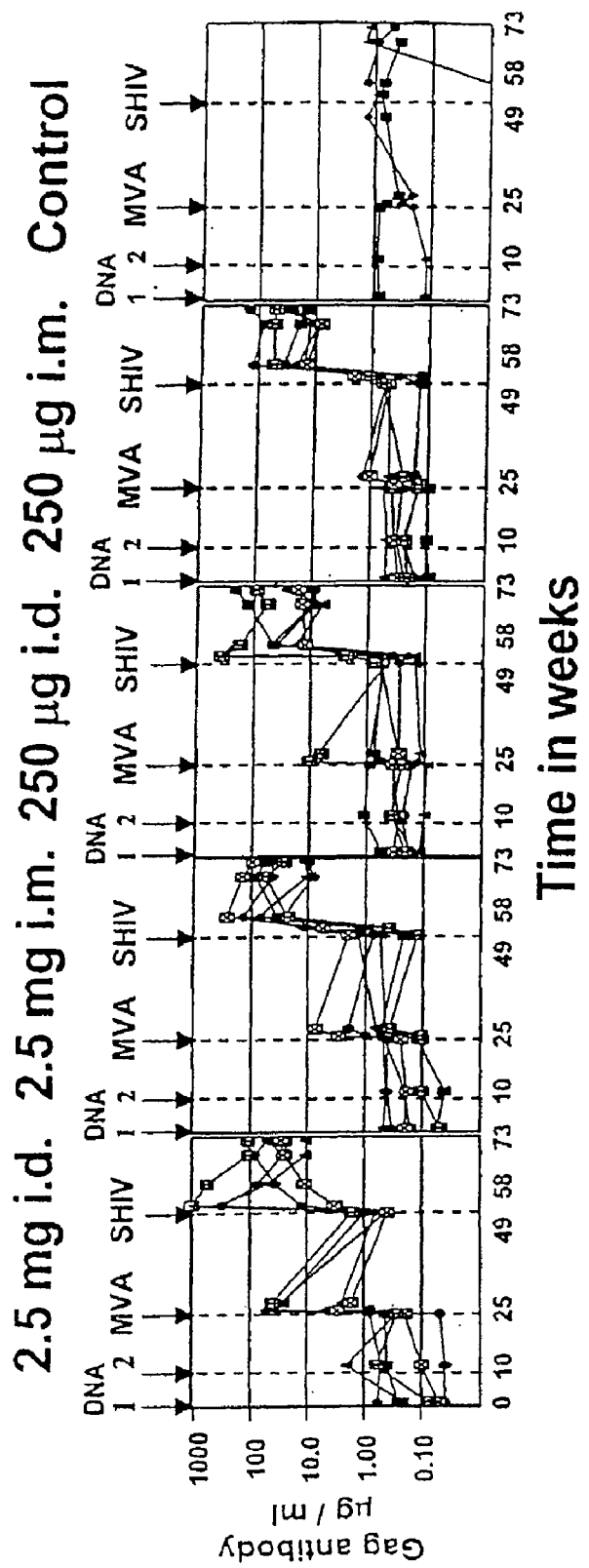
FIGS. 22A-22D show temporal antibody responses following challenge. Micrograms of total Gag (FIG. 22A) or Env (FIG. 22B) antibody were determined using enzyme linked immunosorbent assays (ELISAs). The titers of neutralizing antibody for 89.6 (FIG. 22C) and 89.6P (FIG. 22D) were determined using MT-2 cell killing and neutral red staining. Titers are the reciprocal of the serum dilution giving 50% neutralization of the indicated viruses grown in human PBMC. Symbols for animals are the same as in FIG. 19.
Figure 22B:
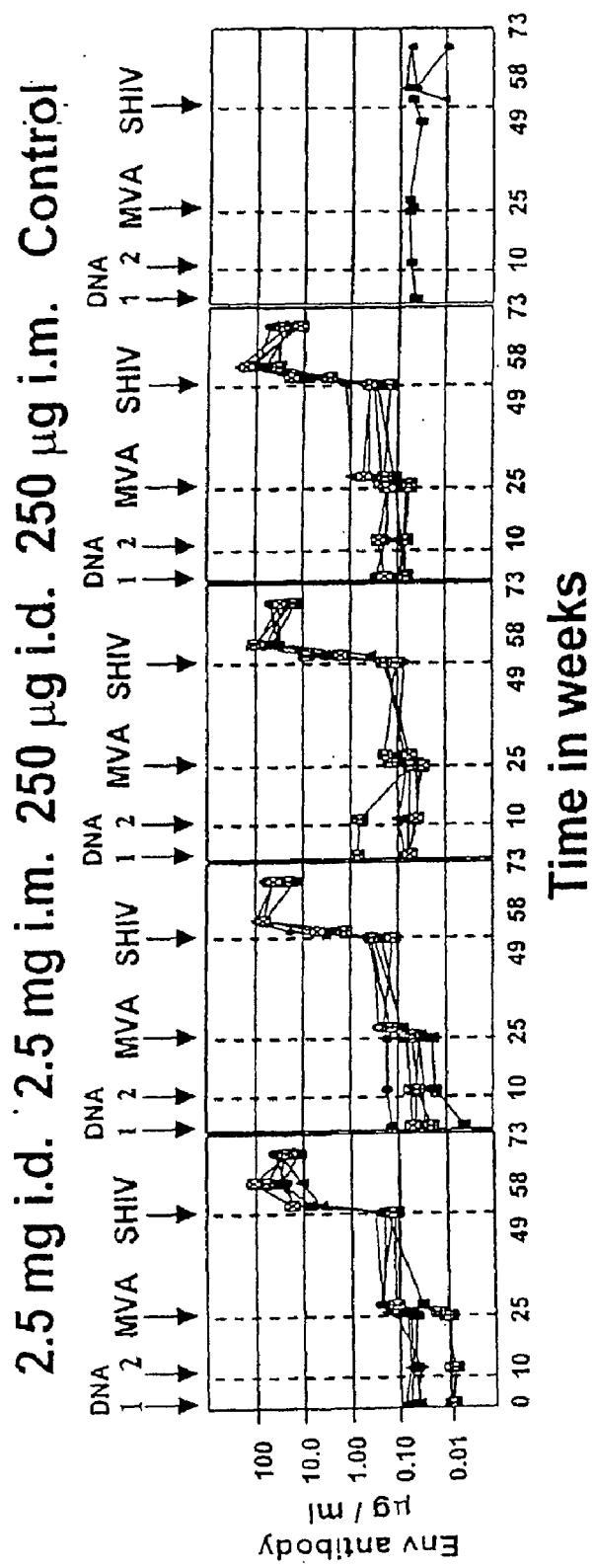
Figure 22C:
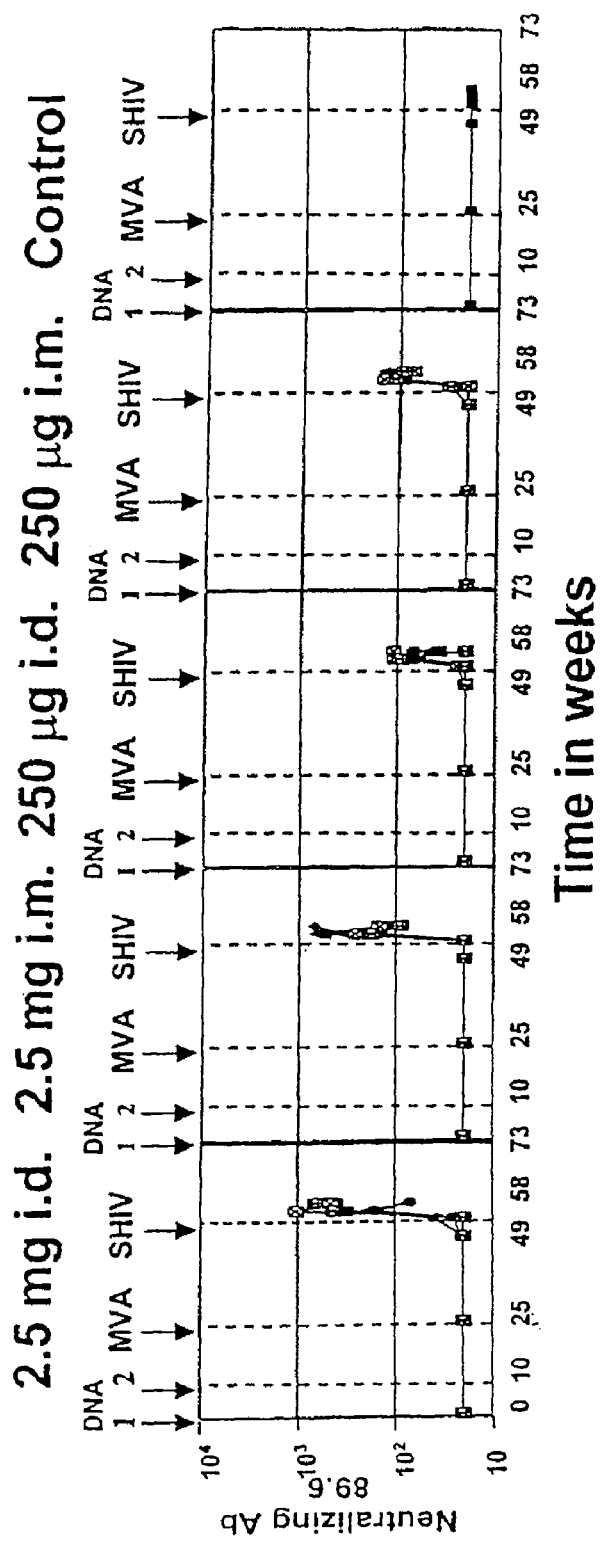
Figure 22D:
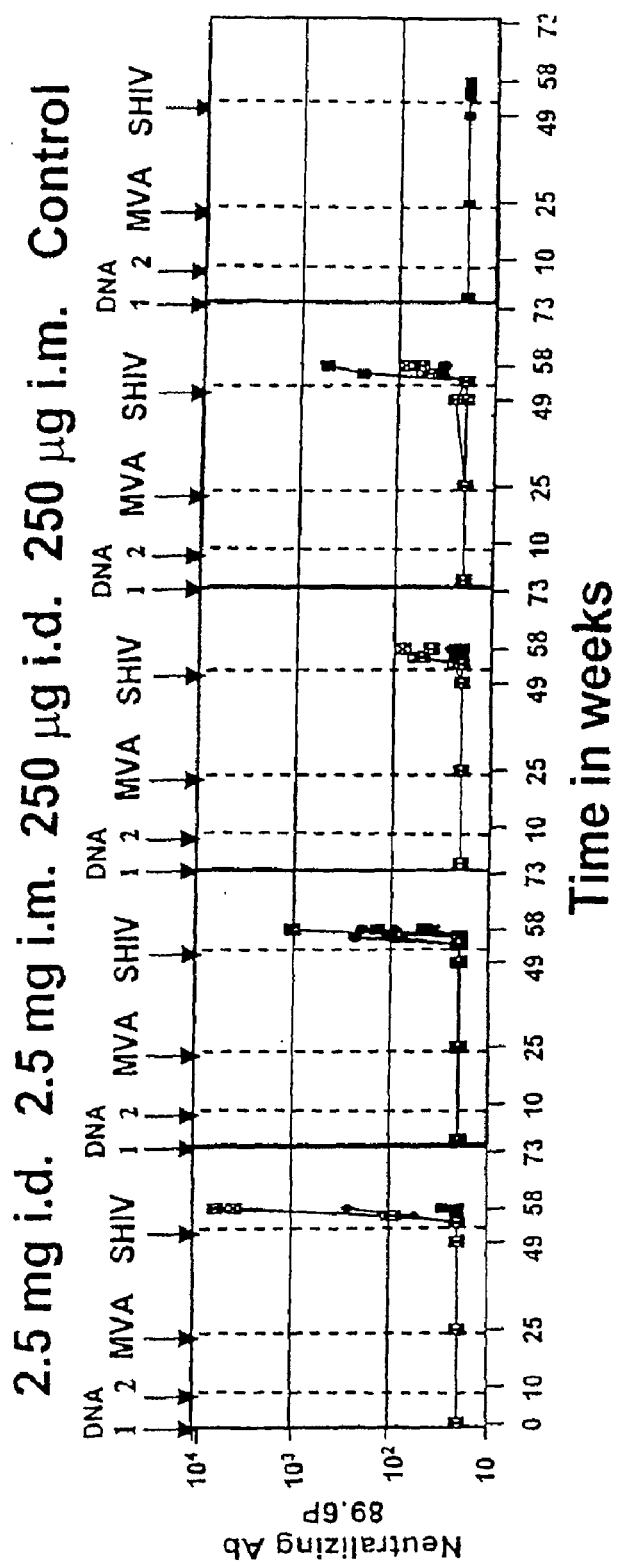
Figure 24A:
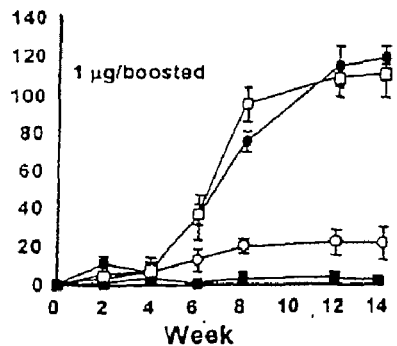
FIG. 24 shows anti-HA IgG raised by gene gun inoculation of DNAs expressing HA proteins.
Figure 24B:
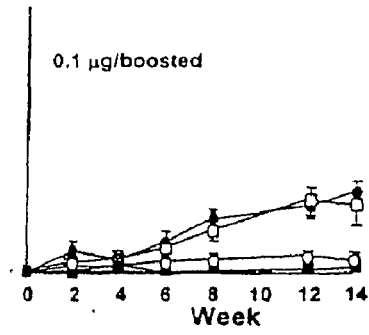
Figure 24C:
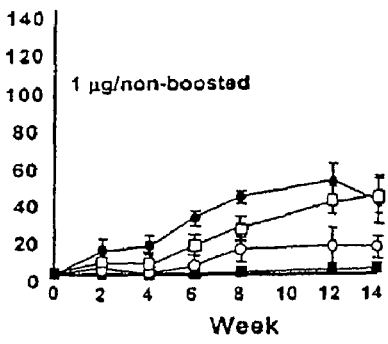
Figure 24D:
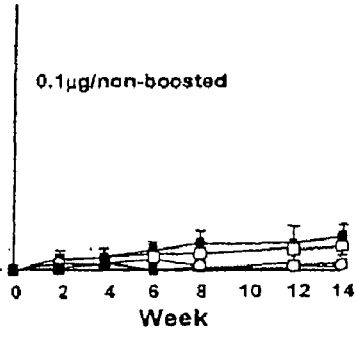
Figure 24E:
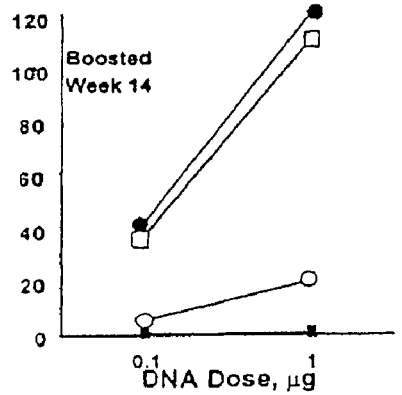
Figure 24F:
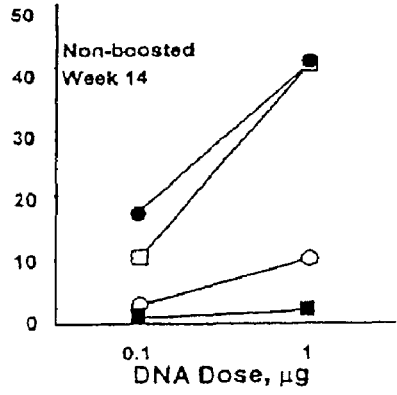
Figure 25A:
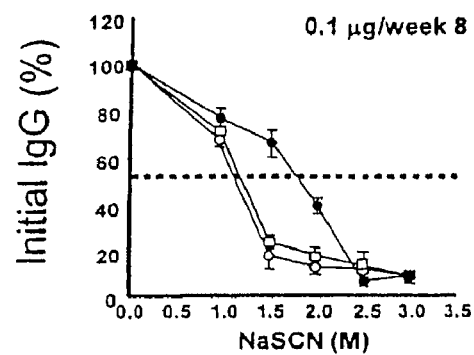
FIG. 25. Shows avidity of the anti HA IgG raised by the three different HA DNA vaccines.
Figure 25B:
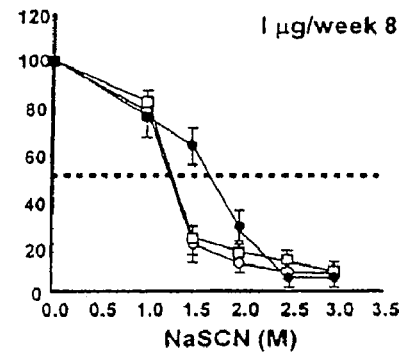
Figure 25C:
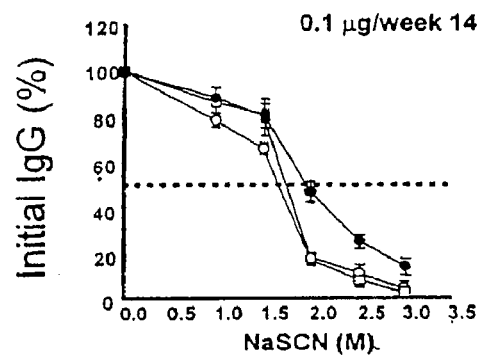
Figure 25D:
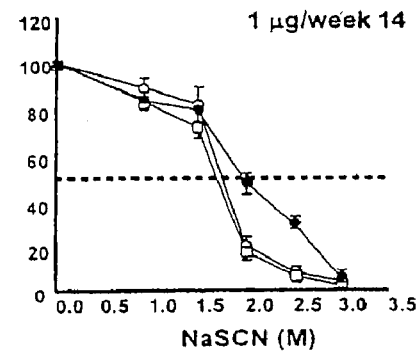

By two weeks post-challenge, neutralizing antibodies for the 89.6 immunogen, but not the SHIV-89.6P challenge were present in the high-dose DNA-primed groups (geometric mean titers of 352 in the i.d. and 303 in the i.m. groups) (FIG. 22C). By 5 weeks post-challenge, neutralizing antibody to 89.6P had been generated (geometric mean titers of 200 in the high-dose i.d. and 126 in the high-dose i.m. group) (FIG. 22D) and neutralizing antibody to 89.6 had started to decline. Thus, priming of an antibody response to 89.6 did not prevent a B cell response leading to neutralizing antibody for SHIV-89.6P. By 16 to 20 weeks post-challenge, antibodies to Gag and Env had fallen in most animals (FIGS. 22A and B). This would be consistent with the control of the virus infection.

T cells correlate with protection. The levels of plasma viral RNA at both two and three weeks post-challenge correlated inversely with the peak pre-challenge frequencies of DNA/MVA-raised IFN-γ ELISPOTs (r=−0.53, P=0.008 and r=−0.70, P=0.0002 respectively) (FIG. 23A).

Importantly, these correlations were observed during the time the immune response was actively reducing the levels of viremia. At later times post-challenge, the clustering of viral loads at or below the level of detection precluded correlations. Correlations also were sought between viral load and post-challenge ELISPOT, proliferative, and neutralizing antibody responses. The levels of IFN-γ ELISPOTS at two weeks post-challenge correlated with the viral load at 3 weeks post-challenge (r=−0.51, P=0.009) (data not shown). Post-challenge proliferative and neutralizing antibody responses did not correlate with viral loads.

Dose and route: The dose of DNA had significant effects on both cellular and humoral responses (P<0.05) while the route of DNA administration had a significant effect only on humoral responses (FIGS. 23 C-E). The intradermal route of DNA delivery was about 10 times more effective than the intramuscular route for generating antibody to Gag (P=0.02) (FIG. 23E). Within our data set, i.d. DNA injections were about 3 times more effective at priming the height and breadth of virus-specific T cells (FIGS. 23C and D). However, these differences were not significant (height, P=0.2; breadth, P=0.08). Interestingly, the route and dose of DNA had no significant effect on the level of protection. At 20 weeks post-challenge, the high-dose DNA-primed animals had slightly lower geometric mean levels of viral RNA ($7 \times 10^2$ and $5 \times 10^2$) than the low-dose DNA-primed animals ($9 \times 10^2$ and $1 \times 10^3$). The animal with the highest intermittent viral loads (macaque 22) was in the low dose i.m.-primed group (FIG. 19D). Thus, the low dose i.m.-primed group, which was slow to control viremia (FIG. 19A), may have poorer long term protection. The breadth of the response did not have an immediate effect on the containment of viral loads, but with time may affect the frequency of viral escape.

These results clearly demonstrate that a multiprotein DNA/MVA vaccine can raise a memory immune response capable of controlling a highly virulent mucosal immunodeficiency virus challenge. Our excellent levels of viral control are more favorable than have been achieved using only DNA or rMVA vaccines (Egan et al., 2000; I. Ourmanov et al., 2000) and comparable to those obtained for DNA immunizations adjuvanted with interleukin-2 (Barouch et al., 2000). All of these previous studies have used more than three vaccine inoculations, none have used mucosal challenges, and most have challenged at peak effector responses and not allowed a prolonged post vaccination period to test for "long term" efficacy as was done in our study. Our results also demonstrate for the first time that vaccine-raised T cells, as measured by IFN-γ ELISPOTs, are a correlate for the control of viremia. This relatively simple assay can now be used for preclinical evaluation of DNA and MVA immunogens for HIV-1, and should be able to be used as a marker for the efficacy of clinical trials in humans.

The DNA/MVA vaccine did not prevent infection. Rather, the vaccine controlled the infection, rapidly reducing viral loads to near or below 1000 copies of viral RNA per ml of blood. Containment, rather than prevention of infection, affords the virus the opportunity to establish a chronic infection (Chun et al., 1998). Nevertheless, by rapidly reducing viral loads, a multiprotein DNA/MVA vaccine will extend the prospect for long-term non-progression and limit HIV transmission.

EXAMPLE 16

Gag-Pol Vaccine Trial

Figure 27:
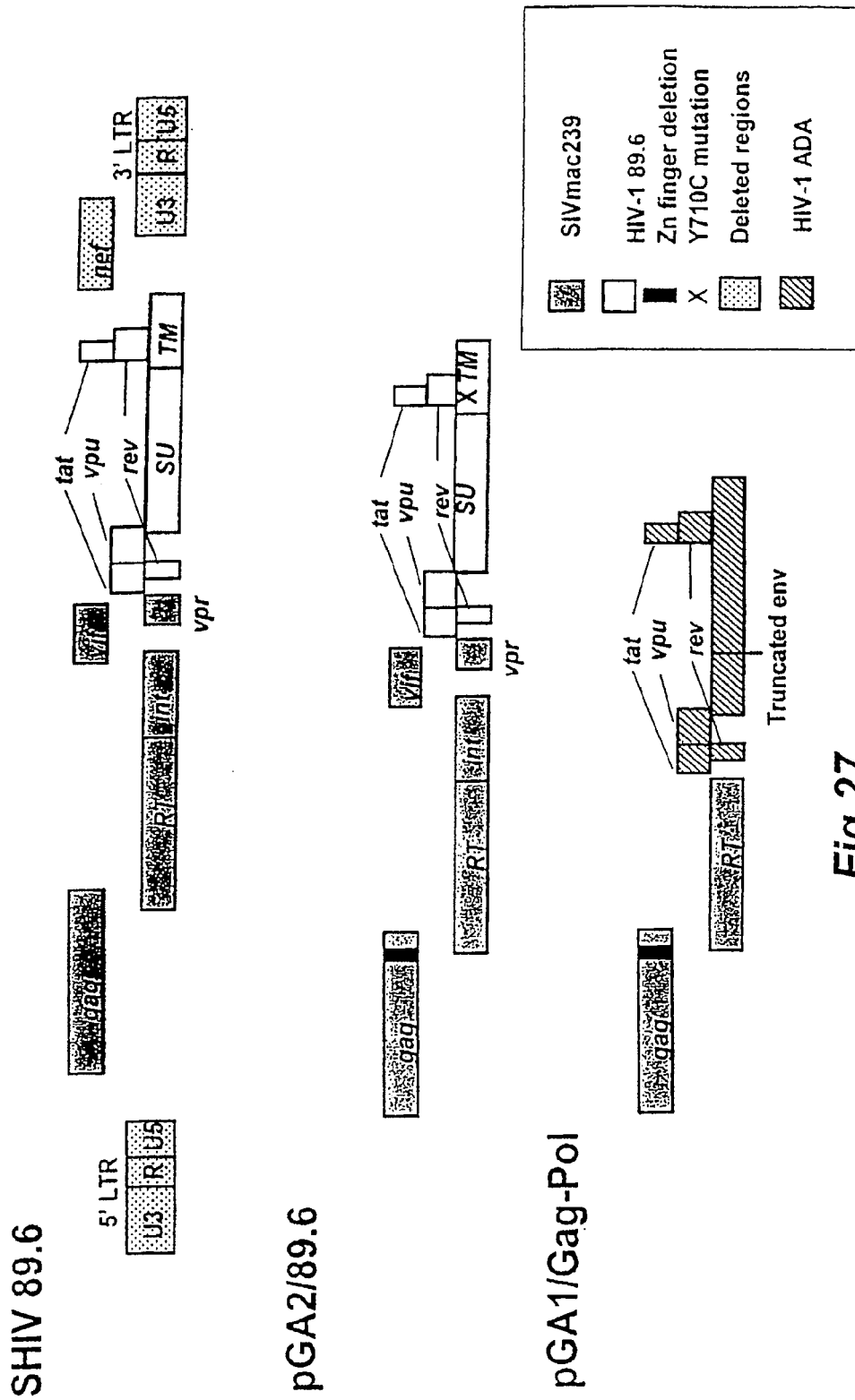
FIG. 27 illustrates the importance of including Env in the vaccine.

A trial using Gag-Pol rather than Gag-Pol-Env expressing immunogens was conducted to determine the importance of including Env in the vaccine (see FIG. 27 for constructs). A vaccine that did not include Env would have certain advantages in the field, such as the ability to screen for anti-Env antibody as a marker for infection. This trial used pGA1/Gag-Pol and a rMVA expressing the Gag-Pol sequences of SIV239 (MVA/Gag-Pol) supplied by Dr. Bernard Moss (NIH-NI-AID)

The "Gag-Pol" immunogens were administered using the schedule described in Example 13 above for the "Gag-Pol-Env" (pGA2/89.6 MVA/89.6) immunogens (see Table 4, Groups 5 and 6). The same doses of DNA, 2.5 mg and 250 µg, were used to prime a high dose and a low dose group and administration was via an intradermal route. As in the previous vaccine trial described in examples 13-15, two to three mamu A*01 macaques were included in each trial group. T cell responses were followed for those specific for the p11c-m epitope using the p11c-m tetramers and using ELISPOTs stimulated by pools of overlapping peptides, as described in the above Examples.

Figure 28A:
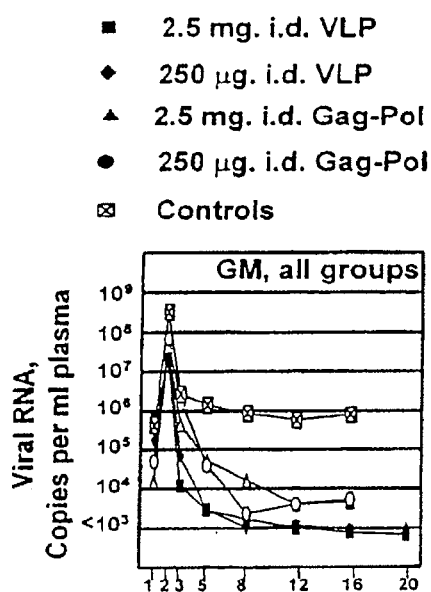
Figure 28B:
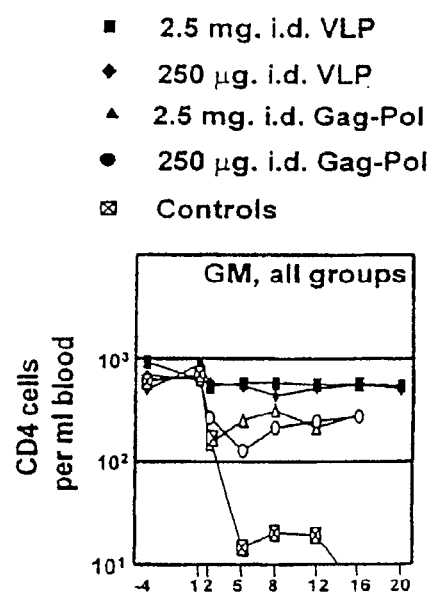
Figure 28D:
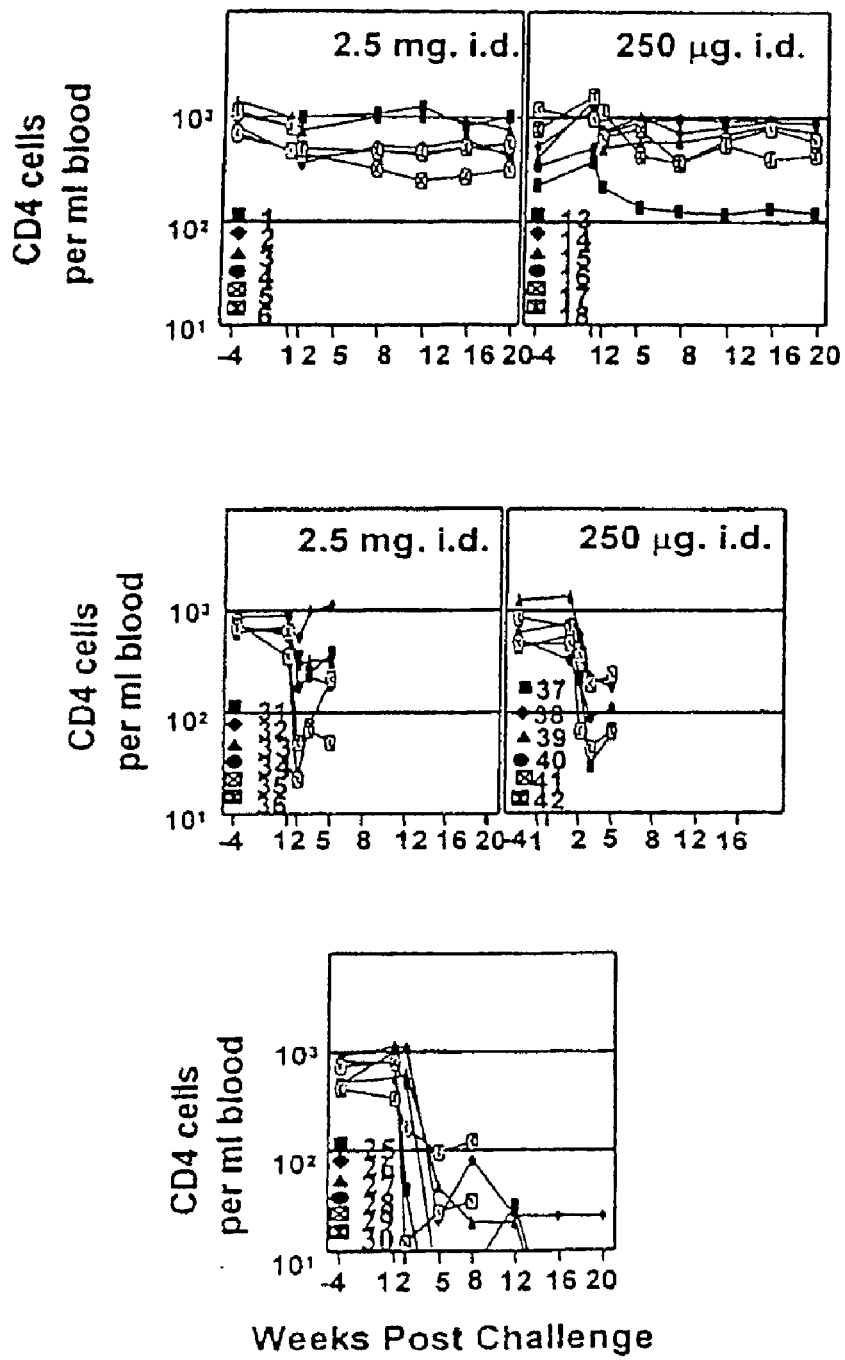

Following immunization, vaccine recipients showed anti-Gag T cell responses similar to those observed in the Gag-Pol-Env vaccine trial. Animals were challenged intrarectally with SHIV-89.6P at 7.5 months following the rMVA booster (FIG. 28). In contrast to the Gag-Pol-Env vaccine protocol, which protected animals against the rapid loss of CD4 cells, the Gag-Pol animals uniformly lost CD4 cells (FIGS. 28B and 28D). This loss was most pronounced in the group receiving the low dose i.d. DNA prime. Consistent with the loss of CD4 cells, the Gag-Pol DNA-immunized groups were also less effective at reducing their viral loads than the Gag-Pol-Env groups (FIGS. 28A and 28C). Geometric mean viral loads for these groups were 10-100-fold higher at 3 weeks post challenge and 10 fold higher at 5 weeks post challenge. These results demonstrate that the Env gene plays an important role in protecting CD4 cells and reducing the levels of viral RNA in challenged animals. The results also show that Gag-Pol-Env DNA/MVA vaccines function more effectively than Gag-Pol DNA/MVA vaccines in protecting recipients against a virulent challenge.

EXAMPLE 17

Measles Inserts

A DNA vaccine expressing a fusion of measles H and the C3d component of complement was used to determine if vaccination could achieve earlier and more efficient anti-H antibody responses. In prior studies in mice by Dempsey et al., the fusion of two or three copies of C3d to a model antigen, hen egg lysozyme increased the efficiency of immunizations by more than 1000-fold (Dempsey et al, 1996). This resulted in more rapid appearance of hemagglutination inhibition (HI) activity and protective immunity (Ross et al, 2000 and Ross et al., 2001).

In the human immune system, one consequence of complement activation is the covalent attachment of the C3d fragment of the third complement protein to the activating protein. C3d in turn binds to CD21 on B lymphocytes, a molecule with B cell stimulatory functions that amplify B lymphocyte activation. In a measles H-C3d fusion protein, the H moiety of the fusion would bind to anti-H Ig receptors on B cells and signal through the B cell receptor, while the C3d moiety of the fusion would bind to CD21 and signal through CD19. In this hypothesis, a B cell responding to an H-C3d fusion protein would undergo more effective signaling than a B cell responding to H alone. Mice vaccinated with DNA expressing a secreted H-fused to three copies of C3d (sH-3C3d) generated a more rapid appearance and higher levels of neutralizing antibody activity than DNA expressing sH only.

Plasmid DNA: pTR600, a eukaryotic expression vector, was constructed to contain two copies of the cytomegalovirus immediate-early promoter (CMV-IE) plus intron A (IA) for initiating transcription of eukaryotic inserts and the bovine growth hormone polyadenylation signal (BGH poly A) for termination of transcription. The vector contains a multi-cloning site for the easy insertion of gene segments and the Col E1 origin of replication for prokaryotic replication and the Kanamycin resistance gene (Kan') for selection in antibiotic media (FIG. 29A).

Figures 29A, 29B:
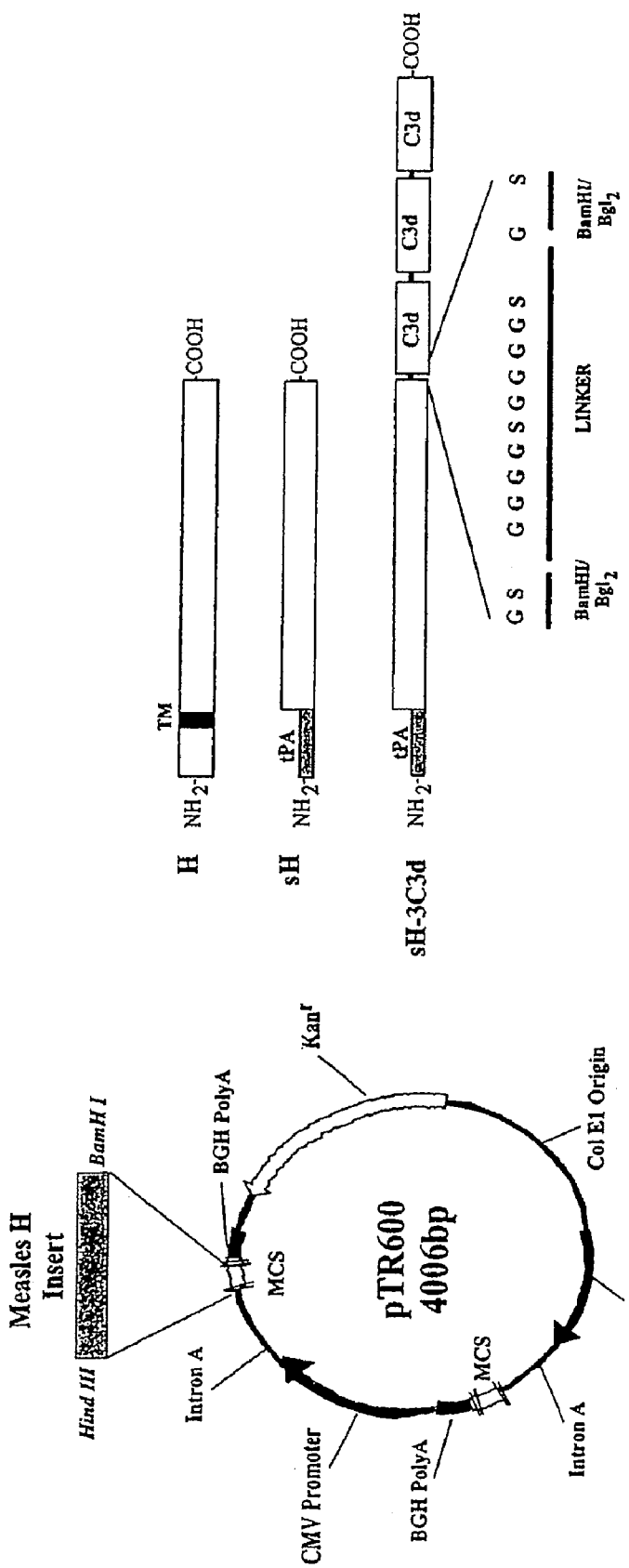
FIG. 29 is a schematic representation of vector DNA vaccine constructs.

Hemagglutinin (H) cDNA sequences from the Edmonton strain and C3d sequences were cloned as previously described and transferred into the pTR600 vaccine vector using unique restriction endonuclease sites (FIG. 29B). The secreted version was generated by deleting the transmembrane and cytoplasmic domains of H. This was accomplished using PCR to clone a fragment of the H gene in frame with an N-terminal synthetic mimic of the tissue plasminogen activator (tpA) leader sequence (Torres, et al, 2000).

The vectors expressing sH-C3d fusion proteins were generated by cloning three tandem repeats of the mouse homologue of C3d in frame at the 3' end of the sH gene as previously described (Dempsey, 1996; Ross et al, 2000; and Ross et al, 2001). The construct design was based upon Dempsey et al. and used sequences from pSLG-C3d. Linkers composed of two repeats of 4 glycines and a serine $\{(G_4S)_2\}$ were fused at the junctures of H and C3d and between each C3d repeat. Potential proteolytic cleavage sites between the junctions of C3d and the junction of sH and C3d were mutated by using Bam HI and Bgl II fusion to mutate an Arg codon to a Gly codon.

The plasmids were amplified in *Escherichia coli* strain, DH5α, purified using anion-exchange resin columns (Qiagen, Valencia, Calif.) and stored at −20° C. in $dH_2O$.

Plasmids were verified by appropriate restriction enzyme digestion and gel electrophoresis. Purity of DNA preparations was determined by optical density reading at 260 nm and 280 nm.

Mice and DNA immunizations: Six to 8 week old BALB/c mice (Harlan Sprague Dawley, Indianapolis, Ind.) were used for inoculations. Briefly, mice were anesthetized with 0.03-0.04 ml of a mixture of 5 ml ketamine HCl (100 mg/ml) and 1 ml xylazine (20 mg/ml). Mice were immunized with two gene gun doses containing 0.5 µg of DNA per 0.5 mg of approximately 1-µm gold beads (DeGussa-Huls Corp., Ridgefield Park, N.J.) at a helium pressure setting of 400 psi.

Transfections and expression analysis: The human embryonic kidney cell line 293T ($5\times10^5$ cells/transfection) was transfected with 2 µg of DNA using 12% lipofectamine according to the manufacture's guidelines (Life Technologies, Grand Island, N.Y.). Supernatants were collected and stored at −20° C. Quantitative antigen capture ELISAs for H were conducted as previously described (Cardoso et al, 1998).

For western hybridization analysis, 15 µl of supernatant or cell lysate was diluted 1:2 in SDS sample buffer (Bio-Rad, Hercules, Calif.) and loaded onto a 10% polyacrylamide/SDS gel. The resolved proteins were transferred onto a nitrocellulose membrane (Bio-Rad, Hercules, Calif.) and incubated with a 1:1000 dilution of polyclonal rabbit anti-HA antisera in PBS containing 0.1% Tween 20 and 1% nonfat dry milk. After extensive washing, bound rabbit antibodies were detected using a 1:2000 dilution of horseradish peroxidase-conjugated goat anti-rabbit antiserum and enhanced chemiluminescence (Amersham, Buckinghamshire, UK).

Antibody assays: A quantitative ELISA was performed to assess anti-H specific IgG levels. Briefly, Ltk⁻ cells constitutively expressing the H protein of MV (24) were grown in 96-well plates. Antisera dilutions were incubated with the intact cells expressing H antigen. The anti-H antibodies were allowed to bind to the cells for 30 min following which the cells were fixed in acetone (80%). The specific antibody responses were detected with biotinylated anti-mouse IgG antibodies and the streptavidine-phosphatase alkaline system (Sigma). Antibody binding to Ltk⁻ cells not expressing H antigen was used to standardize the system. The results were expressed as the endpoint dilution titer.

Neutralization assays. Neutralization assays were conducted on Vero cells grown in six well plates (25). Briefly, 100-200 p.f.u. of the Edmonton strain of measles virus were mixed with serial dilution of sera, incubated for 1 h at 37° C. and then inoculated onto plates. Plates were incubated at 37° C. for 48 h and plaques were counted. Neutralization titers are defined as the reciprocal dilution of sera required to reduce plaque formation by 50% or 90%. Preimmune sera served as negative controls.

Results: Two hemagglutinin-expressing vaccine plasmids were constructed in the pTR600 vector to express either a secreted form of H (sH) from the Edmonston strain or a C3d-fusion of the secreted form of H (sH-3C3d) (FIG. 29). The sH represented the entire ectodomain of H, but excluded the transmembrane and cytoplasmic region. The cloning placed the N-terminal synthetic mimic of the tissue plasminongen activator (tPA) leader sequence in frame with the H sequence. The tPA leader and H sequences were fused immediately 3' to the transmembrane domain of H. The sH-3C3d fusion protein was generated by cloning three tandem repeats of the mouse homologue of C3d in frame with the secreted H gene (FIG. 29B). The proteolytic cleavage sites, found at the junction between each C3d molecule as well as the junction between the H protein and the first C3d coding region, were destroyed by mutagenesis.

Figure 30:
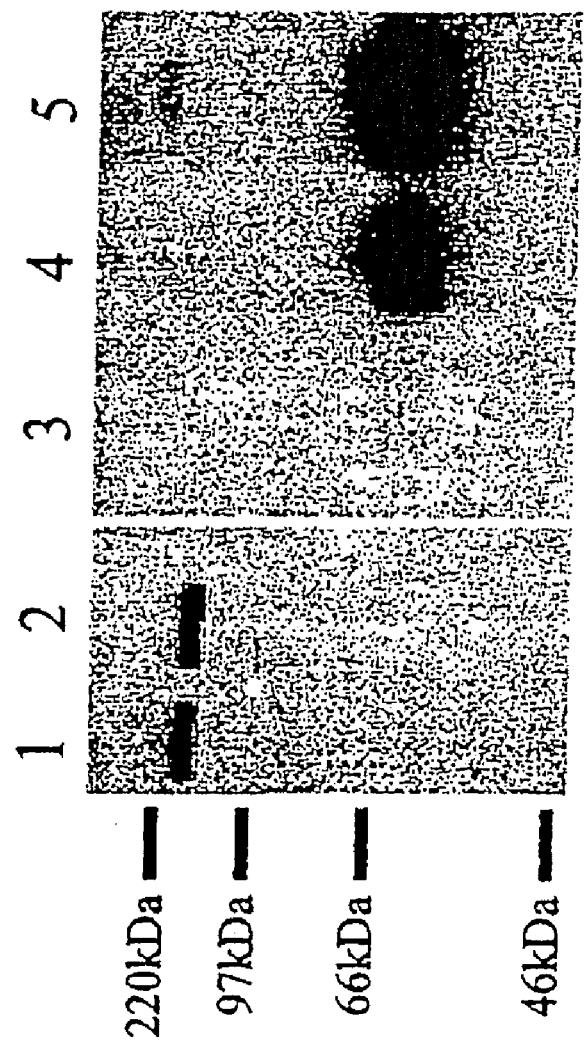
FIG. 30 shows Western blot results showing expression of vaccine constructs in vitro.

Western blot analyses revealed sH and sH-3C3d proteins of the expected sizes. Using a rabbit polyclonal antibody to MV H antisera, western blot analysis showed a broad band of ~70 kD corresponding to the secreted form of H in the supernatant of transfected cells. A higher molecular weight band at ~190 kD is consistent with the projected size of the sH-3C3d fusion protein (FIG. 30). No evidence for the proteolytic cleavage of the sH-C3d fusion protein was seen by western analysis.

Measles virus H was expressed at slightly lower levels by plasmids containing either the sH or sH-3C3d compared to transmembrane-associated forms of the antigen. Human 293T cells were transiently transfected with 2 µg of plasmid and both supernatants and cell lysates were assayed for H using an antigen capture ELISA. Approximately 75% of the H protein was secreted into the supernatant for both sH-DNA and sH-3C3d-DNA transfected cells. As expected, ~99% of the H antigen was detected in the cell lysate of cells transfected with plasmids expressing transmembrane form of H.

Antibody Response to Measles H DNA Immunizations: The sH-3C3d expressing DNA plasmids raised higher titers of ELISA antibody than sH DNA. BALB/c mice were vaccinated by DNA coated gold particles via gene gun with either a 0.1 µg or a 1 µg inoculum. At 4 and 26 weeks post vaccination, mice were boosted with the same dose of DNA given in the first immunization. The temporal pattern for the appearance of anti-H antibody showed a faster onset in mice vaccinated with the C3d fusion expressing DNA compared to mice vaccinated with sH DNA. Good titers of antibody were raised by the first immunization. These were boosted by the $2^{nd}$ and $3^{rd}$ immunizations following the third immunization, titers were 5-6 times higher in the sH-3C3D vaccinated mice than in those vaccinated with sH DNA.

Neutralization assays: Examination of the serum for MV neutralization showed titers up to 1700 after the second inoculation of 0.1 µg of sH-3C3d expressing DNA. Neutralizing antibody studies performed on Vero cells detected higher titers of neutralizing activity against the prototype MV Edmonton strain in mouse sera elicited by the sH-3C3d constructs than in the sera of mice vaccinated with sH expressing DNA. Mice vaccinated with sH-3C3d expressing plasmids had a sharp rise in neutralizing antibody levels that reached a plateau by week 14. In contrast, it took a third vaccination with sH expressing DNA to elicit detectable levels of neutralizing antibodies. After 28 weeks post-vaccination, sera from mice vaccinated with sH-3C3d-DNA had neutralizing titers (>250) that could reduce plaque formation of MV infection by 90%.

The increase in height of the antibody response to H was 7-15 fold higher in mice vaccinated with the C3d protein expressing constructs compared to mice vaccinated with DNA expressing sH only. The increase in antibody response with DNA expressing sH-3C3d is even more intriguing, since this plasmid expressed ~60% as much protein as plasmid expressing sH only.

Figure 31:
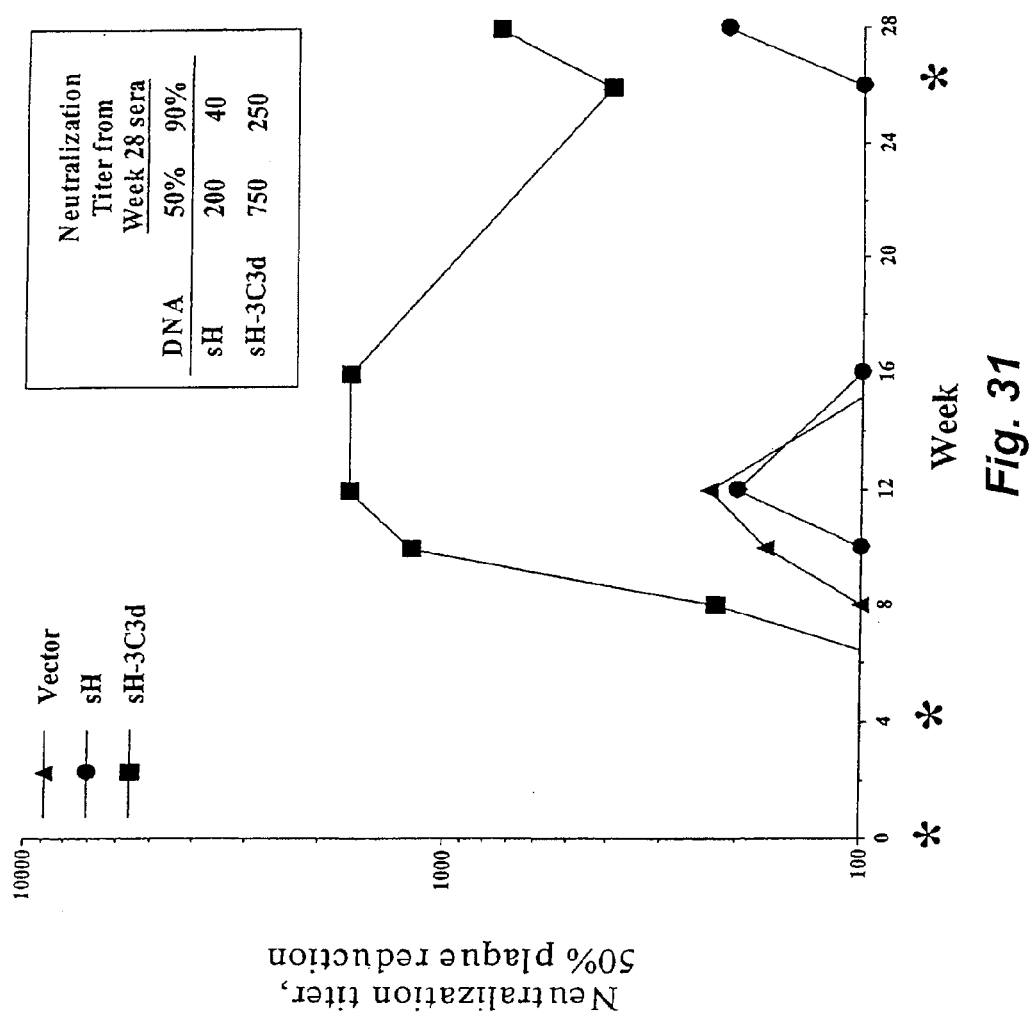
FIG. 31 is a temporal curve of measles virus neutralizing antibody.

In addition to the increase in the overall antibody level, there was a faster onset of antibodies that could specifically neutralize MV in an in vitro infection assay. After the second immunization, detectable levels of neutralizing antibodies were observed in mice vaccinated with DNA expressing sH-3C3d. The titer of the neutralizing antibody peaked at week 14 (1700 for 50% plaque reduction), which are substantially above the minimum correlate for protection (>120 for 50% plaque reduction). In contrast, mice vaccinated with sH expressing DNA had low levels of neutralizing antibody even after the third vaccination (180 for 50% plaque reduction) (FIG. 31).

EXAMPLE 18

Influenza Inserts with and without -C3d

Plasmid vector construction and purification procedures have been previously described for JW4303 (Torres, et al. 1999; Pertmer et al. 1995; Feltquate et al. 1997). In brief, influenza hemagglutinin (HA) sequences from A/PR/8/34 (H1N1) were cloned into either the pJW4303 or pGA eukaryotic expression vector using unique restriction sites.

Figures 26A, 26B:
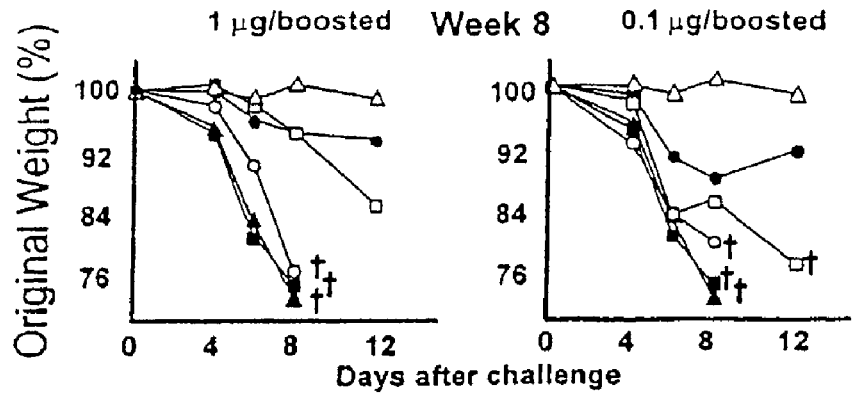
FIG. 26 shows protection from weight loss after virus challenge.
Figures 26C, 26D:
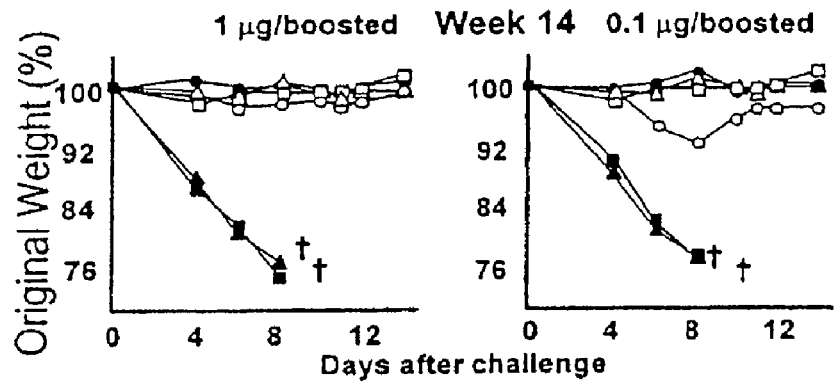
Figures 26E, 26F:
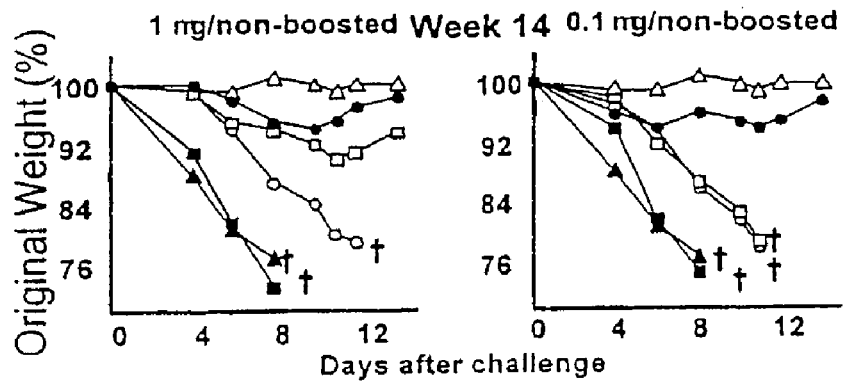

Two versions of HA, a secreted(s) and a transmembrane (tm) associated, have been previously described (Torres et al. 1999; Feltquate et al., 1997). Vectors expressing sHA or tmHA in pJW4303 were designated pJW/sHA and pJW/tmHA respectively and the vectors expressing sHA, tmHA, or sHA-3C3d in pGA were designated pGA/sHA, pGA/tmHA, and pGA/sHA-3C3d respectively.

Vectors expressing HA-C3d fusion proteins were generated by cloning three tandem repeats of the mouse homolog of C3d and placing the three tandem repeats in-frame with the secreted HA gene. The construct designed was based upon Dempsey et al. (1996). Linkers composed of two repeats of 4 glycines and a serine [$(G_4S)_2$] were fused at the joints of each C3d repeat. The pGA/sHA-3C3d plasmid expressed approximately 50% of the protein expressed by the pGA/sHA vector. However, the ratio of sHA-3C3d found in the supernatant vs. the cell lysate was similar to the ratio of antigen expressed by pGA/sHA. More than 80% of the protein was secreted into the supernatant. In western analysis, a higher molecular weight band was detected at 120 kDa and represented the sHA-3C3d fusion protein. Therefore, the sHA-3C3d fusion protein is secreted into the supernatant as efficiently as the sHA antigen.

Mice and DNA immunizations. Six to 8 week old BALB/c mice (Harlan Sprague Dawley, Indianapolis, Ind.) were used for inoculations. Mice, housed in microisolator units and allowed free access to food and water, were cared for under USDA guidelines for laboratory animals. Mice were anesthetized with 0.03-0.04 ml of a mixture of 5 ml ketamine HCl (100 mg/ml) and 1 ml xylazine (20 mg/ml). Gene gun immunizations were performed on shaved abdominal skin using the hand held Accell gene delivery system and immunized with two gene gun doses containing 0.5 μg of DNA per 0.5 mg of approximately 1-μm gold beads (DeGussa-Huls Corp., Ridgefield Park, N.J.) at a helium pressure setting of 400 psi.

Influenza virus challenge. Challenge with live, mouse-adapted, influenza virus (A/PR/8/34) was performed by intranasal instillation of 50 μl allantoic fluid, diluted in PBS to contain 3 lethal doses of virus, into the nares of ketamine-anesthetized mice. This method leads to rapid lung infections and is lethal to 100% of non-immunized mice. Individual mice were challenge at either 8 or 14 weeks after vaccination and monitored for both weight loss and survival. Data were plotted as the average individual weight in a group, as a percentage of pre-challenge weight, versus days after challenge.

Antibody response to the HA DNA Immunization protocol: The tmHA and sHA-3C3d expressing DNA plasmids raised higher titers of ELISA antibody than the sHA DNA. BALB/c mice were vaccinated by DNA coated gold particles via gene gun with either a 0.1 μg or 1 μg dose inoculum. At 4 weeks post vaccination, half of the mice in each group were boosted with the same dose of DNA given in the first immunization. Total anti-HA IgG induced by the sHA-3C3d- and tmHA-expressing plasmids were similar in the different experimental mouse groups and 3-5 times higher then the amount raised by the sHA expressing plasmids (FIG. 24). In addition, the amount of anti-HA antibody elicited increased relative to the amount of DNA used for vaccination in a dose dependent manner (FIG. 24E-24F). Overall, the dose response curves and temporal pattern for the appearance of anti-HA antibody were similar in the mice vaccinated with tmHA-DNA or sHA-3C3d-DNA, but lower and slower, in the mice vaccinated with sHA-DNA. As expected, the booster immunization both accelerated and increased the titers of antibodies to HA.

Avidity of mouse HA antiserum. Sodium thiocyanate (NaSCN) displacement ELISAs demonstrated that the avidity of the HA-specific antibody generated with sHA-3C3d expressing DNA was consistently higher than antibodies from sHA-DNA or tmHA-DNA vaccinated mice (FIG. 25). The avidity of specific antibodies to HA was compared by using graded concentrations NaSCN, a chaotropic agent, to disrupt antigen-antibody interactions. The binding of antibodies with less avidity to the antigen is disrupted at lower concentrations of NaSCN than that of antibodies with greater avidity to the antigen. The effective concentration of NaSCN required to release 50% of antiserum ($ED_{50}$) collected at 8 weeks after vaccination from sHA-DNA or tmHA-DNA boosted mice (0.1 μg dose or 1 μg dose) was ~1.20 M (FIG. 25A). In contrast, antiserum from mice vaccinated and boosted with sHA-3C3d-DNA had an $ED_{50}$ of ~1.75 M (FIG. 25B). At the time of challenge (14 weeks after vaccination), the $ED_{50}$ had increased to ~1.8 M for antibodies from both sHA-DNA and tmHA-DNA vaccinated mice (FIG. 25C). Antibodies from mice vaccinated with sHA-3C3d-DNA had increased to an $ED_{50}$ of ~2.0 M (FIG. 25D). These results suggest that the antibody from sHA-3C3d-DNA vaccinated mice had undergone more rapid affinity maturation than antibody from either sHA-DNA or tmHA-DNA vaccinated mice. The difference between the temporal avidity maturation of antibody for sHA-3C3d and tmHA was independent of the level of the raised antibody. Both of these plasmids had similar temporal patterns for the appearance of antibody and dose response curves for the ability to raise antibody (FIG. 25).

Hemagglutinin-Inhibition (HI) titers. Hemagglutination-inhibition assays (HI) were performed to evaluate the ability of the raised antibody to block binding of A/PR/8/34 (H1N1) to sialic acid. The HI titers were measured from serum samples harvested from mice at 8 and 14 weeks after vaccination. All boosted mice had measurable HI titers at week 14 regardless of the dose or vaccine given. The highest titers (up to 1:1200) were recorded for the sHA-3C3d-DNA vaccinated mice. Nonboosted mice showed more variation in HI titers. Nonboosted mice vaccinated with a 0.1 μg dose of either sHA-DNA or tmHA-DNA expressing plasmids had low HI titers of 1:10. In contrast, mice vaccinated with sHA-3C3d-DNA had titers greater than 1:640. The only vaccinated mice that had a measurable HI titer (1:160) at week 8 were boosted mice vaccinated with 1 μg dose sHA-3C3d-DNA. These results indicate that C3d, when fused to sHA, is able to stimulate specific B cells to increase the avidity maturation of antibody and thus the production of neutralizing antibodies to HA.

Protective efficacy to influenza challenge. Consistent with eliciting the highest titers of HI antibody, the sHA-3C3d DNA raised more effective protection than the sHA or tmHA DNAs. To test the protective efficacy of the various HA-DNA vaccines, mice were challenged with a lethal dose of A/PR/8/34 influenza virus (H1N1) and monitored daily for morbidity (as measured by weight loss) and mortality. Weight loss for each animal was plotted as a percentage of the average pre-challenge weight versus days after challenge (FIG. 26). Virus-challenged naive mice and pGA vector only vaccinated mice showed rapid weight loss with all the mice losing >20% of their body weight by 8 days post-challenge (FIG. 26). In contrast, PBS mock-challenged mice showed no weight loss over the 14 days of observation. All boosted mice survived challenge, 14 weeks after vaccination, regardless of the dose of DNA plasmid administered. However, boosted mice vaccinated with a 0.1 µg dose of sHA-DNA did drop to 92% of their initial body weight at 8 days post-challenge before recovering (FIG. 26). In contrast, when 1 µg dose, boosted mice were challenged at 8 weeks after vaccination, the only mice to survive challenge were sHA-3C3d- and tmHA-DNA vaccinated mice, albeit with greater weight loss than was observed from mice challenged at 14 weeks after vaccination. The only 0.1 µg dose, boosted mice to survive challenge at 8 weeks after vaccination were the sHA-3C3d vaccinated mice (FIG. 26).

Among the nonboosted, 0.1 µg dose immunizations, only the sHA-3C3d-DNA vaccinated mice survived challenge at 14 weeks after vaccination (FIG. 26). All mice administered a single DNA vaccination lost weight. However, of these, the sHA-3C3d-DNA vaccinated mice lost the least weight and these mice were the only mice to survive the lethal challenge (FIG. 26). These results demonstrate the that 3C3d protein, when fused to HA, increased the efficiency of a DNA vaccine, allowing for the reduction in dose of DNA and the number of vaccinations needed to afford protection to a lethal influenza virus challenge.

EXAMPLE 19

HIV Gp120-C3d Fusion Constructs

In this study, a similar approach to that described in Example 18 was used to fuse three copies of murine C3d to the carboxyl terminus of HIV Env gp120 subunit. Using DNA vaccination, BALB/c mice were inoculated and assayed for enhanced immune responses. The fusion constructs induced higher antibody responses to Env and a faster onset of avidity maturation than did the respective wild-type gp120 sequences. These results suggest that the efficacy of DNA vaccines for raising antibody can be significantly improved by fusing proteins with C3d.

Plasmid DNA: pGA was constructed as described in Example 1 to contain the cytomegalovirus immediate-early promoter (CMV-IE) plus intron A (IA) for initiating transcription of eukaryotic inserts, and the bovine growth hormone polyadenylation signal (BGH polyA) for termination of transcription. HIV envelope sequences from the isolates ADA, IIIB and 89.6, encoding almost the entire gp120 region, and C3d sequences were cloned into the pGA vaccine vector using unique restriction endonuclease sites. The gp120 segment encoded a region from amino acid 32 to amino acid 465 and ended with the amino acid sequence VAPTRA (SEQ ID NO:45). The first 32 amino acids were deleted from the N-terminus of each sgp120 and replaced with a leader sequenced from the tissue plasminogen activator (tpA). The vectors expressing sgp120-C3d fusion proteins were generated by cloning three tandem repeats of the mouse homologue of C3d in frame with the sgp120 expressing DNA. The construct design was based upon Dempsey et al. (1996). Linkers composed of two repeats of four glycine residues and a serine {$G_4S$)$_2$} were fused at the junctures of HA and C3d and between each C3d repeat. Potential proteolytic cleavage sites between the junctions of C3d and the junction of 3C3d were mutated by ligating Bam HI and Bgl II restriction endonuclease sites to mutate an Arg codon to a Gly codon.

The plasmids were amplified in *Escherichia coli* strain-DH5α, purified using anion-exchange resin columns (Qiagen, Valencia, Calif.) and stored at −20° C. in dH$_2$0. Plasmids were verified by appropriate restriction enzyme digestion and gel electrophoresis. Purity of DNA preparations was determined by optical density reading at 260 nm and 280 nm.

Mice and DNA immunizations: Six to 8 week old BALB/c mice (Harlan Sprague Dawley, Indianapolis, Ind.) were vaccinated as described in Example 17 above. Briefly, mice were immunized with two gene gun doses containing 0.5 µg of DNA per 0.5 mg of approximately 1-µm gold beads (De-Gussa-Huls Corp., Ridgefield Park, N.J.) at a helium pressure setting of 400 psi.

Transfections and expression analysis and western hybridization experiments were conducted as described in Example 17, except that the nitrocellulose membranes were incubated with a 1:1000 dilution of polyclonal human HIV-infected patient antisera in PBS containing 0.1% Tween 20 and 1% nonfat dry milk. After extensive washing, bound human antibodies were detected using a 1:2000 dilution of horseradish peroxidase-conjugated goat anti-human antiserum and enhanced chemiluminescence (Amersham, Buckinghamshire, UK).

ELISA and avidity assays: An endpoint ELISA was performed to assess the titers of anti-Env IgG in immune serum using purified HIV-1-IIIB gp120 CHO-expressed protein (Intracell) to coat plates as described (Richmond et al., 1998). Alternatively, plates were coated with sheep anti-Env antibody (International Enzymes Inc., Fallbrook, Calif.) and used to capture sgp120 produced in 293T cells that were transiently transfected with sgp120 expression vectors. Mouse sera from vaccinated mice was allowed to bind and subsequently detected by anti-mouse IgG conjugated to horseradish peroxidase. Endpoint titers were considered positive that were two fold higher than background. Avidity ELISAs were performed similarly to serum antibody determination ELISAs up to the addition of samples and standards. Samples were diluted to give similar concentrations of specific IgG by O.D. Plates were washed three times with 0.05% PBS-Tween 20. Different concentrations of the chaotropic agent, sodium thiocyanate (NaSCN) in PBS, were then added (0M, 1 M, 1.5 M, 2 M, 2.5 M, and 3 M NaSCN). Plates were allowed to stand at room temperature for 15 minutes and then washed six times With PBS-Tween 20. Subsequent steps were performed similarly to the serum antibody determination ELISA and percent of initial IgG calculated as a percent of the initial O.D. All assays were done in triplicate.

Neutralizing antibody assays: Antibody-mediated neutralization of HIV-1 IIIB and 89.6 was measured in an MT-2 cell-killing assay as described previously (Montefiori et al., 1988). Briefly, cell-free virus (50 µl containing $10^8$ TCID$_{50}$ of virus) was added to multiple dilutions of serum samples in 100 µl of growth medium in triplicate wells of 96-well microtiter plates coated with poly-L-lysine and incubated at 37° C. for 1 h before MT-2 cells were added ($10^5$ cells in 100 □l added per well). Cell densities were reduced and the medium was replaced after 3 days of incubation when necessary. Neutralization was measured by staining viable cells with Finter's neutral red when cytopathic effects in control wells were >70% but less than 100%. Percentage protection was determined by calculating the difference in absorption (A$_{540}$) between test wells (cells+virus) and dividing this result by the difference in absorption between cell control wells (cells only) and virus control wells (virus only). Neutralizing titers are expressed as the reciprocal of the plasma dilution required to protect at least 50% of cells from virus-induced killing.

Results: Env was expressed at overall similar levels by plasmids containing either the secreted form of the antigen, but at a two-four-fold lower level by the sgp120-C3d expressing plasmids. Human 293T cells were transiently transfected with 2 μg of plasmid and both supernatants and cell lysates were assayed for gp120 using an antigen capture ELISA. The sgp120 constructs expressed from 450 to 800 ng per ml, whereas the 3C3d fusions expressed from 140 to 250 ng per ml. Approximately 90% of the Env protein was present in the supernatant for both sgp120 and sgp120-3C3d-DNA transfected cells (data not shown). The approximately 2-fold differences in the levels of expression of the different sgp120s is likely a reflection in differences in the Env genes as well as differences in the efficiency that the capture and detection antibodies recognized the different Envs.

Western blot analyses revealed sgp120 and sgp120-3C3d proteins of the expected sizes. Using human patient polyclonal antisera, western blot analysis showed the expected broad band of 115-120 kD corresponding to gp120. A higher molecular weight band at ~240 kD was consistent With the projected size of the sgp120-3C3d fusion protein. Consistent with the antigen-capture assay, intense protein bands were present in the supernatants of cells transfected with sgp120-DNA, whereas less intense bands were present in the supernatants of cells transfected with sgp120-3C3d-DNA (data not shown). No evidence for the proteolytic cleavage of the sgp120-C3d fusion protein was seen by western analysis.

Antibody response to Env gp120 DNA immunizations: The sgp120-3C3d expressing DNA plasmids raised higher titers of ELISA antibody than the sgp120 DNA. BALB/c mice were vaccinated by DNA coated gold particles via gene gun with a 1 μg dose inoculum. Mice were vaccinated at day 1 and then boosted at 4, 14, and 26 weeks with the same DNA given in the first immunization. When sera were assayed on gp120-IIIB-coated plates, mice vaccinated with the DNAs expressing the C3d fusion proteins had anti-Env antibodies 3-7 times higher then the amount of antibody raised by the counterpart sgp120 expressing plasmids. Among the C3d constructs, mice vaccinated with sgp120-(IIIB)-3C3d had the highest levels of antibody and mice vaccinated with sgp120-(ADA)-3C3d expressing DNA had the lowest levels of anti-Env antibodies. The temporal pattern for the appearance of anti-Env antibody revealed titers being boosted at each of the inoculations for all constructs tested.

Differences in the levels of the antibody raised by the different Envs appeared to be determined by the specificity of the raised antibody. Using an alternative ELISA protocol, in which antibody was captured on the homologous Env, all of the C3d-fusions appeared to raise'similar levels of antibody. In this assay, sheep anti-Env antibody was used to capture transiently produced sgp120 proteins. This assay revealed low, but similar levels of antibody raised by each of the sgp120-3C3d constructs. The lower levels of antibody detected in this assay are likely to reflect the levels of transfection-produced Env used to capture antibody being lower than in the assays using commercially produced IIIB gp120 to coat plates. As expected using either ELISA method, booster immunizations were necessary to achieve even the most modest antibody response.

Avidity of mouse Env antiserum: Sodium thiocyanate (NaSCN) displacement ELISAs demonstrated that the avidity of the antibody generated with sgp120-3C3d expressing DNA was consistently higher than that from sgp120-DNA vaccinated mice. Avidity assays were conducted on sera raised by sgp120-(IIIB) and sgp120-(IIIB)-3C3d because of the type specificity of the raised antisera and the commercial availability of the IIIB protein (but not the other proteins) for use as capture antigen. The avidity of specific antibodies to Env was compared by using graded concentrations NaSCN, a chaotropic agent, to disrupt antigen-antibody interaction. Results indicated that the antibody from sgp120-3C3d-DNA vaccinated mice underwent more rapid affinity maturation than antibody from sgp120-DNA vaccinated mice.

Env-3C3d expressing plasmids elicit modest neutralizing antibody: Neutralizing antibody studies performed on MT-2 cells detected higher titers of neutralizing activity in the sera generated by the gp120-3C3d constructs than in the sera generated by the sgp120 constructs. Sera were tested against two syncytium inducing, IIIB (X4) and 89.6 (X4R5) viruses. Mice vaccinated with sgp120-3C3d expressing plasmids had very modest levels of neutralizing antibody to the homologous strain of HIV tested by the protection of MT-2 cells from virus-induced killing as measured by neutral red uptake. Titers of neutralizing antibody raised by the gp120-expressing DNAs were at the background of the assay.

The results of this study showed that fusions of HIV-1 Env to three copies of murine C3d enhanced the antibody response to Env in vaccinated mice. Mice vaccinated with any of the three DNA plasmids expressing sgp120 sequence had low or undetectable levels of antibody after 4 vaccinations (28 weeks post-prime). In contrast, mice vaccinated with DNA expressing the fusion of sgp120 and 3C3d proteins elicited a faster onset of antibody (3 vaccinations), as well as higher levels of antibodies.

In contrast to the enhancement of antibody titers and avidity maturation of antibodies to Env, the amount of neutralizing-antibody elicited in the vaccinated mice was low. Mice vaccinated with plasmids expressing sgp120 had low levels of neutralizing antibody that were only modestly increased in mice vaccinated with sp120-3C3d expressing plasmids. However, the levels of neutralizing antibodies did apparently increase after the fourth immunization. The poor titers of neutralizing antibody could have reflected an inherent poor ability of the sgp120-3C3d fusion protein to raise neutralizing antibody because of the failure to adequately expose neutralizing epitopes to responding B cells. The intrinsic high backgrounds for HIV-1 neutralization assays in mouse sera also may have contributed to the poor neutralization titers.

The results demonstrate the effectiveness of C3d-fusions as a molecular adjuvant in enhancing antibody production and enhancing antibody maturation. In addition, the neutralizing antibody response to Env was modestly increased in mice vaccinated with C3d-fusion vaccines. Similar to results seen in Examples 17 and 18, using secreted versions of HA from measles and influenza viruses, C3d-enhanced antibody responses were achieved with plasmids expressing only half as much protein as plasmids expressing non-fused sgp120.

REFERENCES

Amara, R., et al. (2001). Control of a mucosal challenge and prevention of AIDS by a multiprotein DNA/MVA Vaccine. Submitted.

Andre, S., Seed, B., Eberle, J., Schraut, W., Bultmann, A., and Haas, J. (1998). Increased immune response elicited by DNA vaccination with a synthetic gp120 sequence with optimized codon usage. J Virol 72(2), 1497503.

Asakura, Y., Hinkula, J., Leandersson, A. C., Fukushima, J., Okuda, K., and Wahren, B. (1997). Induction of HIV-1 specific mucosal immune responses by DNA vaccination. Scand J Immunol 46(4), 326-30.

Bachmann M F, Zinkernagel R M. Neutralizing antiviral B cell responses. Annu Rev Immunol 1997; 15:235-70.

Barouch. D. H. et al., 2000. Science 290: 486-92.

Barry, M. A., Lai, W. C., and Johnston, S. A. (1995). Protection against mycoplasma infection using expression library immunization. Nature 377(6550), 632-5.

Berger E A (1997). HIV entry and tropism: the chemokine receptor connection. AIDS 11 Suppl A:S3-16

Bohm, W., Kuhrober, A., Paier, T., Mertens, T., Reimann, J., and Schirmbeck, R. (1996). DNA vector constructs that prime hepatitis B surface antigen-specific cytotoxic T lymphocyte and antibody responses in mice after intramuscular injection. J Immunol Methods 193(1), 29-40.

Bohm, W., Mertens, T., Schirmbeck, R., and Reimann, J. (1998). Routes of plasmid DNA vaccination that prime murine humoral and cellular immune responses. Vaccine 16(9-10), 949-54.

Bolivar F, Rodriguez R L, Greene P J, Betlach M C, Heyneker H L, Boyer H W (1977). Construction and characterization of new cloning vehicles. II. A multipurpose cloning system. Gene 2(2):95-113

Boyer, J. D., Ugen, K. E., Wang, B., Agadjanyan, M., Gilbert, L., Bagarazzi, M. L., Chattergoon, M., Frost, P., Javadian, A., Williams, W. V., Refaeli, Y., Ciccarelli, R. B., McCallus, D., Coney, L., and Weiner, D. B. (1997). Protection of chimpanzees from high-dose heterologous HIV-1 challenge by DNA vaccination. Nat Med 3(5), 526-32.

Boyle, J. S., Koniaras, C., and Lew, A. M. (1997). Influence of cellular location of expressed antigen on the efficacy of DNA vaccination: cytotoxic T lymphocyte and antibody responses are suboptimal when antigen is cytoplasmic after intramuscular DNA immunization. Int Immunol 9(12), 1897-906.

Burton, D. R., and Montefiori, D. C. (1997). The antibody response in HIV-1 infection [see comments]. Aids 11(Suppl A), S87-98.

Calarota, S., Bratt, G., Nordlund, S., Hinkula, J., Leandersson, A. C., Sandstrom, E., and Wahren, B. (1998). Cellular cytotoxic response induced by DNA vaccination in HIV-1-infected patients. *Lancet* 351(9112), 1320-5.

Cardoso, A. I, Blixenkrone-Moller, M., Fayolle, J., Liu, M., Buckland, R., and Wild, F. T. Immunization with plasmid DNA encoding for the measles virus hemagglutinin and nucleoprotein leads to humoral and cell-mediated immunity. 1998. Virology. 225:293-299.

Chapman B S, Thayer R M, Vincent K A, Haigwood N L. Effect of intron A from human cytomegalovirus (Towne) immediate-early gene on heterologous expression in mammalian cells. Nucleic Acids Research 1991; 19(14):3979-86.

Chen, S. C., Jones, D. H., Fynan, E. F., Farrar, G. H., Clegg, J. C., Greenberg, H. B., and Herrmann, J. E. (1998a). Protective immunity induced by oral immunization with a rotavirus; DNA vaccine encapsulated in microparticles. *J Virol* 72(7), 5757-61.

Chun. T. W. et al., 1998. Proc Natl Acad Sci U S A 95: 8869-73.

Collman R, Balliet J W, Gregory S A, Friedman H, Kolson D L, Nathanson N, et al. An infectious molecular clone of an unusual macrophage-tropic and highly cytopathic strain of human immunodeficiency virus type 1. J Virol 1992; 66(12):7517-21.

Condon C, Watkins S C, Celluzzi C M, Thompson K, Falo L D, Jr. DNA-based immunization by in vivo transfection of dendritic cells. Nat Med 1996; 2(10):1122-8.

Corr M, Lee D J, Carson D A, Tighe H. Gene vaccination with naked plasmid DNA: mechanism of CTL priming. J Exp Med 1996; 184(4):1555-60.

Dempsey P W, Allison M E, Akkaraju S, Goodnow C C, Fearon D T (1996). C3d of complement as a molecular adjuvant: bridging innate and acquired immunity. Science 271:348-50.

Egan, M. A. et al., (2000) J Virol 74: 7485-95.

Evans D T, O'Connor D H, Jing P, Dzuris J L, Sidney J, da Silva J, et al. Virus-specific cytotoxic T-lymphocyte responses select for amino-acid variation in simian immunodeficiency virus Env and Nef. Nat Med 1999; 5(11): 1270-6.

Feltquate, D. M., Heaney, S., Webster, R. G., and Robinson, H. L. (1997). Different T helper cell types and antibody isotypes generated by saline and gene gun DNA immunization. *Journal of Immunology* 158(5), 2278-84.

Fomsgaard, A., Nielsen, H. V., Bryder, K., Nielsen, C., Machuca, K, Bruun, L., Hansen, J., and Buus, S. (1998). Improved humoral and cellular immune responses against the gp120 V3 loop of HIV-I following genetic immunization with a chimeric DNA vaccine encoding the V3 inserted into the hepatitis B surface antigen. *Scand J Immunol* 47(4), 289-95.

Fu T M, Ulmer J B, Caulfield M J, Deck R R, Friedman A, Wang S, et al. Priming of cytotoxic T lymphocytes by DNA vaccines: requirement for professional antigen presenting cells and evidence for antigen transfer from myocytes. Mol Med 1997; 3(6):362-71.

Fynan, E. F., Webster, R. G., Fuller, D. H., Haynes, J. R., Santoro, J. C., and Robinson, H. L. (1993). DNA vaccines: protective immunizations by parenteral, mucosal, and gene-gun inoculations. *Proc Natl Acad Sci USA* 90(24), 11478-82.

Gromkowski, S. H., Nabel, G. J., and et al. (1995). Cancer gene therapy using plasmid DNA: pharmacokinetic study of DNA following injection in mice [see comments]. *Hum Gene Ther* 6(5), 553-64.

Hakim, I., Levy, S., and Levy, R. (1996). A nine-amino acid peptide from IL-1 beta augments antitumor immune responses induced by protein and DNA vaccines. *J Immunol* 157(12), 5503-11.

Hanke T, Samuel R V, Blanchard T J, Neumann V C, Allen T M, Boyson J E, Sharpe S A, Cook N, Smith G L, Watkins D I, Cranage M P, McMichael (1999). Effective induction of simian immunodeficiency virus-specific cytotoxic T lymphocytes in macaques by using a multiepitope gene and DNA prime-modified vaccinia virus Ankara boost vaccination regimen. *J Virol* 73(9):7524-32

Hanke, T., Blanchard, T. J., Schneider, J., Hannan, C. M., Becker, M., Gilbert S. C., Hill, A. V., Smith, G. L., and McMichael, A. (1998a). Enhancement of MHC class I-restricted peptide-specific T cell induction by a DNA prime/MVA boost vaccination regime. *Vaccine* 16(5), 439-45.

Hanke, T., Schneider, J., Gilbert S. C., Hill, A. V., and McMichael, A. (1998b). DNA multi-CTL epitope vaccines for EIIV and Plasmodium falciparum: immunogenicity in mice. *Vaccine* 16(4), 426-35.

Hartikka, J., Sawdey, M., Comefert-Jensen, F., Margalith, M., Barnhart, K., Nolasco, M., Vahlsing, H. L., Meek, J., Marquet, M., Hobart, P., Norman, J., and Manthorpe, M. (1996). An improved plasmid DNA expression vector for direct injection into skeletal muscle. *Hum Gene Ther* 7(10), 1205-17.

Inchauspe, G., Vitvitski, L., Major, M. E., Jung, G., Spengler, U., Maisonnas, M., and Trepo, C. (1997). Plasmid DNA expressing a secreted or a nonsecreted form of hepatitis C virus nucleocapsid: comparative studies of antibody and T-helper responses following genetic immunization. *DNA Cell Biol* 16(2), 185-95.

Iwasaki A, Torres C A, Ohashi P S, Robinson H L, Barber B H. (1997b) The dominant role of bone marrow-derived cells in CTL induction following plasmid DNA immunization at different sites. *J Immunol* 159(1):11-4.

Iwasaki, A., Stiernholm, B. J., Chan, A. K., Berinstein, N. L., and Barber, B. H. (1997a). Enhanced CTL responses mediated by plasmid DNA immunogens encoding costimulatory molecules and cytokines. *J Immunol* 158(10), 4591-601.

Jones, D. H., Corris, S., McDonald, S., Clegg, J. C., and Farrar, G. H. (1997). Poly(DL-lactide-co-glycolide) encapsulated plasmid DNA elicits systemic and mucosal antibody responses to encoded protein after oral administration. *Vaccine* 15(8), 814-7.

Kawabata, K., Takakura, Y., and Hashida, M. (1995). The fate of plasmid DNA after intravenous injection in mice: involvement of scavenger receptors in its hepatic uptake. *Pharm Res* 12(6), 825-30.

Kent S. J., Zhao, A., Best, S. J., Chandler, J. D., Boyle, D. B., and Ramshaw, 1. A. (1998). Enhanced T-cell immunogenicity and protective efficacy of a human immunodeficiency virus type I vaccine regimen consisting of consecutive priming with DNA and boosting with recombinant fowlpox virus. J *Virol* 72(12), 10180-8.

Kuroda M J, Schmitz J E, Barouch D H, Craiu A, Allen T M, Sette A, et al. Analysis of Gag-specific cytotoxic T lymphocytes in simian immunodeficiency virus-infected rhesus monkeys by cell staining with a tetrameric major histocompatibility complex class I-peptide complex. Journal of Experimental Medicine 1998; 187(9):1373-81.

Letvin, N. L., Montefiori, D. C., Yasutomi, Y., Perry, H. C., Davies, M. E., Lekutis, C., Alroy, M., Freed, D. C., Lord, C. I., Handt, L. K., Liu, M. A., and Shiver, J. W. (1997). Potent, protective anti-HIV immune responses generated by bimodal HIV envelope DNA plus protein vaccination. *Proceedings of the National Academy of Sciences of the United States of America* 94(17), 9378-83.

Lew, D., Parker, S. E., Latimer, T., Abai, A. M., Kuwahara-Rundell, A., Doh, S. G., Yang, Z. Y., Laface, D., Gromkowski, S. H., and Nabel, G. J., et al. (1995). Cancer gene therapy using plasmid DNA: Pharmakinetic study of DNA following injection in mice [see comments]. *Hum. Gene Ther.* 6:553.

Li J, Lord C I, Haseltine W, Letvin N L, Sodroski J. Infection of cynomolgus monkeys with a chimeric HIV-1/SIVmac virus that expresses the HIV-1 envelope glycoproteins. Journal of Acquired Immune Deficiency Syndromes 1992; 5(7):639-46.

Livingston, J. B., Lu, S., Robinson, H. L., and Anderson, D. J. (1995). The induction of mucosal immunity in the female genital tract using gene-gun technology. Part 1: Antigen expression. *Annals of the New York Academy of Sciences* 772, 265-7.

Lu, S., Manson, K., Wyand, M., and Robinson, H. L. (1997). SIV DNA vaccine trial in macaques: post-challenge necropsy in vaccine and control groups. *Vaccine* 15(g), 920-3.

MacGregor, R. R., Gluckman, S., Lacy, K., Kaniefski, B., Boyer, J., Wang, B., Bagarazzi, M., William, W. V., Francher, D., Ginsberg, R., Higgins, T., and Weiner, D. (1996). First human trial of a facilitated DNA plasmid vaccine for HIV-1: safety and host response. *Int Conf AIDS* 11(2), 23 (abstract no. We.B.293).

Maecker, H. T., Umetsu, D. T., De Kruyff, R. H., and Levy, S. (1997). DNA vaccination with cytokine fusion constructs biases the immune response to ovalbumin. *Vaccine* 15(15), 1687-96.

Maecker, H. T., Umetsu, D. T., DeKruyff, R. H., and Levy, S. (1998). Cytotoxic T cell responses to DNA vaccination: dependence on antigen presentation via class II MHC. *J Immunol* 161(12), 6532-6.

Manthorpe, M., Comefert-Jensen, F., Hartikka, J., Feigner, J., Rundell, A., Margalith, M., and Dwarki, V. (1993). Gene therapy by intramuscular injection of plasmid DNA: studies on firefly luciferase gene expression in mice. *Hum Gene Ther* 4(4), 419-31.

McCluskie, M. J., Chu, Y., Xia, J. L., Jessee, J., Gebyehu, G., and Davis, H. L. (1998). Direct gene transfer to the respiratory tract of mice with pure plasmid and lipid-formulated DNA [In Process Citation]. *Antisense Nucleic Acid Drug Dev* 8(5), 401-14.

Montefiori, D. C., W. E. Robinson, S. S. Schuffman, and W. M. Mitchell, 1988. Evaluation of antiviral drugs and neutralizing antibodies to HIV by a rapid and sensitive microtiter infection assay. J. Clin. Microbiol. 26:231-237.

Montgomery, D. L., Shiver, J. W., Leander, K. R., Perry, H. C., Friedman, A., Martinez, D., Ulmer, J. B., Donnelly, J. J., and Liu, M. A. (1993). Heterologous and homologous protection against influenza A by DNA vaccination: optimization of DNA vectors. *DNA Cell Biol* 12(9), 777-83.

Moore, J. P., and Ho, D. D. (1995). HIV-1 neutralization: the consequences of viral adaptation to growth on transformed T cells. Aids 9(Suppl A), S 117-36.

Murali-Krishna K, Altman J D, Suresh M, Sourdive D J, Zajac A J, Miller J D, et al. Counting antigen-specific CD8 T cells: a reevaluation of bystander activation during viral infection. Immunity 1998; 8(2):177-87.

Ourmanov. I. et al. 2000. J Virol 74: 2740-51.

Pertmer, T. M., Eisenbraun, M. D., McCabe, D., Prayaga, S. K., Fuller, D. H., and Haynes, J. R. (1995). Gene gunbased nucleic acid immunization: elicitation of humoral and cytotoxic T lymphocyte responses following epidermal delivery of nanogram quantities of DNA. *Vaccine* 13(15), 1427-30.

Pertmer, T. M., Roberts, T. R., and Haynes, J. R. (1996). Influenza virus nucleoprotein-specific immunoglobulin G subclass and cytokine responses elicited by DNA vaccination are dependent on the route of vector DNA delivery. *J Virol* 70(9), 6119-25.

Pertmer, T. M. and Robinson, H. L. (In press). Studies on antibody responses following neonatal immunization with influenza hemagglutinin DNA or protein. *Virology*.

Poignard P, Sabbe R, Picchio G R, Wang M, Gulizia R J, Katinger H, Parren P W, Mosier D E, Burton D R (1999). Neutralizing antibodies have limited effects on the control of established HIV-1 infection in vivo. *Immunity* 10(4): 431-8

Porgador A, Irvine K R, Iwasaki A, Barber B H, Restifo N P, Germain R N. Predominant role for directly transfected dendritic cells in antigen presentation to CD8+ T cells after gene gun immunization. J Exp Med 1998; 188(6):1075-82.

Reimann K A, Li J T, Veazey R, Halloran M, Park I W, Karlsson G B, et al. A chimeric simian/human immunodeficiency virus expressing a primary patient human immunodeficiency virus type 1 isolate env causes an AIDS-like disease after in vivo passage in rhesus monkeys. Journal of Virology 1996; 70(10):6922-8.

Reimann K A, Li J T, Voss G, Lekutis C, Tenner-Racz K, Racz P, et al. An env gene derived from a primary human immunodeficiency virus type 1 isolate confers high in vivo replicative capacity to a chimeric simian/human immunodeficiency virus in rhesus monkeys. Journal of Virology 1996; 70(5):3198-206.

Richmond, J. F., Lu, S., Santoro, J. C., Weng, J., Hu, S. L., Montefiori, D. C., and Robinson, H. L. (1998). Studies of the neutralizing activity and avidity of anti-human immunodeficiency virus type 1 Env antibody elicited by DNA priming and protein boosting. J Virol 72(11), 9092-9100.

Robinson, H. L. and Pertmer, T. M. (2000). DNA vaccines: Basic studies and applications. In Advances in Virus Research. Academic Press,. Vol. 53 (in press).

Robinson, H. L, Montefiori, D. C., Johnson, R. P., Manson, K. H., Kalish, M. L., Lifson, J. D., Rizvi, T. A., Lu, S., Hu, S. L., Mazzara, G. P., Panicali, D. L., Herndon, J. G., Glickman, R., Candido, M. A., Lydy, S. L., Wand, M. S., and McClure, H. M. (1999). Neutralizing antibody-independent containment of immunodeficiency virus challenges by DNA priming and recombinant pox virus booster immunizations. Nat. Med. 5:526.

Robinson, H. L., and Pertmer, T. M. (1998). Nucleic Acid Immunizations. In "Current Protocols in Immunology" (R. Coico, Ed.), Vol. 1, pp. 2.14.1-2.14.19. 3 vols. John Wiley & Sons, Inc., New York.

Robinson, H. L., Ginsberg, H. S., Davis, H. L., Johnston, S. A., and Liu, M. A. (1997). The Scientific Future of DNA for Immunization. American Academy of Microbiology. May 31-Jun. 2-1996.

Robinson, H. L., Hunt, L. A., and Webster, R. G. (1993). Protection against a lethal influenza virus challenge by immunization with a haemagglutinin-expressing plasmid DNA. Vaccine 11(9), 957-60.

Rodriguez, F., Zhang, J., and Whitton, J. L. (1997). DNA immunization: ubiquitination of a viral protein enhances cytotoxic T-lymphocyte induction and antiviral protection but abrogates antibody induction. J Virol 71(11), 8497-503.

Ross, T. M., Y. Xu, R. A. Bright, and H. L. Robinson. C3d enhancement of antibodies to Hemagglutinin accelerates protection against influenza virus challenge. Nat. Immunol. 2000. 1:127-131.

Ross, T. M., Y. Xu, T. D. Green, D. C. Montefiori, and H. L. Robinson. 2001. Enhanced Avidity maturation of Antibody to Human Immunodeficiency Virus envelope: DNA Vaccination with gp120-C3d Fusion Proteins. AIDS Res. Human Retro. In press.

Sasaki, S., Hamajima, K., Fukushima, J., Ihata, A., Ishii, N., Gorai, I., Hirahara, F., Mohri, H., and Okuda, K. (1998b). Comparison of intranasal and intramuscular immunization against human immunodeficiency virus type I with a DNA-monophosphoryl lipid A adjuvant vaccine. Infect Immun 66(2), 823-6.

Schneider, J., Gilbert, S. C., Blanchard, T. J., Hanke, T., Robson, K. J., Hannan, C. M., Becker, M., Sinden, R_Smith, G. L., and Hill, A. V. (1998). Enhanced immunogenicity for CD8+ T cell induction and complete protective efficacy of malaria DNA vaccination by boosting with modified vaccinia virus Ankara. Nat Med 4(4), 397-402.

Scholtissek S, Grosse F. A cloning cartridge of lambda t(o) terminator. Nucleic Acids Res 1987; 15(7):3185.

Sizemore, D. R., Branstrom, A. A., and Sadoff, J. C. (1997). Attenuated bacteria as a DNA delivery vehicle for DNA-mediated immunization. Vaccine 15(8), 804-7.

Sizemore, D. R., Branstrom, A. A., and Sadoff, J. C. (1995). Attenuated Shigella as a DNA delivery vehicle for DNA-mediated immunization. Science 270(5234), 299-302.

Staprans, S., B. Corliss, J. Guthrie, M. B. Feinberg, in *Viral Genome Methods* K. Adolph, Ed. (CRC Press, Boca Raton, Fla., 1996) pp. 167-184.

Subbarao S, Schochetman G. Genetic variability of HIV-1. Aids 1996; 10(Suppl A):S13-23.

Sutcliffe, et al. 1978. Cold Spring Harbor Quant. Biol. 43:77-90

Tang, D. C., De Vit, M., and Johnston, S. A. (1992). Genetic immunization is a simple method for eliciting an immune response. Nature 356(6365), 152-4.

Thomson, S. A., Sherritt, M. A., Medveczky, J., Elliott, S. L., Moss, D. J., Fernando, G. J., Brown, L. E., and Suhrbier, A. (1998). Delivery of multiple CD8 cytotoxic T cell epitopes by DNA vaccination. J Immunol 160(4), 1717-23.

Tobery, T. W., and Siliciano, R. F. (1997). Targeting of FHV-I antigens for rapid intracellular degradation enhances cytotoxic T lymphocyte (CTL) recognition and the induction of de novo CTL responses in vivo after immunization. J Exp Med 185(5), 909-20.

Torres C A, Yang K, Mustafa F, Robinson H L (2000). DNA immunization: effect of secretion of DNA-expressed hemagglutinins on antibody responses. Vaccine 18: 805-14

Torres C A, Iwasaki A, Barber B H, Robinson H L. Differential dependence on target site tissue for gene gun and intramuscular DNA immunizations. J Immunol 1997; 158(10): 4529-32.

Uchijima, M., Yoshida, A., Nagata, T., and Koide, Y. (1998). Optimization of codon usage of plasmid DNA vaccine is required for the effective MIIC class I-restricted T cell responses against an intracellular bacterium. J Immunol 161(10), 5594-9.

Ulmer, J. B., Donnelly, J. J., Parker, S. E., Rhodes, G. H., Felgner, P. L., Dwarki, V. J., Gromkowski, S. H., Deck, R. R., De Witt, C. M., Friedman, A., and et al. (1993). Heterologous protection against influenza by injection of DNA encoding a viral protein. Science 259(5102), 1745-9.

Wild, J., Gruner, B., Metzger, K., Kuhrober, A., Pudollek, H. P., Hauser, H., Schirmbeck, R., and Reimann, J. (1998). Polyvalent vaccination against hepatitis B surface and core antigen using a dicistronic expression plasmid. Vaccine 16(4), 353-60.

Wolff, J. A., Malone, R_W., Williams, P., Chong, W., Acsadi, G., Jani, A., and Felgner, P. L. (1990). Direct gene transfer into mouse muscle in vivo. Science 247(4949 Pt 1), 1465-8.

Wu, Y., and Kipps, T. J. (1997). Deoxyribonucleic acid vaccines encoding antigens with rapid proteasomedependent degradation are highly efficient inducers of cytolytic T lymphocytes. J Immunol 159(12), 603743.

Xiang, Z., and Ertl, H. C. (1995). Manipulation of the immune response to a plasmid-encoded viral antigen by coinoculation with plasmids expressing cytokines. Immunity 2(2), 129-35.

Yamamoto S, Folks T M, Heneine W. Highly sensitive qualitative and quantitative detection of reverse transcriptase activity: optimization, validation, and comparative analysis with other detection systems. J Virol Methods 1996; 61(1-2): 135-43.

What is claimed is:

1. A vector comprising:
   (a) a gene encoding kanamycin resistance;
   (b) Col E1 replicator;
   (c) a lambda T0 terminator operably linked to the gene encoding kanamycin resistance; and
   (d) a eukaryotic transcription cassette comprising a CMV immediately early promoter, a polyadenylation signal sequence, and a nucleic acid sequence encoding: an HIV gag protein; an HIV pol protein fragment lacking the integrase domain and having amino acid changes at Asp185, Trp266, and Glu478; an HIV tat protein; an HIV rev protein; an HIV vpu protein; and an HIV env protein.

2. The vector of claim 1, wherein the HIV proteins are HIV clade B proteins.

3. The vector of claim 2, HIV Glade B proteins are HIV BH10 proteins or HIV ADA proteins.

4. The vector of claim 1, wherein the eukaryotic transcription cassette further comprises intron A of the CMV immediate early promoter.

5. The vector of claim 1, wherein the polyadenylation sequence is the rabbit beta globin polyadenylation sequence.

6. The vector of claim 1, wherein the polyadenylation sequence is the bovine growth hormone polyadenylation sequence.

7. A vector comprising the nucleotide sequence of SEQ ID NO:2.

8. The vector of claim 1, wherein Asp185 is changed to Asn, Trp266 is changed to Thr, and Glu478 is changed to Gln.

9. The vector of claim 1 or 8, wherein the HIV gag protein has amino acid changes at Cys392, Cys395, Cys413 and Cys416.

10. The vector of claim 9, wherein Cys392 is changed to Ser, Cys395 is changed to Ser, Cys413 is changed to Ser and Cys416 is changed to Ser.

* * * * *

UNITED STATES PATENT AND TRADEMARK OFFICE
CERTIFICATE OF CORRECTION

PATENT NO.         : 7,795,017 B2                                    Page 1 of 1
APPLICATION NO.    : 11/009063
DATED              : September 14, 2010
INVENTOR(S)        : Harriet L. Robinson et al.

It is certified that error appears in the above-identified patent and that said Letters Patent is hereby corrected as shown below:

On the Title Page, Column 2 (Abstract), line 12-13, delete "histocompatability" and insert
-- histocompatibility --

Signed and Sealed this

Fourteenth Day of December, 2010

David J. Kappos
*Director of the United States Patent and Trademark Office*